US011324594B2

(12) United States Patent
Ratz et al.

(10) Patent No.: US 11,324,594 B2
(45) Date of Patent: May 10, 2022

(54) PROSTHETIC HEART VALVE

(71) Applicant: inQB8 Medical Technologies LLC, Winchester, MA (US)

(72) Inventors: J. Brent Ratz, Winchester, MA (US); Arshad Quadri, West Hartford, CT (US)

(73) Assignee: inQB8 Medical Technologies, LLC, Wilmington, DE (US)

( * ) Notice: Subject to any disclaimer, the term of this patent is extended or adjusted under 35 U.S.C. 154(b) by 0 days.

(21) Appl. No.: 16/836,882

(22) Filed: Mar. 31, 2020

(65) Prior Publication Data
US 2020/0306044 A1 Oct. 1, 2020

Related U.S. Application Data

(63) Continuation of application No. PCT/US2020/024765, filed on Mar. 25, 2020.
(Continued)

(51) Int. Cl.
*A61F 2/24* (2006.01)
*A61F 2/00* (2006.01)

(52) U.S. Cl.
CPC .......... *A61F 2/2463* (2013.01); *A61F 2/2436* (2013.01); *A61F 2002/0081* (2013.01);
(Continued)

(58) Field of Classification Search
CPC ........ A61F 2/24; A61F 2/2412; A61F 2/2418; A61F 2/2469; A61F 2220/0008; A61F 2230/0069; A61F 2/2463; A61F 2/2436; A61F 2/2466; A61F 2002/0081; A61F 2210/009; A61F 2250/001; A61F 2250/0098
See application file for complete search history.

(56) References Cited

U.S. PATENT DOCUMENTS

| 10,617,519 B2 | 4/2020 | Vidlund et al. |
| 10,687,939 B2 | 6/2020 | Cooper et al. |

(Continued)

FOREIGN PATENT DOCUMENTS

EP 2777617 A1 9/2014

OTHER PUBLICATIONS

International Search Report and Written Opinion of the ISA/US in PCT/US2020/024765, dated Oct. 1, 2020, 12 pages.

*Primary Examiner* — Diane D Yabut
*Assistant Examiner* — Brigid K Byrd
(74) *Attorney, Agent, or Firm* — Wolf, Greenfield & Sacks, P.C.

(57) ABSTRACT

This disclosure relates generally to prosthetic valves and methods and systems for deploying, positioning, and recapturing the same. A prosthetic valve includes one or more support structures. At least one of the one or more support structures defines an elongate central passageway of the prosthetic valve. The prosthetic valve can also include a plurality of leaflet elements attached to at least one of the one or more support structures and disposed within the elongate central passageway for control of fluid flow through the elongate central passageway. At least one of the one or more support structures is configured to biodynamically fix the prosthetic valve within a native valve such as, for example, a native tricuspid valve of a heart.

30 Claims, 95 Drawing Sheets

Related U.S. Application Data

(60) Provisional application No. 62/823,365, filed on Mar. 25, 2019.

(52) U.S. Cl.
CPC . *A61F 2210/009* (2013.01); *A61F 2230/0069* (2013.01); *A61F 2250/001* (2013.01); *A61F 2250/0098* (2013.01)

(56) References Cited

U.S. PATENT DOCUMENTS

| | | | |
|---|---|---|---|
| 2002/0055775 A1* | 5/2002 | Carpentier | A61F 2/2427 623/2.17 |
| 2008/0071368 A1* | 3/2008 | Tuval | A61F 2/2409 623/2.17 |
| 2009/0005863 A1* | 1/2009 | Goetz | A61F 2/2439 623/2.18 |
| 2012/0035722 A1* | 2/2012 | Tuval | A61F 2/2412 623/2.37 |
| 2013/0325114 A1 | 12/2013 | McLean et al. | |
| 2014/0277427 A1 | 9/2014 | Ratz et al. | |
| 2015/0342733 A1 | 12/2015 | Alkhatib et al. | |
| 2016/0095700 A1* | 4/2016 | Righini | A61F 2/2418 623/2.11 |
| 2017/0071733 A1* | 3/2017 | Ghione | A61F 2/2418 |
| 2017/0095328 A1* | 4/2017 | Cooper | A61F 2/2418 |
| 2017/0100236 A1* | 4/2017 | Robertson | A61F 2/2409 |
| 2018/0055629 A1* | 3/2018 | Oba | A61F 2/2418 |
| 2018/0289485 A1 | 10/2018 | Rajagopal et al. | |

\* cited by examiner

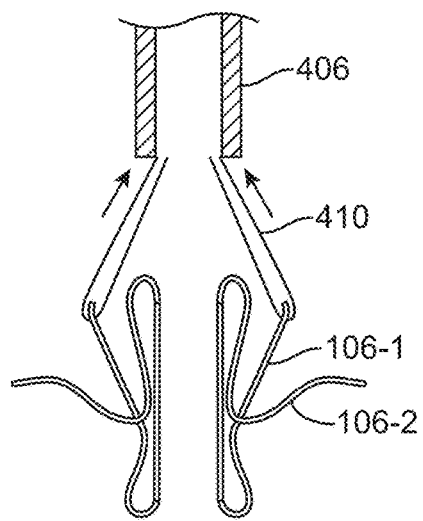 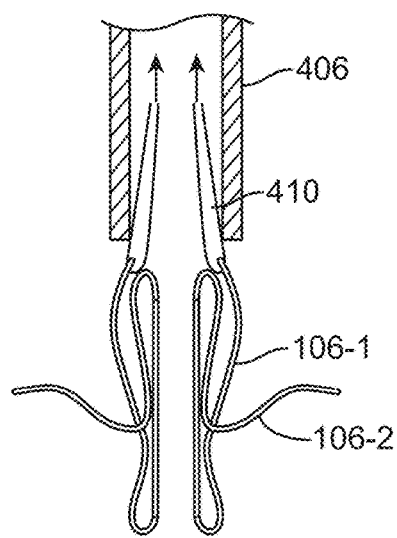 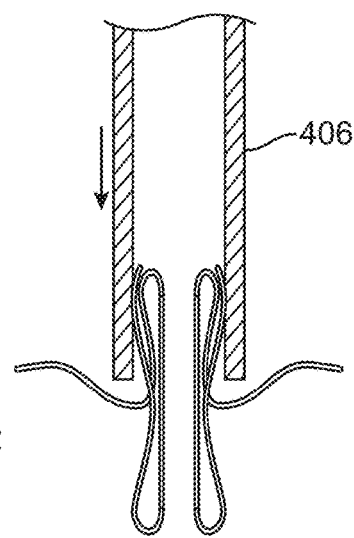
FIG. 9　　　　　FIG. 10　　　　　FIG. 11
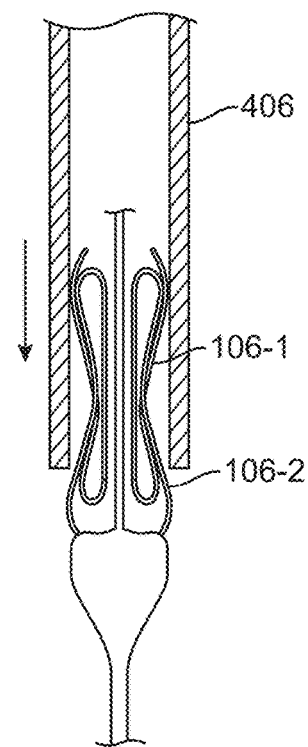
FIG. 12

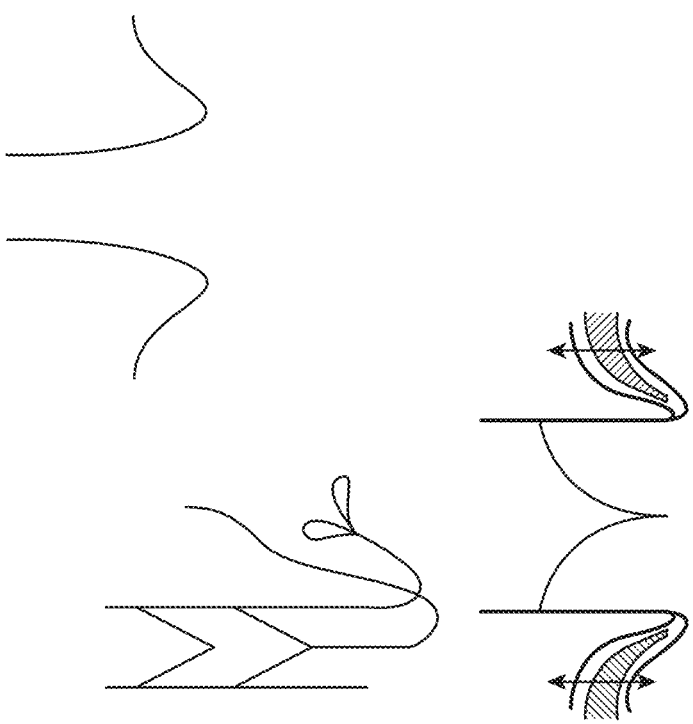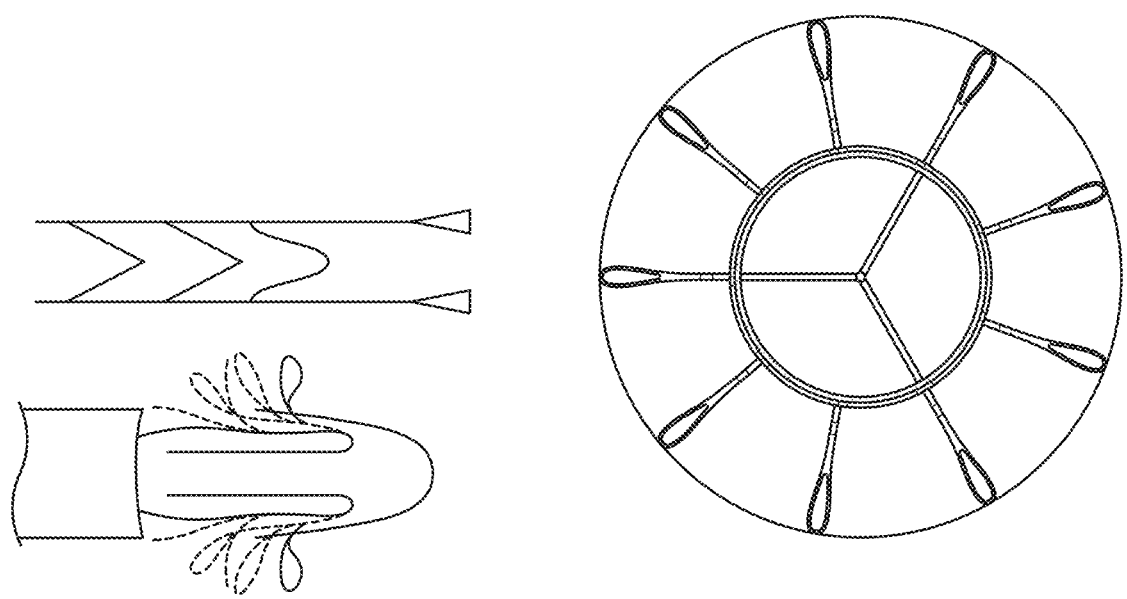
FIG. 28

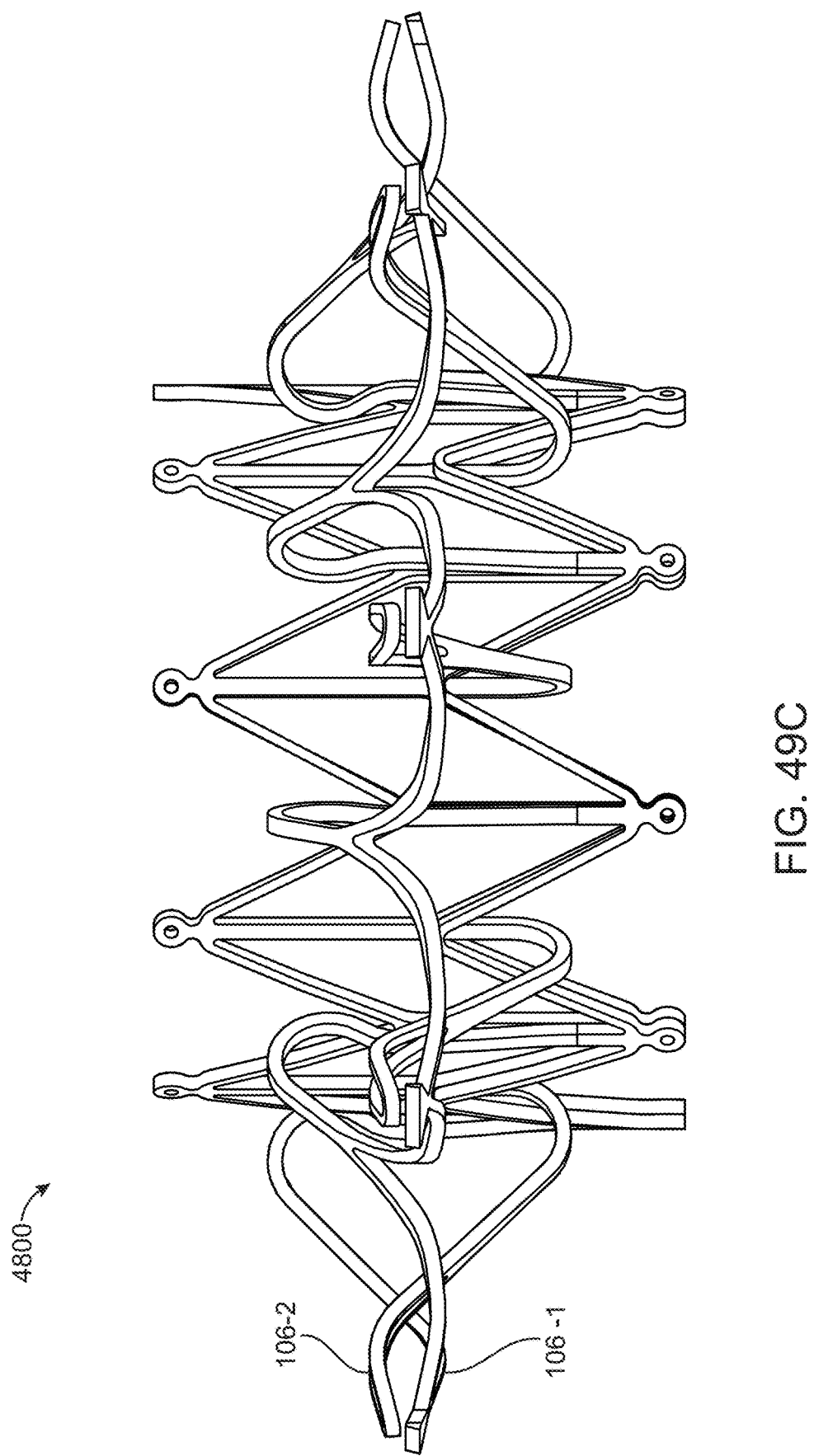

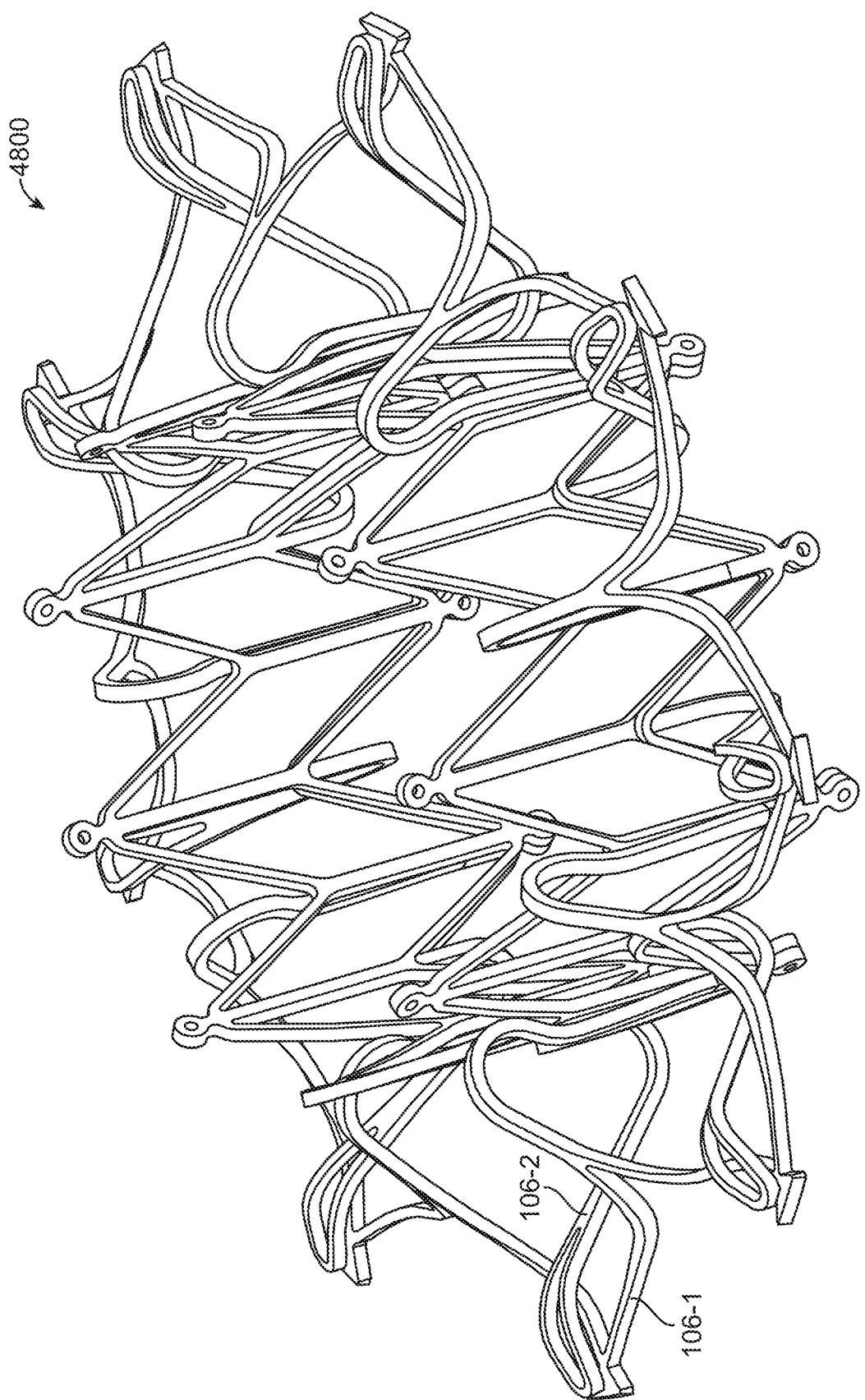

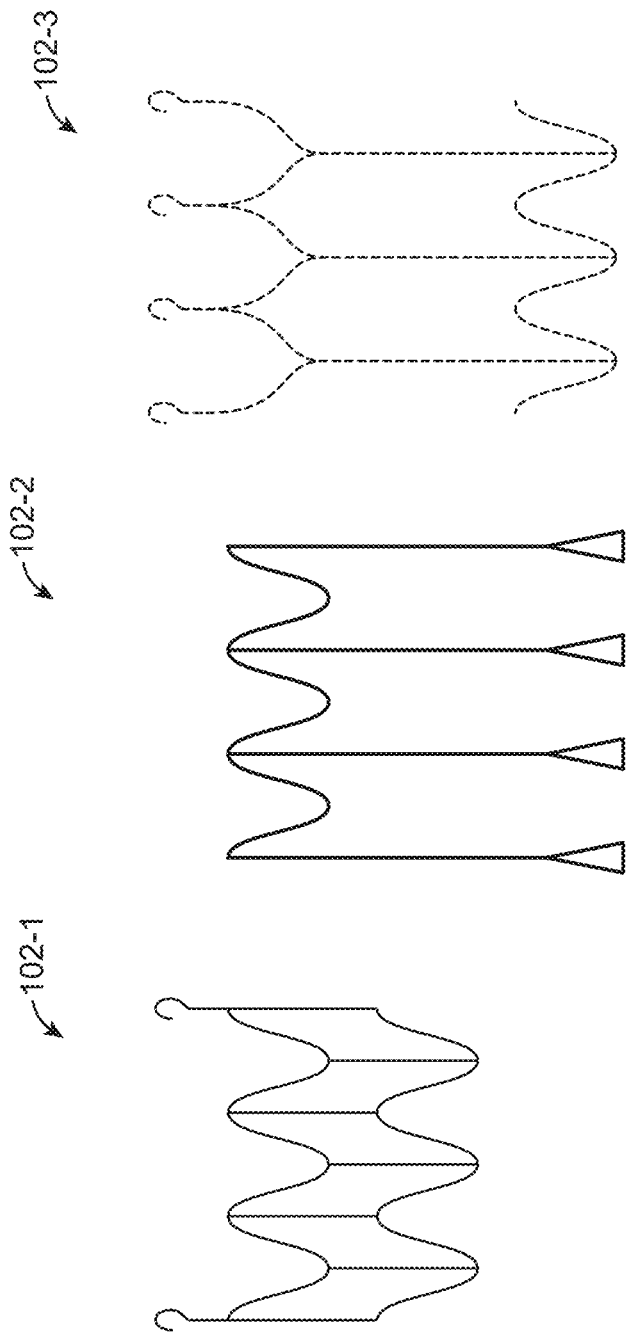
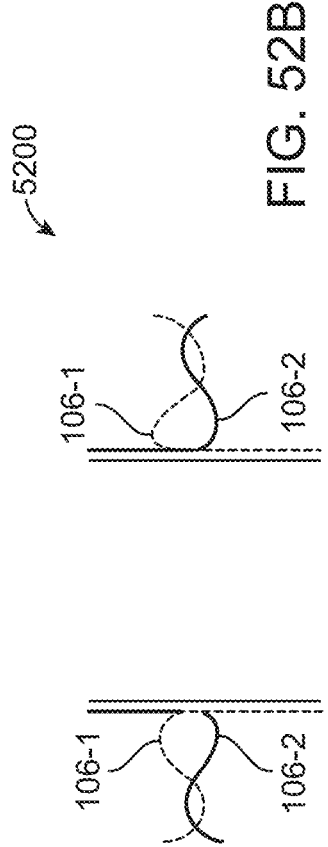
FIG. 52A
FIG. 52B

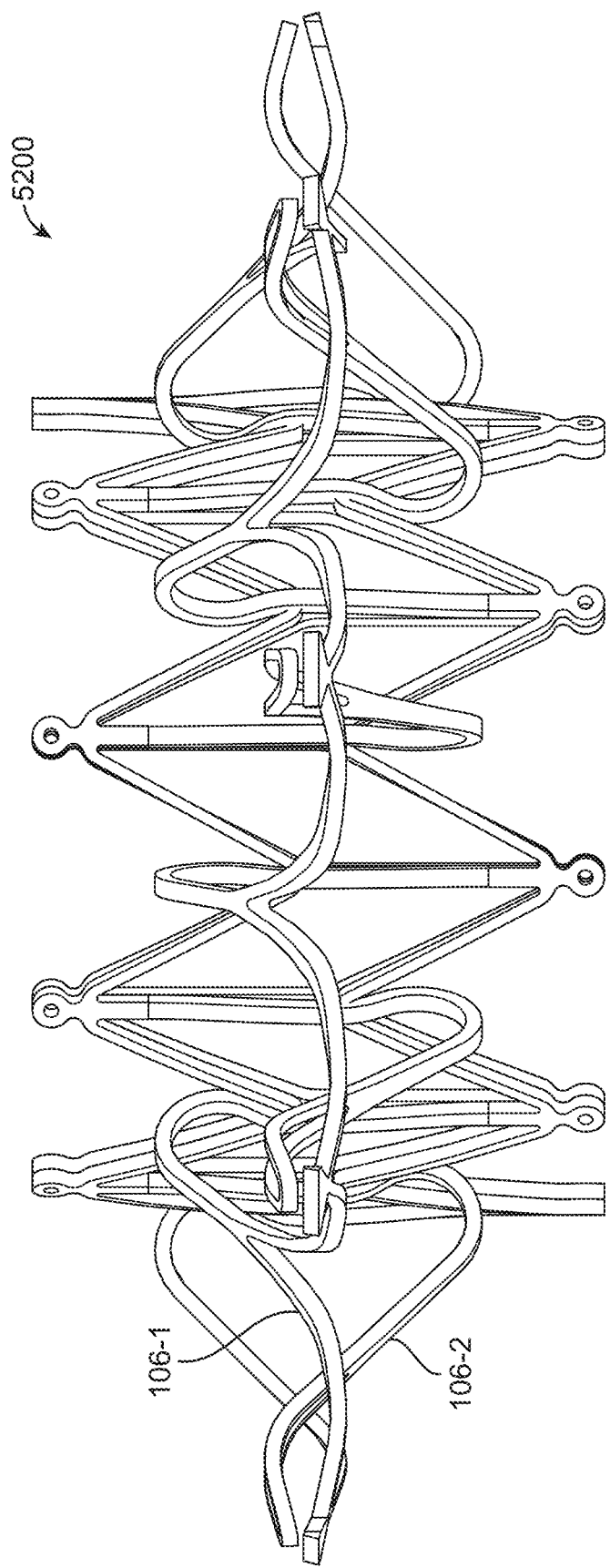

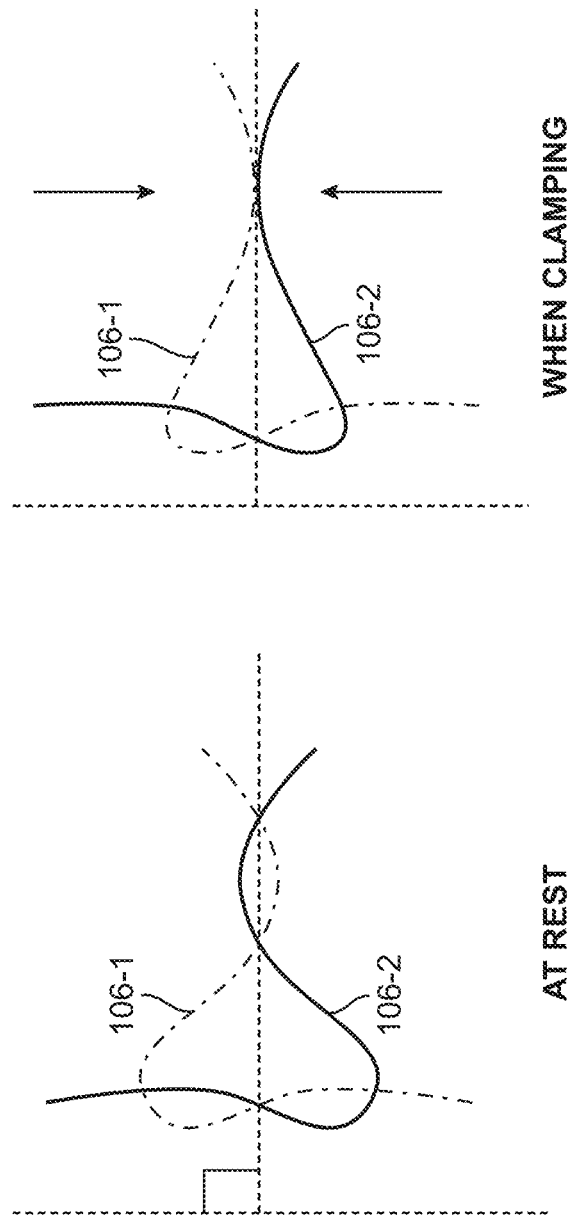

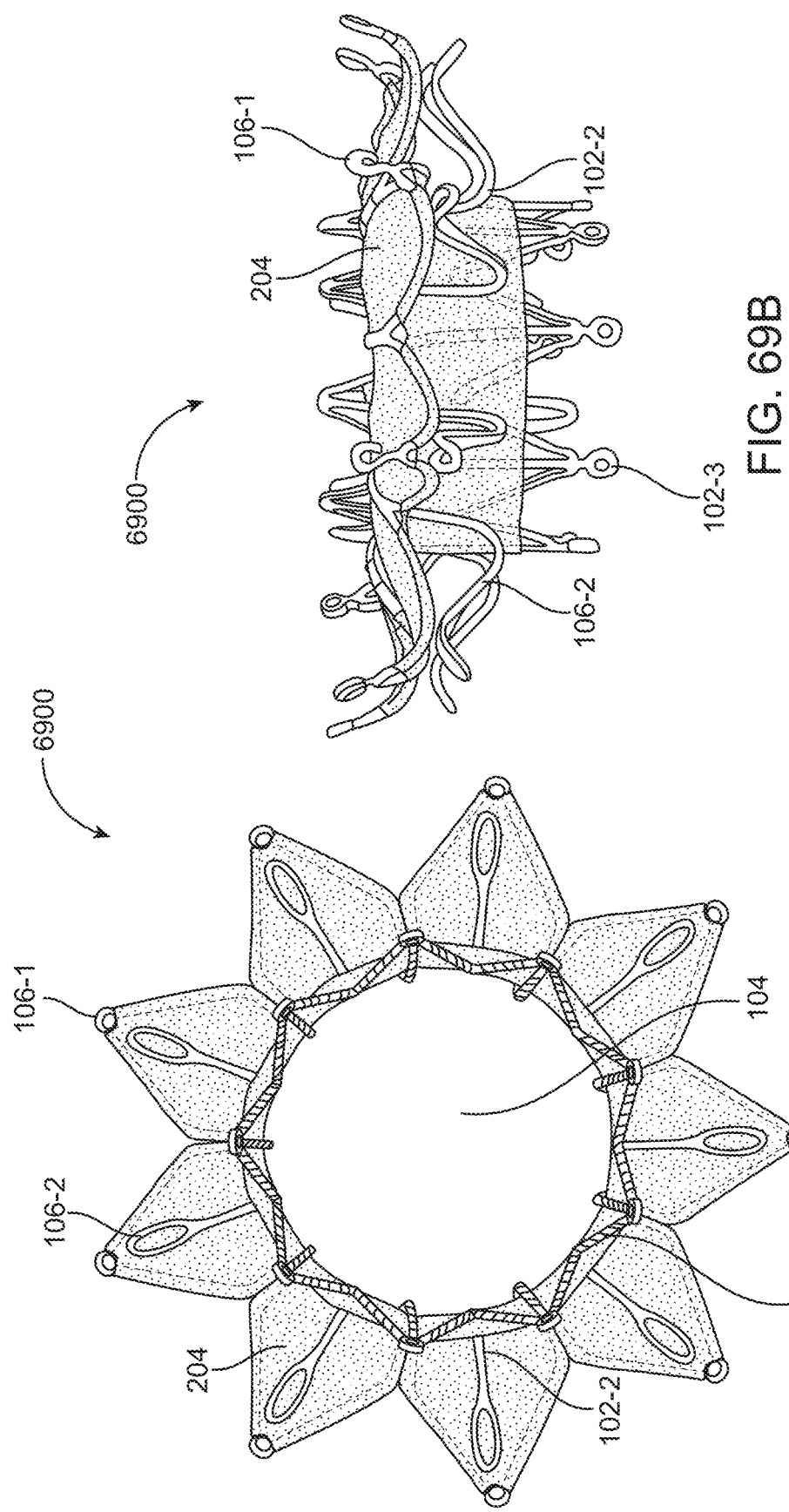

PROSTHETIC HEART VALVE

CROSS-REFERENCE TO RELATED APPLICATION

This application is a continuation application of International Application No. PCT/US2020/24765, filed on Mar. 25, 2020, which claims the benefit of U.S. Provisional Application No. 62/823,365, filed on Mar. 25, 2019, all of which are hereby incorporated by reference in their entirety.

TECHNICAL FIELD

The present disclosure generally relates to implantable cardiac devices and, more particularly, to prosthetic tricuspid valves.

BACKGROUND

Significant advancements have been made in the transcatheter treatment of heart valve disease. Initial clinical efforts focused on the pulmonary valve and were quickly followed by devices focused on the percutaneous replacement of the aortic valve to treat Aortic Stenosis. In parallel there were numerous programs that attempted to address Mitral Regurgitation through transcatheter repair technologies and later through transcatheter mitral valve replacement.

Tricuspid valve disease is a condition in which the tricuspid valve located between the right ventricle and the right atrium of the heart of does not function properly. There are multiple forms of tricuspid valve disease, including, for example, tricuspid valve regurgitation, in which blood flows backwards from the right ventricle into the right atrium, tricuspid valve stenosis, in which the tricuspid valve is narrowed, thereby decreasing blood flow from the right atrium to the right ventricle, and tricuspid atresia, which is congenital non-formation or mal-formation of the tricuspid valve, thereby blocking or decreasing blood flow from the right atrium to the right ventricle. Tricuspid valve disease has been largely ignored as a "lesser" valve disease, relative to Aortic Stenosis (greatest level of mortality) and Mitral Regurgitation (greatest prevalence).

There are currently few tricuspid-specific prosthetic tricuspid valves. In many cases tricuspid valve defects have been treated using repurposed prosthetic aortic and mitral valves. Prosthetic aortic and mitral valves that have been repurposed for use in the tricuspid valve rigidly fix by asserting pressure on the native annulus of the tricuspid valve, making the prosthetic valve immobile. Because of the tricuspid valve's proximity to conductive regions of the heart, this rigid fixation of a prosthetic valve within the tricuspid valve can lead to heart block and/or other conduction abnormalities.

There is a need for prosthetic valves specifically designed for the repair of the tricuspid valve, as replacement of the tricuspid presents unique issues.

SUMMARY

The invention provides a prosthetic tricuspid valve that is not rigidly fixed within a native tricuspid valve. This biodynamic valve design prevents heart blockage and/or other dangerous conduction abnormalities. The prosthetic tricuspid valve provided herein is able to remain in place stably, but not rigidly throughout the cardiac cycles of the heart is also needed.

The biodynamic prosthetic heart valve of the invention provides the necessary solutions by allowing the needed movement which characterizes the native tricuspid valve. In one aspect, the invention comprises a prosthetic heart valve including one or more support structures. At least one of the one or more support structure defines an elongate central passageway. The prosthetic heart valve can also include a plurality of leaflet elements attached to at least of the one or more support structures and disposed within the elongate central passageway for control of blood flow through the elongate central passageway. At least one of the one or more support structures is configured to biodynamically fix the prosthetic heart valve to native leaflets of a native heart valve of a heart. Specifically, in some embodiments, the at least one support structure is configured to biodynamically fix the prosthetic heart valve to the native leaflets of the native heart valve such that the at least one support structure is moveable within a native annulus of the native heart valve responsive to changes in pressure on one or more sides of the native heart valve.

As referred to herein, the term "biodynamic" with regard to a prosthetic heart valve, refers to a configuration of the prosthetic heart valve that allows the prosthetic heart valve to maintain axial stabilization within a native heart valve of a heart, while also moving within the native heart valve. This allows the valve to be responsive to alternating pressure differentials on either side of the native heart valve during cardiac cycles of the heart. This is accomplished without directly attaching to a native annulus or native chords of the native heart valve, thereby preserving the natural motion of the native annulus. Specifically, the prosthetic heart valve is axially stabilized within the native heart valve by grasping the native leaflets of the native heart valve, rather than relying on annular force or direct annular or chordal attachment. As referred to herein, the term "axial stabilization" with regard to a prosthetic heart valve located within a native heart valve refers to a portion of the prosthetic heart valve being interposed between any two diametrically opposed points on a native annulus of the native heart valve.

Many features of the prosthetic heart valve described herein enable this biodynamic movement of the prosthetic heart valve. In some embodiments, at least one of the one or more support structures of the prosthetic heart valve includes a cylindrical portion having an atrial end and a ventricular end. The elongate central passageway of the prosthetic heart valve is defined by the cylindrical portion of the at least one support structure. In some embodiments, at least one support structure of the one or more support structures comprises an atrial set of arms. Additionally, in some embodiments, at least one support structure of the one or more support structures comprises a ventricular set of arms. Each arm of the atrial set of arms and the ventricular set of arms can include a proximal segment that is proximal to the cylindrical portion of the at least one support structure and a distal segment that is distal to the cylindrical portion of the at least one support structure.

In some embodiments, the distal segment of each arm of the atrial set of arms and the ventricular set of arms can extend perpendicularly away from a central axis of the elongate central passageway. Furthermore, the atrial set of arms can be configured to contact the native leaflets on an atrial side of the native heart valve, and the ventricular set of arms can be configured to contact the native leaflets on a ventricular side of the native heart valve. As referred to herein, a distal segment of an arm extending "perpendicularly" away from the central axis of the elongate central passageway refers to the distal segment of the arm extending away from the central axis of the elongate central passageway such that that a line drawn from a point of contact of the distal segment with an object (e.g., a native heart valve leaflet) to a longitudinal position along the exterior surface of the cylindrical portion of the at least one support structure from which the distal segment extends, is oriented approximately 90°+/−45° from the central axis of the elongate central passageway. As discussed below, this approximate perpendicularity of the line from the point of contact of the distal segment to the longitudinal position along the exterior surface of the cylindrical portion from which the distal segment extends enables axial stabilization of the prosthetic heart valve within the native heart valve.

Specifically, in some embodiments, the atrial and ventricular sets of arms are bent such that in an implanted configuration in which the at least one support structure biodynamically fixes the prosthetic heart valve to the native leaflets of the native heart valve, in the event of motion of the cylindrical portion of the at least one support structure toward the atrial side of the native heart valve due to a ventricular systolic pressure load, one or more arms of the ventricular set of arms resist the motion while one or more arms of the atrial set of arms relax to maintain contact with the atrial side of the native leaflets. Similarly, in the event of motion of the cylindrical portion of the at least one support structure toward the ventricular side of the native heart valve due to a ventricular diastole pressure load and/or an elimination of a previously applied ventricular systolic load, one or more arms of the atrial set of arms resist the motion while one or more arms of the ventricular set of arms relax to maintain contact with the ventricular side of the native leaflets. This also creates a trampoline effect where the ventricular systolic pressure load can be partially absorbed by the atrial motion of the native leaflets.

In some embodiments, the arms of the atrial set of arms alternate with the arms of the ventricular set of arms around a circumference of the cylindrical portion of the at least one support structure.

In some embodiments, overbite can exist between the atrial set of arms and the ventricular set of arms. Specifically, in some embodiments, the arms of the atrial set of arms and the arms of the ventricular set of arms can extend across a cross-sectional plane of the cylindrical portion of the at least one support structure. As referred to herein, a "cross-sectional plane" with regard to a cylindrical portion of at least one support structure is a cross-sectional plane of the cylindrical portion of the at least one support structure that is perpendicular to a central axis of a elongate central passageway defined by the cylindrical portion of the at least one support structure. In some further embodiments, the distal segments of the arms of the atrial set of arms that extend perpendicularly away from the central axis of the elongate central passageway extend toward the ventricular end of the cylindrical portion of the at least one support structure, thereby enabling the distal segments of the arms of the atrial set of arms that extend perpendicularly away from the central axis of the elongate central passageway to clamp the native leaflets on the atrial side of the native heart valve. Additionally, the distal segments of the arms of the ventricular set of arms that extend perpendicularly away from the central axis of the elongate central passageway can extend toward the atrial end of the cylindrical portion of the at least one support structure, thereby enabling the distal segments of the arms of the ventricular set of arms that extend perpendicularly away from the central axis of the elongate central passageway to clamp the native leaflets on the ventricular side of the native heart valve.

Upon implantation of the prosthetic heart valve, this overbite between the atrial arms and the ventricular arms will result in additional clamping action and further tensioning of the native leaflets because the distal segments of the atrial arms on the atrial side of the native leaflets will be actively pushing down towards the ventricle of the heart, while the distal segments of the ventricular arms on the ventricular side of the native leaflets will be actively pushing up towards the atrium of the heart, thereby effectively creating a corrugated effect in the native leaflets like a ruffled collar. This tensioning effect from the opposing forces on either side of the native leaflets will help to further axially stabilize the prosthetic heart valve within the native heart valve. The amount of overbite between the atrial arms and the ventricular arms of the prosthetic heart valve determines the magnitude of the clamping force of the arms on the native leaflet of the native heart valve. Furthermore, the magnitude of the clamping force of the arms on the native leaflets of the native heart valve determines the amount of axial stabilization and biodynamic movement of the prosthetic heart valve within the native heart valve throughout cardiac cycles of the heart. Specifically, greater clamping forces of the arms on the native leaflets of the native heart valve yields greater axial stabilization and less biodynamic movement of the prosthetic heart valve within the native heart valve throughout cardiac cycles of the heart.

In some embodiments, the distal segments of the arms of the atrial set of arms that extend perpendicularly away from the central axis of the elongate central passageway each have a tip that curves toward the atrial end of the cylindrical portion of the at least one support structure, thereby reducing trauma to the native leaflets on the atrial side of the native heart valve at the points of contact of the atrial set of arms. Furthermore, in some embodiments, the distal segments of the arms of the ventricular set of arms that extend perpendicularly away from the central axis of the elongate central passageway each have a tip that curves toward the ventricular end of the cylindrical portion of the at least one support structure, thereby reducing trauma to the native leaflets on the ventricular side of the native heart valve at the points of contact of the ventricular set of arms.

In some embodiments, the cylindrical portion of the at least one support structure can be radially collapsible for transcatheter implantation. Additionally, the distal segments of the atrial and ventricular sets of arms that extend perpendicularly away from the central axis of the elongate central passageway can be resiliently straightenable.

In certain embodiments, the distal segments of one or more arms of the ventricular set of arms (e.g., ventricular-directed arms) that extend perpendicularly away from the central axis of the elongate central passageway, can extend toward the ventricular end of the cylindrical portion of the at least one support structure, thereby enabling the distal segments of the ventricular-directed arms that extend perpendicularly away from the central axis of the elongate central passageway to contact one of the native leaflets on the atrial side of the native heart valve rather than on the ventricular side of the native heart valve, thereby holding the native leaflet radially outward from the native heart valve in an open position. Configuring the ventricular-directed arms to hold a native leaflet radially outward from a native heart valve in an open position can be useful in many different embodiments. For example, configuring the ventricular-directed arms to hold a native leaflet radially outward from a native heart valve in an open position can be useful in embodiments in which the native leaflet is difficult to capture by the arms for one reason or another (e.g., if the native leaflet is too small or restricted). As another example, configuring the ventricular-directed arms to hold a native leaflet radially outward from a native heart valve in an open position can be useful in minimizing a number of echocardiography planes and/or viewpoints required during implantation of the prosthetic heart valve (thereby simplifying the implantation procedure).

In some embodiments, the prosthetic heart valve described herein can further include one or more covers that extend within the elongate central passageway and over one or more of the atrial set of arms and the ventricular set of arms. In some such embodiments, a portion of the one or more covers can include a fenestration feature. In an implanted configuration in which the at least one support structure biodynamically fixes the prosthetic heart valve to native leaflets of a native heart valve, the fenestration feature can be disposed between the elongate central passageway and a native annulus of the native heart valve. In some embodiments, the fenestration feature can be at least one of a radiopaque marker, an opening, a magnetic element, a one-way valve, a pop-up valve, a mechanically resizable opening, and increased porosity.

In certain embodiments, the atrial set of arms of the prosthetic heart valve can be attached to the ventricular end of the cylindrical portion of the at least one support structure, while the ventricular set of arms can be attached to the atrial end of the cylindrical portion of the at least one support structure. In other words, in certain embodiments, the atrial set of arms and the ventricular set of arms of the prosthetic heart valve can originate from opposing ends of the cylindrical portion of the at least one support structure. In such embodiments, the one or more covers can initiate at and attach to the distal segment of each arm of the atrial set of arms, extend to and attach to the proximal segment of each arm of the ventricular set of arms, extend through the cylindrical portion of the at least one support structure within the elongate central passageway, and extend around the cylindrical portion of the at least one support structure to attach to the proximal segment of each of the atrial set of arms. In some embodiments, the one or more covers can terminate at and attach to a location along the proximal segment of each arm of the atrial set of arms that is a common distance from the cylindrical portion of the at least one support structure. In alternative embodiments, the one or more covers can further extend and attach to the distal segment of each arm of the ventricular set of arms. In some embodiments, the one or more covers can extend asymmetrically and/or non-circularly within the elongate central passageway and over one or more of the atrial set of arms and the ventricular set of arms.

In some embodiments, the atrial set of arms can be attached to the atrial end of the cylindrical portion of the at least one support structure, while the ventricular set of arms can be attached to the ventricular end of the cylindrical portion of the at least one support structure. In alternative embodiments, such as the embodiment mentioned above, the atrial set of arms can be attached to the ventricular end of the cylindrical portion of the at least one support structure, while the ventricular set of arms can be attached to the atrial end of the cylindrical portion of the at least one support structure.

In embodiments in which the atrial set of arms is attached to the ventricular end of the cylindrical portion of the at least one support structure, and the ventricular set of arms is attached to the atrial end of the cylindrical portion of the at least one support structure, the proximal segment of each arm of the atrial set of arms can extend from the ventricular end of the cylindrical portion of the at least one support structure toward the atrial end of the cylindrical portion of the at least one support structure along an exterior surface of the cylindrical portion of the at least one support structure, and the distal segment of each arm of the atrial set of arms can extend perpendicularly away from the central axis of the elongate central passageway. Similarly, the proximal segment of each arm of the ventricular set of arms can extend from the atrial end of the cylindrical portion of the at least one support structure toward the ventricular end of the cylindrical portion of the at least one support structure along an exterior surface of the cylindrical portion of the at least one support structure, and the distal segment of each arm of the ventricular set of arms can extend perpendicularly away from the central axis of the elongate central passageway.

In further embodiments, in which the atrial set of arms is attached to the ventricular end of the cylindrical portion of the at least one support structure, and the ventricular set of arms is attached to the atrial end of the cylindrical portion of the at least one support structure, the distal segments of the arms of the atrial set of arms that extend perpendicularly away from the central axis of the elongate central passageway can extend from an atrial longitudinal position along the exterior surface of the cylindrical portion of the at least one support structure, and the distal segments of the arms of the ventricular set of arms that extend perpendicularly away from the central axis of the elongate central passageway can extend from a ventricular longitudinal position along the exterior surface of the cylindrical portion of the at least one support structure, where the atrial longitudinal position is in closer proximity to the atrial end of the cylindrical portion of the at least one support structure than the ventricular longitudinal position is to the atrial end of the cylindrical portion of the at least one support structure.

In further embodiments in which the ventricular set of arms is attached to the atrial end of the cylindrical portion of the at least one support structure, in an implanted configuration in which the at least one support structure biodynamically fixes the prosthetic heart valve to native leaflets of a native heart valve, the ventricular set of arms can extend from the atrial end of the cylindrical portion of the at least one support structure, through a native annulus of the native heart valve, and into the ventricular side of the native heart valve to contact the native leaflets on the ventricular side of the native heart valve.

In further embodiments in which the atrial set of arms is attached to the ventricular end of the cylindrical portion of the at least one support structure, in an implanted configuration in which the at least one support structure biodynamically fixes the prosthetic heart valve to native leaflets of a native heart valve, the atrial set of arms extend from the ventricular end of the cylindrical portion of the at least one support structure, through a native annulus of the native heart valve, and into the atrium of the heart to contact the native leaflets on the atrial side of the native heart valve.

These various embodiments in which the atrial set of arms is attached to the ventricular end of the cylindrical portion of the at least one support structure and the ventricular set of arms is attached to the atrial end of the cylindrical portion of the at least one support structure serve to provide further overbite between the atrial arms and the ventricular arms, as discussed above. Furthermore, these various embodiments in which the atrial set of arms is attached to the ventricular end of the cylindrical portion of the at least one support structure and the ventricular set of arms is attached to the atrial end of the cylindrical portion of the at least one support structure can enable improved distribution of forces received by the atrial and ventricular arms throughout the prosthetic heart valve, thereby reducing breakability of the prosthetic heart valve, and particularly the atrial and ventricular arms.

In certain embodiments, the cylindrical portion of the at least one support structure can be a cylindrical cage structure with openings. In such embodiments, at least some portions of the cylindrical cage structure and the openings can be configured to receive bends of one or more arms of the atrial set of arms and the ventricular set of arms where the arms extend perpendicularly away from the central axis of the elongate central passageway. By configuring the cylindrical portion of the at least one support structure to receive bends of one or more arms of the atrial set of arms and the ventricular set of arms where the arms extend perpendicularly away from the central axis of the elongate central passageway, the at least one support structure can provide additional support to the atrial set of arms and the ventricular set of arms, and can enable improved load distribution throughout the prosthetic heart valve, thereby reducing breakability of the prosthetic heart valve, and particularly the atrial and ventricular arms. This improved load distribution throughout the prosthetic heart valve is particularly important in the biodynamic prosthetic heart valve disclosed herein, because continual biodynamic motion of the prosthetic heart valve with a native heart valve during cardiac cycles of the heart can increase load on the prosthetic heart valve and thus opportunities for breakability of the prosthetic heart valve. Additionally, by providing additional support to the atrial set of arms and the ventricular set of arms, the arms can be further stabilized as they come into contact with native heart valve leaflets, thereby enabling axial stabilization of the prosthetic heart valve within a native heart valve.

In some embodiments, the prosthetic heart valve can include one support structure. However, in alternative embodiments, to further improve load distribution of the prosthetic heart valve, the prosthetic heart valve can include more than one support structure. In such embodiments, the prosthetic heart valve can include two, three, or more than three support structures. In such multi-support structure embodiments of the prosthetic heart valve, the multiple support structures can be configured to fit together (e.g., to snap into place) such that one or more of the multiple support structures receives support and load distribution benefits from one or more of the other multiple support structures, as described above. In some embodiments, to configure multiple support structures of a prosthetic heart valve to fit together, a minimum inner diameter of the cylindrical portion of the at least one support structure that defines the elongate central passageway can be less than a maximum outer diameter of the elongate central passageway. In additional embodiments, a minimum diameter of a radius of curvature of each bend of the one or more arms of the atrial set of arms and the ventricular set of arms, where the arms extend perpendicularly away from the central axis of the elongate central passageway, can be less than the maximum outer diameter of the elongate central passageway.

In another aspect, the invention comprises a prosthetic heart valve including one or more support structures that define an elongate central passageway, and a valve structure attached to at least one of the one or more support structures and disposed within the elongate central passageway for control of blood flow through the elongate central passageway. At least one of the one or more support structures includes a plurality of arms that extend away from the elongate central passageway for attachment of the at least one support structure to native leaflets of a native heart valve of a heart.

In some embodiments, the plurality of arms can include an atrial set of arms that extend from an atrial end of at least one support structure before curving to extend away from the elongate central passageway, and a ventricular set of arms that extend from a ventricular end of at least one support structure before curving to extend away from the elongate central passageway. In some such embodiments, the atrial arms and the ventricular arms can be configured to cooperate to hold the native leaflets of the native heart valve to maintain the elongate central passageway in a native annulus of the native heart valve without any direct attachment to the native annulus or to native cords associated with the native heart valve.

In another aspect, the invention comprises a prosthetic heart valve including one or more support structures that define an elongate central passageway, and a plurality of leaflet elements attached to at least one of the one or more support structures and disposed within the elongate central passageway. At least one of the one or more support structures is configured to biodynamically fix the prosthetic heart valve within, and separated from, a native annulus of a native heart valve of a heart.

In some embodiments, at least one support structure of the one or more support structures comprises a cylindrical portion comprising an atrial end and a ventricular end. The elongate central passageway can be defined by the cylindrical portion of the at least one support structure. Additionally, the cylindrical portion of the at least one support structure can be expandable to a maximum radial width that is less than a minimum radial width of the native annulus of the native heart valve.

In some embodiments, to biodynamically fix the prosthetic heart valve within, and separated from, the native annulus of the native heart valve, at least one of the one or more support structures of the prosthetic heart valve is configured to grasp native leaflets of the native heart valve, without direct attachment to the native annulus or native cords associated with the native heart valve.

In some embodiments, the native heart valve can be the tricuspid heart valve.

In another aspect, the invention comprises a method of transcatheter implantation of a prosthetic heart valve. The prosthetic heart valve includes at least one support structure having a cylindrical portion. The cylindrical portion of the at least one support structure defines an elongate central passageway of the prosthetic heart valve. The prosthetic heart valve also includes an atrial plurality of arms extending from a ventricular end of the cylindrical portion of the at least one support structure. Each arm of the atrial plurality of arms includes a proximal segment that is proximal to the cylindrical portion of the at least one support structure, and a distal segment that is distal to the cylindrical portion of the at least one support structure. The prosthetic heart valve also includes a ventricular plurality of arms extending from an atrial end of the cylindrical portion of the at least one support structure. Each arm of the ventricular plurality of arms includes a proximal segment that is proximal to the cylindrical portion of the at least one support structure, and a distal segment that is distal to the cylindrical portion of the at least one support structure.

The method of transcatheter implantation of the prosthetic heart valve includes guiding the prosthetic heart valve into a native valve of a heart of a patient via a vein of the patient while the prosthetic heart valve is in a contracted configuration in which the elongate central passageway has an atrial diameter, each arm of the ventricular plurality of arms is held against an exterior surface of the cylindrical portion of the at least one support structure by a sheath, and each arm of the atrial plurality of arms is held within the sheath and against the exterior surface of the cylindrical portion of the at least one support structure by a respective restraint of a plurality of restraints. The method further includes retracting the sheath to allow each arm of the ventricular plurality of arms to bend such that a distal segment of each arm of the ventricular plurality of arms extends away from the cylindrical portion of the at least one support structure. The method further includes retracting the prosthetic heart valve along with the sheath until the distal segment of each arm of the ventricular plurality of arms contacts native leaflets of the native heart valve on a ventricular side of the native heart valve. The method further includes expanding the cylindrical portion of the at least one support structure from the contracted configuration with the atrial diameter to an expanded configuration with a larger ventricular diameter to form the elongate central passageway. The method further includes advancing the plurality of restraints to allow each arm of the atrial plurality of arms to bend such that a distal segment of each arm of the atrial plurality of arms extends away from the cylindrical portion of the at least one support structure and captures the native leaflets of the native heart valve on an atrial side of the native heart valve against the distal segment of the ventricular plurality of arms contacting the native leaflets of the native heart valve on the ventricular side of the native heart valve.

In some embodiments, retracting the sheath to allow each arm of the ventricular plurality of arms to bend such that the distal segment of each arm of the ventricular plurality of arms extends away from the cylindrical portion of the at least one support structure further includes allowing each arm of the ventricular plurality of arms to bend such that the proximal segment of each arm of the ventricular plurality of arms extends along the exterior surface of the cylindrical portion of the at least one support structure. Additionally, in such embodiments, advancing the plurality of restraints to allow each arm of the atrial plurality of arms to bend such that the distal segment of each arm of the atrial plurality of arms extends away from the cylindrical portion of the at least one support structure can further include allowing each arm of the atrial plurality of arms to bend such that the proximal segment of each arm of the atrial plurality of arms extends along the exterior surface of the cylindrical portion of the at least one support structure.

In some embodiments, the method can further include detaching the plurality of restraints from the atrial plurality of arms.

In some embodiments, the method can further include repositioning the prosthetic heart valve within the native heart valve by retracting the plurality of restraints from the atrial plurality of arms to straighten each arm of the atrial plurality of arms against the exterior surface of the cylindrical portion of the at least one support structure to release the native leaflets of the native heart valve, while pushing the at least one support structure toward the ventricular side of the native heart valve with a plurality of spreader arms.

In some embodiments, the method can further include re-capturing and removing the prosthetic heart valve from the native heart valve by advancing the sheath to straighten each arm of the ventricular plurality of arms and compress the cylindrical portion of the at least one support structure for removal of the prosthetic heart valve from the native heart valve via the vein of the patient while the prosthetic heart valve is in a contracted configuration.

In some embodiments, advancing the plurality of restraints can include advancing the restraints while maintaining contact with the at least one support structure with a plurality of spreader arms.

In some embodiments, the plurality of spreader arms can extend from a mid layer within the sheath. In certain embodiments, each restraint of the plurality of restraints can extend from the sheath between a pair of the plurality of spreader arms. In certain embodiments, each spreader arm of the plurality of spreader arms can include an interlocking mechanism that maintains contact with the atrial end of the cylindrical portion of the at least one support structure.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 9-12 illustrate a prosthetic heart valve in various stages of removal, in accordance with an embodiment.

FIGS. 27-30 illustrate various aspects of a prosthetic heart valve having another support structure, in accordance with an embodiment.

FIG. 49C illustrates a CAD drawing of a side view of a prosthetic tricuspid valve having two support structures, in accordance with an embodiment.

FIG. 49E illustrates a CAD drawing of a tilted side view of a prosthetic tricuspid valve having two support structures, in accordance with an embodiment.

FIG. 52A illustrates a view of flattened support structures of a prosthetic tricuspid valve having three support structures, in accordance with an embodiment.

FIG. 52B illustrates a side view of a prosthetic tricuspid valve having three support structures and configured for implantation in a native tricuspid valve, in accordance with an embodiment.

FIG. 53D illustrates a CAD drawing of a side view of a prosthetic tricuspid valve having three support structures, in accordance with an embodiment.

FIG. 54A illustrates a side view of overbite between an atrial arm and a ventricular arm of a prosthetic tricuspid valve at rest, in accordance with an embodiment.

FIG. 54B illustrates a side view of an atrial arm and a ventricular arm of a prosthetic tricuspid valve when a prosthetic tricuspid valve is implanted in a native tricuspid valve, in accordance with an embodiment.

FIG. 69A is an image of a bottom-up view of support structures of a prototype prosthetic tricuspid valve, in accordance with an embodiment.

FIG. 69B is an image of a side view of support structures of a prototype prosthetic tricuspid valve, in accordance with an embodiment.

DETAILED DESCRIPTION

Figure 1:
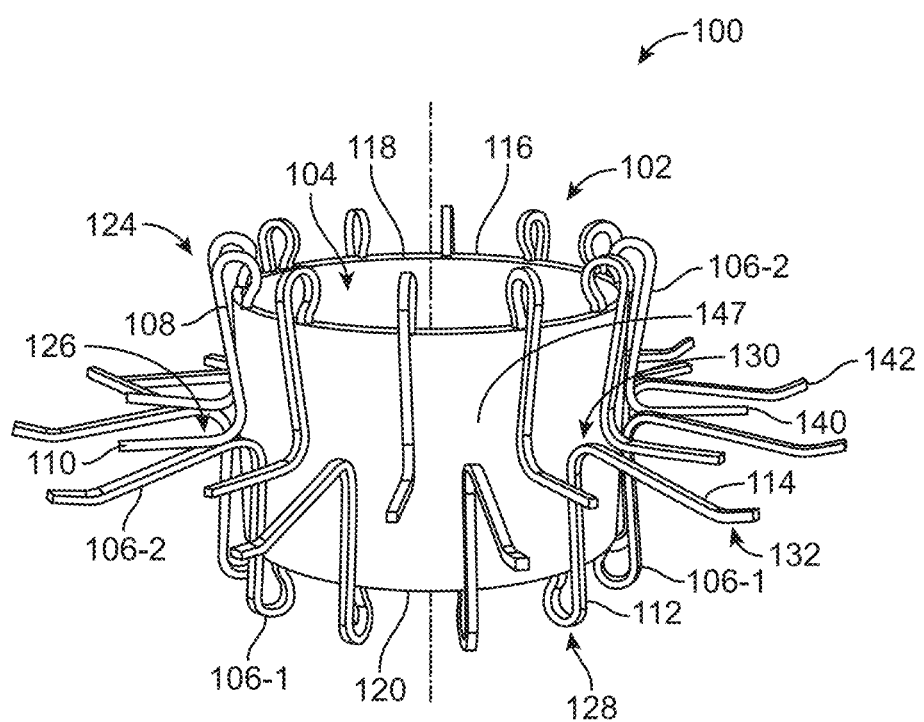
FIG. 1 is a schematic perspective view of a support structure for a prosthetic heart valve, in accordance with an embodiment.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Because aortic and mitral valve replacements have generally been the focus of device development, the need for a solution for Tricuspid Regurgitation (TR) remains unaddressed, particularly because there is growing evidence showing that TR is associated with higher mortality rates and should not be left untreated even if the other heart valves have been addressed.

Like the mitral valve, the tricuspid valve is in an atrio-ventricular position. Consequently, it might be expected that a mitral valve replacement could be repurposed for use in the tricuspid position. However, specific aspects of the tricuspid valve anatomy and the surrounding anatomy (e.g. the tricuspid valve's larger size and proximity to conductive regions of the heart) make a dedicated solution more favorable than such a repurposing of mitral valve devices.

In accordance with aspects of the disclosure, a biodynamic prosthetic tricuspid valve is provided herein. As mentioned above, as referred to herein, the term "biodynamic" with regard to a prosthetic tricuspid valve, refers to a configuration of the prosthetic tricuspid valve that allows the prosthetic tricuspid valve to maintain axial stabilization within a native tricuspid valve of a heart, but to move within the native tricuspid valve responsive to alternating pressure differentials on either side of the native tricuspid valve during cardiac cycles of the heart, without directly attaching to a native annulus or native chords of the native tricuspid valve, thereby preserving the natural motion of the native annulus. Specifically, the prosthetic tricuspid valve is axially stabilized within the native tricuspid valve by grasping the native leaflets of the native tricuspid valve, rather than relying on annular force or direct annular or chordal attachment. As referred to herein, the term "axial stabilization" with regard to a prosthetic tricuspid valve located within a native tricuspid valve refers to a portion of the prosthetic tricuspid valve being interposed between any two diametrically opposed points on a native annulus of the native tricuspid valve.

The prosthetic tricuspid valve includes one or more support structures. For example, as discussed in further detail below, the prosthetic tricuspid valve can include one, two, three, or more than three support structures. At least one of the one or more support structures includes a cylindrical portion having an atrial end and a ventricular end. The cylindrical portion of the at least one support structure defines an elongate central passageway of the prosthetic tricuspid valve. A central axis of the elongate central passageway extends within the elongate central passageway from the atrial end of the cylindrical portion to the ventricular end of the cylindrical portion. When the prosthetic tricuspid valve is in an implanted configuration in a native tricuspid valve of a heart, blood flows through the elongate central passageway of the prosthetic tricuspid valve from an atrium of the heart to a ventricle of the heart, along the central axis of the elongate central passageway. Furthermore, a plurality of leaflet elements attach to the at least one support structure and are disposed within the elongate central passageway for control of blood flow through the elongate central passageway.

Ventricular arms extending from a first end of the cylindrical portion of the at least one support structure extend into the ventricle of the heart to contact the ventricular surface of the native leaflets, while atrial arms extending from a second end opposite the first end of the cylindrical portion of the at least one support structure extend into the atrium to contact the atrial surface of the native leaflets. Various features of the prosthetic tricuspid valve configure the valve for transcatheter implantation, re-positioning, and/or removal. The prosthetic tricuspid valve described herein can be easily positioned and deployed in a wide range of patients with the ability to control the deployment, assess complete functionality, and maintain the ability to recapture and remove the implant prior to full release.

Although various examples are described herein in which prosthetic tricuspid valves are configured for replacement of the native tricuspid valve, it should be appreciated that appropriate modifications can be made for use of the prosthetic tricuspid valves disclosed herein to replace other native heart valves and/or in any other non-heart valves.

FIG. 1 illustrates an example prosthetic tricuspid valve 100 in accordance with aspects of the disclosure. In the example of FIG. 1, prosthetic tricuspid valve 100 includes a support structure 102 having a cylindrical portion 116 that defines an elongate central passageway 104. Cylindrical portion 116 has an atrial end 118 configured to be disposed in the atrium of the heart, and a ventricular end 120 configured to be disposed in the ventricle of the heart. A central axis of the elongate central passageway 104 along which blood flows from the atrium of the heart to the ventricle of the heart is depicted in FIG. 1 by a dotted line.

Although cylindrical portion 116 is shown as a solid cylindrical structure, it should be appreciated that the cylindrical portion 116 can be formed from other structures such as, for example, a radially expandable and compactable cylindrical cage structure with openings that can be balloon expandable or self-expanding. In such embodiments, the cylindrical cage structure can be made of laser cut metal, polymer tubing, and/or wire-formed material. In this example, some of the openings (not shown in FIG. 1, see FIG. 15, 16, 21 or 22) may be positioned to receive one or more bends of one or more of arms 106 described below, to maintain uniformity and symmetry during loading and recapturing of the prosthetic tricuspid valve 100, and/or to enable load distribution from the one or more arms 106 throughout the support structure 102 of the prosthetic tricuspid valve 100. In various structural implementations, cylindrical portion 116 is radially collapsible (e.g., into elongate central passageway 104) for transcatheter implantation.

Cylindrical portion 116 is undersized relative to a native tricuspid valve annulus so as not to put any radial force on the annulus. Specifically, in the example of FIG. 1 and various other examples described herein, cylindrical portion 116 is expandable to a maximum radial width that is less than the minimum radial width of the native annulus of the native tricuspid valve. As described in detail below, the arms 106 are configured to cooperate to hold the native leaflets of the native tricuspid valve to maintain the elongate central passageway 104 in the native annulus of the native tricuspid valve without any direct attachment to the native annulus or cords so that prosthetic tricuspid valve 100 is biodynamically fixed within, and separated from, the native annulus of the native tricuspid valve. However, it should be appreciated that some portions of the prosthetic tricuspid valve 100 can extend to or beyond the native annulus. For example, and as discussed in further detail hereinafter, the prosthetic tricuspid valve 100 may include an atrial sealing skirt that extends to or beyond the native annulus for anchoring and/or to fully cover the commissures of the native tricuspid valve for leak prevention.

Cylindrical portion 116 is depicted in FIG. 1 as having a circular cross section, but it should be appreciated that cylindrical portion 116 can have a generally cylindrical shape without a perfectly circular cross section. For example, cylindrical portion 116 can have a cross section that is circular or non-circular (e.g. D-shaped, triangular, oval, or any other cross-sectional geometry), and can be configured such that one prosthetic tricuspid valve size accommodates all patients (e.g., with different sizing only for the arms 106 and an atrial sealing skirt to be described hereinafter) or with a range of prosthetic tricuspid valve sizes depending on patient anatomy.

Although not shown in FIG. 1, a plurality of leaflet elements can be attached to support structure 102 and disposed within the elongate central passageway 104 for control of blood flow through the elongate central passageway. These leaflet elements replace the function of the native leaflets once the prosthetic tricuspid valve 100 is installed.

As shown in FIG. 1, the prosthetic tricuspid valve 100 is biodynamically fixed within, and separated from, a native annulus of a native tricuspid valve by fixing the prosthetic tricuspid valve 100 to native leaflets of the native tricuspid valve using a plurality of ventricular arms 106-1 and atrial arms 106-2. Specifically, the plurality of ventricular arms 106-1 extend from a first end of the cylindrical portion 116 of the support structure 102 and contact a ventricular side of the native leaflets of the native tricuspid valve. Similarly, the plurality of atrial arms 106-2 extend from a second end opposite the first end of the cylindrical portion 116 of the support structure 102 and contact an atrial side of the native leaflets of the native tricuspid valve. As shown in FIG. 1, the atrial arms 106-1 may alternate with the ventricular arms 106-2 around a circumference of the cylindrical portion 116 of the support structure 102.

Each arm 106 comprises a proximal segment and a distal segment. The proximal segment of each arm 106 is proximal to the cylindrical portion 116 of the support structure 102. Specifically, the proximal segment of each arm 106 is the segment of the arm 106 that is attached to the cylindrical portion 116 of the support structure 102. The proximal segment of each arm 106 extends from its attachment point at the cylindrical portion 116 along an exterior surface 147 of the cylindrical portion 116, and ends at (and includes) a secondary bend that directs the distal segment of the arm away from and perpendicular to the central axis of the elongate central passageway 104. The secondary bend directs the distal segment of the arm away from and perpendicular to the central axis of the elongate central passageway 104 at a longitudinal position along the exterior surface 147 of the cylindrical portion 116. In some embodiments (e.g., the embodiment of the prosthetic tricuspid device 100 in FIG. 1), the proximal segment of each arm 106 also includes an initial bend that directs the proximal segment of the arm 106 along the exterior surface 147 of the cylindrical portion 116.

Each atrial arm 106-1 has a proximal segment 112 and each ventricular arm 106-2 has a proximal segment 108. As shown in FIG. 1 and as discussed in further detail below, the optional initial bend of the proximal segment 112 of each atrial arm 106-1 is an initial bend 128, and the secondary bend of the proximal segment 112 of each atrial arm 106-1 is a secondary bend 130. Similarly, the optional initial bend of the proximal segment 108 of each ventricular arm 106-2 is an initial bend 124, and the secondary bend of the proximal segment 108 of each ventricular arm 106-2 is a secondary bend 126.

The distal segment of each arm 106 is distal to the cylindrical portion 116 of the at least one support structure 102. Specifically, the distal segment of each arm 106 is the segment of the arm 106 that contacts an object (e.g., the native leaflets of the native tricuspid valve). The distal segment of an arm 106 contacts an object (e.g., the native leaflets of the native tricuspid valve) at a point of contact along the distal segment of the arm 106. The distal segment of each arm 106 extends from (and does not include) the secondary bend of the arm 106, extends away from and perpendicular to the central axis of the elongate central passageway 104, and ends at (and includes) a tip. As mentioned above, the distal segment of the arm extends away from and perpendicular to the central axis of the elongate central passageway 104 from a longitudinal position along the exterior surface 147 of the cylindrical portion 116.

In some embodiments discussed in detail below with regard to FIG. 24, the distal segment of each arm can include an extended segment having a third bend. Each atrial arm 106-1 has a distal segment 114 and each ventricular arm 106-2 has a distal segment 110. As discussed in further detail below, the tip of the distal segment 114 of each atrial arm 106-1 is a tip 142, and the tip of the distal segment 110 of each ventricular arm 106-2 is a tip 140.

In the example of FIG. 1, the proximal segment 108 of each ventricular arm 106-2 extends from the atrial end 118 of cylindrical portion 116 and has the initial bend 124 of 180°+/−45° that directs the proximal segment 108 of the ventricular arm 106-2 along the exterior surface 147 of cylindrical portion 116, through the native annulus (outside of the elongate central passageway 104), and sufficiently towards the ventricular end 120. Then, following the secondary bend 126 in the proximal segment 108 of the ventricular arm 106-2, the distal segment 110 of the ventricular arm 106-2 extends away from and perpendicular to the central axis of the elongate central passageway 104, from a longitudinal position along the exterior surface 147 of the cylindrical portion 116.

FIG. 1 also shows how the proximal segment 112 of each atrial arm 106-1 extends from the ventricular end 120 of cylindrical portion 116 and has the initial bend 128 of 180°+/−45° that directs the proximal segment 112 of the atrial arm 106-1 along the exterior surface 147 of cylindrical portion 116, through the native annulus (outside of the elongate central passageway 104), and sufficiently towards the atrial end 118 of the cylindrical portion 116. Then, following the secondary bend 130 in the proximal segment 112 of the atrial arm 106-1, the distal segment 114 of the atrial arm 106-1 extends away from and perpendicular to the central axis of the elongate central passageway 104, from a longitudinal position along the exterior surface 147 of the cylindrical portion 116. As mentioned above, in some embodiments, the proximal segments of one or more arms 106 do not include an initial bend.

As mentioned above, the distal segment of each arm 106 extends perpendicularly away from the central axis of the elongate central passageway 104 for attachment of the support structure 102 to the native leaflets of the native tricuspid valve. As referred to herein, a distal segment of an arm 106 extending "perpendicularly" away from the central axis of the elongate central passageway 104 refers to the distal segment of the arm 160 extending away from the central axis of the elongate central passageway 104 such that that a line drawn from a point of contact of the distal segment with an object (e.g., a native tricuspid valve leaflet) to a longitudinal position along the exterior surface 147 of the cylindrical portion 116 of the at least one support structure 102 from which the distal segment extends, is oriented approximately 90°+/−45° from the central axis of the elongate central passageway 104. In some embodiments, the point of contact of a distal segment of an arm 106 can be the tip 140 or 142 of the arm 106. In alternative embodiments in which a distal segment of an arm 106 includes an extended segment having a third bend, the points of contact of the distal segment of the arm can be the extended segment, or more particularly, the third bend, of the arm 106. The point of contact of a distal segment of an arm 106 can also be any other portion of the distal segment of the arm 106. As discussed in further detail below, this approximate perpendicularity of the line from the point of contact of the distal segment to the longitudinal position along the exterior surface 147 of the cylindrical portion 116 from which the distal segment extends enables axial stabilization of the prosthetic tricuspid valve within the native tricuspid valve.

The distal segment 114 of each atrial arm 106-1 and the distal segment 110 of each ventricular arm 106-2 that extend perpendicularly away from the central axis of the elongate central passageway 104 are resiliently straightenable (e.g., against the exterior surface 147 of cylindrical portion 116 of the support structure 102) with or without extending beyond the length of the cylindrical portion 116. In this way, prosthetic tricuspid valve 100 is configured to have a reduced length to facilitate navigation of curves or bends along an insertion pathway (e.g., within the vasculature (e.g., vein or artery) of the patient and into the heart).

In the example of FIG. 1, the ventricular arms 106-2 extend from the atrial end 118 of the cylindrical portion 116, the atrial arms 106-1 extend from the ventricular end 120 of the cylindrical portion 116, and relative locations of the secondary bends 126 and 130 are such that the location of the secondary bend 126 of each ventricular arm 106-2 is closer in proximity to the ventricular end 120 of the cylindrical portion 116 than the secondary bend 130 of each atrial arm 106-1. In other words, in the example of FIG. 1, the atrial arms 106-1 and the ventricular arms 106-2 extend across a cross-sectional plane of the cylindrical portion 116 of the at least one support structure 102 such that there is overbite between the atrial arms 106-1 and the ventricular arms 106-2 over the cross-sectional plane. As referred to herein, a "cross-sectional plane" with regard to a cylindrical portion of at least one support structure is a cross-sectional plane of the cylindrical portion of the at least one support structure that is perpendicular to a central axis of a elongate central passageway defined by the cylindrical portion of the at least one support structure. As a result of this overbite between the atrial arms 106-1 and the ventricular arms 106-2, in vivo, the ventricular arms 106-2 extending from the atrial end 118 of the cylindrical portion 116 extend down into the ventricle of the heart to contact the ventricular surface of the native leaflets, while the atrial arms 106-1 extending from the ventricular end 120 of the cylindrical portion 116 extend up into the atrium of the heart to contact the atrial surface of the native leaflets.

Additionally, in some embodiments, the relative bend angle of the secondary bends 126 and 130 can each or either be slightly greater than 90°, such that the tip 140 of each ventricular arm 106-2 is closer in proximity to the atrial end 118 of the cylindrical portion 116 than the tip 142 of each atrial arm 106-1. This arrangement further contributes to the overbite of the atrial arms 106-1 and the ventricular arms 106-2 described above. Upon implantation, this overbite of the atrial arms 106-1 and the ventricular arms 106-2 will result in additional clamping action and further tensioning of the native leaflets because the distal segments 114 of the atrial arms 106-1 on the atrial side of the native leaflets will be actively pushing down towards the ventricle of the heart, while the distal segments 110 of the ventricular arms 106-2 on the ventricular side of the native leaflets will be actively pushing up towards the atrium of the heart, thereby effectively creating a corrugated effect in the native leaflets like a ruffled collar. This tensioning effect from the opposing forces on either side of the native leaflets will help to axially stabilize the prosthetic tricuspid valve 100 within the native tricuspid valve.

Securing prosthetic tricuspid valve 100 to either side of the native leaflets in this way also creates a trampoline effect where ventricular systolic pressure load can be partially absorbed by the upward (atrial) motion and tensioning of the native leaflets. Specifically, in this example, the arms 106 are bent such that, in the event of motion of the cylindrical portion 116 of the support structure 102 toward the atrial side 118 of the native tricuspid valve (e.g., due to a ventricular systolic pressure load), the ventricular arms 106-2 resist the motion while the atrial arms 106-1 relax to maintain contact with the atrial side of the native leaflets. Additionally, in the event of motion of the cylindrical portion 116 of the support structure 102 toward the ventricular side 120 of the native tricuspid valve, the atrial arms 106-1 resist the motion while the ventricular arms 106-2 relax to maintain contact with the ventricular side of the native leaflets. Furthermore, as a result of the trampoline effect, force from the distal segment 110 of each ventricular arm 106-2 against the ventricular side of the native leaflets can be further distributed throughout an atrial sealing skirt to minimize the risk of erosion through the native leaflets. In this way, the prosthetic tricuspid valve 100 is biodynamically fixed within the native tricuspid valve during the cardiac cycle.

It should be appreciated that, although tips 140 and 142 of arms 106-2 and 106-1 are depicted in FIG. 1 as having a square cross-section, in other implementations the cross-sectional configuration of the tips 140 and 142 of arms 106-2 and 106-1 can have a circular or another non-circular shape (e.g., in order to provide improved attachment and/or leak prevention such as in the presence of an atrial sealing skirt as discussed in further detail hereinafter). The relative lengths of the distal segments 114 of the atrial arms 106-1 and/or the distal segments 110 of the ventricular arms 106-2 can also be modified for improved attachment and/or leak prevention.

Figure 2:
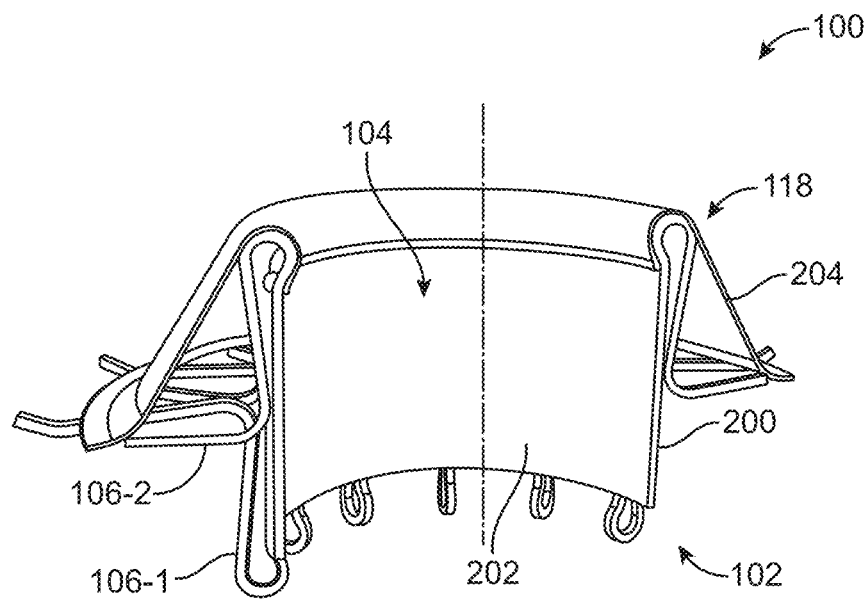
FIG. 2 is a schematic cross-sectional perspective view of a prosthetic heart valve, in accordance with an embodiment.

FIG. 2 shows an example of a cover 200 that can be provided over support structure 102. Cover 200 can be made from bioprosthetic tissue (e.g. bovine, porcine, etc.) or can be made from synthetic material (e.g. polyurethane, ePTFE, proprietary hydrogel materials, etc.). As shown, cover 200 can include a cylindrical portion 202 that defines the elongate central passageway 104 and to which prosthetic leaflet elements (not shown) can be attached. Cover 200 can also include an atrial sealing skirt 204 that extends over the atrial end 118 of support structure 102 and at least partially over the atrial arms 106-1.

The atrial sealing skirt 204 may also facilitate the recapturable nature of the prosthetic tricuspid valve 100. For example, reduction of the atrial arm 106-1 length while maintaining contact with the atrial end 118 of the cylindrical portion 116 of the support structure 102, may fold up the atrial sealing skirt 204 and then allow for an outer sheath (see 406 of FIG. 4) to be advanced toward the ventricular side of the native tricuspid valve, in order to recapture the ventricular arms 106-2 contacting the ventricular side of the native leaflets of the native tricuspid valve, and fully reposition or remove the implant prior to final release.

Figure 3:
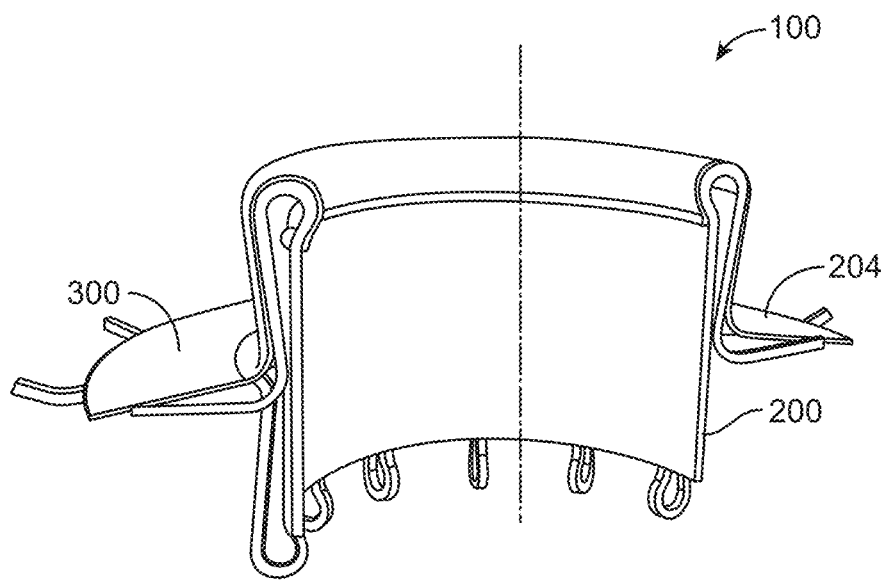
FIG. 3 is another schematic cross-sectional perspective view of a prosthetic heart valve, in accordance with an embodiment.

In these examples, a portion of the atrial sealing skirt 204 that is relatively proximal to the atrial side of the native tricuspid valve may be attached to the proximal segment 108 of each ventricular arm 106-2 (see, e.g., FIG. 3), and a portion of the atrial sealing skirt 204 that is relatively distal to the atrial side of the native tricuspid valve may be attached to the distal segment 114 of each atrial arm 106-1. The cover 200 may extend down through the cylindrical portion 116 of the support structure 102 within the elongate central passageway 104. In the examples of FIGS. 2 and 3, portion 202 of cover 200 that extends down through the cylindrical portion 116 of the support structure 102 to help define elongate central passageway 104 ends at or near the ventricular end 120 of cylindrical portion 116. However, in some implementations (see, e.g., FIGS. 17 and 18), cover 200 wraps around the ventricular end 120 of the cylindrical portion 116 and terminates along the proximal segment 112 of each atrial arm 106-1 (e.g., just before the secondary bend 130). In other examples, not explicitly shown, the cover 200 can extend beyond the proximal segment 112 of each atrial arm 106-1 and terminate along the distal segment 110 of each ventricular arm 106-2. In either implementation, cover 200 may form a continuous "webbing" of atrial sealing skirt 204 on the atrial end 118 of the cylindrical portion 116 of the support structure 102 that helps to generate a seal, and also serves as a backstop to the pressure from the ventricular arms 106-2 on the ventricular side of the native tricuspid valve leaflets, and prevents the ventricular arms 106-2 from eroding through the native leaflets. Atrial sealing skirt 204 may extend to or beyond the native annulus of the native tricuspid valve for anchoring and to fully cover the commissures of the native tricuspid valve for sufficient leak prevention.

In various examples, atrial sealing skirt 204 may initiate at, and be attached to, the distal segment 114 of each atrial arm 106-1, then switch to be attached to the proximal segment 108 of each ventricular arm 106-2, then extend down through the elongate central passageway 104, around to the proximal segment 112 of each atrial arm 106-1, and either terminate prior to the second bend 130 of each atrial arm 106-1 (e.g., along the proximal segment of each atrial arm 106-1 at a common distance from the cylindrical portion 116), or further extend to the distal segment 110 of each ventricular arm 106-2 before terminating, in various implementations.

In some embodiments, the cover 200 can extend asymmetrically and/or non-circularly within the elongate central passageway 104 and over one or more of the atrial arms 106-1 and/or the ventricular arms 106-2. For example, in some embodiments, the cover 200 can extend in a "D" shape within the elongate central passageway 104 and over one or more of the atrial arms 106-1 and/or the ventricular arms 106-2.

Figure 13:
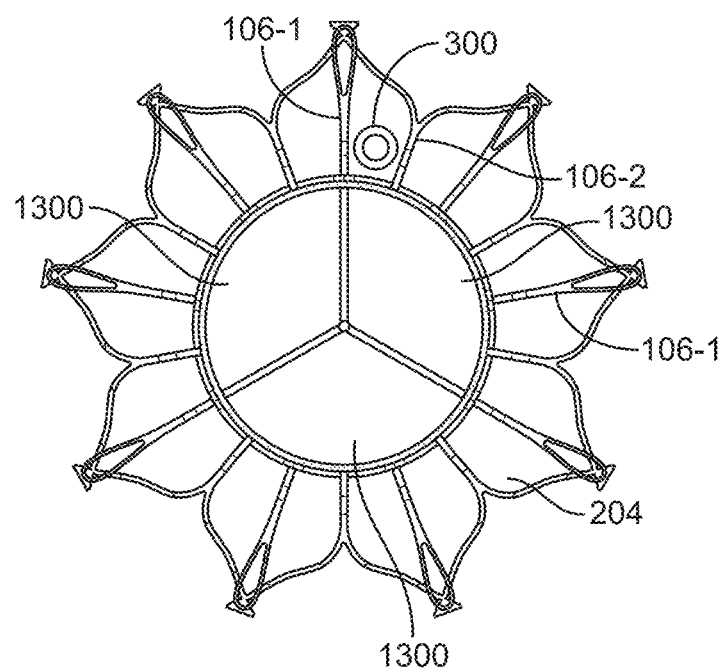
FIG. 13 illustrates a top view of a prosthetic heart valve, in accordance with an embodiment.

FIG. 3 also shows how prosthetic tricuspid valve 100 may include a fenestration feature 300 in a portion of the cover 200 (see also, FIG. 13). Fenestration feature 300 may include, for example, a radiopaque marker, an opening, a magnetic element, a one-way valve, a pop-up valve, a mechanically resizable opening, and increased porosity. In an implanted configuration in which the support structure 102 biodynamically fixes the prosthetic tricuspid valve 100 to native leaflets of a native tricuspid valve, the fenestration feature 300 can be disposed between the elongate central passageway 104 and a native annulus of the native tricuspid valve.

Fenestration feature 300 may, for example, be a hole or a vent that allows for passing a guidewire and ancillary devices (e.g. a pacing lead, ICD lead, or another device) through cover 200 and/or the native tricuspid valve into the ventricle (e.g., for right ventricle and/or pulmonary artery access and beyond). In this way, additional devices can access the right ventricle and/or the pulmonary artery without the need to go through elongate central passageway 104 of the prosthetic tricuspid valve 100 so as to avoid insufficiency, thrombosis risk, and/or valve damage.

Fenestration feature 300 may include a hole that is identified with a radiopaque marker. Fenestration feature 300 may also have a magnetic element or other mechanism to help with alignment and engagement of a secondary system (e.g. similar to a trans-septal puncture needle) for passing through the atrial sealing skirt 204 and the native tricuspid valve to reach the ventricle and beyond. Fenestration feature 300 may be formed from the same material as the atrial sealing skirt 204 or a different material (e.g., ePTFE, silicone, or the like) in order to facilitate sealing of the fenestration feature 300 pre- and post-passing of a device therethrough. Similarly, the fenestration feature 300 can include a one-way valve that is separate from the valve structures (e.g., leaflet elements) in the elongate central passageway 104. In some implementations, fenestration feature 300 may be initially sealed, and configured in such a way that it is easily identifiable and able to be punctured. In other implementations, the entire atrial sealing skirt 204 may be manufactured from a material that allows for puncture by a standard or custom ancillary device, and then maintains a sufficient seal to prevent undesirable regurgitant flow after a lead or other catheter is passed through.

It should also be appreciated that fenestration feature 300 and/or one or more other features of atrial sealing skirt 204 can be arranged to permanently or temporarily allow a controlled amount of regurgitant flow therethrough (e.g., to allow relief permanently or temporarily of a pressure increase in the ventricle that may be caused by sealing of the native tricuspid valve by the prosthetic tricuspid valve 100).

In other embodiments, one or more fenestration features, including the fenestration feature 300, may be located radially along the elongate central passageway 104 in positions that allow a controlled amount of regurgitant flow therethrough, while bypassing the cover 200. For example, fenestration feature 300 may be implemented as a permanent opening of a predetermined size or a mechanically controllable opening (e.g., an iris or other opening having a diameter, width, or other dimension that is mechanically controllable and/or changeable at the time of implantation and/or after implantation). As another example, fenestration feature 300 may be a portion of atrial sealing skirt 204 that is more porous than other portions of atrial sealing skirt 204. A fenestration feature 300 that is implemented as a portion of atrial sealing skirt 204 with increased porosity may have a permanently increased porosity or may be formed from a material having a porosity that is initially increased, but decreases (e.g., endothelializes) over time in the implanted environment to allow a controlled reduction of regurgitant flow. Alternatively, the entire atrial sealing skirt 204 may be porous to control the amount of regurgitant flow, and/or may allow a decrease in porosity over time (e.g., through endothelialization) to gradually reduce regurgitant flow. In some implementations, fenestration feature 300 may have a pressure-controlled component such as a pop-up valve that allows regurgitant flow when a pressure in the ventricle rises above a predetermined threshold.

Figure 4:
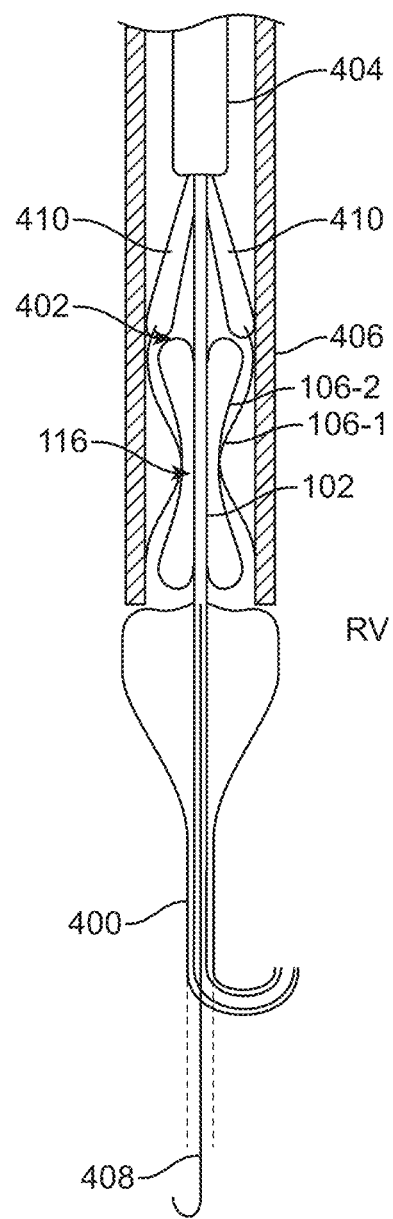
FIGS. 4-8 illustrate a prosthetic heart valve in various stages of implantation, in accordance with an embodiment.

FIGS. 4-8 illustrate various prosthetic tricuspid valves 100 in various stages of implantation into a native tricuspid valve of a heart of a patient. In the example of FIG. 4, prosthetic tricuspid valve 100 is compacted within a delivery sheath 406 such that cylindrical portion 116 (in this example implemented as a cage structure) of support structure 102 is radially compressed within sheath 406, and such that the distal segment 114 of each atrial arm 106-1 and the distal segment 110 of each ventricular arm 106-2 straightened against the exterior surface 147 of cylindrical portion 116 without extending beyond the length of cylindrical portion 116.

FIG. 4 also shows a mid layer 404 within sheath 406, a plurality of restraints 410, each attached to the distal segment 114 of an atrial arm 106-1, an inner nose cone 402, and an outer nose cone 400 (e.g., a pigtail nose cone configured to be guided along a guidewire 408 and/or separate from the guidewire 408). Guidewire 408 may be used to guide prosthetic tricuspid valve 100 into a native tricuspid valve of a heart of a patient via a vein of the patient while the prosthetic tricuspid valve 100 is in the contracted configuration of FIG. 4 in which the cylindrical portion 116 has a first diameter, each ventricular arm 106-2 is held against an exterior surface 147 of the cylindrical portion 116 by sheath 406, and each atrial arm 106-1 is held within the sheath 406 and against the exterior surface 147 of the cylindrical portion 116 by a respective restraint 410.

Figure 5:
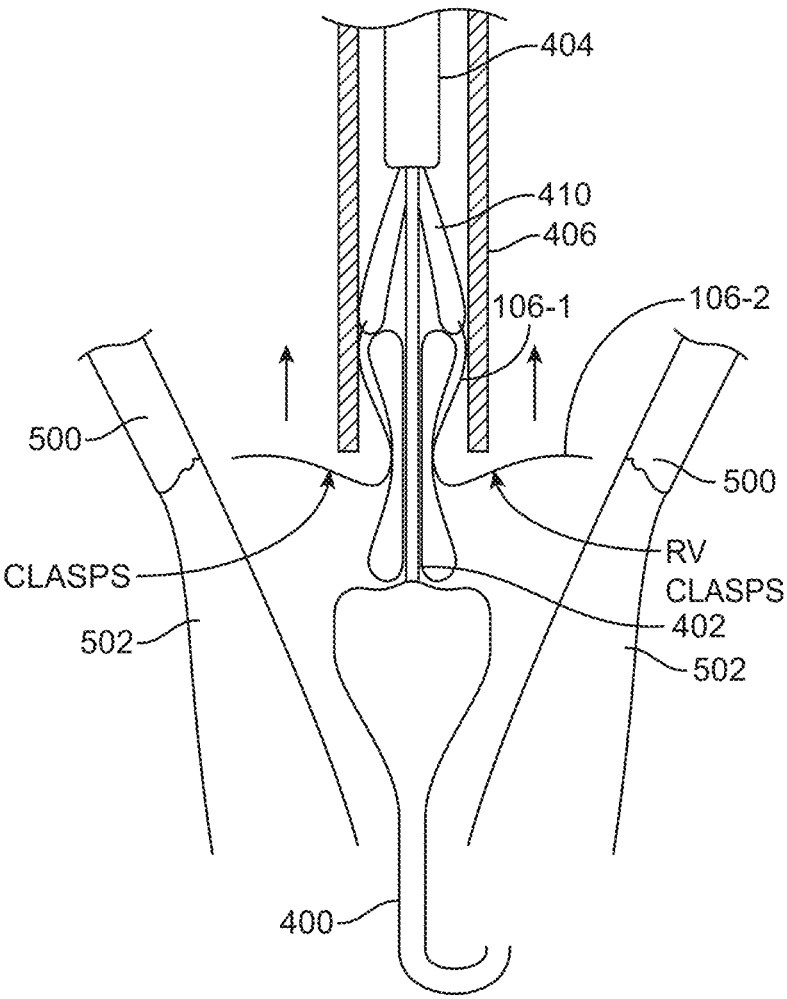

As indicated in FIG. 5, sheath 406 may be retracted to allow the ventricular arms 106-2 to bend such that the proximal segment 108 of each ventricular arm 106-2 extends along the exterior surface 147, and such that the distal segment 110 of each ventricular arm 106-2 extends perpendicularly away from the central axis of cylindrical portion 116. In FIG. 5, prosthetic tricuspid valve 100 has been inserted into the native tricuspid valve. In FIG. 5, native leaflets 500 and native chordae tendineae 502 of the native tricuspid valve are visible.

Figure 6:
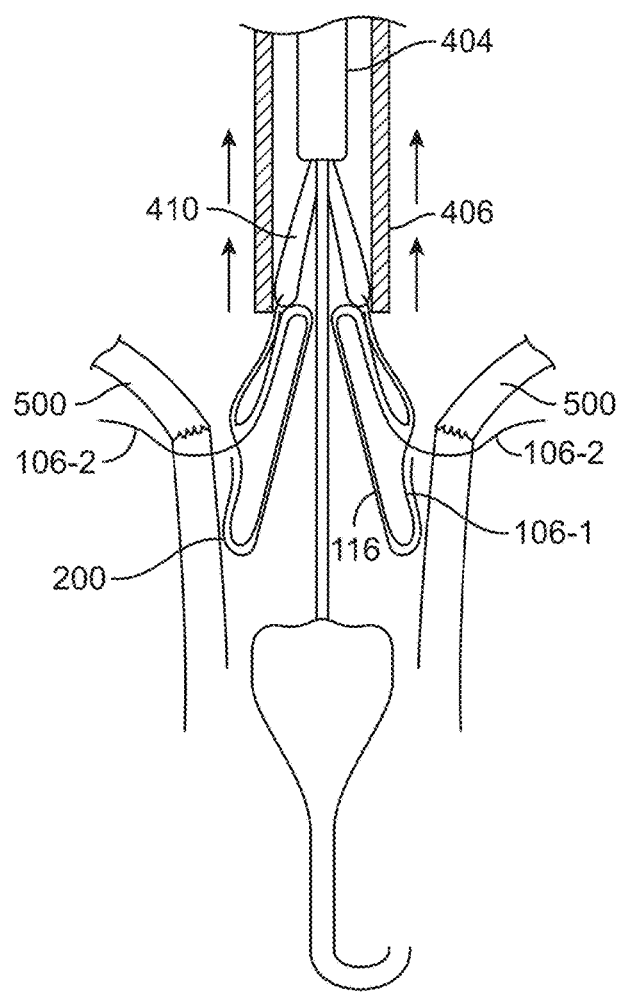

As indicated in FIG. 6, prosthetic tricuspid valve 100 can then be retracted along with the sheath 406 until the distal segment 110 of each ventricular arm 106-2 contacts a ventricular side of native leaflets 500 of the native tricuspid valve. It can be seen in FIG. 6 that cylindrical portion 116 is expanding (e.g., due to shape memory features thereof, balloon expansion, or the like) from the contracted configuration of FIG. 4 having the first diameter, to an expanded configuration with a larger, second diameter to form the elongate central passageway 104 (see also FIGS. 7 and 8).

Figure 7:
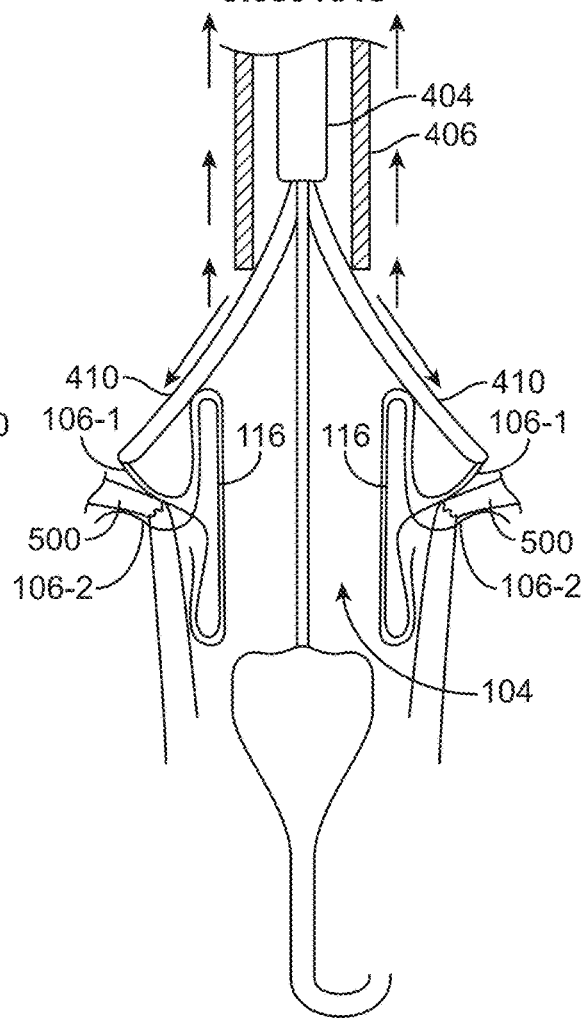
Figure 8:
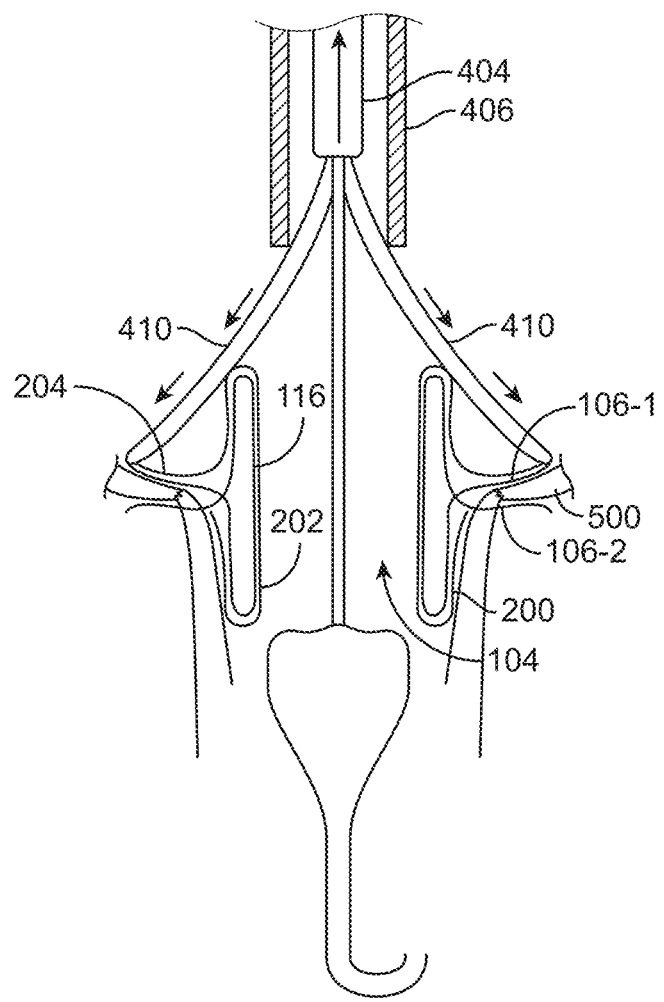

As indicated in FIGS. 7 and 8, restraints 410 can then be advanced to allow the atrial arms 106-1 to bend such that the proximal segment 112 of each atrial arm 106-1 extends along the exterior surface 147 of the cylindrical portion, and such that the distal segment 114 of each atrial arm 106-1 extends perpendicularly away from the central axis of the cylindrical portion 116 to contact an atrial side of the native leaflets 500, and thereby capture the native leaflets 500 against the distal segments 110 of the ventricular arms 106-2.

Restraints 410 may be constructed of suture, polymer, metal, and/or any other material, and can serve as a controllably expandable connection from the delivery system to the tips of the atrial arms 106-1 residing on the atrial side of the native leaflets 500. In this way, the atrial arms 106-1 can be extended and expanded as the final step of deployment prior to assessing valve function, with the connection back to the delivery system maintained even at full diameter. If the result is undesirable and recapturing is required, the restraints 410 can be actuated in the reverse direction to pull the tips of the atrial arms 106-1 back towards the delivery system to reposition and/or recapture the implant. If positioning and valve function is as desired, then the restraints 410 can be released, and the implant can be fully deployed.

For example, if prosthetic tricuspid valve 100 is desirably positioned in the native tricuspid valve, restraints 410 may be detached from the atrial arms 106-1 for release of the prosthetic tricuspid valve 100 in a fully implanted configuration. FIG. 8 shows how support structure 102 (including arms 106-1 and 106-2) is configured to biodynamically fix the prosthetic tricuspid valve 100 within, and separated from, a native annulus of a native tricuspid valve by grasping native leaflets 500 of the native tricuspid valve, without directly attaching to the native annulus or native chordae tendineae associated with the native tricuspid valve.

However, if repositioning or removal of prosthetic tricuspid valve 100 from the configuration of FIG. 8 is desired, FIGS. 9-12 show how restraints 410 can be retracted (FIG. 9) to straighten the atrial arms 106-1 against the exterior surface 147 of the cylindrical portion 116 to release the native leaflets 500, and how sheath 406 can be advanced (FIGS. 10-12) to straighten the ventricular arms 106-2 and compress central cylindrical portion 116 for removal of the prosthetic tricuspid valve 100.

FIGS. 4-12 also illustrate the overbite arrangement of the arms 106 during capture of native leaflets 500. Specifically as shown in FIGS. 4-12, the atrial arms 106-1 extend from the ventricular end 120 of the cylindrical portion 116 and the ventricular arms 106-2 extend from the atrial end 118 of the cylindrical portion 116. Both the atrial arms 106-1 and the ventricular arms 106-2 extend across the cross-sectional plane of the cylindrical portion 116 of the at least one support structure 102 such that there is overbite between the atrial arms 106-1 and the ventricular arms 106-2 over the cross-sectional plane during capture of native leaflets 500. Although support structure 102 can be implemented with arms 106 that do not cross over the cross-sectional plane, and thus do not exhibit overbite (e.g., with atrial arms 106-1 extending from the atrial end 118 of the cylindrical portion 116 and ventricular arms 106-2 extending from the ventricular end 120 of the cylindrical portion 116), the overbite arrangement described herein (see, e.g., FIGS. 1-12) in which the atrial arms 106-1 and the ventricular arms 106-2 cross over twice with respect to the cross-sectional plane of the cylindrical portion 116 has the advantage of facilitating a more robust seal against the native leaflets 500 to prevent paravalvular leak, and also has the advantage of facilitating the proper sequencing of deployment (ventricular arms 106-2 followed by atrial arms 106-1), that allows for full assessment and recapturing of the prosthetic tricuspid valve 100. Furthermore, having the atrial arms 106-1 and the ventricular arms 106-2 extend from opposite ends of the cylindrical portion 116 allows for each set of arms 106-1 and 106-2 to be compressed against the cylindrical portion 116 itself (rather than having to be fully extended beyond each end of the cylindrical portion 116), thereby greatly reducing the overall length of the prosthetic tricuspid valve 100 during delivery, and thereby improving flexibility and ease of positioning and deployment.

FIG. 13 shows a top view of prosthetic tricuspid valve 100 in which leaflet elements 1300 within elongate central passageway 104 can be seen to form an interior of the prosthetic tricuspid valve 100. In the example of FIG. 13, leaflet elements 1300 are coapted to form a complete seal in the closed configuration of prosthetic tricuspid valve 100. However, as noted above in connection with FIG. 3, it may be desirable in some scenarios to permanently or temporarily allow a controlled amount of regurgitant flow through prosthetic tricuspid valve 100. In the example of FIG. 3, various implementations of fenestration feature 300 are described for allowing such a controlled regurgitant flow. However, in other implementations, leaflet elements 1300 may be provided with features or restraints that provide the desired regurgitant flow. For example, a tension line or other mechanical or material features (not shown) may be provided to hold back one or more of the leaflet elements 1300 from completely coapting with the other leaflet elements 1300, to permanently or temporarily allow a controlled amount of regurgitant flow between the leaflet elements 1300. A tension line can later be removed, loosened, or materially altered to reduce or eliminate the regurgitant flow.

Figure 14:
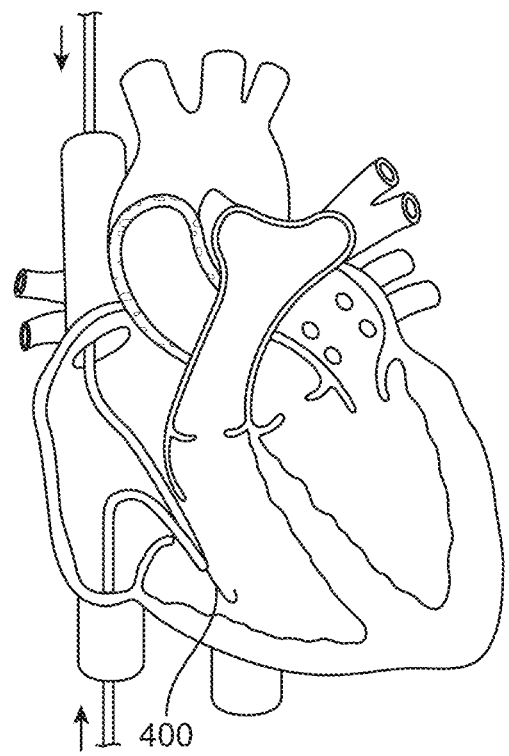
FIG. 14 illustrates various implantation routes for a prosthetic heart valve, in accordance with an embodiment.

Prosthetic tricuspid valve 100 can be delivered into a native tricuspid valve from the inferior vena cava that extends up to the superior vena cava. The distal portion of the delivery system can be extended to allow a capsule to extend away from the main axis of the delivery system with a preset curvature and flex toward the native tricuspid valve for axialization and positioning. Extending further into the inferior vena cava will increase the curve, while pulling the distal portion back will minimize the curve in this example. FIG. 14 illustrates delivery paths from the inferior vena cava and the superior vena cava.

The delivery system for this transcatheter tricuspid valve implant 100 can come from the superior vena cava via the jugular vein, the subclavian vein, or some other vessel, or from the inferior vena cava via the femoral vein or an alternative entry point. Alternatively, access could be achieved through surgical access via the right atrium of the heart.

For example, the deployment sequence can allow for partial deployment within the atrium before advancing into the ventricle to complete the positioning and deployment, or the deployment sequence can allow for full advancement and positioning into the native tricuspid valve before initiating deployment.

The delivery system may be passive or may have multiple planes of steering elements. In some implementations, depth control can be provided by including a steering mechanism of the delivery system that can be shuttled proximally or distally relative to the handle of the delivery system. One example of shuttling the steering mechanism includes allowing for tensioning of the steering mechanism (for example, relative movement between a base laser cut hypotube and a tension wire mounted to the distal end of that hypotube) inside a subcomponent of the handle of the delivery system that, itself, can be linearly translated within the handle while maintaining that same relative tension between the steering mechanism.

Figure 25:
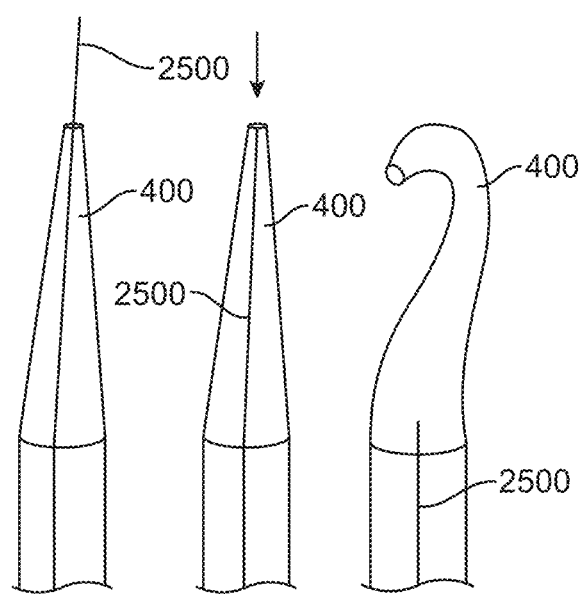
FIGS. 25 and 26 illustrate various views of a nose cone and guidewire for implantation of a prosthetic heart valve, in accordance with an embodiment.
Figure 26:
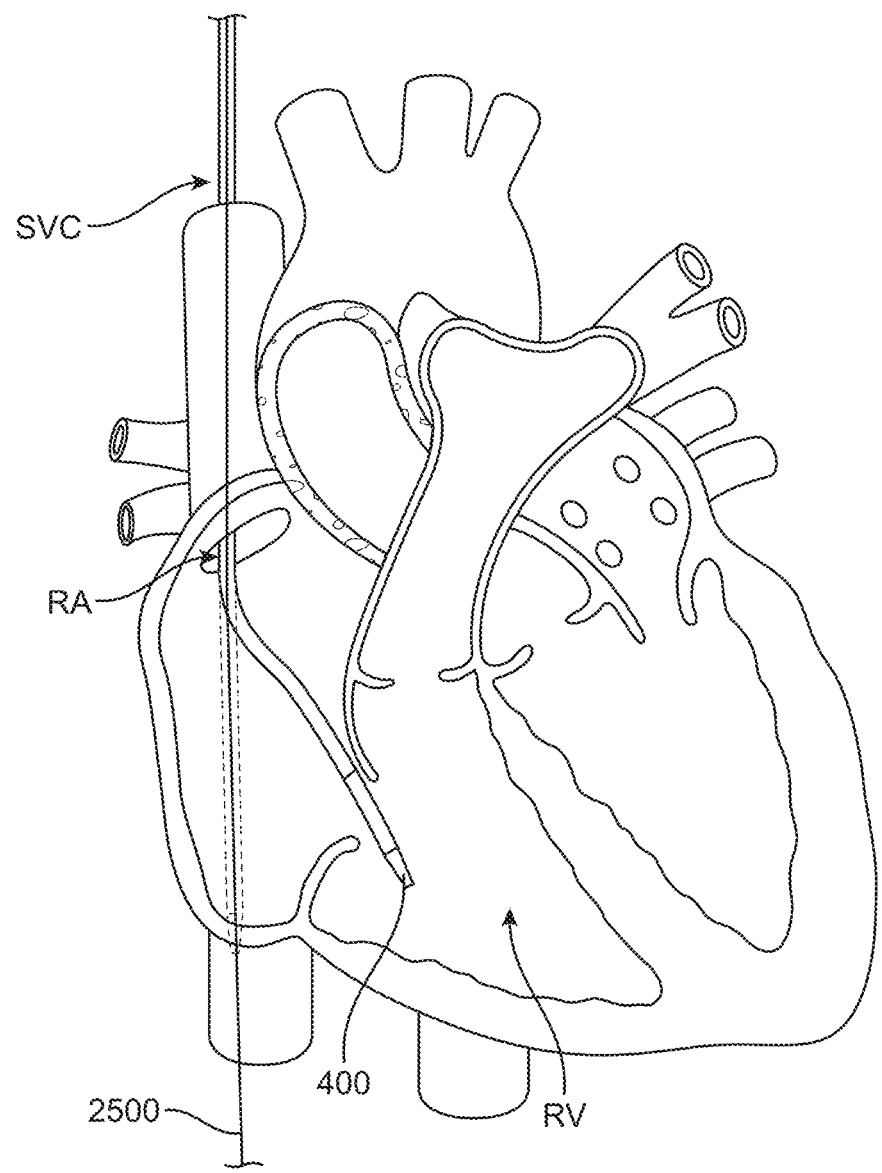

In some scenarios, the delivery system is advanced from the inferior vena cava, past the right atrium and into the superior vena cava along a guidewire extending beyond the superior vena cava, with the prosthetic tricuspid valve 100 being effectively housed in a portion of the delivery system positioned within the right atrium. Then, a distal portion of the delivery system is extended up into the superior vena cava such that the distal portion of the delivery system is released from the proximal portion, and is able to flex away from the main axis of the delivery system and towards the native tricuspid valve annulus. The degree to which the distal portion of the delivery system is extended away from the proximal portion of the delivery system controls the size of the angle between the proximal portion of the distal portion of the delivery system (where the prosthetic tricuspid valve 100 is housed) and the main axis of the proximal portion of the delivery system, until the prosthetic tricuspid valve 100 is co-axially aligned with the native tricuspid valve annulus. Delivery features are further illustrated in FIGS. 25 and 26 which show separation of a pigtail nose cone 400 from a guidewire 408.

Figure 33:
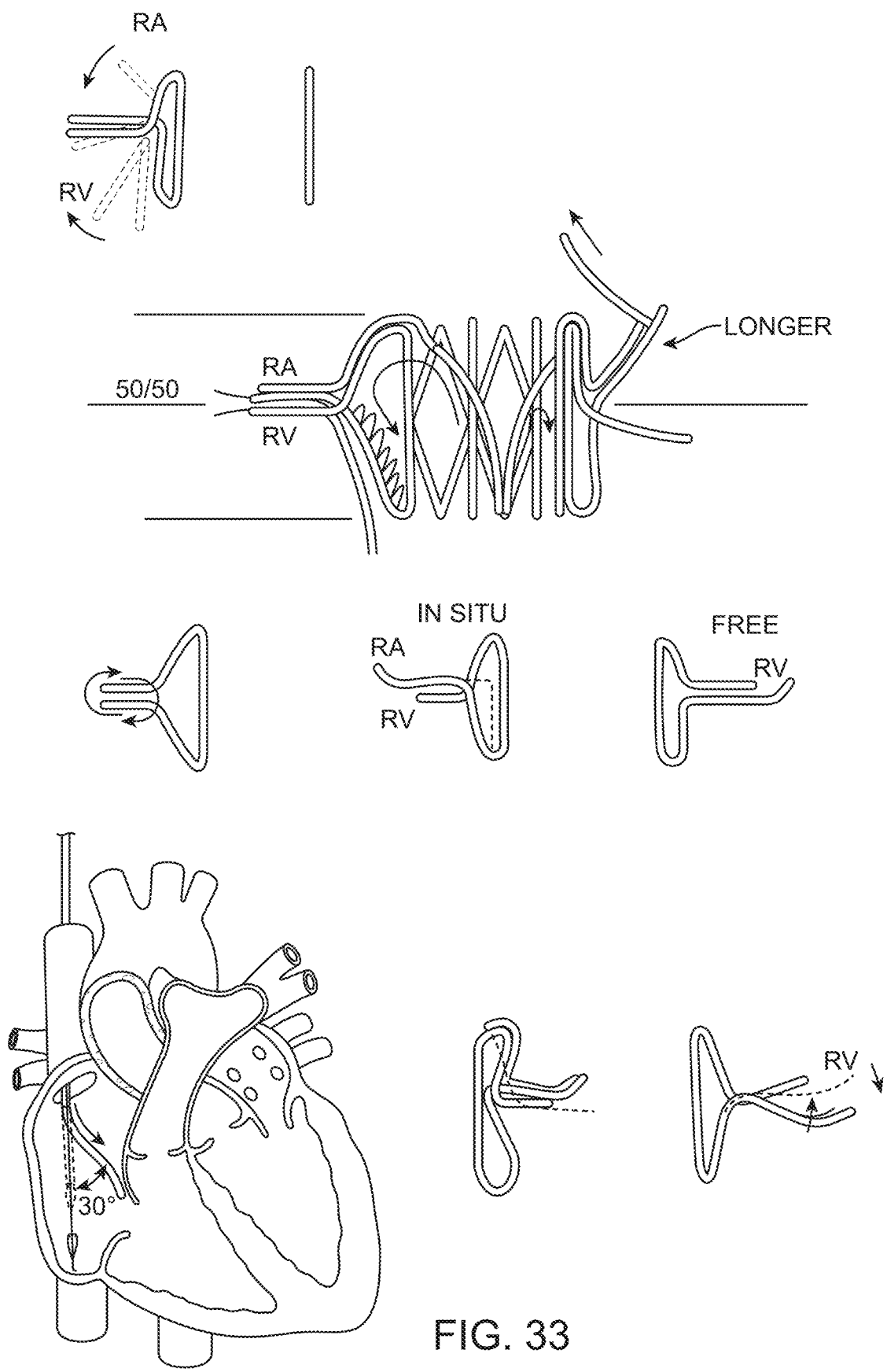
Figure 34:
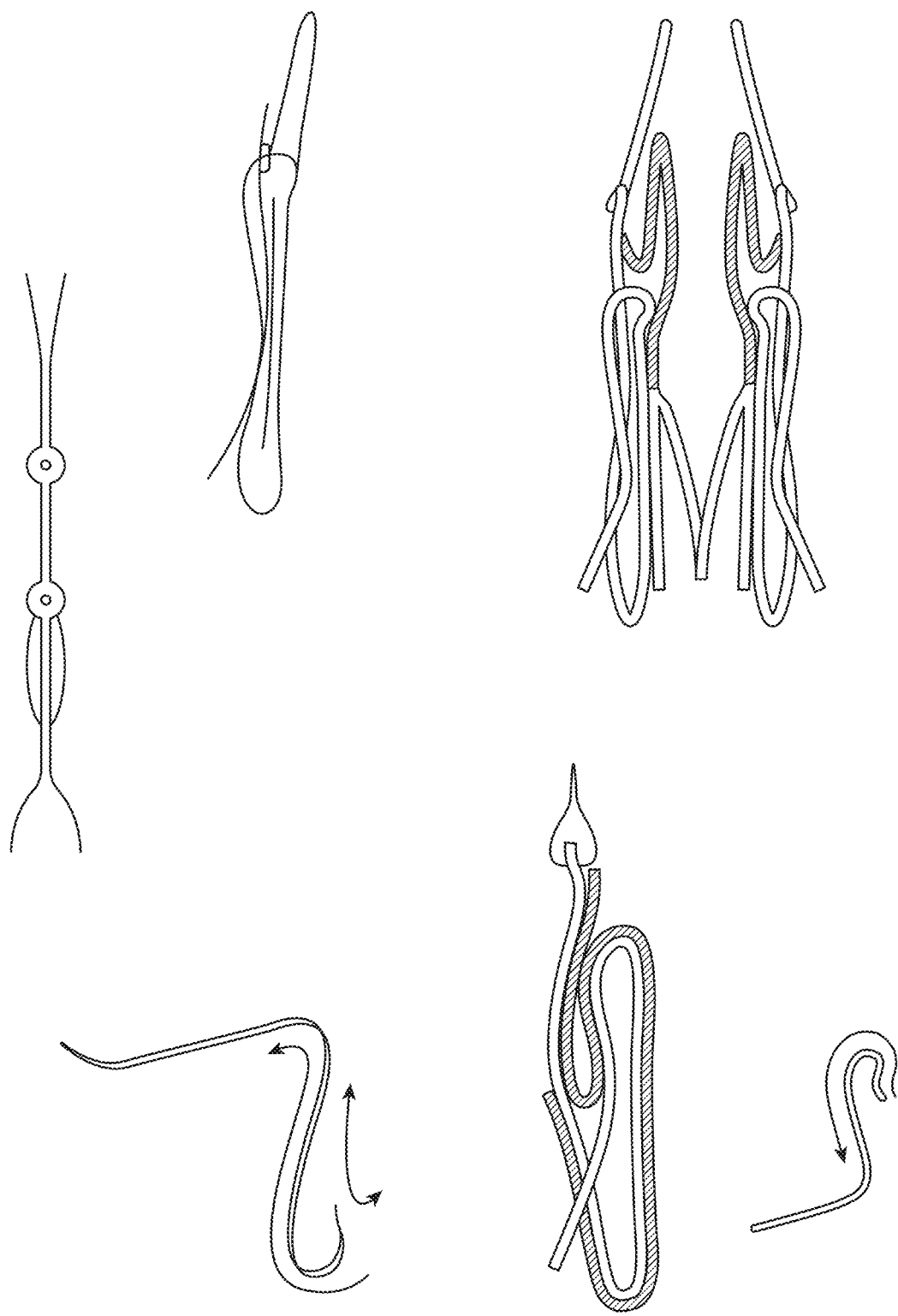

In another example, the delivery system may approach the right atrium from the superior vena cava with a guidewire extending down into the inferior vena cava (see, e.g., lower left of FIG. 33). In this example, as the tip of the delivery system approaches the right atrium, the delivery system may be decoupled from the guidewire so that the delivery system can be directed either passively or with active steering, towards the annulus of the native tricuspid valve. In this way, the guidewire may still be used for stability without having to be advanced into the right ventricle where it could cause complications (e.g., perforation, entanglement, conductivity issues, or otherwise). In this example or others, the outer nose cone 400 of the delivery system may be blunt and rounded like a dome, or may be long and flexible in the shape of pigtail such that it can be advanced atraumatically into the right ventricle without becoming entangled in the chordae of the native tricuspid valve.

Figure 15:
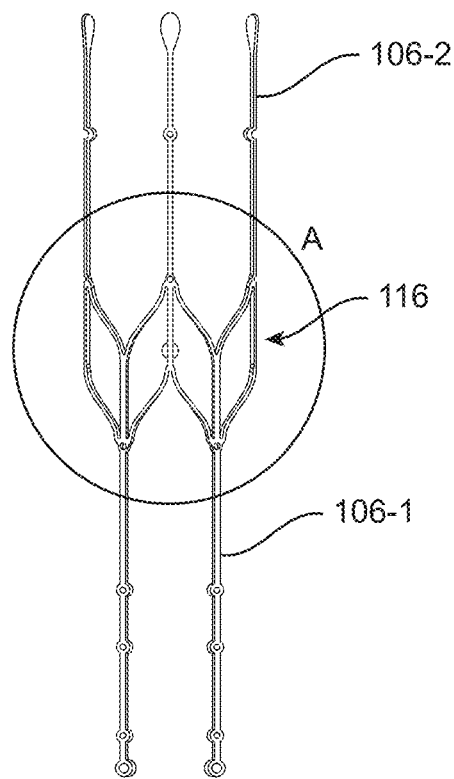
FIGS. 15 and 16 illustrate a portion of support structure for a prosthetic heart valve, in accordance with an embodiment.
Figure 16:
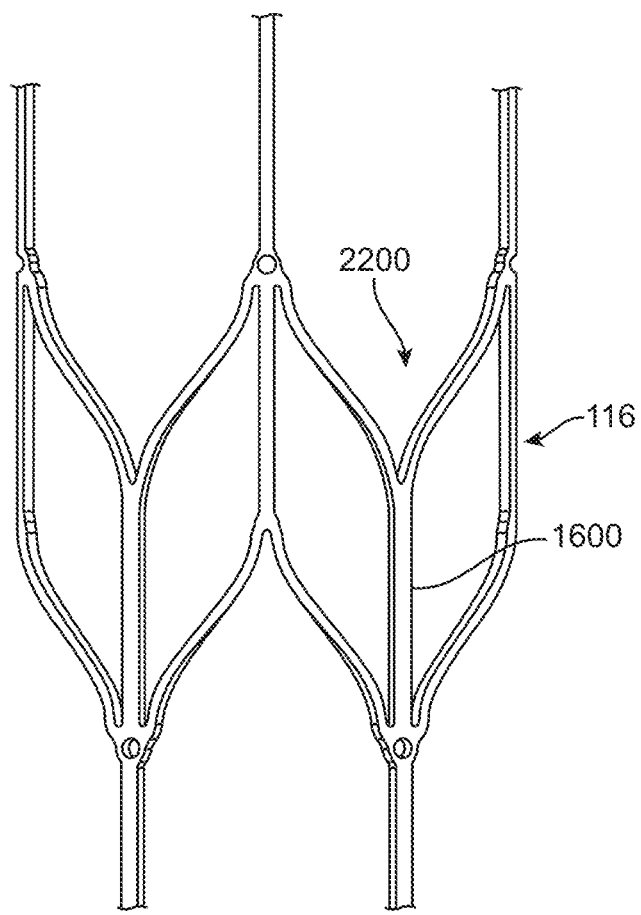

FIGS. 15 and 16 respectively show wide- and near-field views of a portion of support structure 102 in which cylindrical portion 116 is formed by a collapsible cage structure (e.g., having a V-shaped strut 2200 for capture of the secondary bend 130 of an atrial arm 106-1). In the example of FIGS. 15 and 16, the arms 106 are shown before bends 126, 124, 128, and 130 are formed therein.

Figure 17:
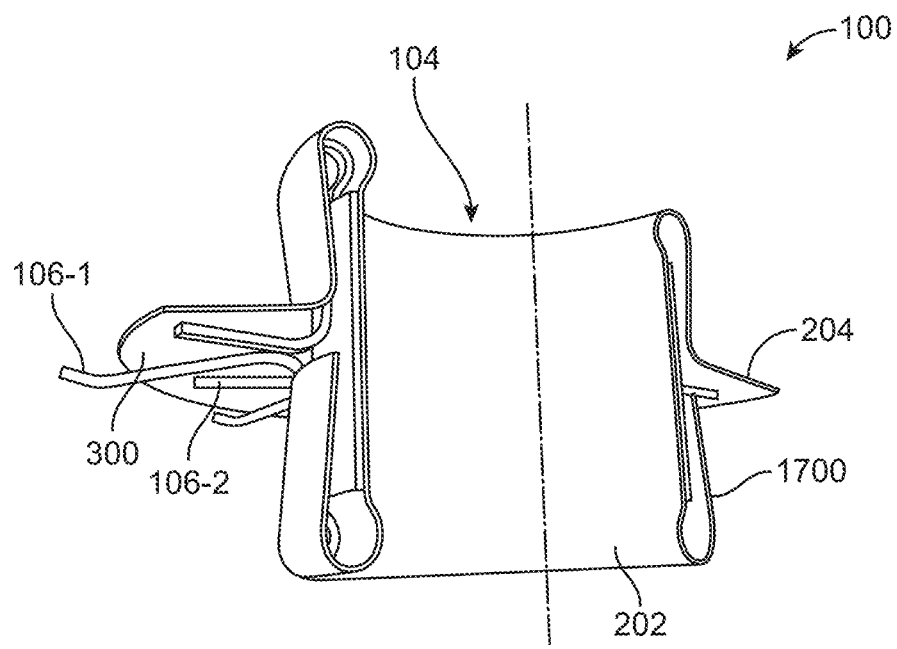
FIG. 17 is another schematic cross-sectional perspective view of a prosthetic heart valve, in accordance with an embodiment.
Figure 18:
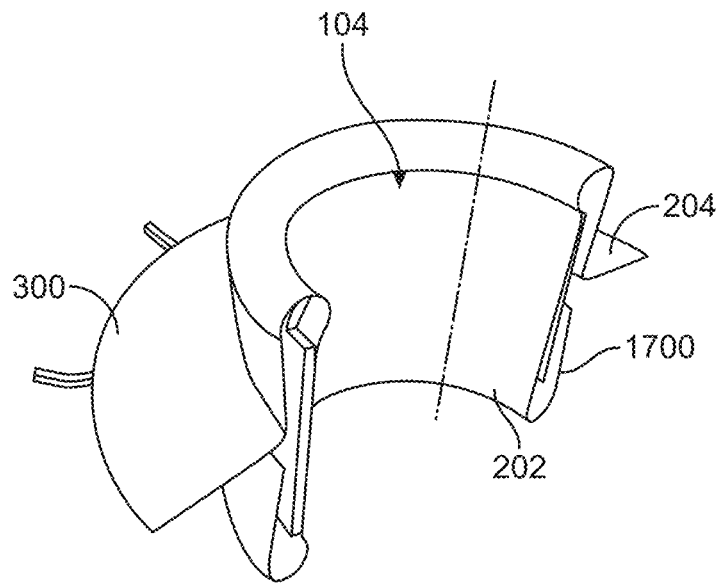
FIG. 18 is another schematic cross-sectional perspective view of a prosthetic heart valve, in accordance with an embodiment.

FIGS. 17 and 18 show other arrangements for cover 200 as described above.

Figure 19:
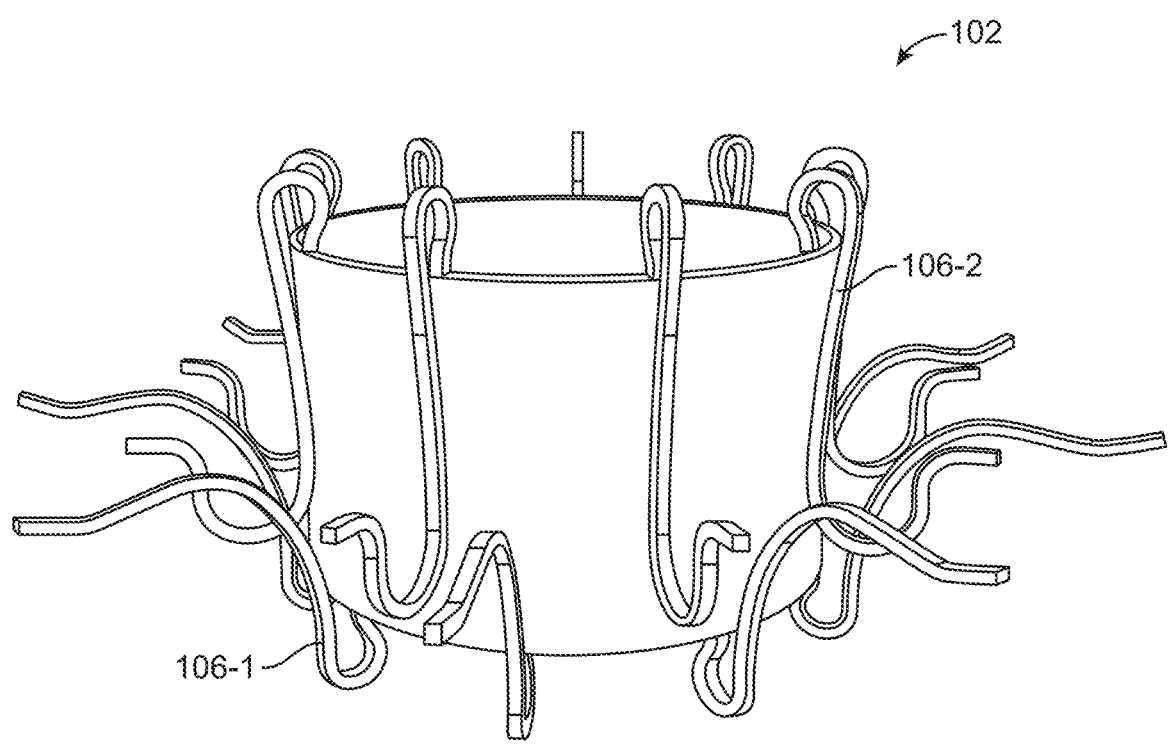
FIG. 19 illustrates another example support structure for a prosthetic heart valve, in accordance with an embodiment.

FIG. 19 shows how the overbite of atrial arms 106-1 and ventricular arms 106-2 may be formed closer to the ventricular end 120 of cylindrical portion 116 than illustrated in FIG. 1. In other words, FIG. 19 shows how the cross-sectional plane of the cylindrical portion 116 over which the atrial arms 106-1 and ventricular arms 106-2 extend may be formed closer to the ventricular end 120 of cylindrical portion 116 than illustrated in FIG. 1

Figure 20:
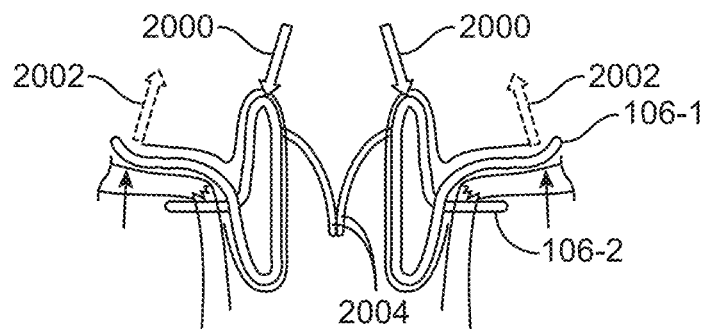
FIG. 20 illustrates various forces that can be applied during implantation of a prosthetic heart valve, in accordance with an embodiment.

FIG. 20 illustrates how forces 2000 (e.g., by mid layer 404) can be provided against the cylindrical portion 116 of the support structure 102 of the prosthetic tricuspid valve 100 in opposition to restraining forces 2002 on atrial arms 106-1 of the support structure 102 for control of the capture of native leaflets.

Figure 21:
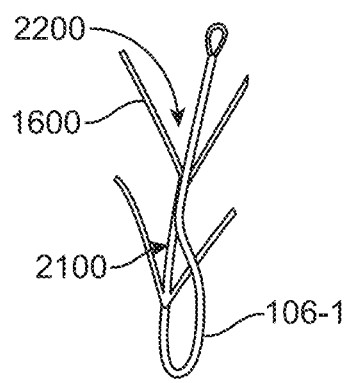
FIGS. 21 and 22 illustrate various implementations of a portion of a support structure for a prosthetic heart valve, in accordance with an embodiment.
Figure 22:
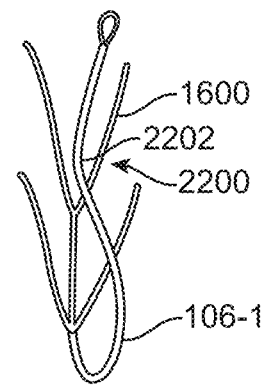

FIG. 21 shows how V-shaped strut 2200 can be formed above the secondary bend 130 of the atrial arm 106-1 which contacts the cylindrical portion 116 of support structure 2100 (e.g., support structure 102), in contrast to the implementation of FIG. 22 in which V-shaped strut 2200 resides below the secondary bend 2202 (e.g., secondary bend 130) of the atrial arm 106-1 and receives the secondary bend 2202 and steadies the position of atrial arm 106-1.

Figure 23:
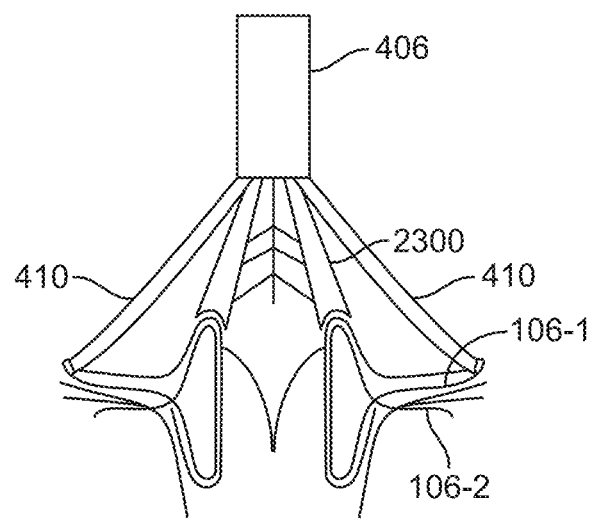
FIG. 23 illustrates various delivery structures for a prosthetic heart valve, in accordance with an embodiment.

FIG. 23 shows spreader arms 2300 that are configured to extend from mid layer 404 to provide force 2000 of FIG. 20 in opposition to the restraining force 2002 of restraints 410. Further details of the arrangement of spreader arms 2300 and restraints 410 are provided hereinafter in connection with FIGS. 35-40.

Figure 24:
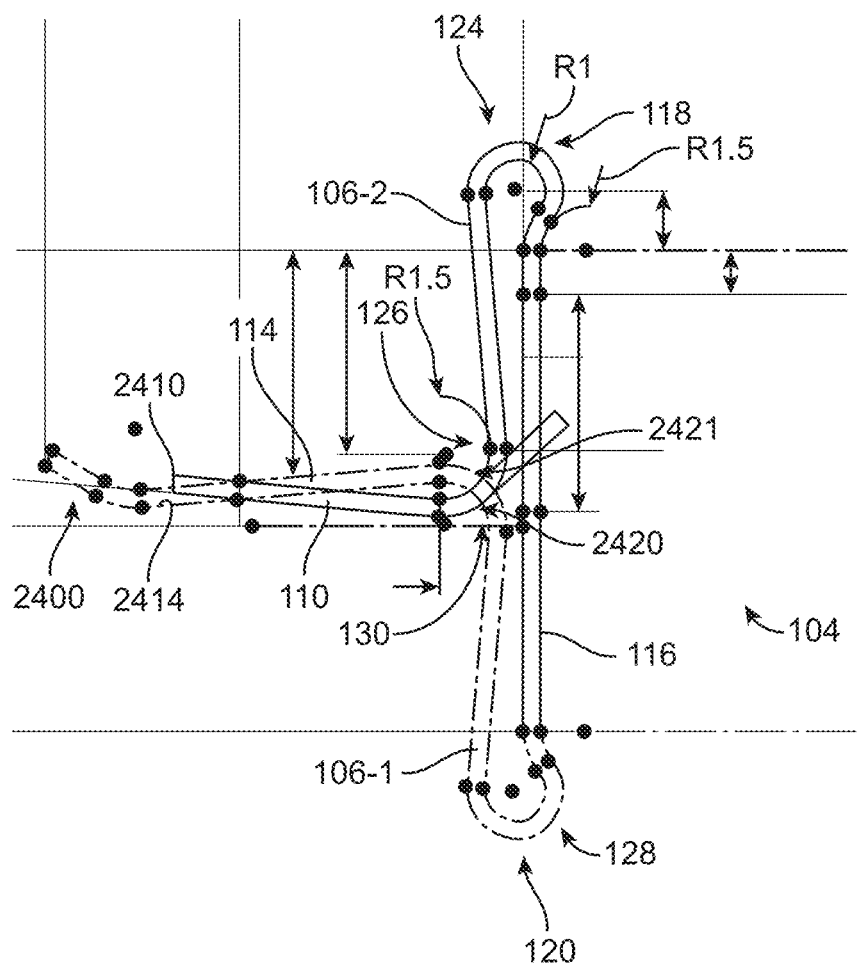
FIG. 24 illustrates a side view of a pair of arms extending from a cylindrical portion of a support structure of a prosthetic heart valve, in accordance with an embodiment.

FIG. 24 shows a side view of a pair of atrial arms 106-1 and ventricular arms 106-2 and illustrates the overbite arrangement of the pair of atrial arms 106-1 and ventricular arms 106-2, for grasping of the native leaflets as in FIG. 8. As shown in FIG. 24, the distal segment 114 of each atrial arm 106-1 that extends perpendicularly away from the central axis of the elongate central passageway 104 extends from a first longitudinal position 2421 along the cylindrical portion 116 of the support structure 102. Similarly, the distal segment 110 of each ventricular arm 106-2 that extends away from the central axis of the elongate central passageway 104 extends from a second longitudinal position 2420 along the cylindrical portion 116 of the support structure 102. As shown in FIG. 24, the first longitudinal position 2421 is nearer to the atrial end 118 of the cylindrical portion 116 of the support structure 102 than the second longitudinal position 2420 is to the atrial end 118 of the cylindrical portion 116 of the support structure 102.

In an implanted configuration of the prosthetic tricuspid valve 100 in which the support structure 102 of the prosthetic tricuspid valve 100 biodynamically fixes the prosthetic tricuspid valve 100 to the native leaflets 500 of the native tricuspid valve, the ventricular arms 106-2 in example of FIG. 24 extend from the atrial end 118 of the cylindrical portion 116, through a native annulus of the native tricuspid valve, and into the ventricle of the heart to contact a ventricular surface of the native leaflets 500. In this implanted configuration, the atrial arms 106-1 extend from the ventricular end 120 of the cylindrical portion 116, through the native annulus of the native tricuspid valve, and into the atrium of the heart to contact an atrial surface of the native leaflets 500.

FIG. 24 also shows how bends 126 and 130 can be greater than 90° so that the distal segment 114 of each atrial arm 106-1 that extends perpendicularly away from the central axis of the elongate central passageway 104 extends toward the ventricular end 120 of the cylindrical portion 116, and so that the distal segment 110 of each ventricular arm 106-2 that extends perpendicularly away from the central axis of the elongate central passageway 104 extends toward the atrial end 118 of the cylindrical portion 116.

FIG. 24 also shows how the distal segment 114 of each atrial arm 106-1 that extends perpendicularly away from the central axis of the elongate central passageway 104 has a tip 142, the distal segment 110 of each ventricular arm 106-2 that extends perpendicularly away from the central axis of the elongate central passageway 104 has a tip 140, and the tips 142 are nearer to the ventricular end 120 of the cylindrical portion 116 than the tips 140 are to the ventricular end 120 of the cylindrical portion 116. However, as indicated in FIG. 24, the distal segment 114 of each atrial arm 106-1 (e.g., the tip 142 of each atrial arm 106-1) may include an extended segment 2400 with a third bend toward the atrial end 118 of the cylindrical portion 116 for more atraumatic engagement of the atrial surfaces of the native leaflets, if desired. It should also be appreciated that distal segment 110 of each ventricular arm 106-2 (e.g., the tip 140 of each ventricular arm 106-2) may also include an extended segment with a third bend (e.g., similar to the third bend of the extended segment 2400 of each atrial arm 106-1) toward the ventricular end 120 of the cylindrical portion 116 for more atraumatic engagement of the ventricular surfaces of the native leaflets, if desired. It should be noted that the aforementioned third bends can also reduce the frictional forces exerted by the prosthetic tricuspid valve 100 on the inner surface of the outer sheath 406 by directing the tips of the arms 106 away from the inner surface of the outer sheath 406 during loading, delivery, and recapturing of the prosthetic tricuspid valve 100.

Referring again to FIGS. 25 and 26, the delivery system can come from a guidewire 2500 (e.g., guidewire 408) running from the inferior vena cava to the superior vena cava, or from the superior vena cava to the inferior vena cava, where the nose cone 400 and distal portion of the delivery system separate from the wire track of the guidewire 2500 to an enter the right atrium, go through the native tricuspid valve annulus, and enter into the right ventricle without the guidewire 2500. This allows leveraging of the stability of the guidewire 2500 along the straight portion without the risk of having a guidewire in the right ventricle, which could excite the electrical system of the heart and cause conduction abnormalities. When the guidewire 2500 is pulled out, the nose cone 400 can revert to a flexible "pigtail" like tip that can easily be passed through the native tricuspid valve annulus without getting tangled in the cords of the native tricuspid valve. In other embodiments, the guidewire 2500 can be extended into the right atrium from either the superior vena cava or the inferior vena cava, and the delivery system can be advanced such that the nose cone 400 reverts to its "pigtail" shape prior to entering the right ventricle.

Figure 27:
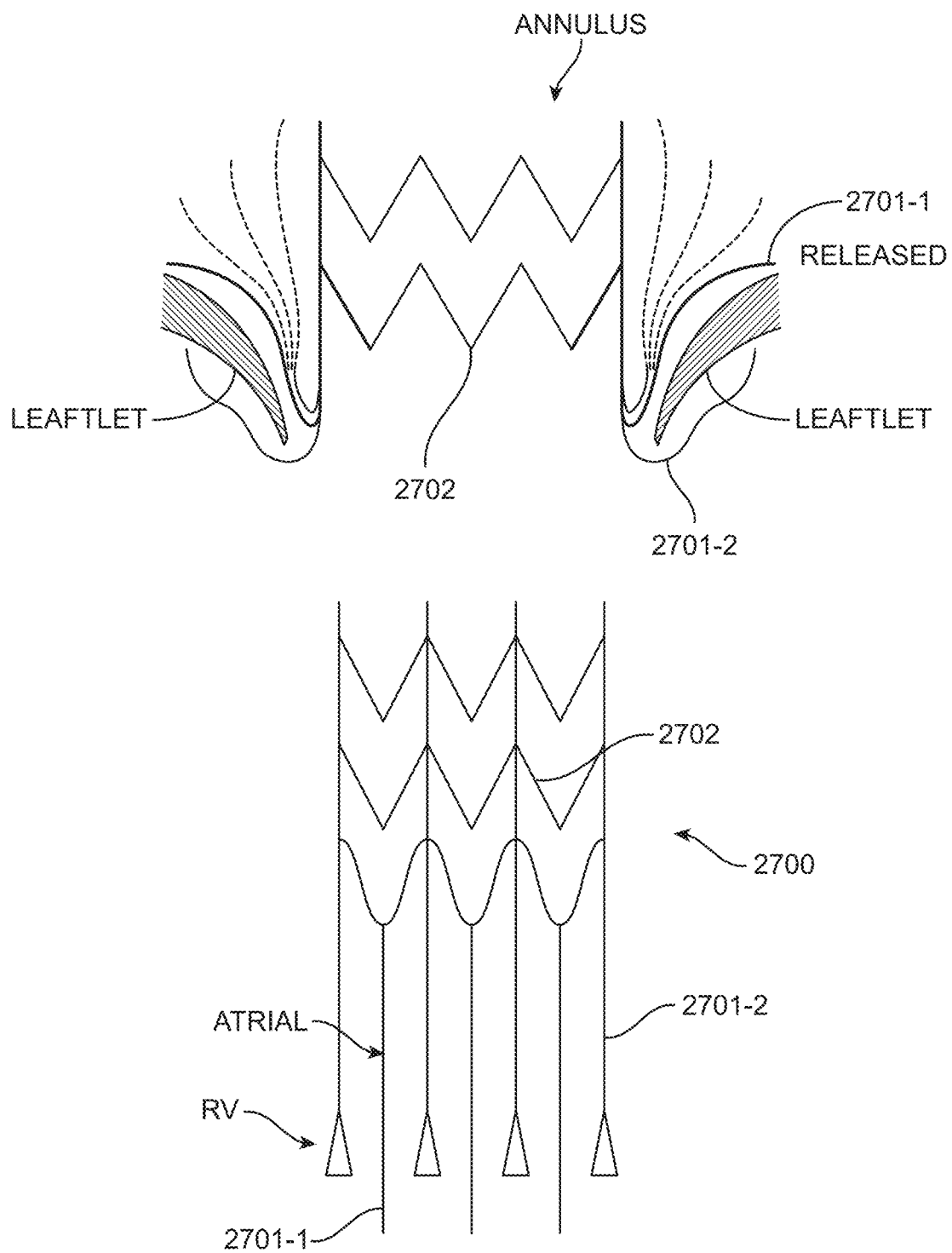
Figure 29:
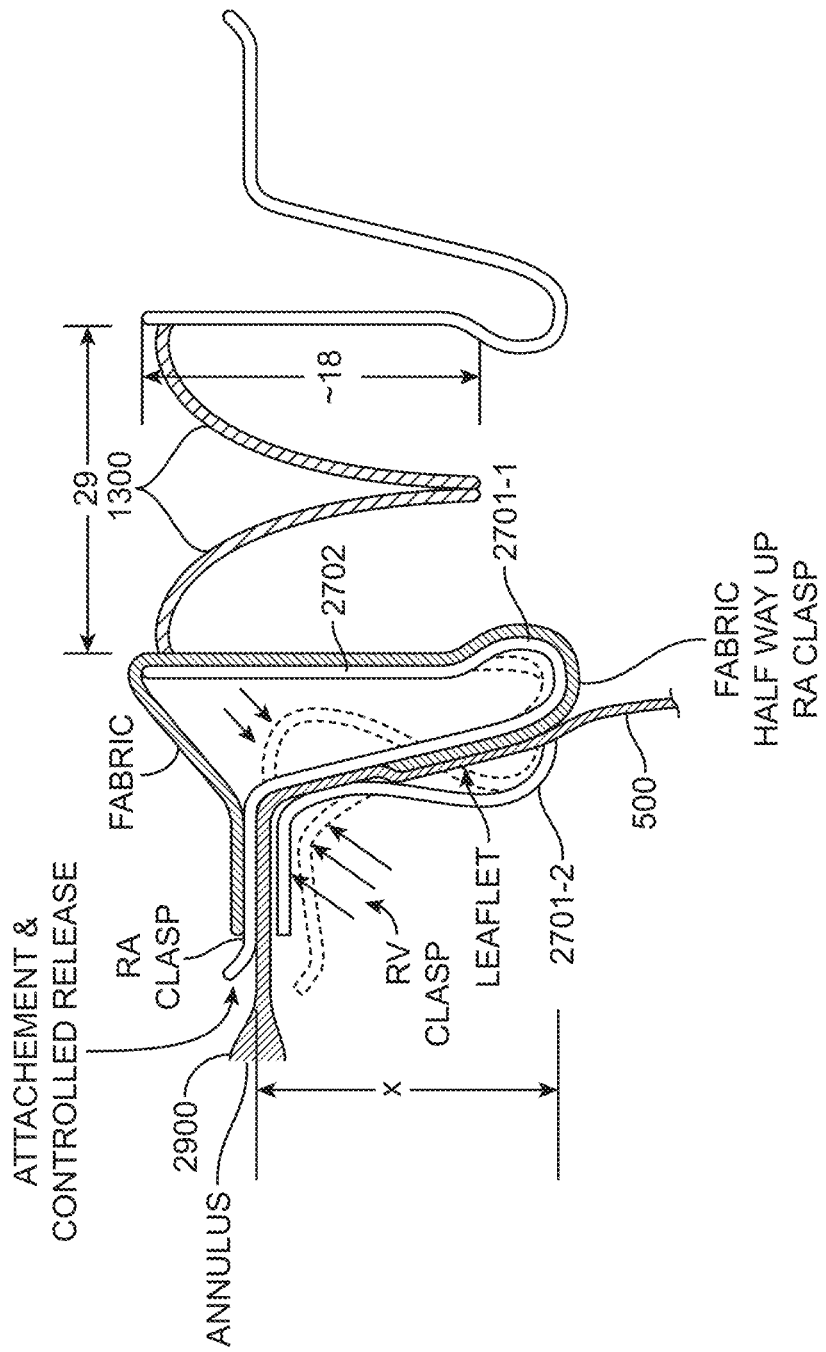

FIGS. 27-29 illustrate another implementation of a support structure 2702 (e.g., support structure 102) for a prosthetic tricuspid valve 2700 in which both atrial arms 2701-1 (e.g., atrial arms 106-1) and ventricular arms 2701-2 (e.g., ventricular arms 106-2) may extend initially from the ventricular end of the support structure 2702, each arm 2701 having an initial bend of 180°+/−45° that directs the arm 2701 back towards the atrial end of the support structure 2702. In this example, each atrial arm 2701-1 extends through an annulus of a native tricuspid valve and has a secondary bend closer in proximity to the atrial end of the support structure 2720 than a secondary bend of each ventricular arm 2701-2. The secondary bend of each arm 2702 is sufficient to position the distal segment of the arm 2702 beyond the secondary bend of the arm 2702 perpendicular to a central axis of an elongate central passageway defined by the support structure 2702. However, in this example, the degrees of the secondary bends of the arms 2702 are such that the tips of the atrial arms 2701-1 are closer in proximity to the ventricular end of the support structure 2702 than the tips of the ventricular arms 2701-2. Thus, the arrangement of the atrial arms 2701-1 and the ventricular arms 2701-2 above and below the native leaflets would again result in the corrugated, ruffled-collar configuration to ensure a tight seal and more stable positioning of the prosthetic tricuspid valve 2700.

Figure 30:
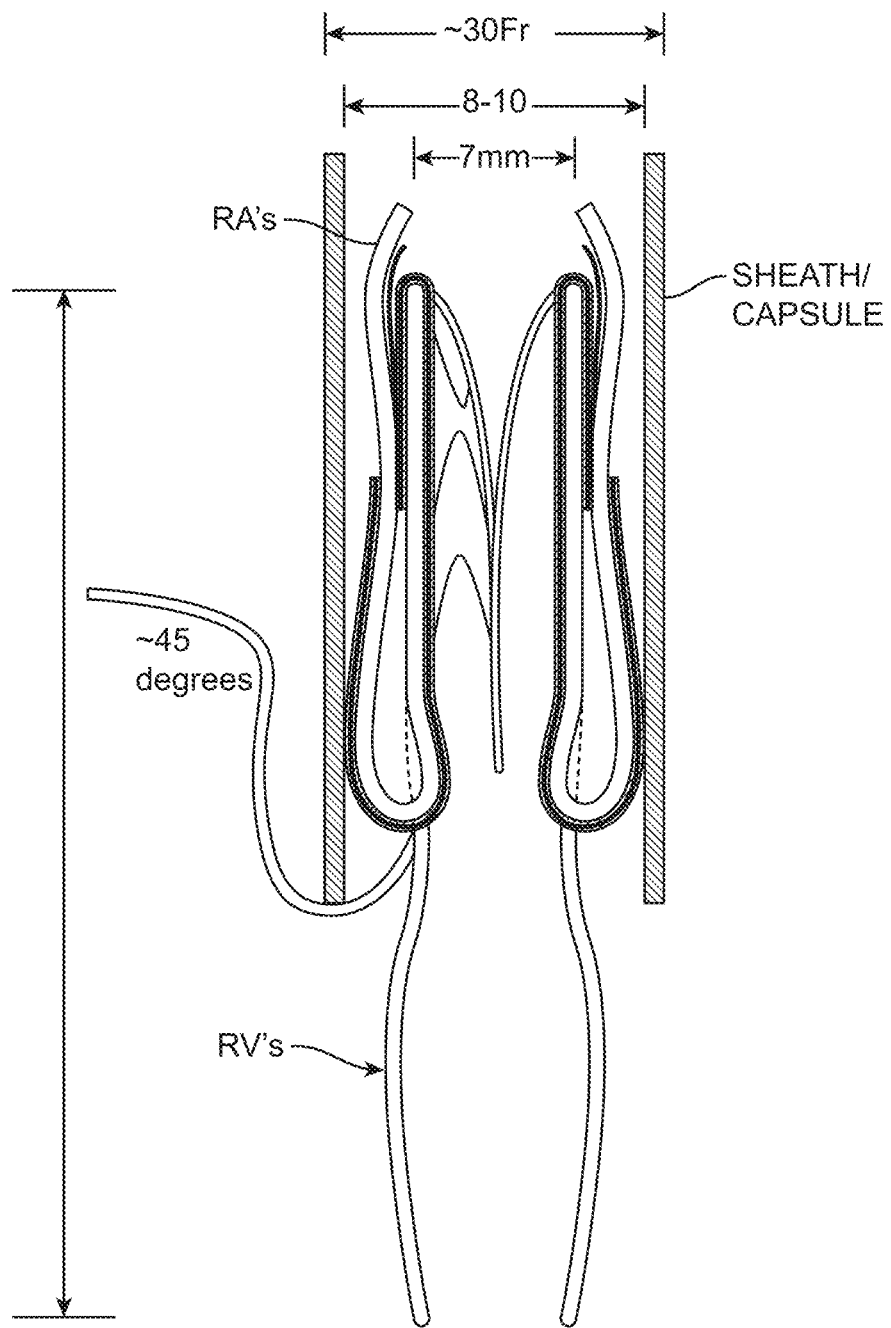
Figure 31:
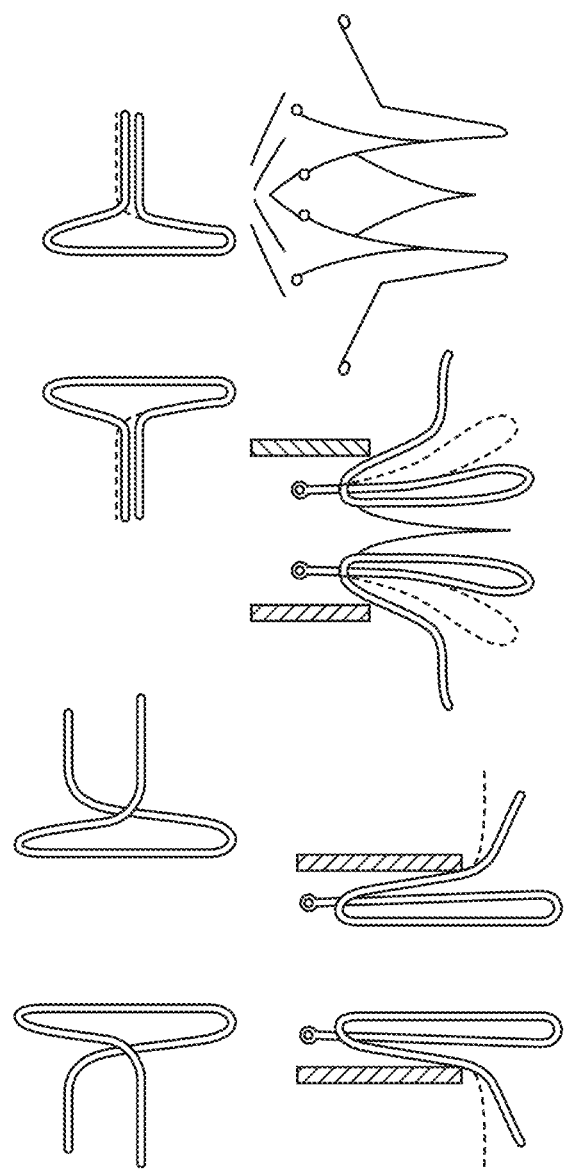
FIGS. 31-34 illustrate various other aspects of prosthetic heart valves that are contemplated herein, in accordance with an embodiment.
Figure 32:
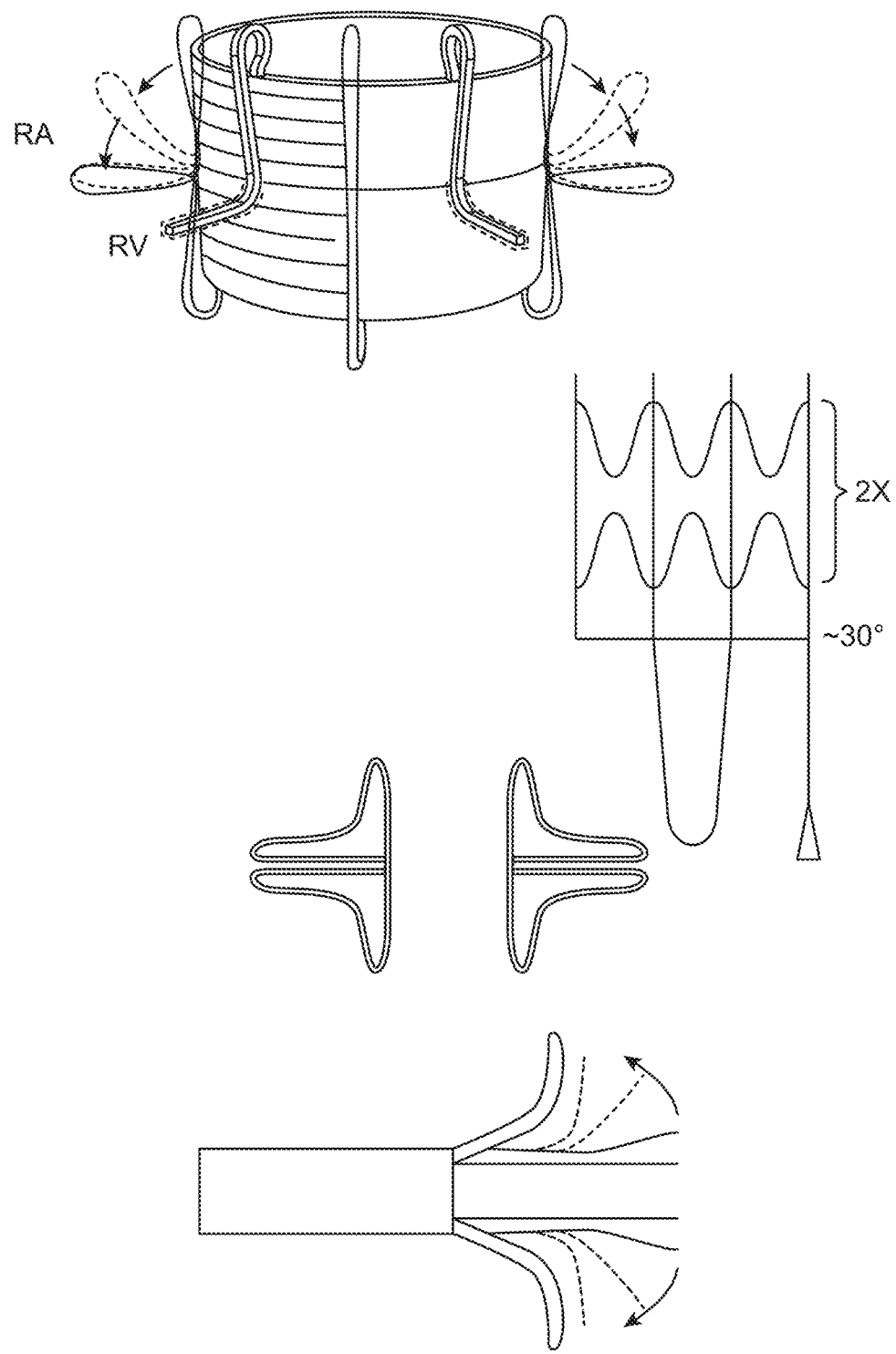

In yet another implementation, both the atrial arms 2701-1 and the ventricular arms 2701-2 extend initially from the atrial end of the support structure 2702. Leaflet elements 1300 described in connection with prosthetic tricuspid valve 100 can also be used with the alternative support structures 2702 of FIGS. 27-30, as indicated in FIG. 29. In one exemplary implementation, as shown in FIG. 30, each atrial arm 2701-1 can be folded up against the exterior surface 147 of the support structure 2702 during loading, while each ventricular arm 2701-2 can be extended down toward and beyond the ventricular end of the support structure 2702 during loading.

FIGS. 31-34 illustrate various features prosthetic tricuspid valves in which atrial and ventricular arms originate and extend from opposite ends of a cylindrical portion of a support structure of the prosthetic tricuspid valves (e.g., in which ventricular arms originate and extend from an atrial end of the cylindrical portion of the support structure and in which atrial arms originate and extend from a ventricular end of the cylindrical portion of the support structure). These various features can applied to any of the implementations described above and below, if desired.

Figure 35:
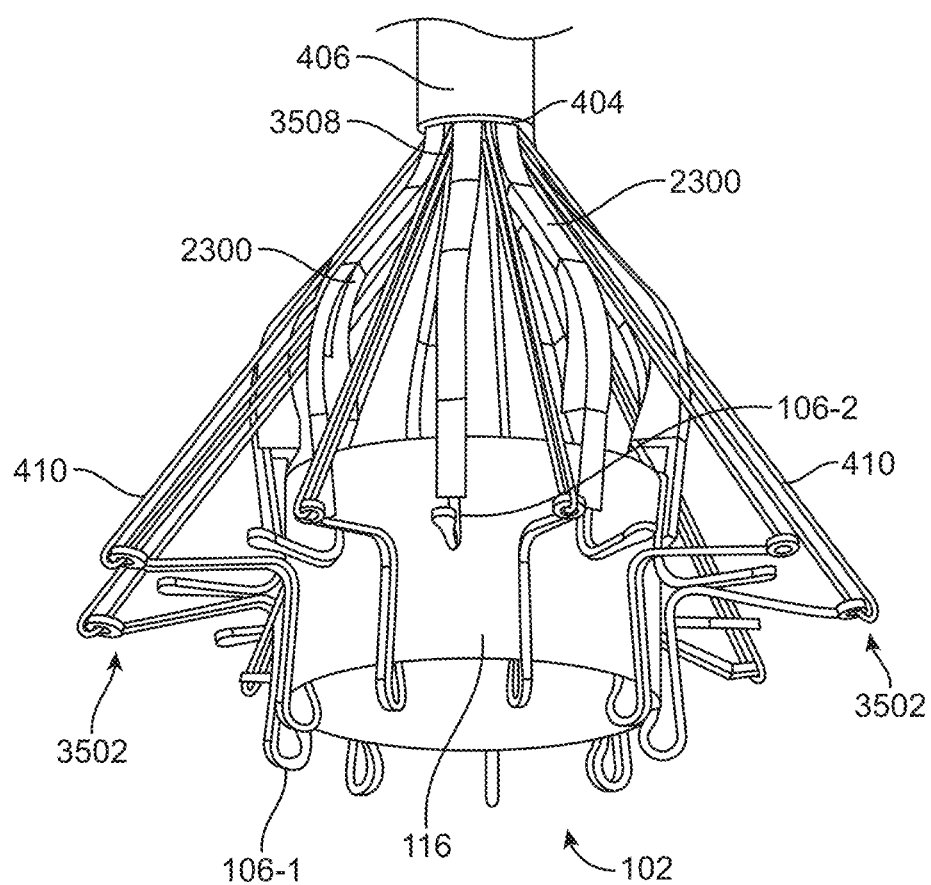
FIG. 35 illustrates a perspective view of the support structure for the prosthetic heart valve interfacing with a delivery system, in accordance with an embodiment.

FIG. 35 illustrates additional features of spreader arms 2300 as described above in connection with FIG. 23 (e.g., for providing forces 2000 and 2002 of FIG. 20 for controlled deployment or retraction of ventricular arms 106-2). As shown in the example of FIG. 35, a plurality of spreader arms 2300 can extend from circumferentially separated locations on mid layer 404 and can be configured to spread radially apart upon retraction of outer sheath 406.

Each spreader arm 2300 can be coupled to the atrial end 118 of the cylindrical portion 116 of the support structure 102 in such a way that the spread of spreader arms 2300 allows cylindrical portion 116 of prosthetic tricuspid valve 100 to expand radially, while spreader arms 2300 provide a force in a ventricular direction against support structure 102, that opposes the atrial-directed force of restraints 410 on atrial arms 106-1. Spreader arms 2300 may be formed from a 3D printed or molded material (e.g., a polymer) that is flexible enough that it can be compressed into sheath 406 and then flare back out naturally into the configuration of FIG. 35 upon retraction of sheath 406. In the example of FIG. 35, each restraint 410 for each atrial arm 106-1 is implemented as a suture that extends from a gap 3508 between spreader arms 2300, through an eyelet 3502 in the atrial arm 106-1, and back through gap 3508 between spreader arms 2300. Once the desired implantation position for prosthetic tricuspid valve 100 is achieved, restraints 410 can be cut and removed.

Figure 36:
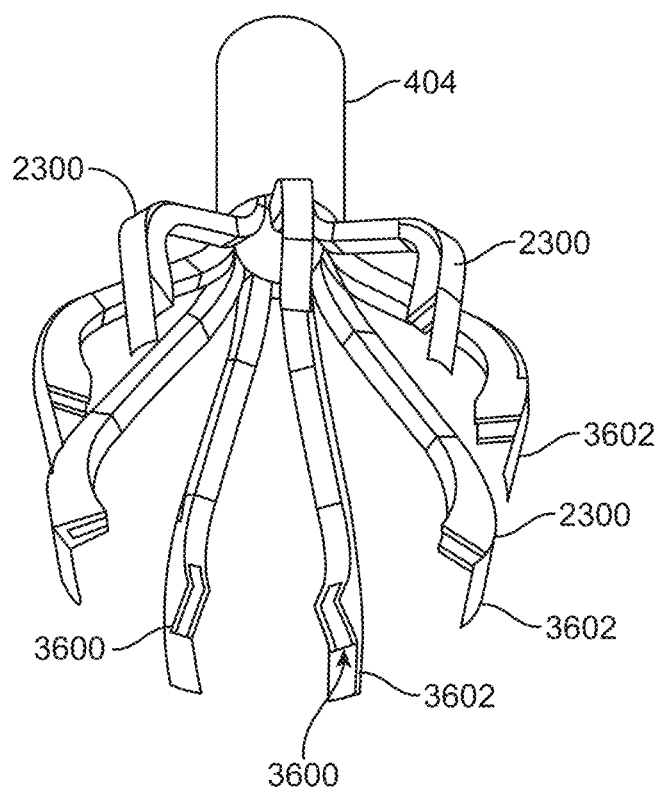
FIG. 36 illustrates a perspective view of the spreader arms of FIG. 35 in accordance with various aspects of the subject technology, in accordance with an embodiment.

FIG. 36 illustrates a perspective view of spreader arms 2300 extending from mid layer 404, in which interlocking mechanisms 3600 for interfacing with the atrial end 118 of the cylindrical portion 116 of the support structure 102 can be seen. Each interlocking mechanism 3600 is configured to maintain contact with the atrial end 118 of the cylindrical portion 116 of the support structure 102 such that spreader arms 2300 can push on the at least one support structure 102 in a ventricular direction. In some embodiments, the interlocking mechanisms 3600 can maintain contact with the atrial end 118 of the cylindrical portion 116 of the support structure 102 both during active pushing of the spreader arms 2300, and during passive rest of the spreader arms 2300. In some embodiments, the interlocking mechanisms 3600 can disengage from the atrial end 118 of the cylindrical portion 116 of the support structure 102 during passive rest of the spreader arms 2300 when mid layer 404 is moved away from support structure 102.

As shown in FIG. 36, each spreader arm 2300 may include an extension 3602 that extends beyond the interlocking mechanism 3600 on the spreader arm, and over the atrial end 118 of the cylindrical portion 116 of the at least one support structure 102. The extension 3602 may serve multiple purposes. First, extension 3602 can serve as a "hood" over the support structure 102 that allows for easier recapturing of the prosthetic tricuspid valve 100 with lower forces by preventing the outer sheath 406 from encountering resistance from an edge of the support structure 102 as the outer sheath 406 is advanced back over the edge of the support structure 102 during recapturing. In addition, extension 3602 can extend to promote pleating of the atrial sealing skirt 204 and to provide a hinge point for controlled folding of the atrial sealing skirt 204, to again reduce loading and recapturing forces that would otherwise cause the atrial sealing skirt 204 to bunch non-uniformly as the atrial arms 106-1 are folded up.

Figure 59:
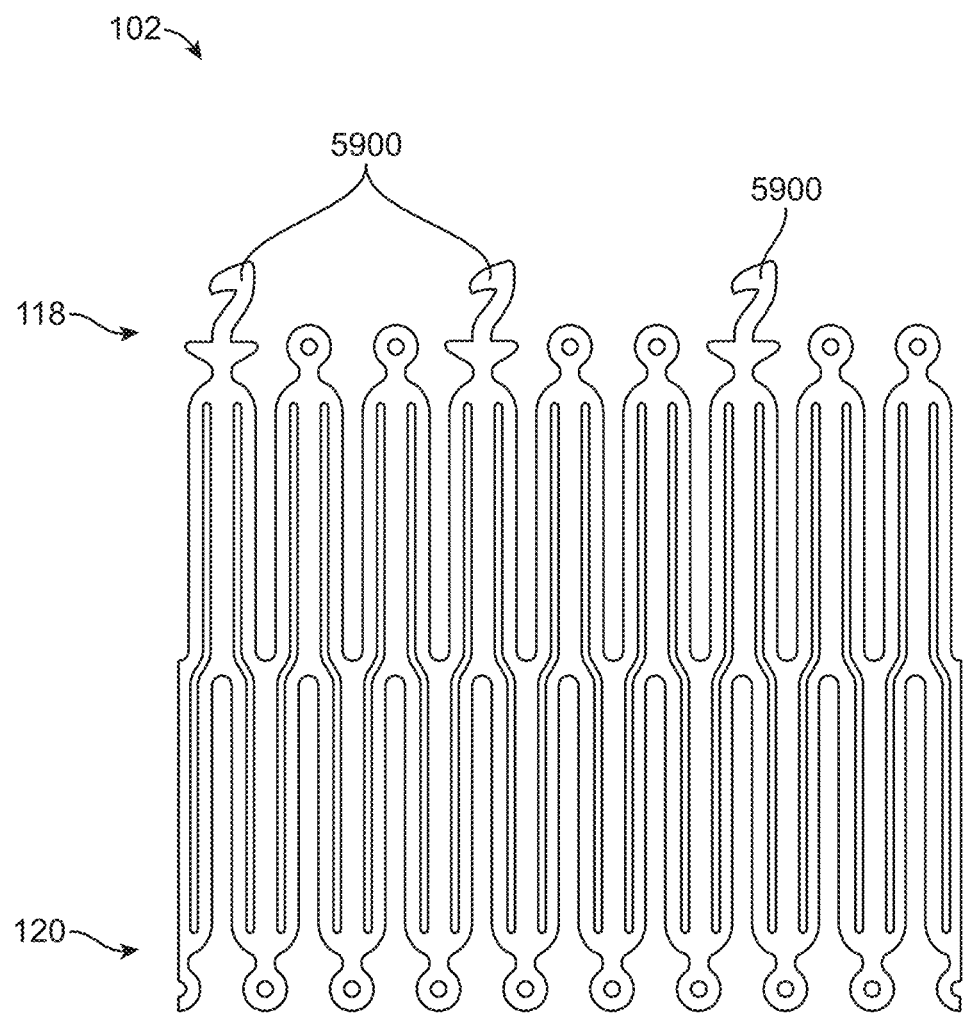
FIG. 59 illustrates a view of a flattened support structure of a prosthetic tricuspid valve, in accordance with an embodiment.
Figure 60:
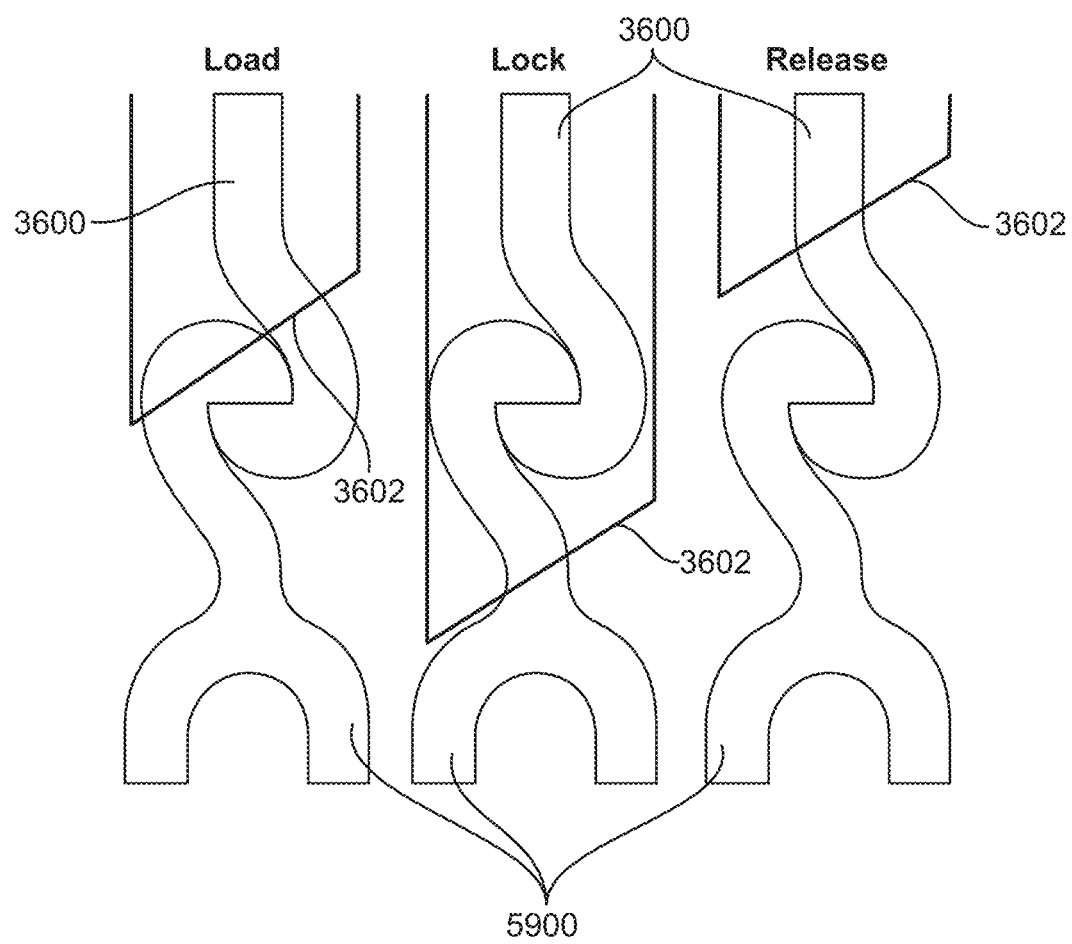
FIG. 60 illustrates loading, locking, and releasing of interlocking mechanisms of a support structure of a prosthetic tricuspid valve, in accordance with an embodiment.

In the examples of FIGS. 35 and 36, spreader arms 2300 engage with the proximal segment 108 of each ventricular arm 106-2 (e.g., the initial bend 124 of each ventricular arm 106-2) at the atrial end 118 of the cylindrical portion 116 of the support structure 102. However, it should be appreciated that spreader arms 2300 can be alternatively or additionally provided to engage with the cylindrical portion 116 of the support structure 102, as shown in the examples of FIGS. 59-60.

Figure 37:
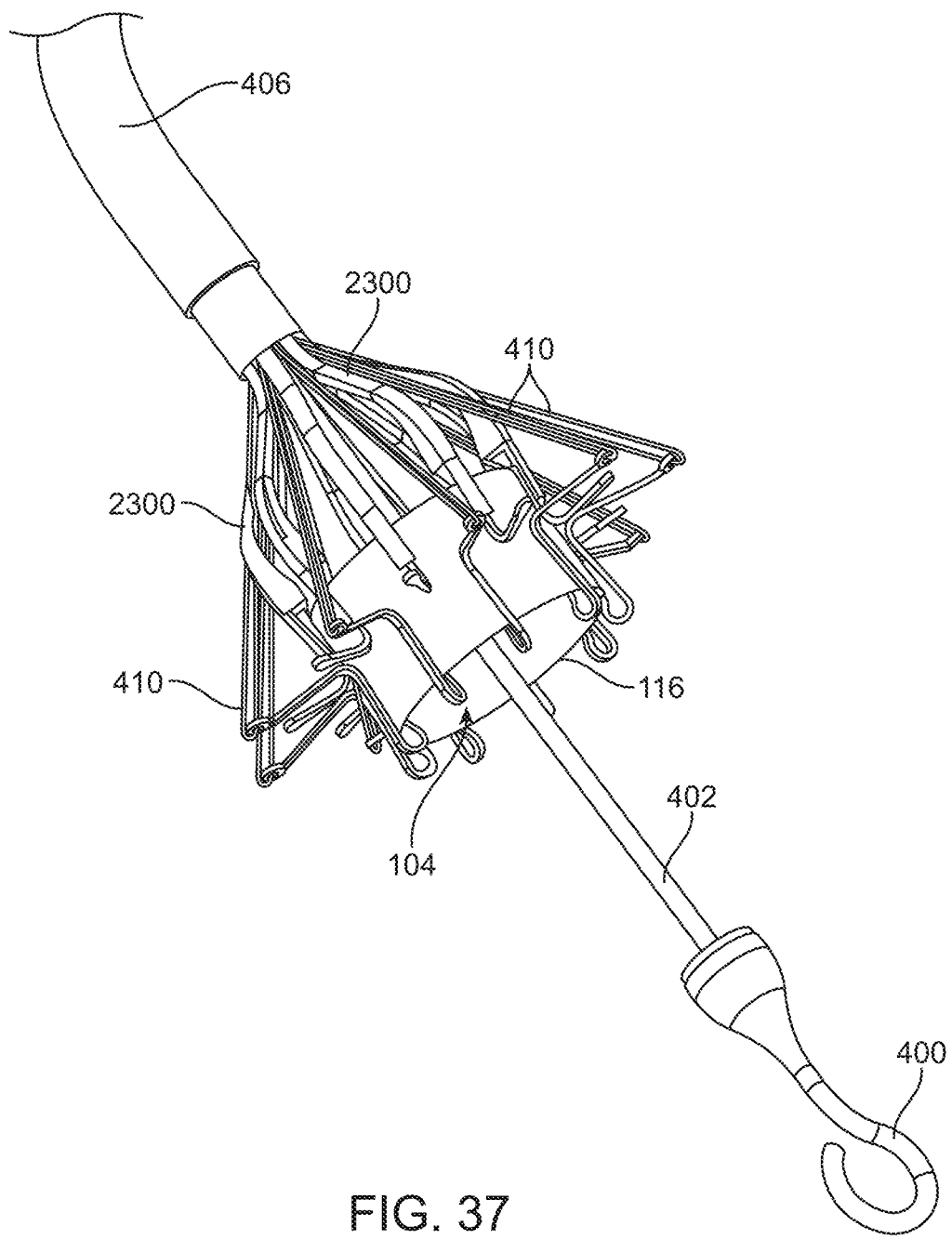
FIG. 37 illustrates a wider perspective view of the support structure for the prosthetic heart valve interfacing with a delivery system in accordance with various aspects of the subject technology, in accordance with an embodiment.

FIG. 37 illustrates a wider perspective view of support structure 102 coupled to restraints 410 and spreader arms 2300 of mid layer 404, in which inner nose cone 402 and outer nose cone 400 can be seen extending through elongate central passageway 104. Prosthetic tricuspid valve 100 may be disposed in the configuration of FIG. 37 during implantation and prior to removal of inner nose cone 402, outer nose cone 400, spreader arms 2300, restraints 410, and sheath 406, to finalize implantation.

Figure 38:
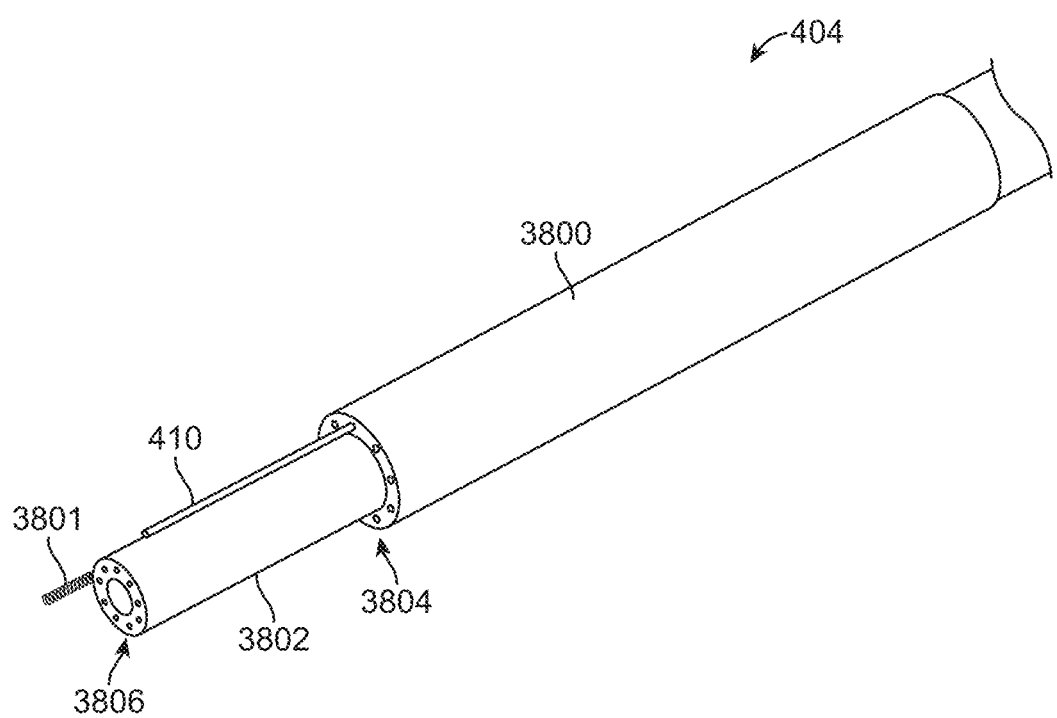
FIG. 38 illustrates a perspective view of a portion of a mid layer of a delivery system for a prosthetic heart valve, in accordance with an embodiment.

FIG. 38 illustrates a perspective view of a portion of mid layer 404 in accordance with aspects of the disclosure. As illustrated by FIG. 38, suture lines that form restraints 410 can run the full length of the delivery system (e.g., within elongate openings 3804 in an outer layer 3800 of mid layer 404). If desired, these suture lines can be coupled to springs 3801 on an end of the delivery system to accommodate any flex in an end of the delivery system that is configured to be proximal to the ventricular side of the native tricuspid valve and that could change in relative length. Springs 3801 may be mounted, for example, in openings 3806 in an inner layer 3802 of mid layer 404. From springs 3801, the suture lines can run down the inner diameter, through one of the arm eyelets 3502 (see FIG. 35), and then back down through the gaps 3508 between spreader arms 2300. In one example implementation, nine spreader arms 2300 can alternate circumferentially with nine suture lines. One end of each suture line can extend from mid layer 404 at an end of the delivery system that is configured to be proximal to the atrial side of the native tricuspid vale, so that the end can be cut to allow the suture line to be pulled out around the inner diameter.

Figure 39:
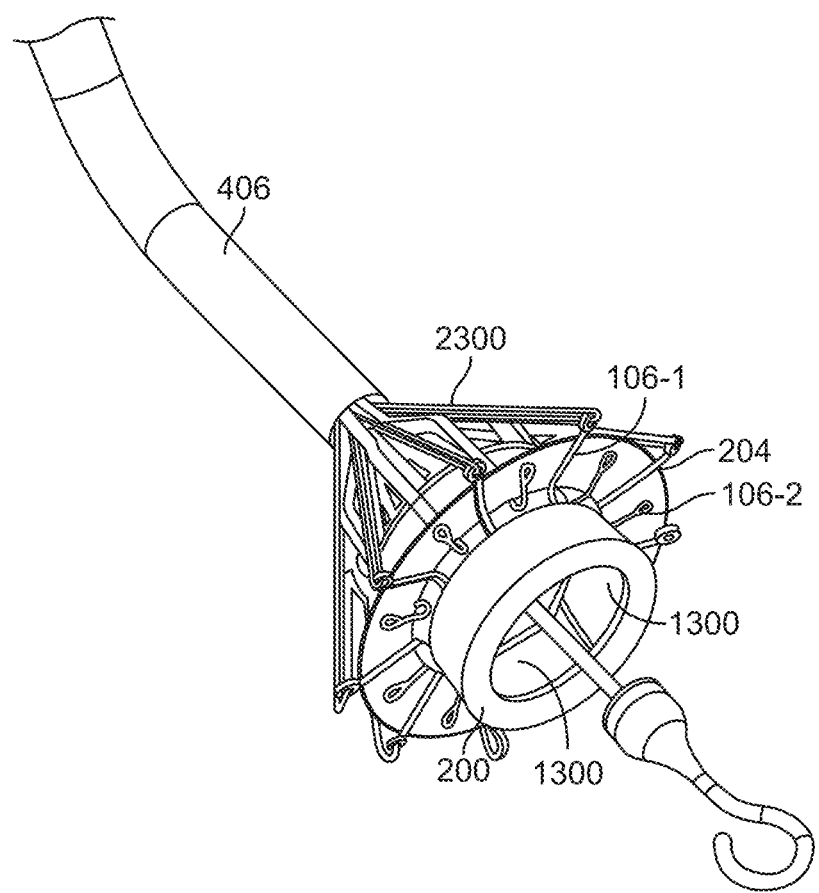
FIG. 39 illustrates a perspective view of a prosthetic heart valve interfacing with a delivery system, in accordance with an embodiment.
Figure 40:
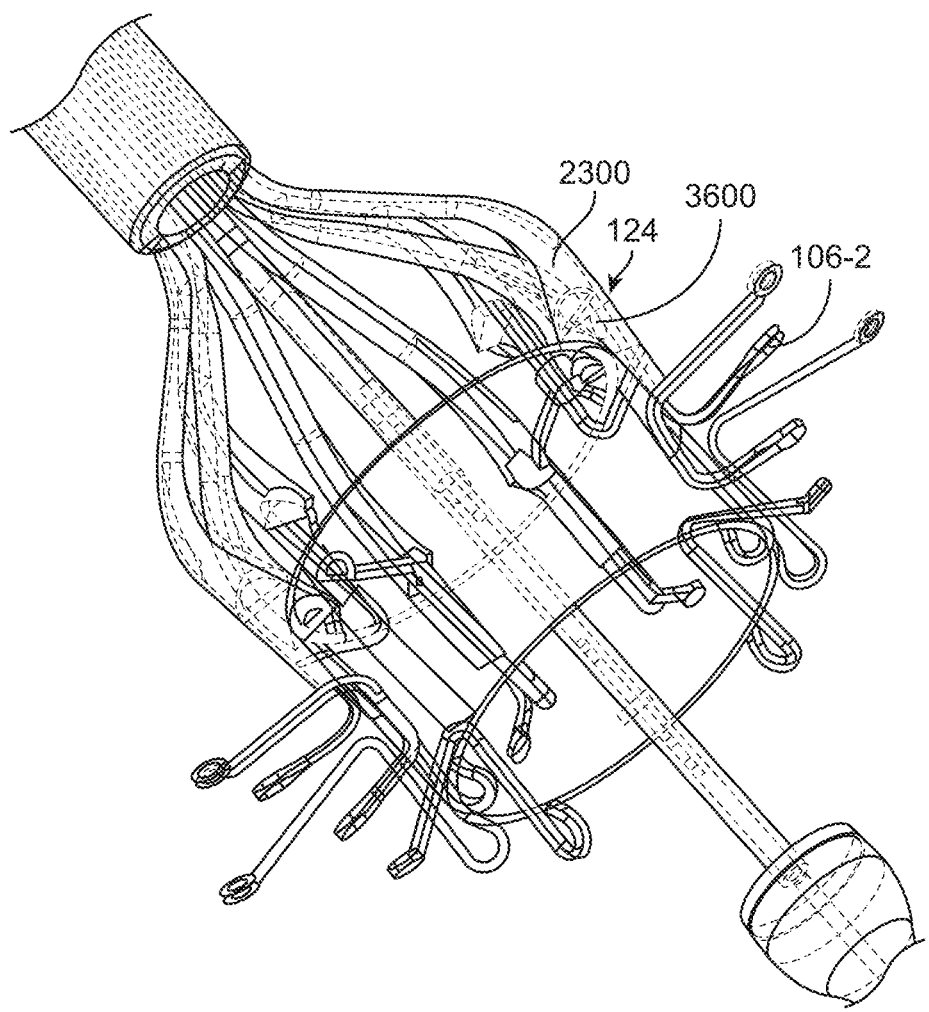
FIG. 40 illustrates a partially transparent perspective view of the support structure for the prosthetic heart valve interfacing with the delivery system, in accordance with an embodiment.

In the examples of FIGS. 35 and 37, support structure 102 of prosthetic tricuspid valve 100 is shown interfacing with spreader arms 2300 and restraints 410 without the other portions of the prosthetic tricuspid valve 100, simply for clarity. FIG. 39 illustrates the complete prosthetic tricuspid valve 100, including leaflet elements 1300 and cover 200, including atrial sealing skirt 204, interfacing with the delivery system. For additional clarity, FIG. 40 illustrates a perspective view of support structure 102 and spreader arms 2300 shown in partial transparency, particularly for clarity of the interfaces between interlocking mechanisms 3600 and bends 124 of ventricular arms 106-2.

Figure 41:
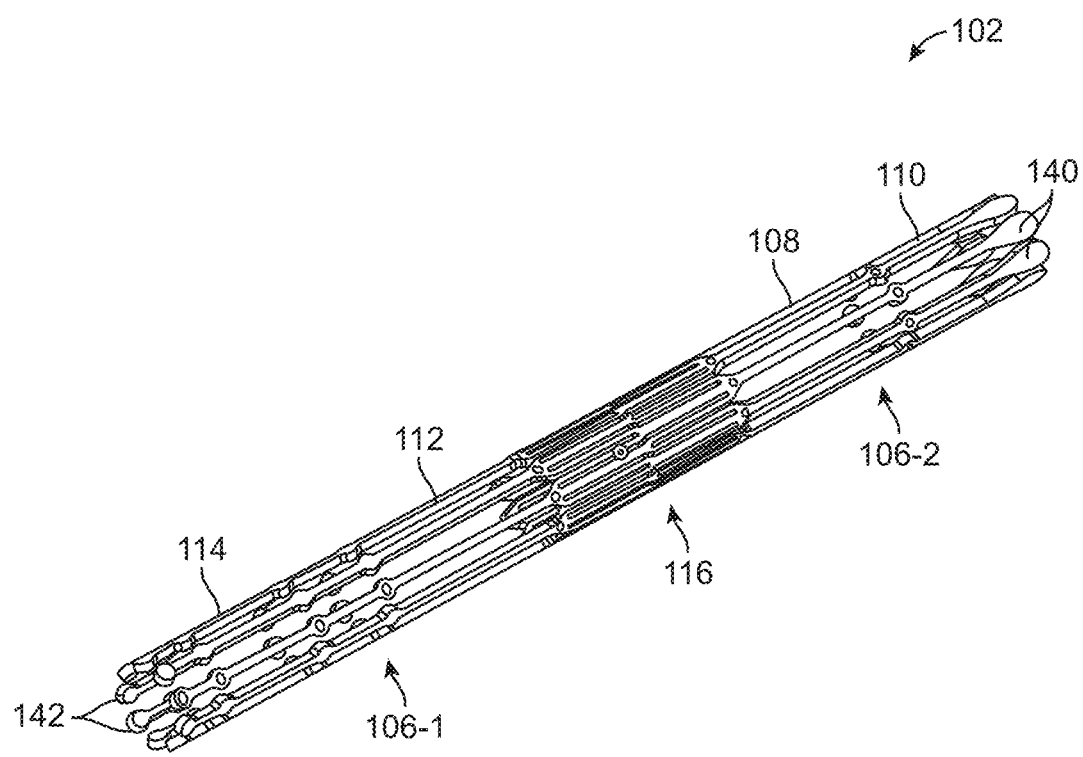
FIG. 41 illustrates a perspective view of a support structure for a prosthetic heart valve prior to formation of bends in arms that extend from a cylindrical portion, in accordance with an embodiment.

FIG. 41 illustrates a perspective view of support structure 102 in a configuration in which atrial arms 106-1, ventricular arms 106-2, and cylindrical portion 116 are cut from a common structure. In the example of FIG. 41, support structure 102 is shown "as-cut" (e.g., with atrial arms 106-1 and ventricular arms 106-2 shown before bends 126, 124, 128, and 130 are formed therein to modify the configuration of segments 108, 110, 112, and 114 to mirror those shown in, for example, FIG. 1). FIG. 41 also illustrates example configurations for ventricular arm tips 140 and atrial arm tips 142. However, the configurations of tips 140 and 142 can be provided with various different geometries to optimize load distribution against the native leaflets. In the configuration of FIG. 41, cylindrical portion 116 is formed from an expandable cage structure that is depicted in a contracted configuration.

Figure 42A:
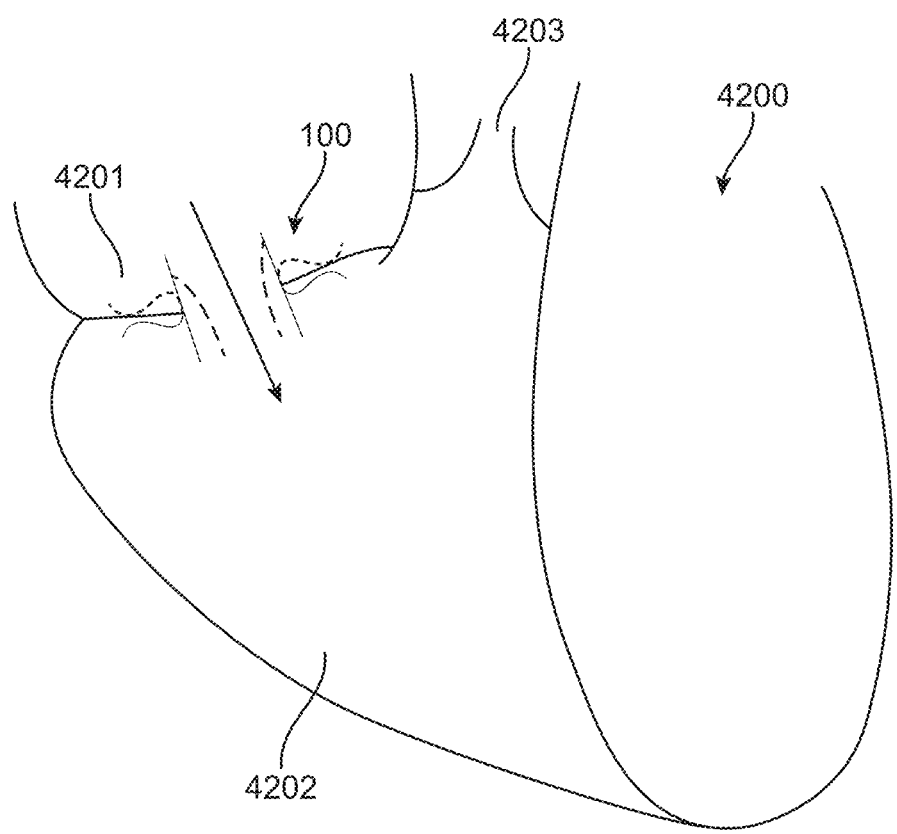
FIG. 42A illustrates a prosthetic tricuspid valve implanted in a native tricuspid valve of a heart during diastolic filling of a ventricle of the heart, in accordance with an embodiment.
Figure 42B:
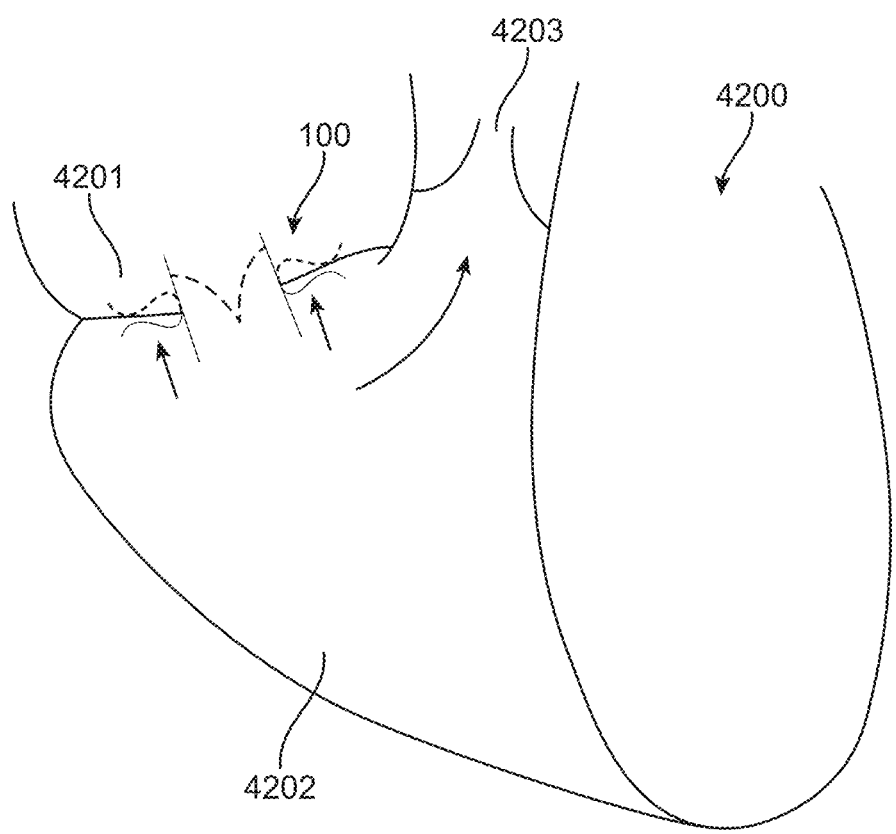
FIG. 42B illustrates a prosthetic tricuspid valve implanted in a native tricuspid valve of a heart during systolic contraction of a ventricle of the heart, in accordance with an embodiment.

FIGS. 42A-B illustrate the prosthetic tricuspid valve 100 implanted in a native tricuspid valve of a heart 4200 throughout alternating pressure differentials on either side of the native tricuspid valve 100 during cardiac cycles of the heart 4200.

Specifically, FIG. 42A illustrates the prosthetic tricuspid valve 100 implanted in the native tricuspid valve of the heart 4200 during diastolic filling of a ventricle 4202 of the heart 4200. During diastolic filling of the ventricle 4202 of the heart 4200, blood flows from an atrium 4201 of the heart 4200, through the elongate central passageway 104 of the prosthetic tricuspid valve 100, and into the ventricle 4202 of the heart 4200. During diastolic filling of the ventricle 4202 of the heart 4200, pressure on the prosthetic tricuspid valve 100 is relieved as the prosthetic tricuspid valve 100 moves slightly towards the ventricle 4202 of the heart 4200. The atrial arms 106-1 resist this motion, while the ventricular arms 106-2 relax to maintain contact with the ventricular side of the native tricuspid valve leaflets.

Conversely, FIG. 42B illustrates the prosthetic tricuspid valve 100 implanted in the native tricuspid valve of the heart 4200 during systolic contraction of the ventricle 4202 of the heart 4200. During systolic contraction of the ventricle 4202 of the heart 4200, blood flows out of the ventricle 4202 of the heart 4200 and into a pulmonary artery 4203 of the heart 4200. During systolic contraction of the ventricle 4202 of the heart 4200, pressure on the prosthetic tricuspid valve 100 moves the prosthetic tricuspid valve 100 slightly towards the atrium 4201 of the heart 4200. The ventricular arms 106-2 resist this motion while the atrial arms 106-1 relax to maintain contact with the atrial side of the native tricuspid valve leaflets. This also creates a trampoline effect where the ventricular systolic pressure load can be partially absorbed by the atrial motion of the native leaflets.

Figure 43A:
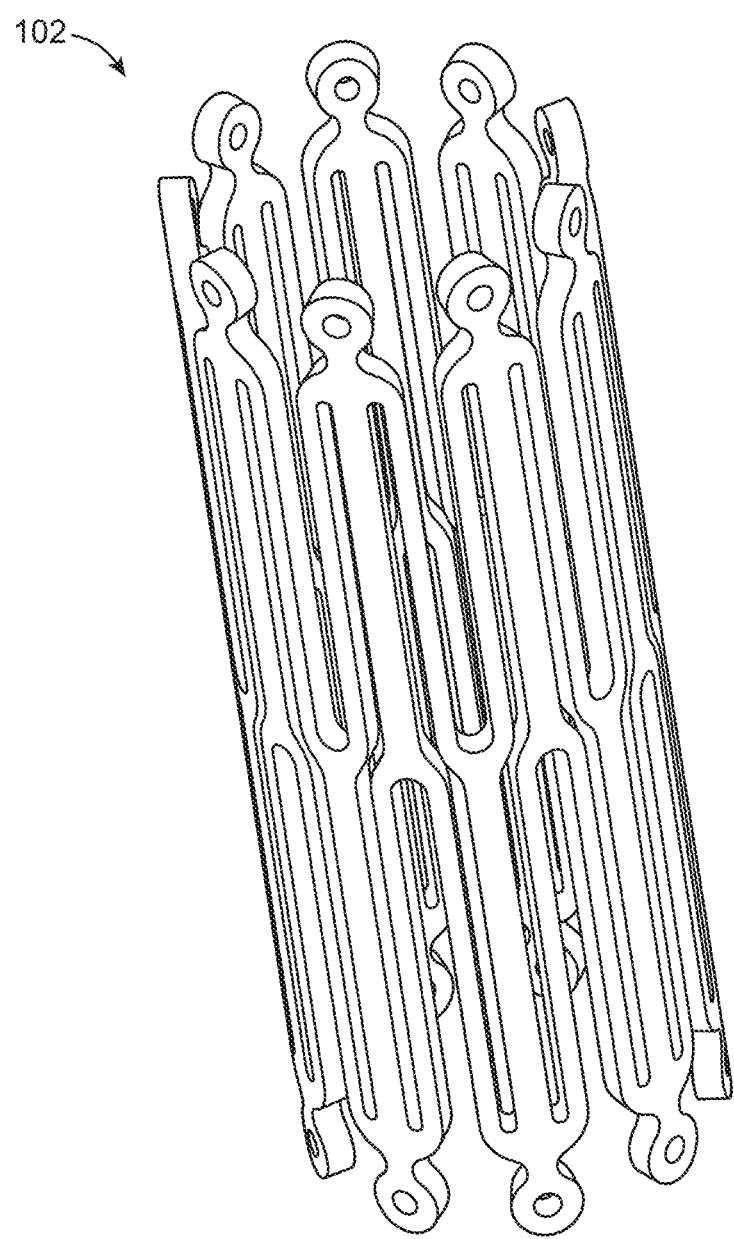
FIG. 43A illustrates another implementation of a support structure for a prosthetic tricuspid valve in a contracted configuration, and defining an elongate central passageway having a first diameter, in accordance with an embodiment.
Figure 43B:
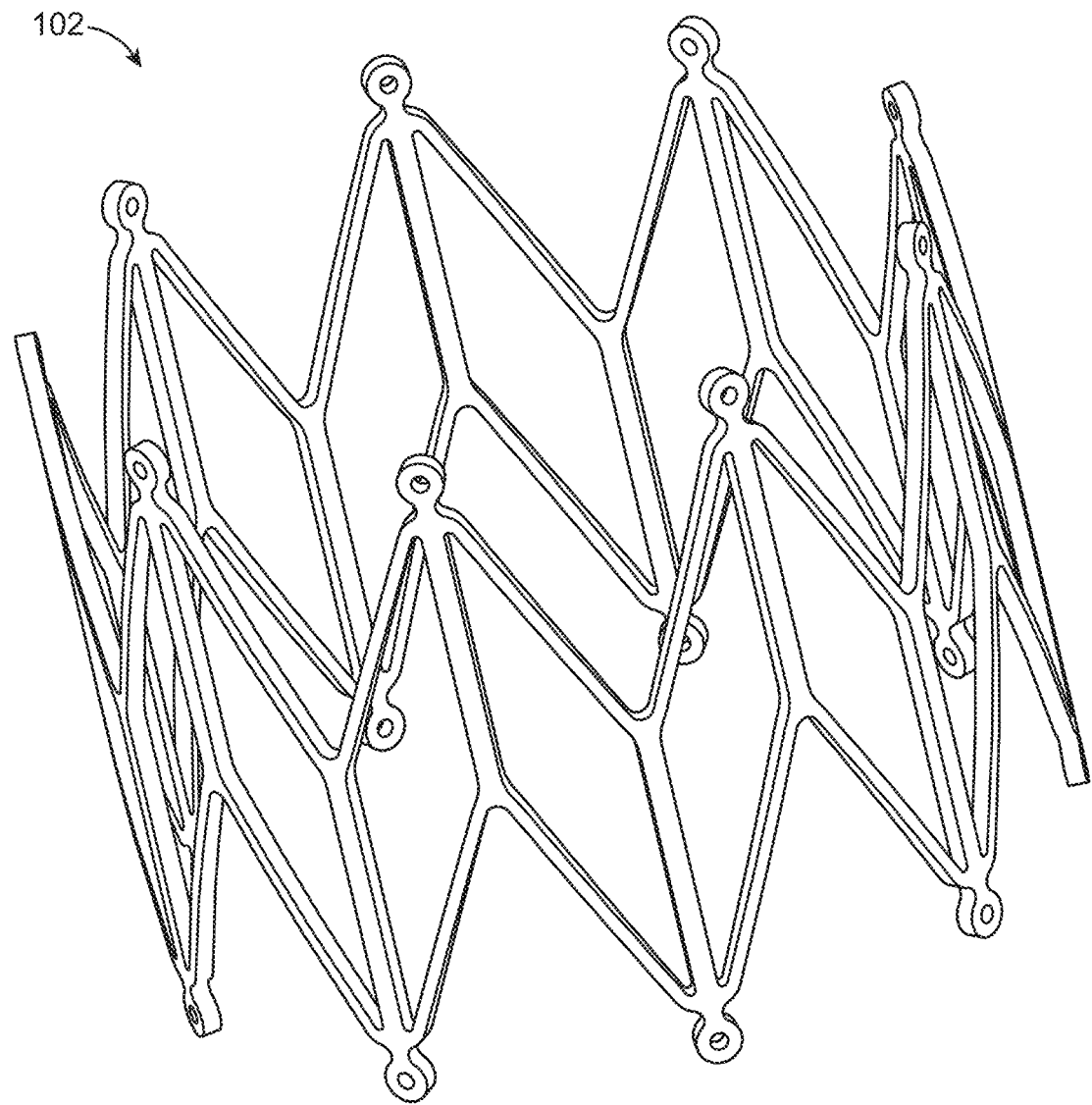
FIG. 43B illustrates another implementation of a support structure for a prosthetic tricuspid valve in an expanded configuration, and defining an elongate central passageway having a second diameter that is larger than the first diameter, in accordance with an embodiment.

FIG. 43A-B illustrate another implementation of a support structure 102 for a prosthetic tricuspid valve, in accordance with an embodiment. Specifically, FIG. 43A illustrates another implementation of a support structure 102 for a prosthetic tricuspid valve in a contracted configuration, and defining an elongate central passageway having a first diameter. FIG. 43B illustrates another implementation of a support structure 102 for a prosthetic tricuspid valve in an expanded configuration, and defining an elongate central passageway having a second diameter that is larger than the first diameter. For example, in the embodiment of FIGS. 43A-B, the first diameter of the elongate central passageway can be 8 mm, while the second diameter of the elongate central passageway can be 25 mm.

As discussed above, a prosthetic tricuspid valve described herein can include one or more support structures. For example, the prosthetic tricuspid valve described herein can include one, two, three, or more than three support structures. At least one of the one or more support structures includes a cylindrical portion having an atrial end and a ventricular end. The cylindrical portion of the at least one support structure defines an elongate central passageway of the prosthetic tricuspid valve. The Detailed Description of certain figures above and below describe exemplar prosthetic tricuspid valves including one support structure. Additionally, the Detailed Description of certain figures above and below describe exemplar prosthetic tricuspid valves including more than one (e.g., two, three, or more than three) support structures. For example, the Detailed Description of FIGS. 46-53 below describe exemplar prosthetic tricuspid valves having two or three support structures. However, many of the features of prosthetic tricuspid valves that are described with reference to a prosthetic tricuspid valve having a particular number of support structures can be included in other prosthetic tricuspid valves having a different number of support structures.

FIGS. 44-45 illustrate different views of an implementation of a prosthetic tricuspid valve 4400 having one support structure 102, in accordance with an embodiment.

Figure 44A:
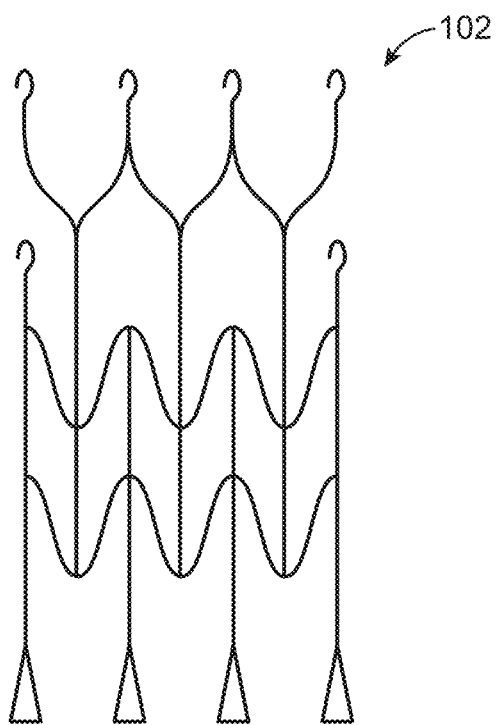
FIG. 44A illustrates a view of a flattened support structure of a prosthetic tricuspid valve having one support structure, in accordance with an embodiment.

FIG. 44A illustrates a view of the flattened support structure 102 of the prosthetic tricuspid valve 4400 having one support structure 102, in accordance with an embodiment.

Figure 44B:
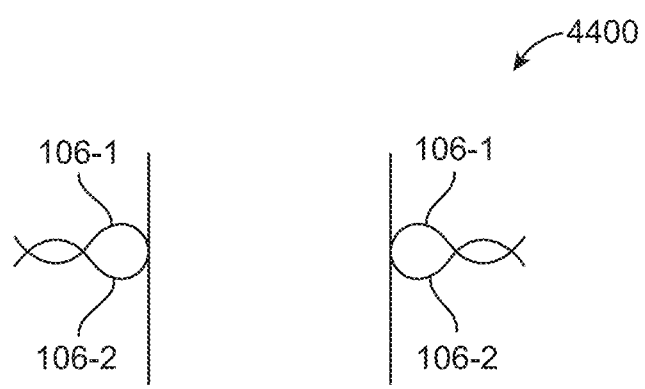
FIG. 44B illustrates a side view of a prosthetic tricuspid valve having one support structure and configured for implantation in a native tricuspid valve, in accordance with an embodiment.

FIG. 44B illustrates a side view of the prosthetic tricuspid valve 4400 having one support structure 102 and configured for implantation in a native tricuspid valve, in accordance with an embodiment.

Figure 45A:
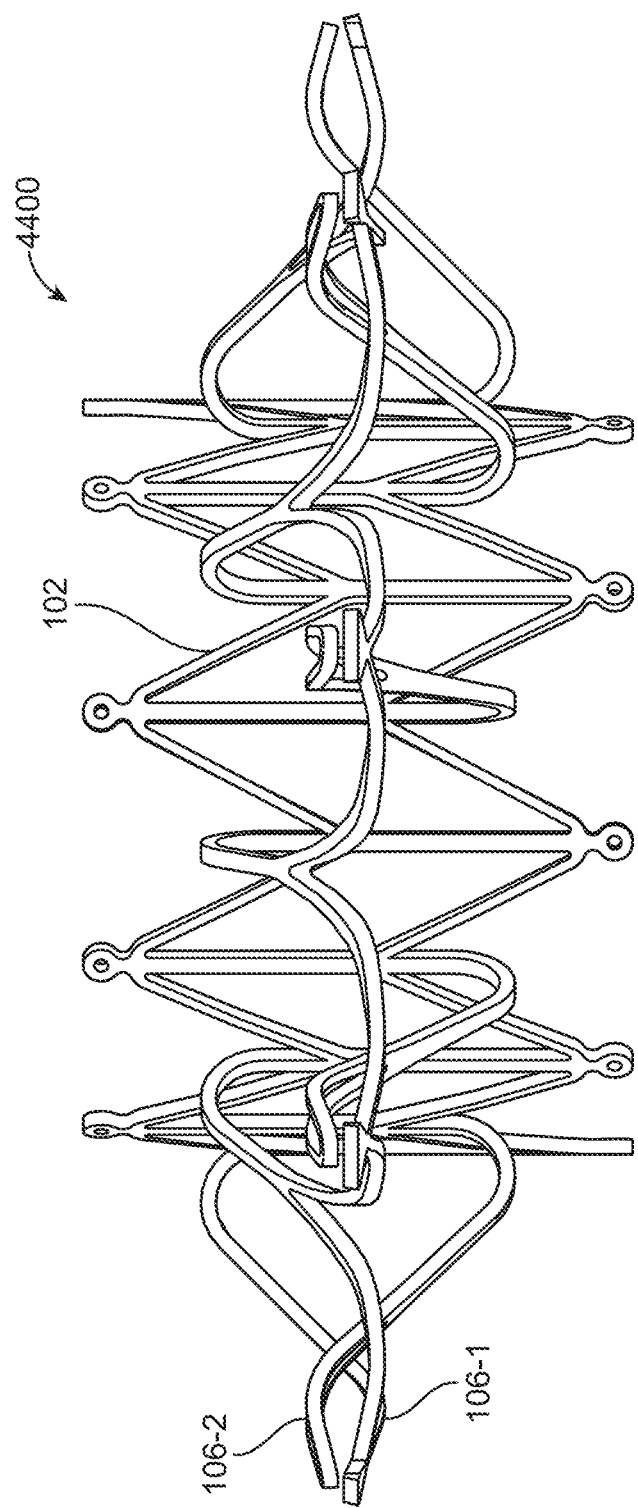
FIG. 45A illustrates a CAD drawing of a side view of a prosthetic tricuspid valve having one support structure, in accordance with an embodiment.
Figure 45B:
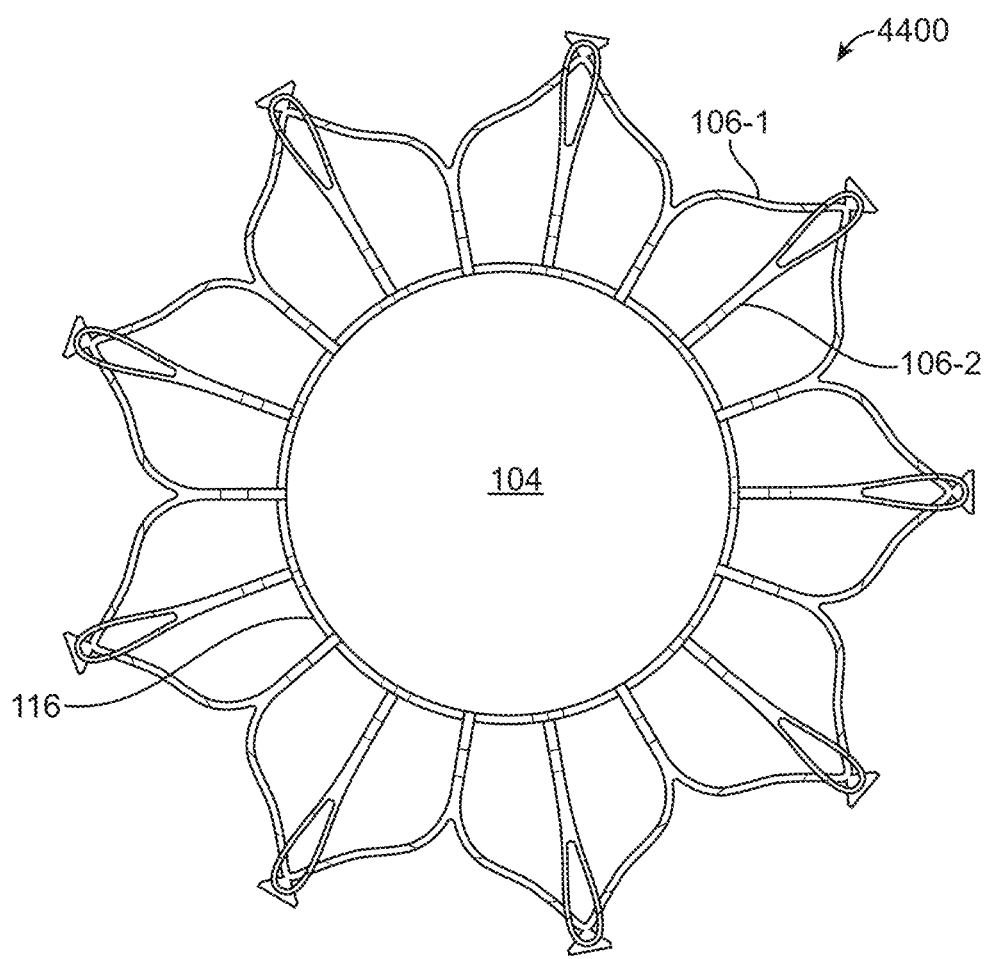
FIG. 45B illustrates a CAD drawing of a top-down view of a prosthetic tricuspid valve having one support structure, in accordance with an embodiment.
Figure 45C:
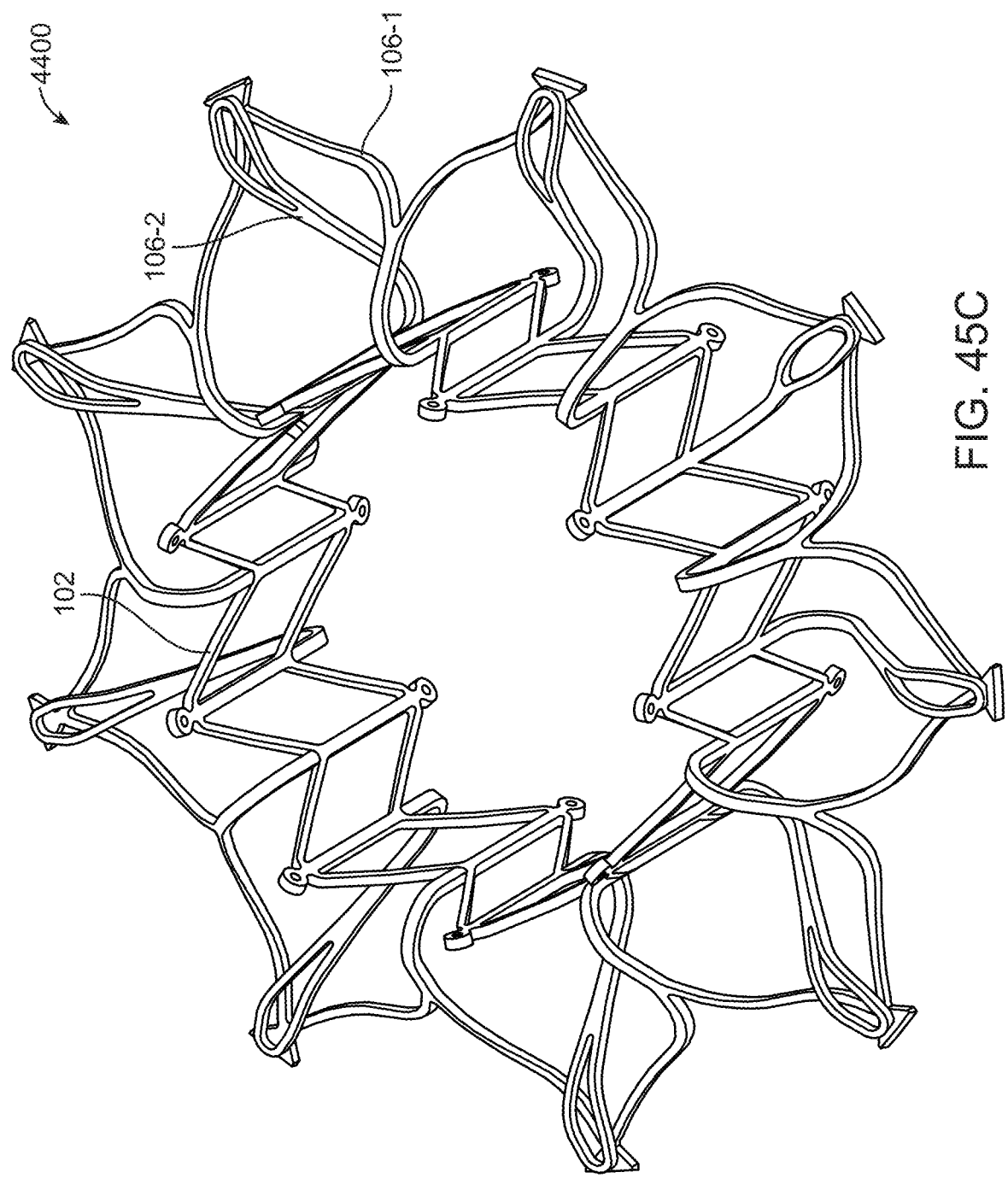
FIG. 45C illustrates a CAD drawing of a titled side view of a prosthetic tricuspid valve having one support structure, in accordance with an embodiment.
Figure 45D:
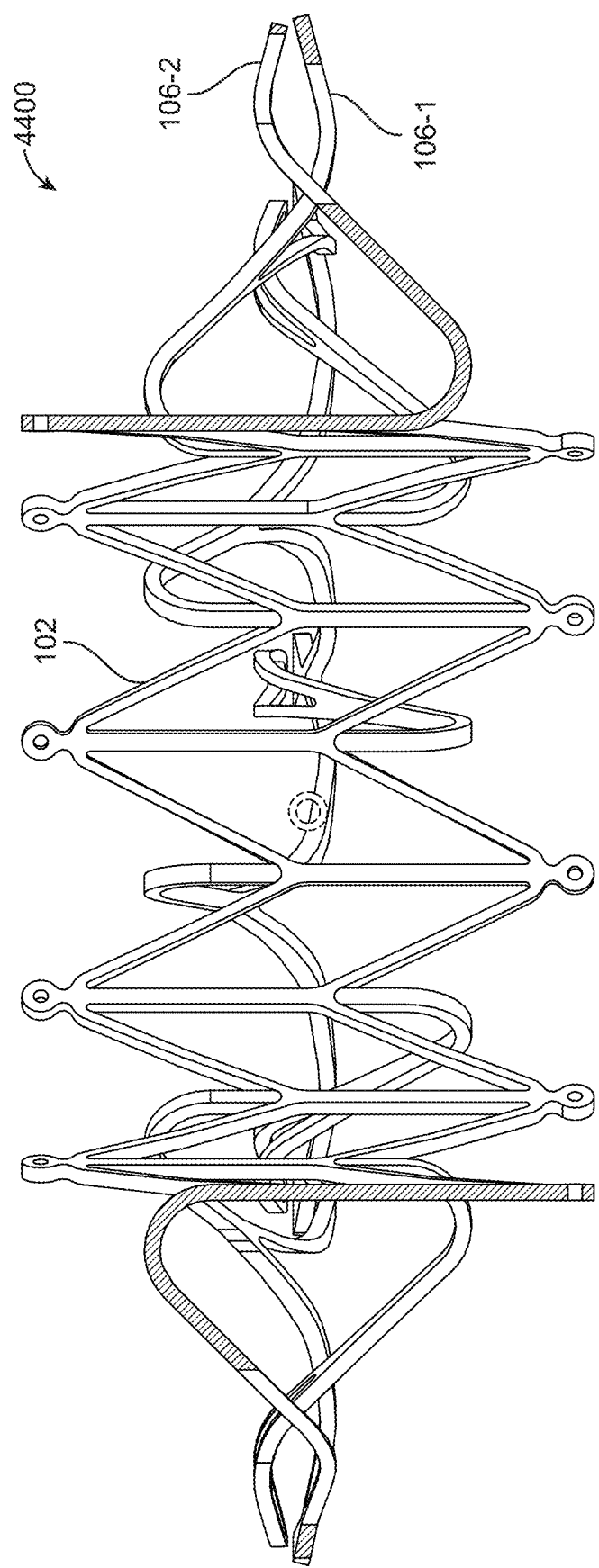
FIG. 45D illustrates a CAD drawing of a side view of a prosthetic tricuspid valve having one support structure, in accordance with an embodiment.

FIGS. 45A-D illustrate computer-aided design (CAD) drawings of different views of the prosthetic tricuspid valve 4400 having one support structure 102, in accordance with an embodiment. FIG. 45A illustrates a CAD drawing of a side view of the prosthetic tricuspid valve 4400 having one support structure 102, in accordance with an embodiment. FIG. 45B illustrates a CAD drawing of a top-down view of the prosthetic tricuspid valve 4400 having one support structure 102, in accordance with an embodiment. FIG. 45C illustrates a CAD drawing of a titled side view of the prosthetic tricuspid valve 4400 having one support structure 102, in accordance with an embodiment. FIG. 45D illustrates a CAD drawing of a side view of the prosthetic tricuspid valve 4400 having one support structure 102, in accordance with an embodiment.

In the embodiment of the prosthetic tricuspid valve 4400 having one support structure 102, both the atrial arms 106-1 and the ventricular arms 106-2 are formed from the one support structure 102. As described throughout this disclosure, the one support structure 102 also includes a cylindrical portion 116 that defines an elongate central passageway 104 of the prosthetic tricuspid valve 4400.

The advantages to forming the prosthetic tricuspid valve 4400 from one support structure 102 include reduction of a diameter of the prosthetic tricuspid valve 4400, and fewer steps for assembly of the prosthetic tricuspid valve 4400. However, one disadvantage to forming the prosthetic tricuspid valve 4400 from one support structure 102 is more complex manufacturing of the prosthetic tricuspid valve 4400. Another disadvantage to forming the prosthetic tricuspid valve 4400 from one support structure 102 is that the prosthetic tricuspid valve 4400 may not distribute load effectively, and thus certain portions of the prosthetic tricuspid valve 4400 may be easily fractured under stress. Specifically, as discussed in further detail below, forming the prosthetic tricuspid valve 4400 from one support structure 102 can result in the prosthetic tricuspid valve 4400 having shorter arms 106, as well as fulcrum points occurring in the same general location as load nodes, effectively yielding less ability for load distribution and thus greater breakability of the prosthetic tricuspid valve 4400.

FIGS. 46-47 illustrate different views of an implementation of a prosthetic tricuspid valve 4600 having two support structures 102-1 and 102-2, in accordance with an embodiment.

Figure 46A:
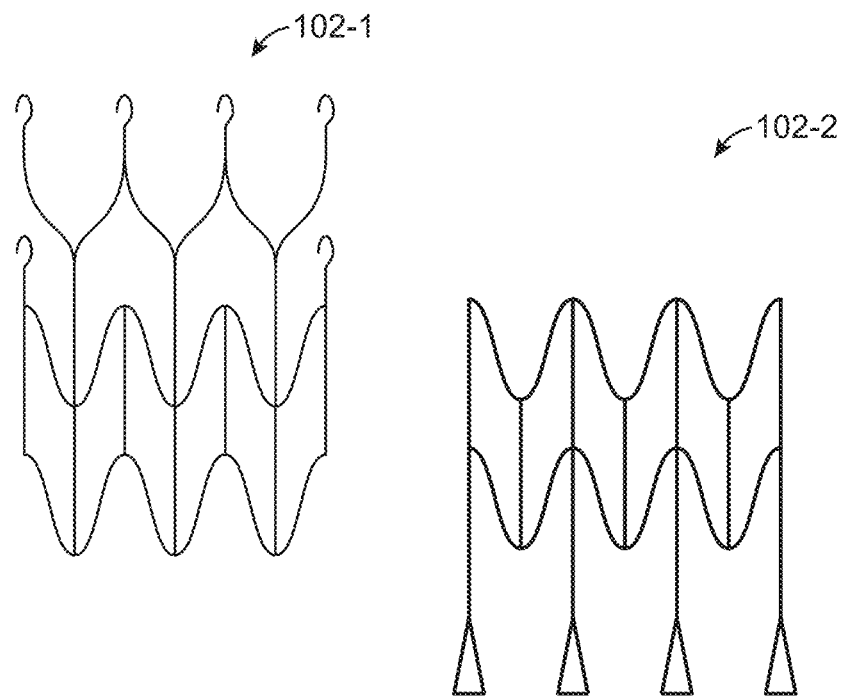
FIG. 46A illustrates a view of flattened support structures and of a prosthetic tricuspid valve having two support structures, in accordance with an embodiment.

FIG. 46A illustrates a view of the flattened support structures 102-1 and 102-2 of the prosthetic tricuspid valve 4600 having two support structures 102-1 and 102-2, in accordance with an embodiment.

Figure 46B:
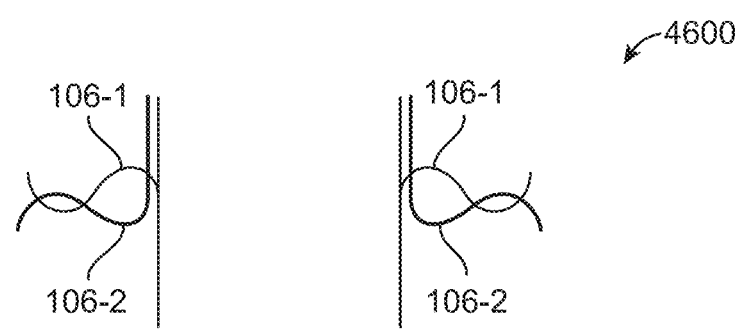
FIG. 46B illustrates a side view of a prosthetic tricuspid valve having two support structures, and configured for implantation in a native tricuspid valve, in accordance with an embodiment.

FIG. 46B illustrates a side view of the prosthetic tricuspid valve 4600 having two support structures 102-1 and 102-2 and configured for implantation in a native tricuspid valve, in accordance with an embodiment.

Figure 47A:
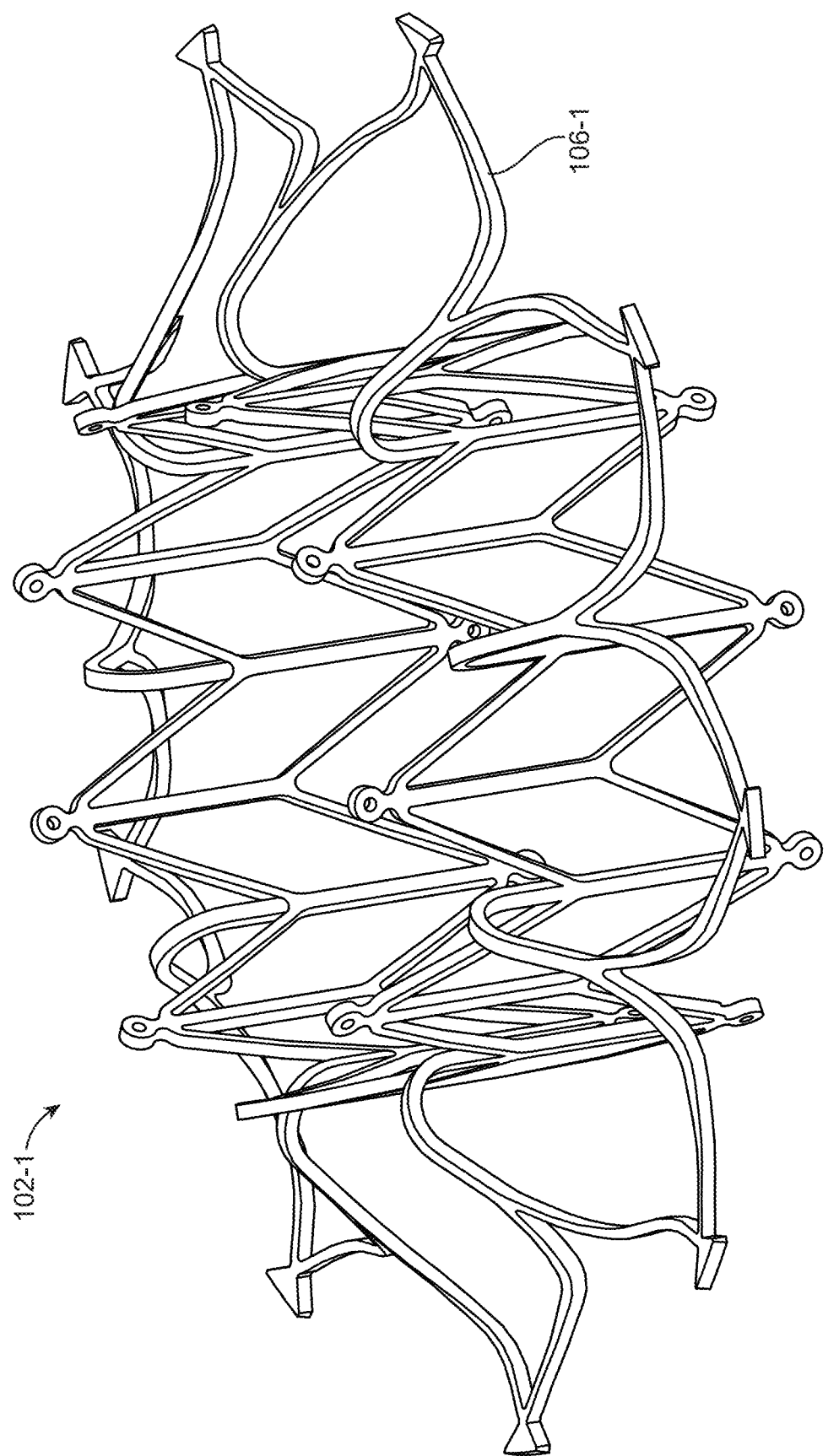
FIG. 47A illustrates a CAD drawing of a tilted side view of a support structure of a prosthetic tricuspid valve having two support structures, in accordance with an embodiment.
Figure 47B:
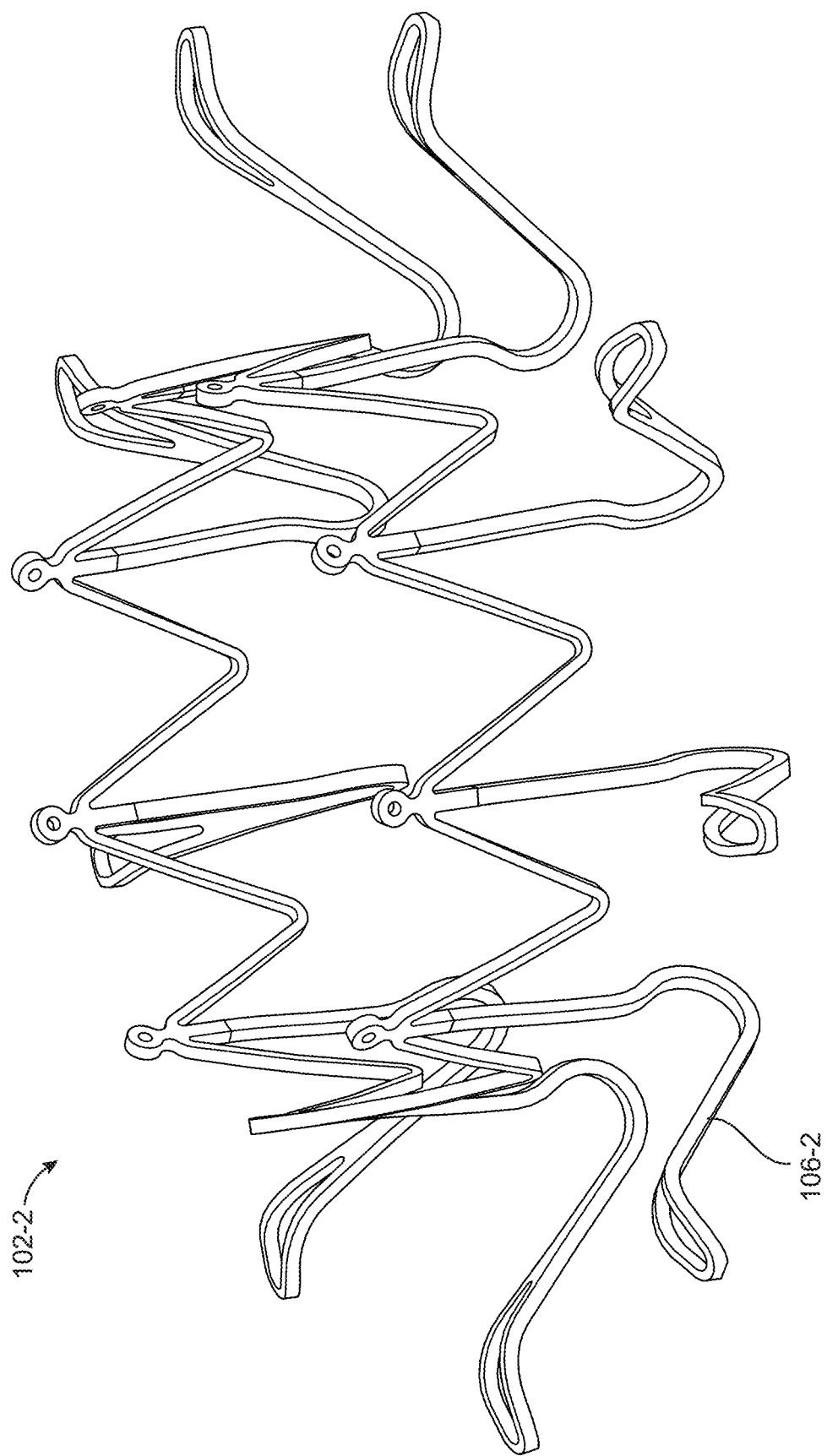
FIG. 47B illustrates a CAD drawing of a tilted side view of a support structure of a prosthetic tricuspid valve having two support structures, in accordance with an embodiment.
Figure 47C:
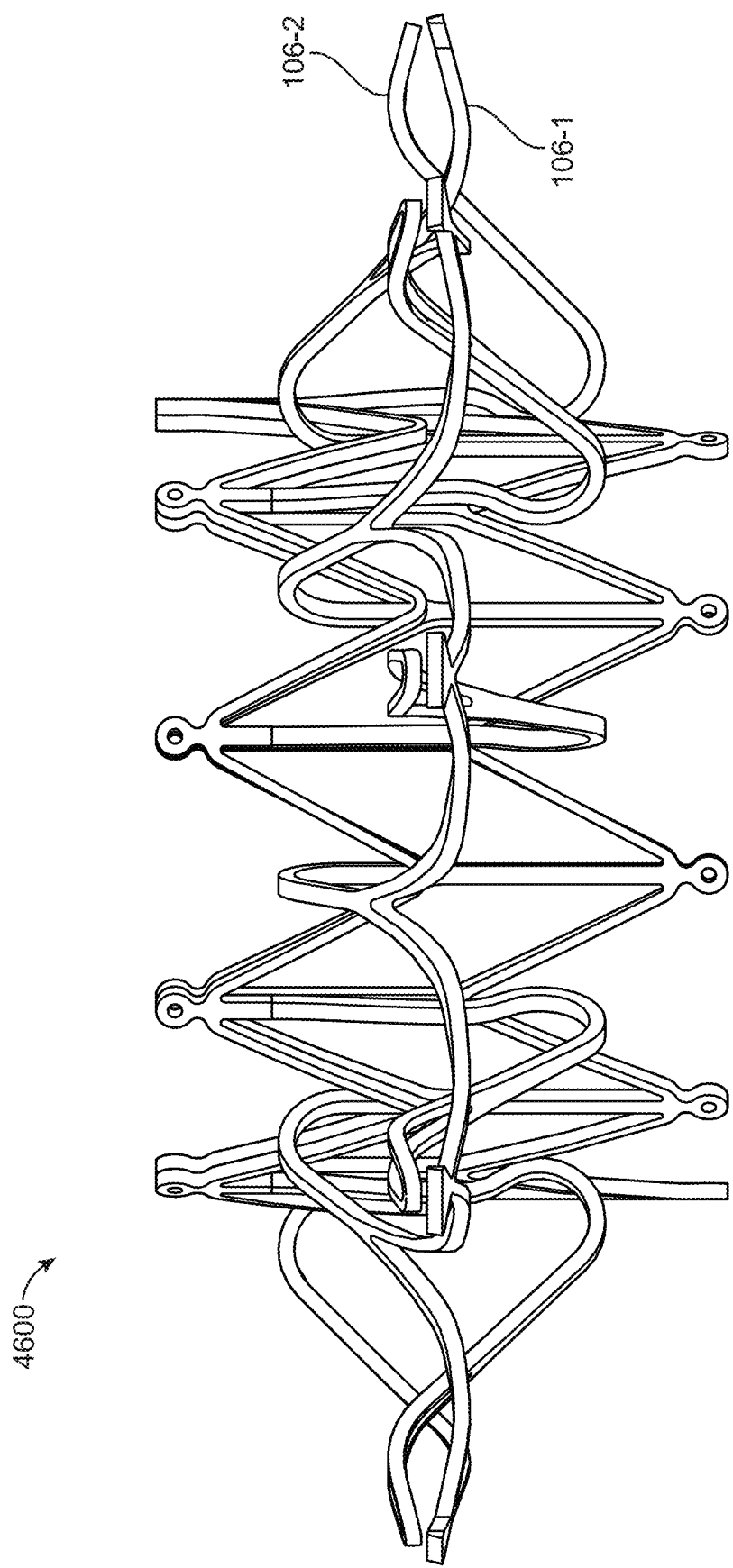
FIG. 47C illustrates a CAD drawing of a side view of a prosthetic tricuspid valve having two support structures, in accordance with an embodiment.
Figure 47D:
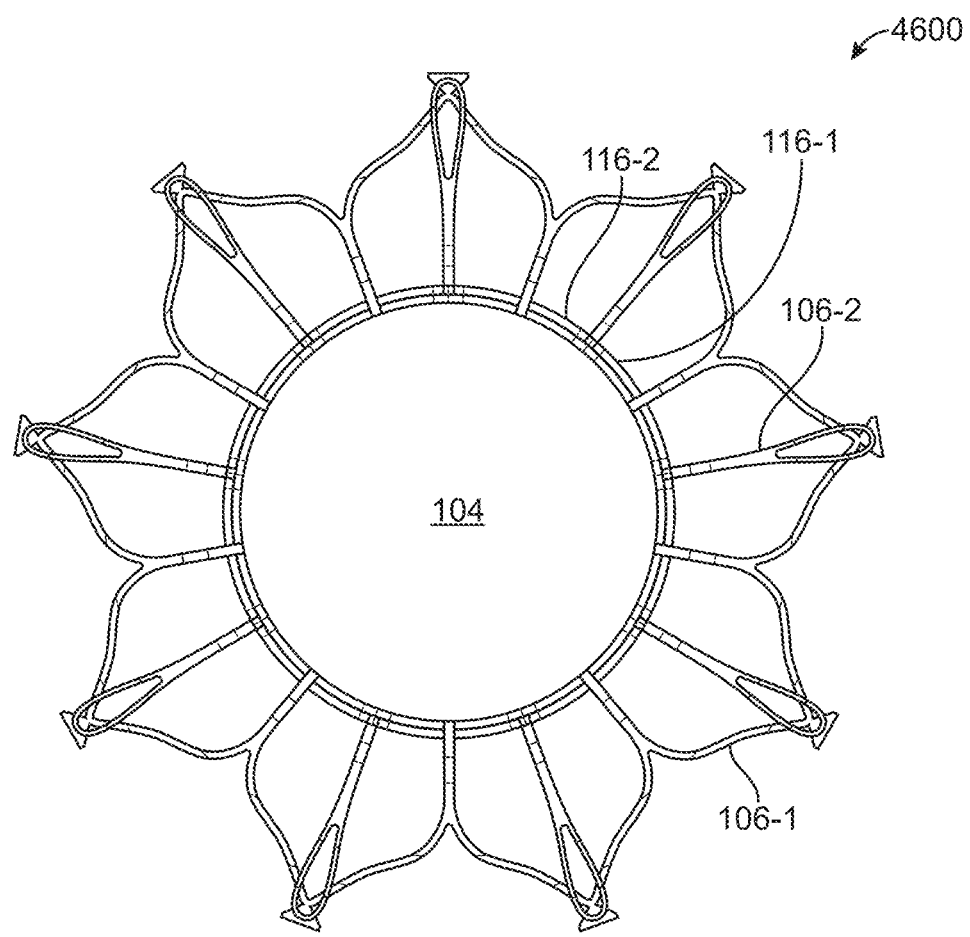
FIG. 47D illustrates a CAD drawing of a top-down view of a prosthetic tricuspid valve having two support structures, in accordance with an embodiment.
Figure 47E:
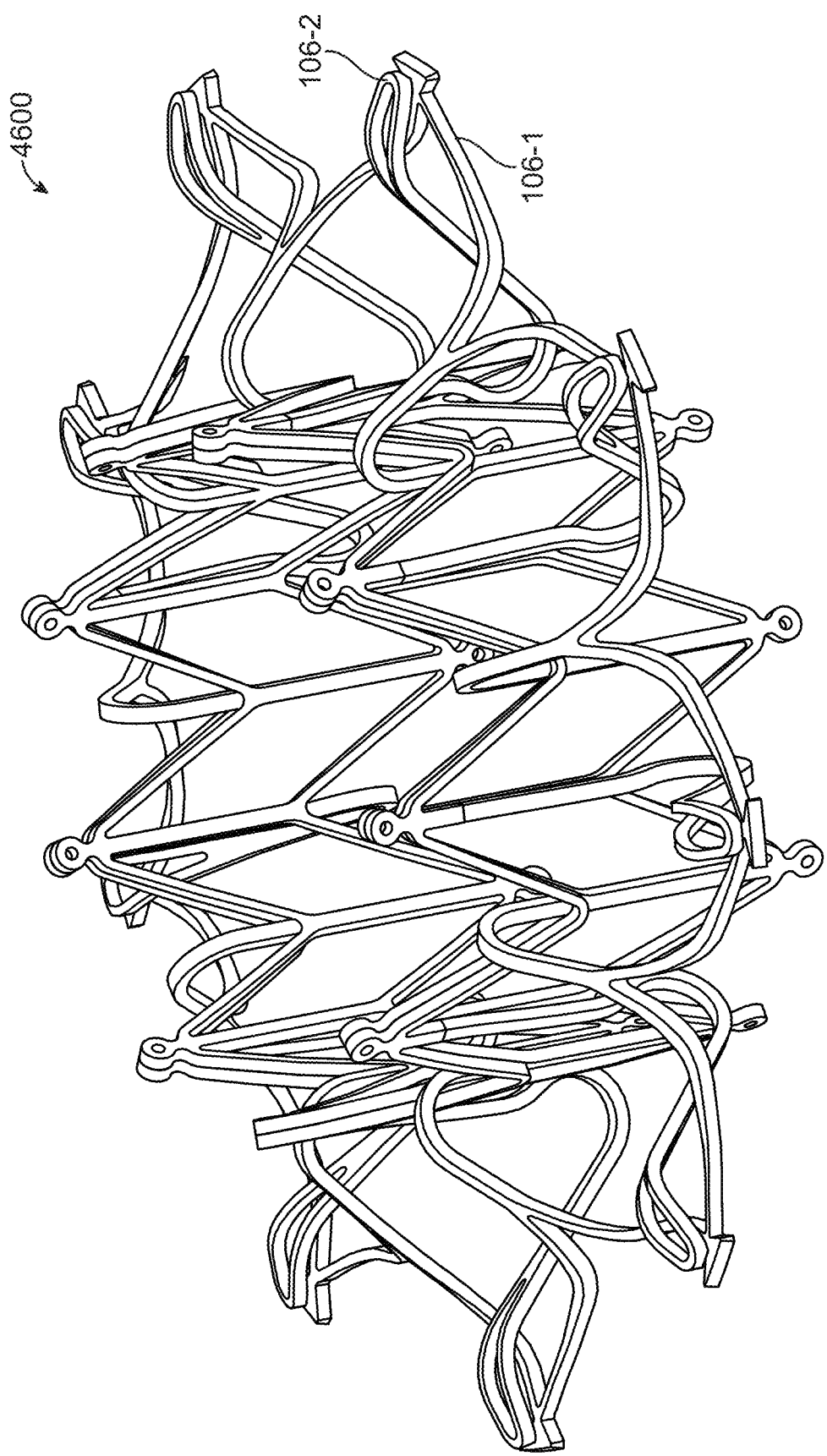
FIG. 47E illustrates a CAD drawing of a tilted side view of a prosthetic tricuspid valve having two support structures, in accordance with an embodiment.
Figure 47F:
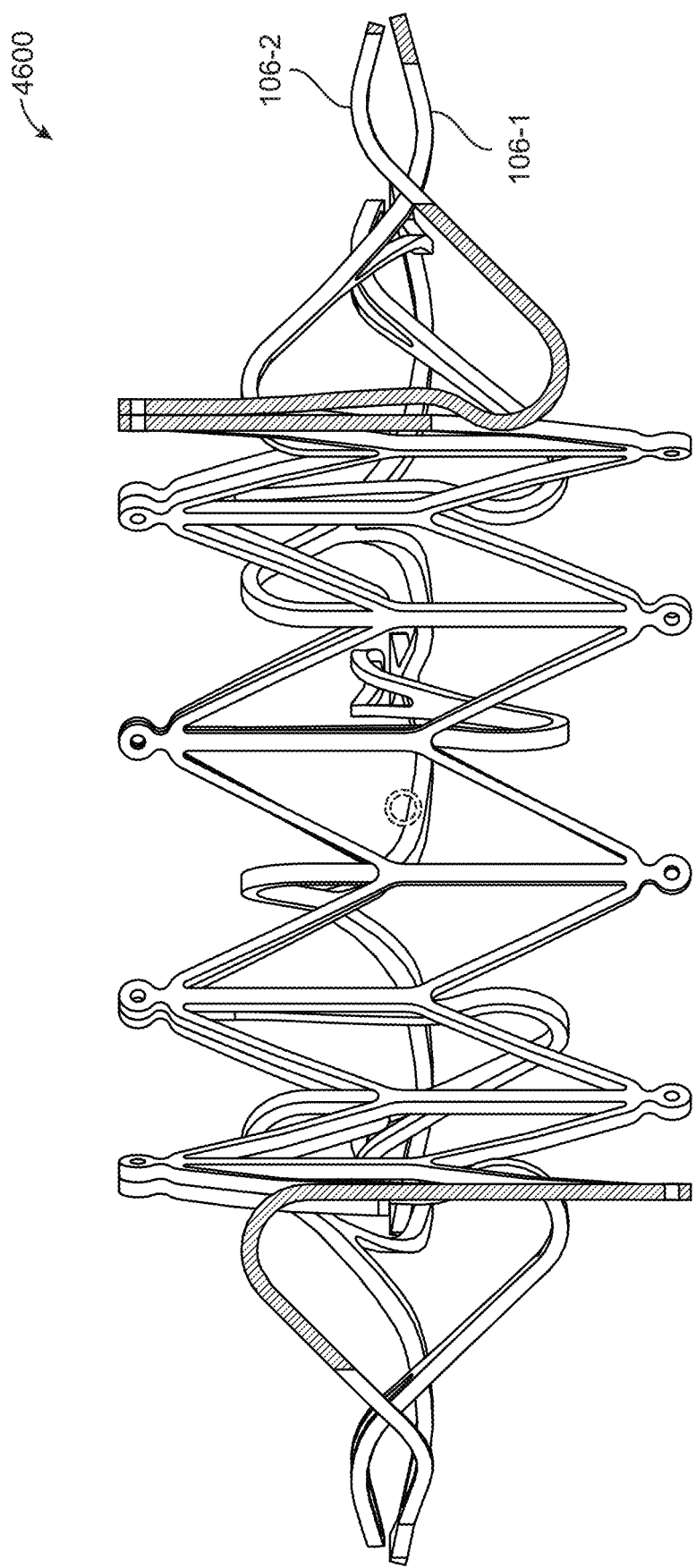
FIG. 47F illustrates a CAD drawing of another side view of a prosthetic tricuspid valve having two support structures, in accordance with an embodiment.

FIGS. 47A-F illustrate CAD drawings of different views of the prosthetic tricuspid valve 4600 having two support structures 102-1 and 102-2, in accordance with an embodiment. FIG. 47A illustrates a CAD drawing of a tilted side view of the support structure 102-1 of the prosthetic tricuspid valve 4600 having two support structures 102-1 and 102-2, in accordance with an embodiment. FIG. 47B illustrates a CAD drawing of a tilted side view of the support structure 102-2 of the prosthetic tricuspid valve 4600 having two support structures 102-1 and 102-2, in accordance with an embodiment. FIG. 47C illustrates a CAD drawing of a side view of the prosthetic tricuspid valve 4600 having two support structures 102-1 and 102-2, in accordance with an embodiment. FIG. 47D illustrates a CAD drawing of a top-down view of the prosthetic tricuspid valve 4600 having two support structures 102-1 and 102-2, in accordance with an embodiment. FIG. 47E illustrates a CAD drawing of a tilted side view of the prosthetic tricuspid valve 4600 having two support structures 102-1 and 102-2, in accordance with an embodiment. FIG. 47F illustrates a CAD drawing of another side view of the prosthetic tricuspid valve 4600 having two support structures 102-1 and 102-2, in accordance with an embodiment.

In the embodiment of the prosthetic tricuspid valve 4600 having two support structures 102-1 and 102-2, the atrial arms 106-1 are formed from the first support structure 102-1 and the ventricular arms 106-2 are formed from the second support structure 102-2. The two support structures 102-1 and 102-2 are configured to fit together to form the prosthetic tricuspid valve 4600. As described throughout this disclosure, at least one of the two support structures 102-1 and 102-2 includes a cylindrical portion that defines an elongate central passageway 104 of the prosthetic tricuspid valve 4600. For example, in the implementation of the prosthetic tricuspid valve 4600 having two support structures 102-1 and 102-2 depicted in FIGS. 46-47, each support structure of the two support structures 102-1 and 102-2 includes a cylindrical portion, 116-1 and 116-2, respectively, that define the elongate central passageway 104 of the prosthetic tricuspid valve 4600. However, in alternative embodiments, only one of the two support structures 102-1 and 102-2 may include a cylindrical portion to define the elongate central passageway 104 of the prosthetic tricuspid valve 4600.

An advantage to forming the prosthetic tricuspid valve 4600 from the two support structures 102-1 and 102-2 includes simpler manufacturing of the prosthetic tricuspid valve 4600. However, a disadvantage to forming the prosthetic tricuspid valve 4600 from the two support structures 102-1 and 102-2 is that assembly of the prosthetic tricuspid valve 4600 includes an additional step of fitting the two support structures 102-1 and 102-2 together to form the prosthetic tricuspid valve 4600. Another advantage to forming the prosthetic tricuspid valve 4600 from the two support structures 102-1 and 102-2 is that there is improved load distribution in the ventricular arms 106-2, which is important because the ventricular arms 106-2 experience greater forces than the atrial arms 106-1 when the prosthetic tricuspid valve 4600 is implanted in vivo.

FIGS. 48-49 illustrate different views of an implementation of a prosthetic tricuspid valve 4800 having two support structures 102-1 and 102-2, in accordance with an embodiment.

Figure 48A:
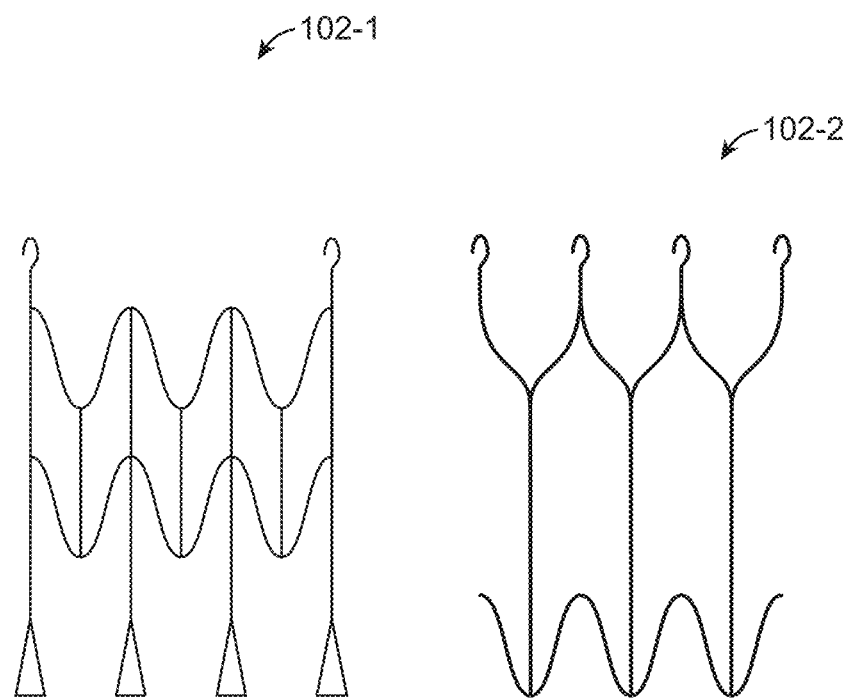
FIG. 48A illustrates a view of flattened support structures of a prosthetic tricuspid valve having two support structures, in accordance with an embodiment.

FIG. 48A illustrates a view of the flattened support structures 102-1 and 102-2 of the prosthetic tricuspid valve 4800 having two support structures 102-1 and 102-2, in accordance with an embodiment.

Figure 48B:
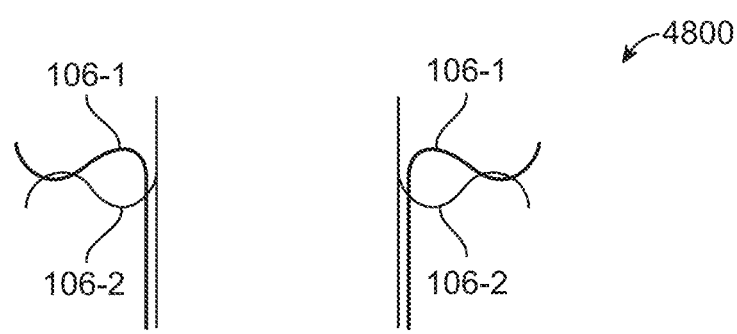
FIG. 48B illustrates a side view of a prosthetic tricuspid valve having two support structures and configured for implantation in a native tricuspid valve, in accordance with an embodiment.

FIG. 48B illustrates a side view of the prosthetic tricuspid valve 4800 having two support structures 102-1 and 102-2 and configured for implantation in a native tricuspid valve, in accordance with an embodiment.

Figure 49A:
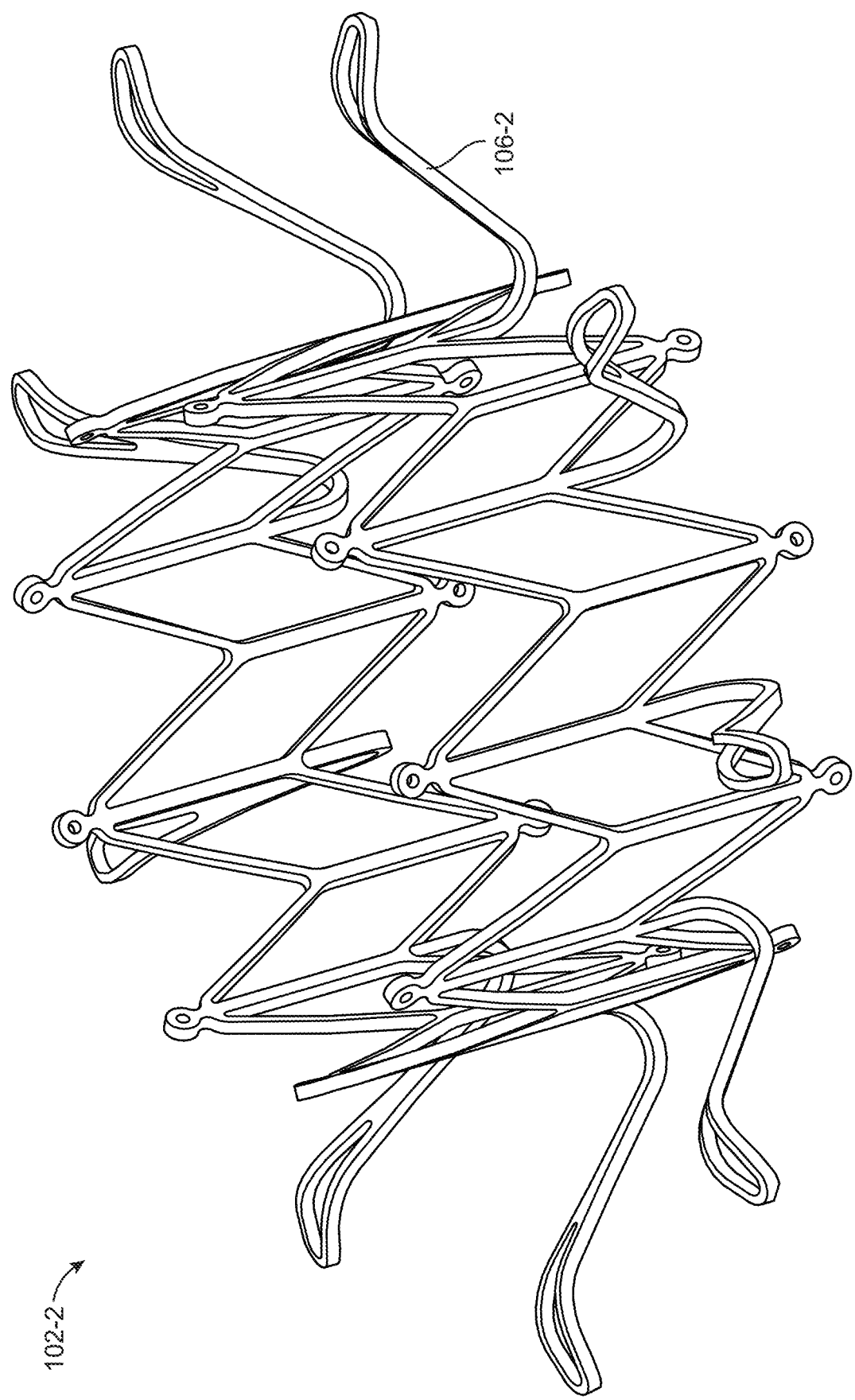
FIG. 49A illustrates a CAD drawing of a tilted side view of a support structure of a prosthetic tricuspid valve having two support structures, in accordance with an embodiment.
Figure 49B:
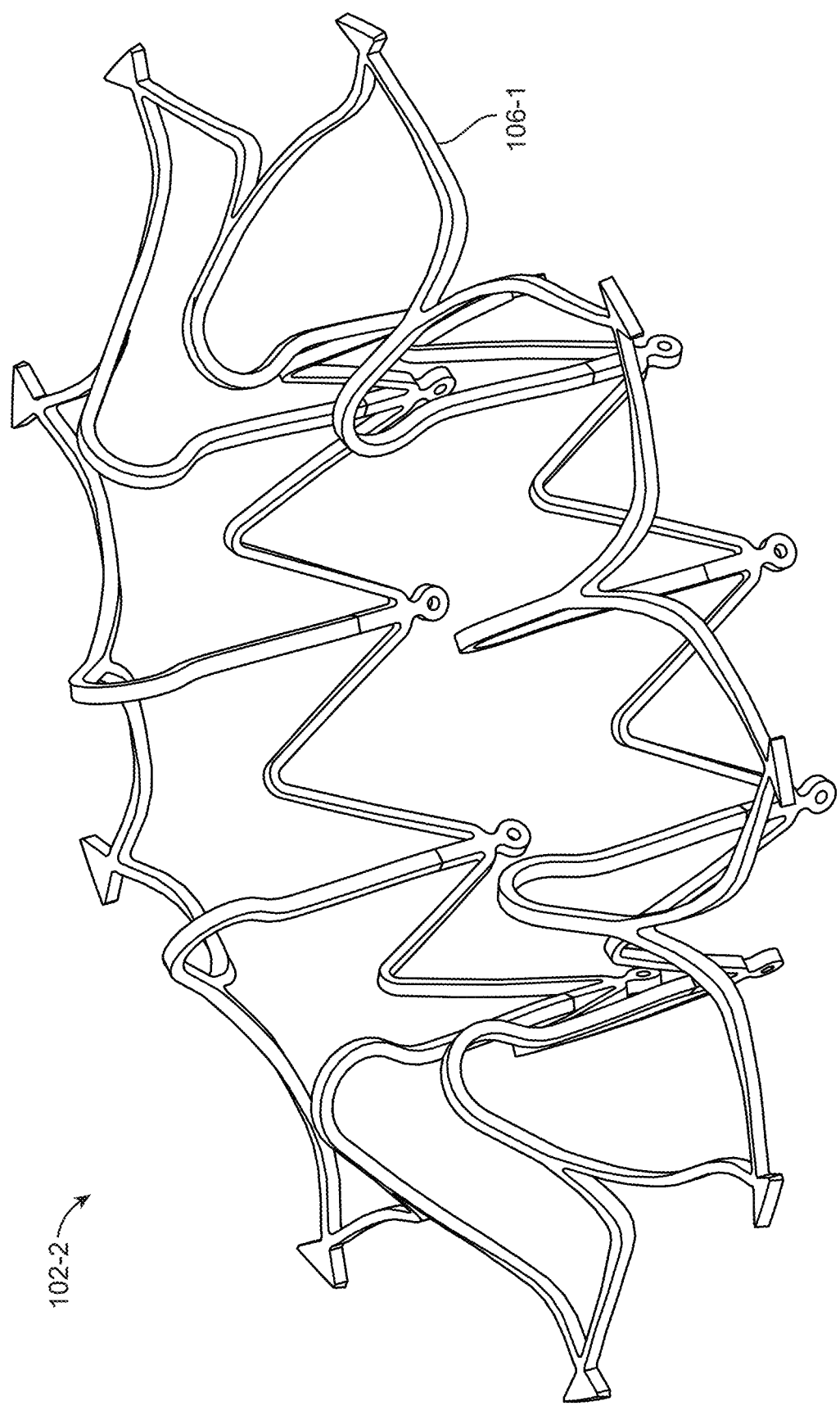
FIG. 49B illustrates a CAD drawing of a tilted side view of a support structure of a prosthetic tricuspid valve having two support structures, in accordance with an embodiment.
Figure 49D:
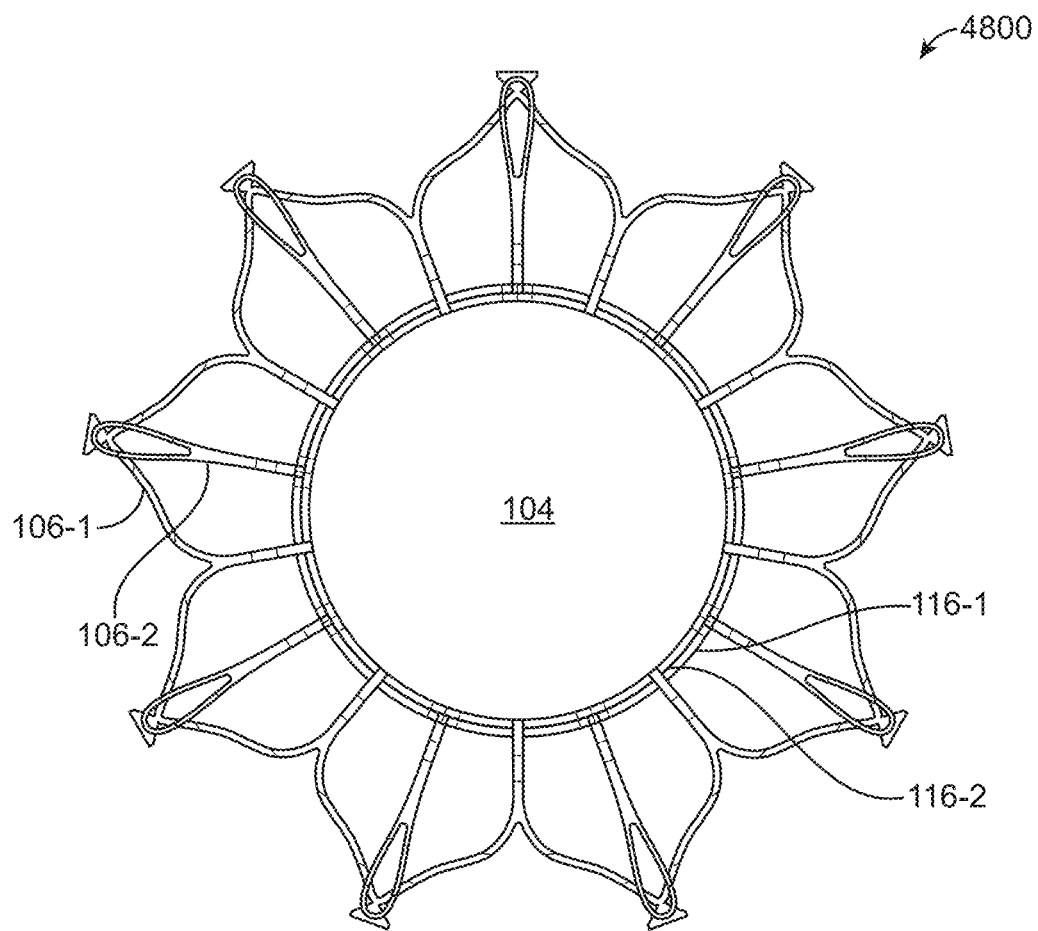
FIG. 49D illustrates a CAD drawing of a top-down view of a prosthetic tricuspid valve having two support structures, in accordance with an embodiment.
Figure 49F:
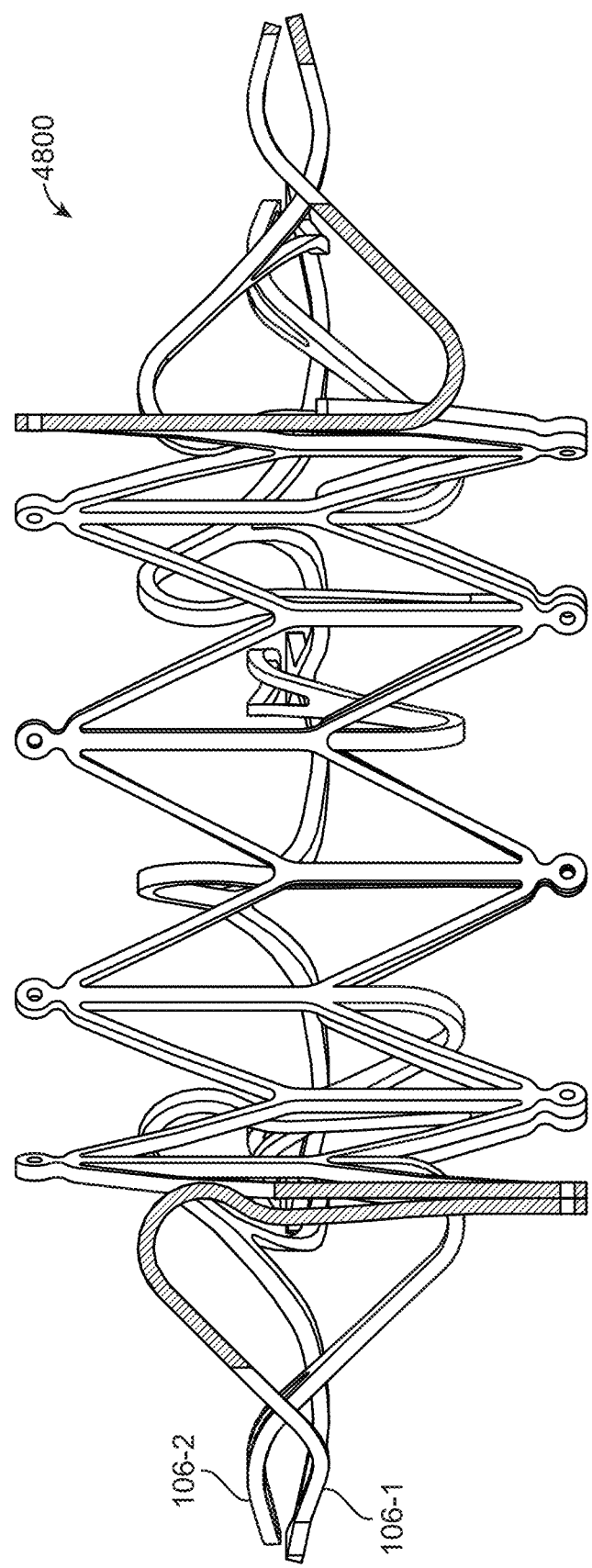
FIG. 49F illustrates a CAD drawing of another side view of a prosthetic tricuspid valve having two support structures, in accordance with an embodiment.

FIGS. 49A-F illustrate CAD drawings of different views of the prosthetic tricuspid valve 4800 having two support structures 102-1 and 102-2, in accordance with an embodiment. FIG. 49A illustrates a CAD drawing of a tilted side view of the support structure 102-1 of the prosthetic tricuspid valve 4800 having two support structures 102-1 and 102-2, in accordance with an embodiment. FIG. 49B illustrates a CAD drawing of a tilted side view of the support structure 102-2 of the prosthetic tricuspid valve 4800 having two support structures 102-1 and 102-2, in accordance with an embodiment. FIG. 49C illustrates a CAD drawing of a side view of the prosthetic tricuspid valve 4800 having two support structures 102-1 and 102-2, in accordance with an embodiment. FIG. 49D illustrates a CAD drawing of a top-down view of the prosthetic tricuspid valve 4800 having two support structures 102-1 and 102-2, in accordance with an embodiment. FIG. 49E illustrates a CAD drawing of a tilted side view of the prosthetic tricuspid valve 4800 having two support structures 102-1 and 102-2, in accordance with an embodiment. FIG. 49F illustrates a CAD drawing of another side view of the prosthetic tricuspid valve 4800 having two support structures 102-1 and 102-2, in accordance with an embodiment.

In the embodiment of the prosthetic tricuspid valve 4800 having two support structures 102-1 and 102-2, the ventricular arms 106-2 are formed from the first support structure 102-1 and the atrial arms 106-1 are formed from the second support structure 102-2. The two support structures 102-1 and 102-2 are configured to fit together to form the prosthetic tricuspid valve 4800. As described throughout this disclosure, at least one of the two support structures 102-1 and 102-2 includes a cylindrical portion that defines an elongate central passageway 104 of the prosthetic tricuspid valve 4800. For example, in the implementation of the prosthetic tricuspid valve 4800 having two support structures 102-1 and 102-2 depicted in FIGS. 48-49, each support structure of the two support structures 102-1 and 102-2 includes a cylindrical portion, 116-1 and 116-2, respectively, that define the elongate central passageway 104 of the prosthetic tricuspid valve 4800. However, in alternative embodiments, only one of the two support structures 102-1 and 102-2 may include a cylindrical portion to define the elongate central passageway 104 of the prosthetic tricuspid valve 4800.

An advantage to forming the prosthetic tricuspid valve 4800 from the two support structures 102-1 and 102-2 includes simpler manufacturing of the prosthetic tricuspid valve 4800, as with the prosthetic tricuspid valve 4600. Another advantage to forming the prosthetic tricuspid valve 4800 from the two support structures 102-1 and 102-2 is that the leaflet elements can be formed from the first support structure 102-1 which forms the ventricular arms 106-2 rather than the atrial arms 106-1, thereby enabling an atrial sealing skirt as discussed above to be formed separately from the leaflet elements, by the second support structure 102-2 forming the atrial arms 106-1. By forming the atrial sealing skirt from the second support structure 102-2, separate from the leaflet elements formed from the first support structure 102-1, assembly of the individual support structures 102-1 and 102-2 is simpler, and the atrial sealing skirt can be laminated. However, assembly of the prosthetic tricuspid valve 4800 still includes an additional step of fitting the two support structures 102-1 and 102-2 together to form the prosthetic tricuspid valve 4800. Another advantage to forming the prosthetic tricuspid valve 4800 from the two support structures 102-1 and 102-2 is that there is improved load distribution, but mainly in the atrial arms 106-1, which is less important because the atrial arms 106-1 experience less force than the ventricular arms 106-2 when the prosthetic tricuspid valve 4800 is implanted in vivo.

FIGS. 50-51 illustrate different views of an implementation of a prosthetic tricuspid valve 5000 having two support structures 102-1 and 102-2, in accordance with an embodiment.

Figure 50A:
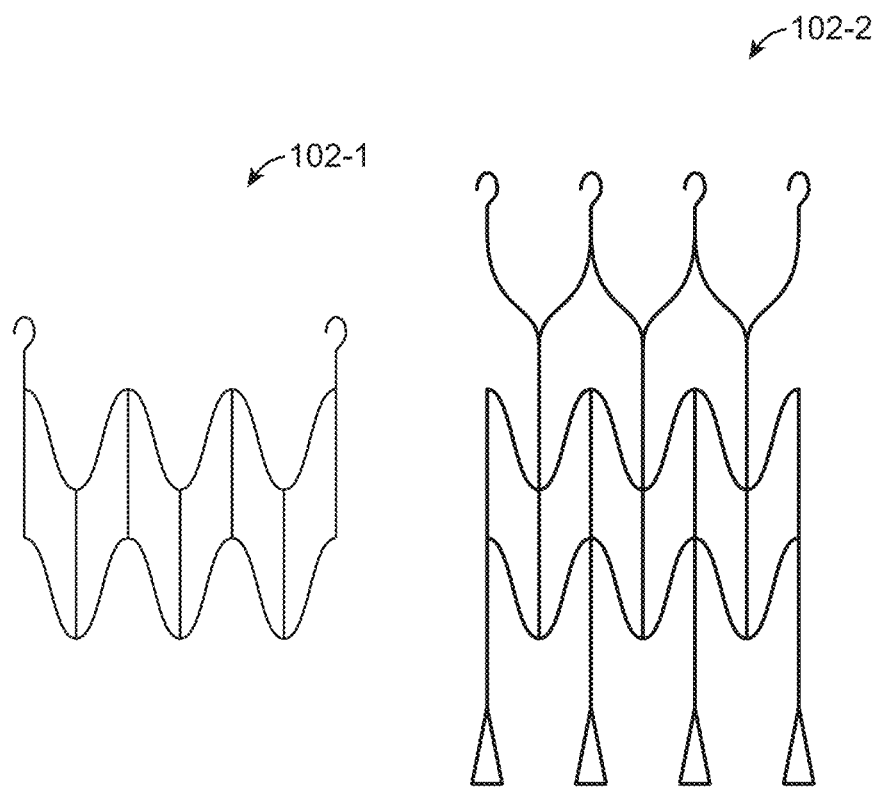
FIG. 50A illustrates a view of flattened support structures of a prosthetic tricuspid valve having two support structures, in accordance with an embodiment.

FIG. 50A illustrates a view of the flattened support structures 102-1 and 102-2 of the prosthetic tricuspid valve 5000 having two support structures 102-1 and 102-2, in accordance with an embodiment.

Figure 50B:
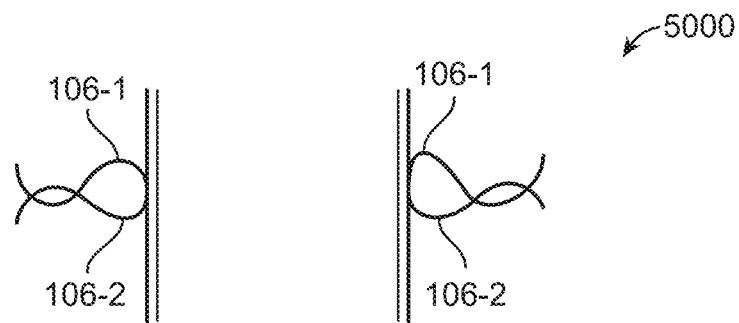
FIG. 50B illustrates a side view of a prosthetic tricuspid valve having two support structures and configured for implantation in a native tricuspid valve, in accordance with an embodiment.

FIG. 50B illustrates a side view of the prosthetic tricuspid valve 5000 having two support structures 102-1 and 102-2 and configured for implantation in a native tricuspid valve, in accordance with an embodiment.

Figure 51A:
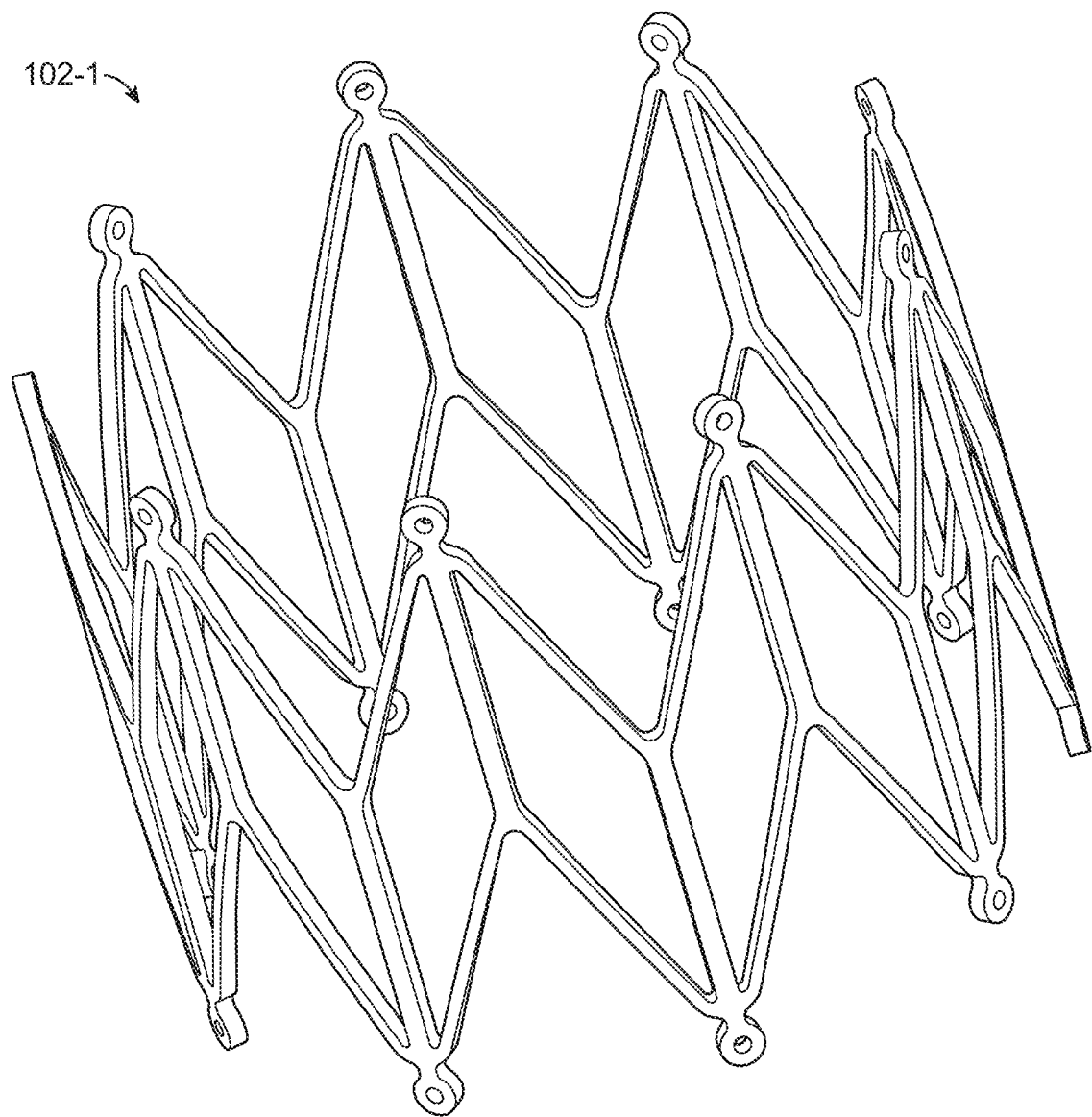
FIG. 51A illustrates a CAD drawing of a tilted side view of a support structure of a prosthetic tricuspid valve having two support structures, in accordance with an embodiment.
Figure 51B:
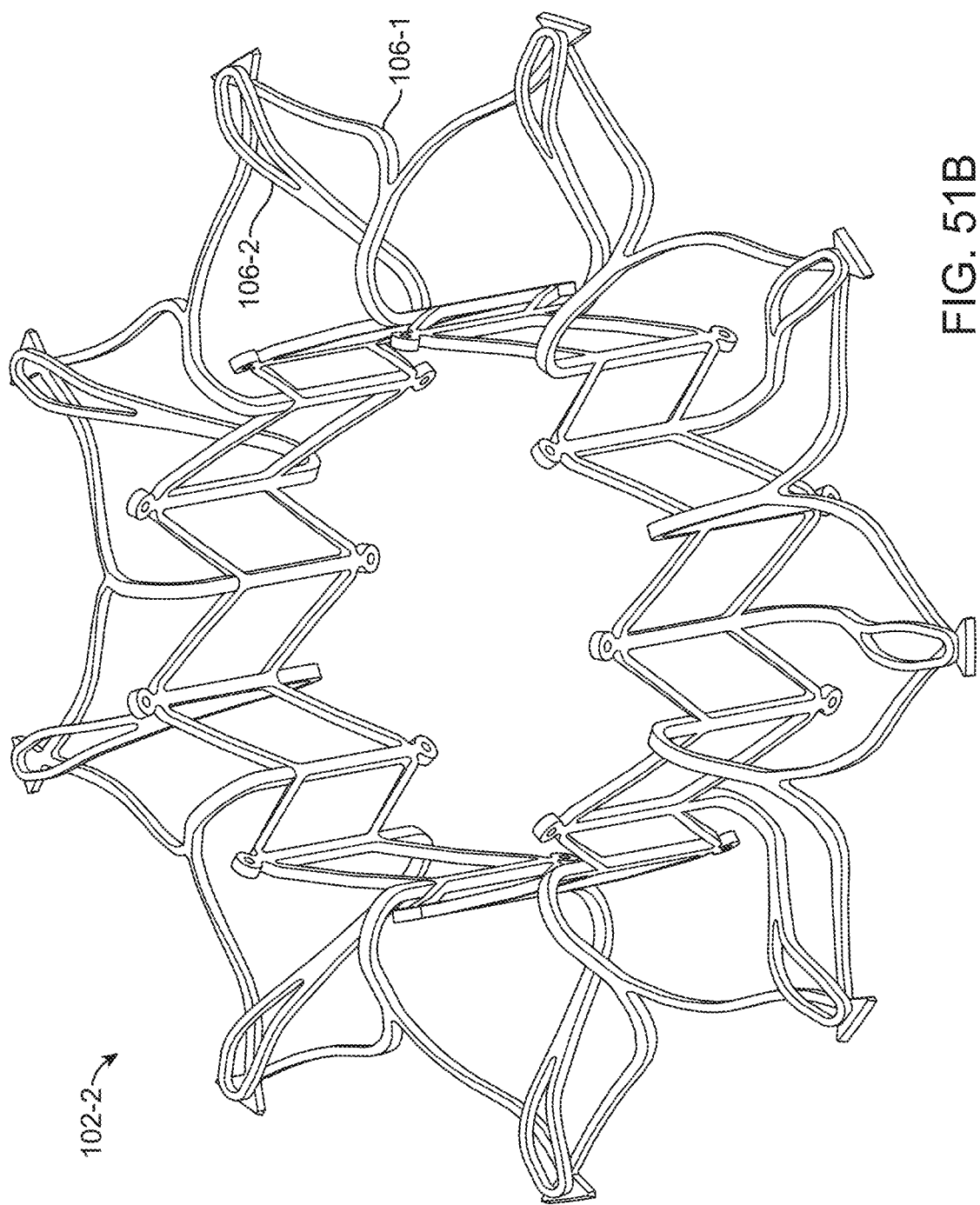
FIG. 51B illustrates a CAD drawing of a tilted side view of a support structure of a prosthetic tricuspid valve having two support structures, in accordance with an embodiment.
Figure 51C:
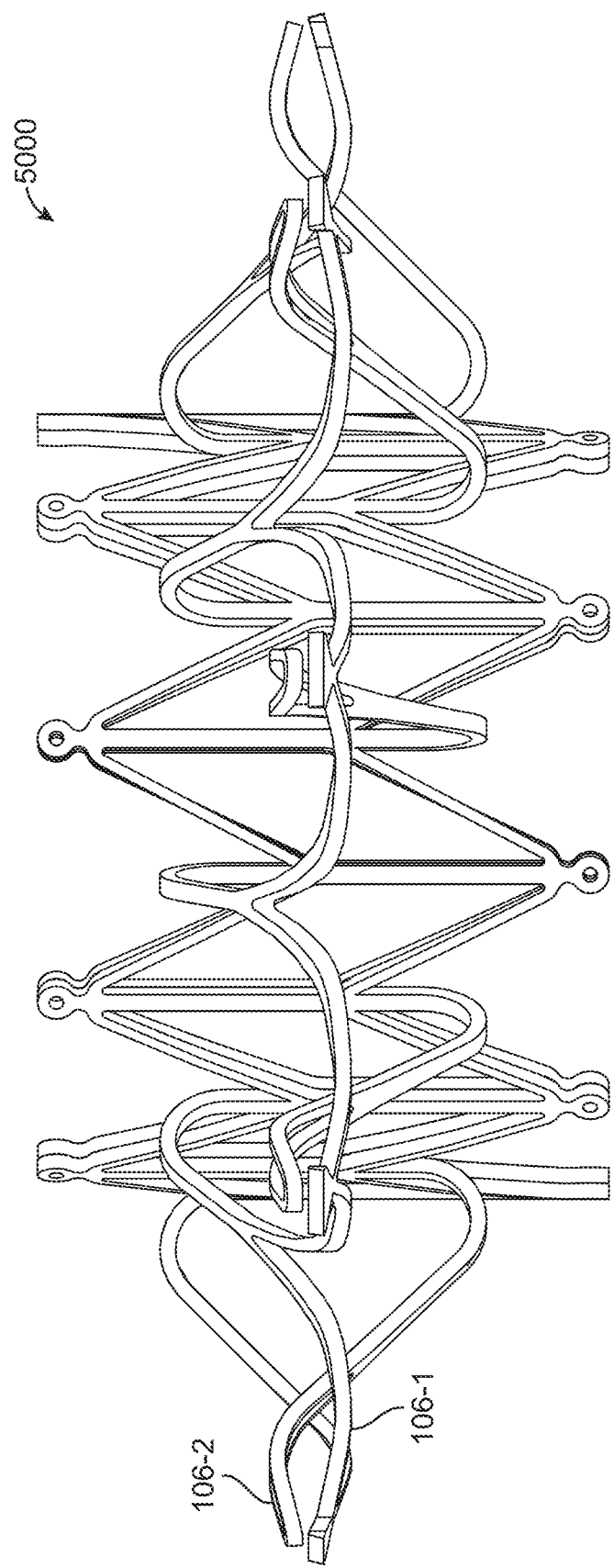
FIG. 51C illustrates a CAD drawing of a side view of a prosthetic tricuspid valve having two support structures, in accordance with an embodiment.
Figure 51D:
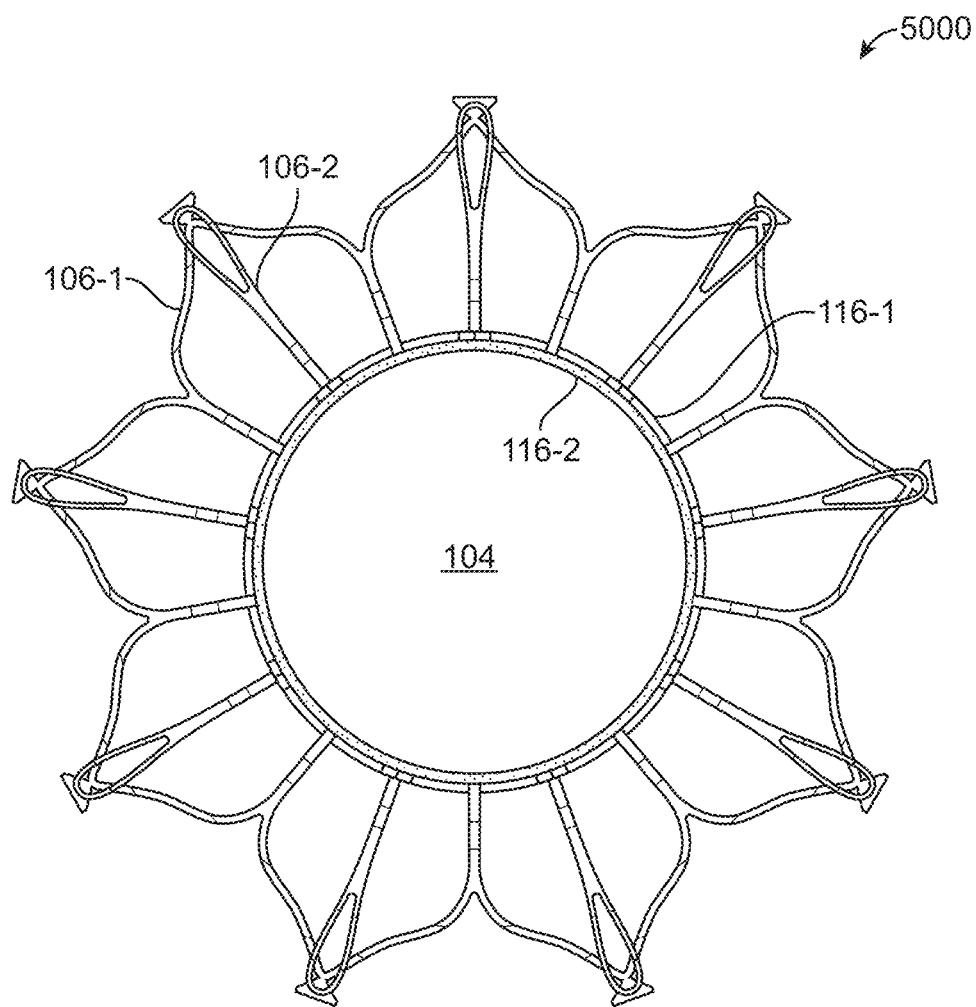
FIG. 51D illustrates a CAD drawing of a top-down view of a prosthetic tricuspid valve having two support structures, in accordance with an embodiment.
Figure 51E:
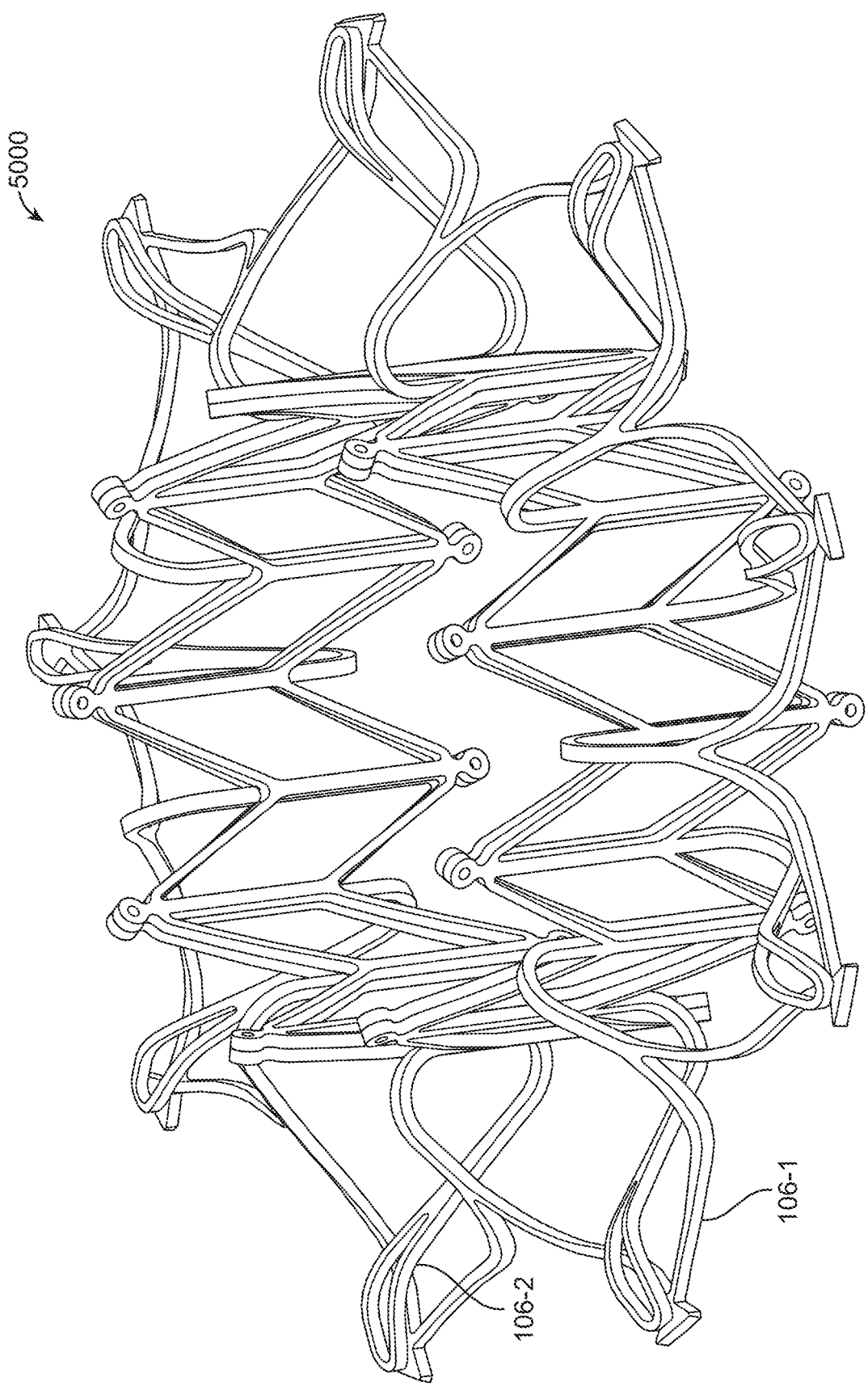
FIG. 51E illustrates a CAD drawing of a tilted side view of a prosthetic tricuspid valve having two support structures, in accordance with an embodiment.
Figure 51F:
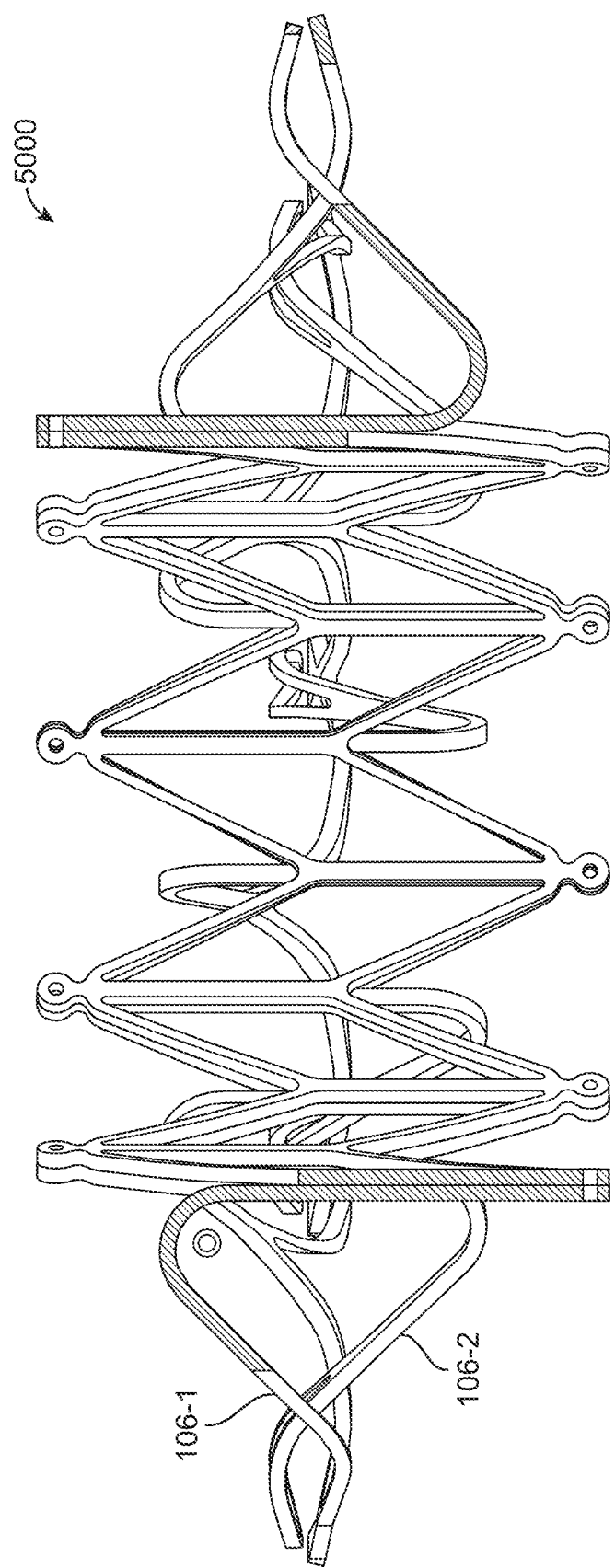
FIG. 51F illustrates a CAD drawing of another side view of a prosthetic tricuspid valve having two support structures, in accordance with an embodiment.

FIGS. 51A-F illustrate CAD drawings of different views of the prosthetic tricuspid valve 5000 having two support structures 102-1 and 102-2, in accordance with an embodiment. FIG. 51A illustrates a CAD drawing of a tilted side view of the support structure 102-1 of the prosthetic tricuspid valve 5000 having two support structures 102-1 and 102-2, in accordance with an embodiment. FIG. 51B illustrates a CAD drawing of a tilted side view of the support structure 102-2 of the prosthetic tricuspid valve 5000 having two support structures 102-1 and 102-2, in accordance with an embodiment. FIG. 51C illustrates a CAD drawing of a side view of the prosthetic tricuspid valve 5000 having two support structures 102-1 and 102-2, in accordance with an embodiment. FIG. 51D illustrates a CAD drawing of a top-down view of the prosthetic tricuspid valve 5000 having two support structures 102-1 and 102-2, in accordance with an embodiment. FIG. 51E illustrates a CAD drawing of a tilted side view of the prosthetic tricuspid valve 5000 having two support structures 102-1 and 102-2, in accordance with an embodiment. FIG. 51F illustrates a CAD drawing of another side view of the prosthetic tricuspid valve 5000 having two support structures 102-1 and 102-2, in accordance with an embodiment.

In the embodiment of the prosthetic tricuspid valve 5000 having two support structures 102-1 and 102-2, the first support structure 102-1 does not form the atrial arms 106-1 or the ventricular arms 106-2. The second support structure 102-2 forms both the atrial arms 106-1 and the atrial arms 106-1. In some embodiments, the second support structure 102-2 forming both the atrial arms 106-1 and the atrial arms 106-1 can be the prosthetic tricuspid valve 4400 having the one support structure 102. The two support structures 102-1 and 102-2 are configured to fit together to form the prosthetic tricuspid valve 5000. As described throughout this disclosure, at least one of the two support structures 102-1 and 102-2 includes a cylindrical portion that defines an elongate central passageway 104 of the prosthetic tricuspid valve 5000. For example, in the implementation of the prosthetic tricuspid valve 5000 having two support structures 102-1 and 102-2 depicted in FIGS. 50-51, each support structure of the two support structures 102-1 and 102-2 includes a cylindrical portion, 116-1 and 116-2, respectively, that define the elongate central passageway 104 of the prosthetic tricuspid valve 5000. However, in alternative embodiments, only one of the two support structures 102-1 and 102-2 may include a cylindrical portion to define the elongate central passageway 104 of the prosthetic tricuspid valve 5000.

Like the prosthetic tricuspid valves 4600 and 4800, an advantage to forming the prosthetic tricuspid valve 5000 from the two support structures 102-1 and 102-2 includes simpler manufacturing of the prosthetic tricuspid valve 5000. Additionally, like the prosthetic tricuspid valve 4800, another advantage to forming the prosthetic tricuspid valve 5000 from the two support structures 102-1 and 102-2 is that the leaflet elements can be formed from the first support structure 102-1 which does not form the atrial arms 106-1, thereby enabling an atrial sealing skirt as discussed above to be formed separately from the leaflet elements, by the second support structure 102-2 forming the atrial arms 106-1. By forming the atrial sealing skirt from the second support structure 102-2, separate from the leaflet elements formed from the first support structure 102-1, assembly of the individual support structures 102-1 and 102-2 is simpler, and the atrial sealing skirt can be laminated. However, assembly of the prosthetic tricuspid valve 5000 still includes an additional step of fitting the two support structures 102-1 and 102-2 together to form the prosthetic tricuspid valve 5000. Another advantage to forming the prosthetic tricuspid valve 5000 from the two support structures 102-1 and 102-2 is that there is improved load distribution because the first support structure 5000-1 can provide additional reinforcement to the atrial arms 106-1 and to the ventricular arms 106-2 formed from the second support structure 5000-2. However, the arms 106 are not still not extended, and the fulcrum points still occur in the same general location as load nodes, effectively yielding less ability for load distribution and thus greater breakability of the prosthetic tricuspid valve 5000.

FIGS. 52-53 illustrate different views of an implementation of a prosthetic tricuspid valve 5200 having three support structures 102-1, 102-2, and 102-3, in accordance with an embodiment.

FIG. 52A illustrates a view of the flattened support structures 102-1, 102-2, and 102-3 of the prosthetic tricuspid valve 5200 having three support structures 102-1, 102-2, and 102-3, in accordance with an embodiment.

FIG. 52B illustrates a side view of the prosthetic tricuspid valve 5200 having three support structures 102-1, 102-2, and 102-3 and configured for implantation in a native tricuspid valve, in accordance with an embodiment.

Figure 53A:
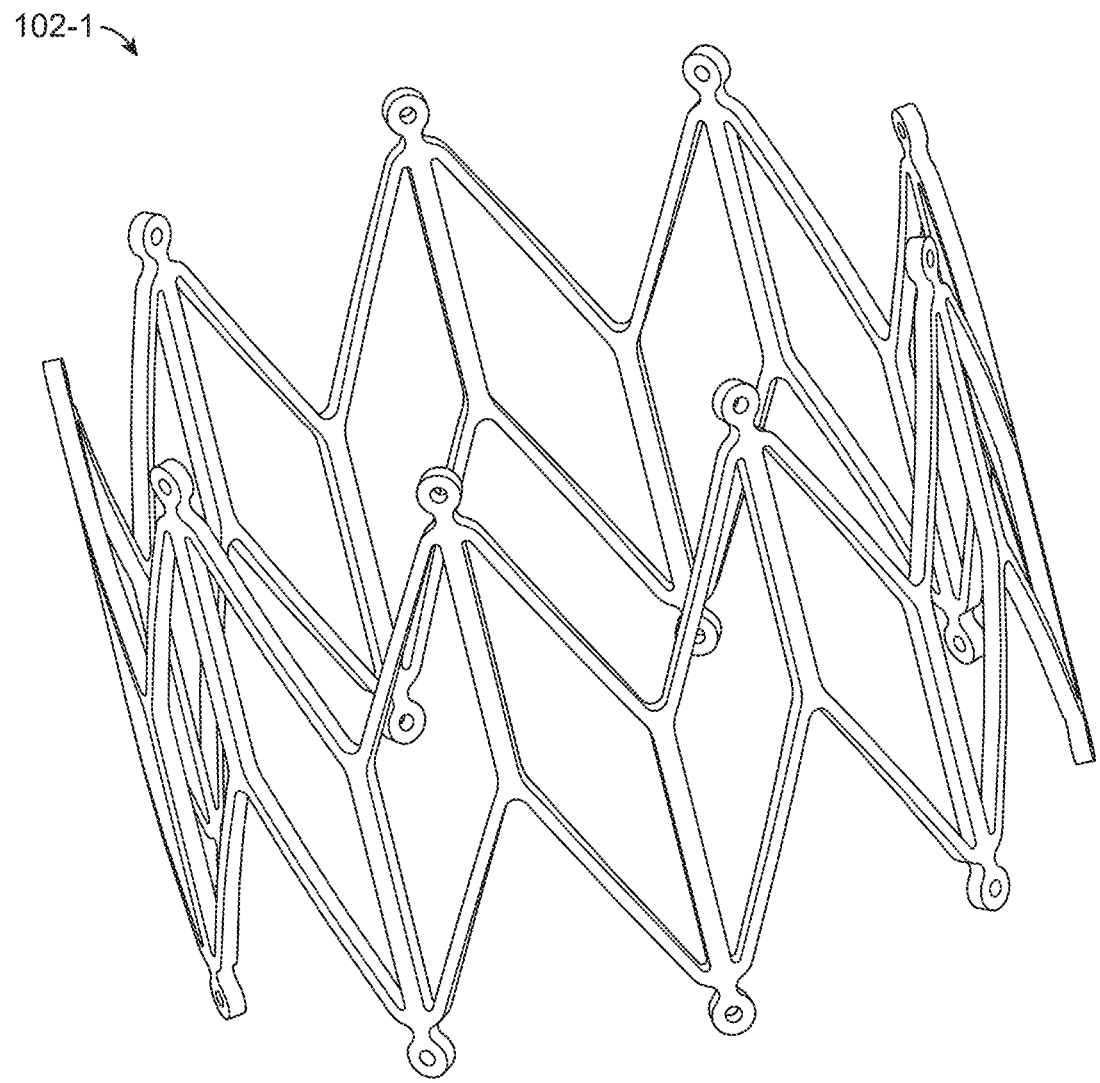
FIG. 53A illustrates a CAD drawing of a tilted side view of a support structure of a prosthetic tricuspid valve having three support structures, in accordance with an embodiment.
Figure 53B:
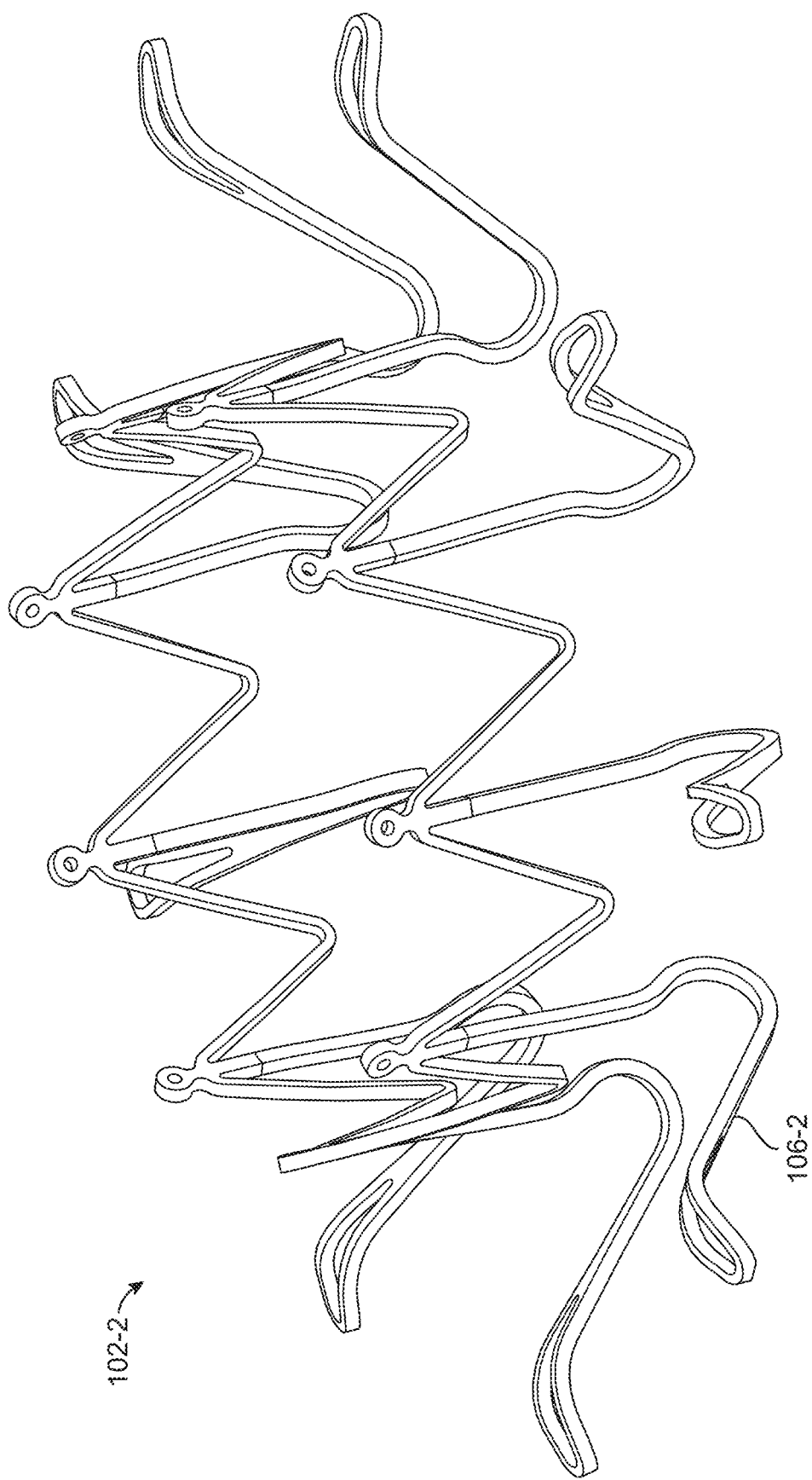
FIG. 53B illustrates a CAD drawing of a tilted side view of a support structure of a prosthetic tricuspid valve having three support structures, in accordance with an embodiment.
Figure 53C:
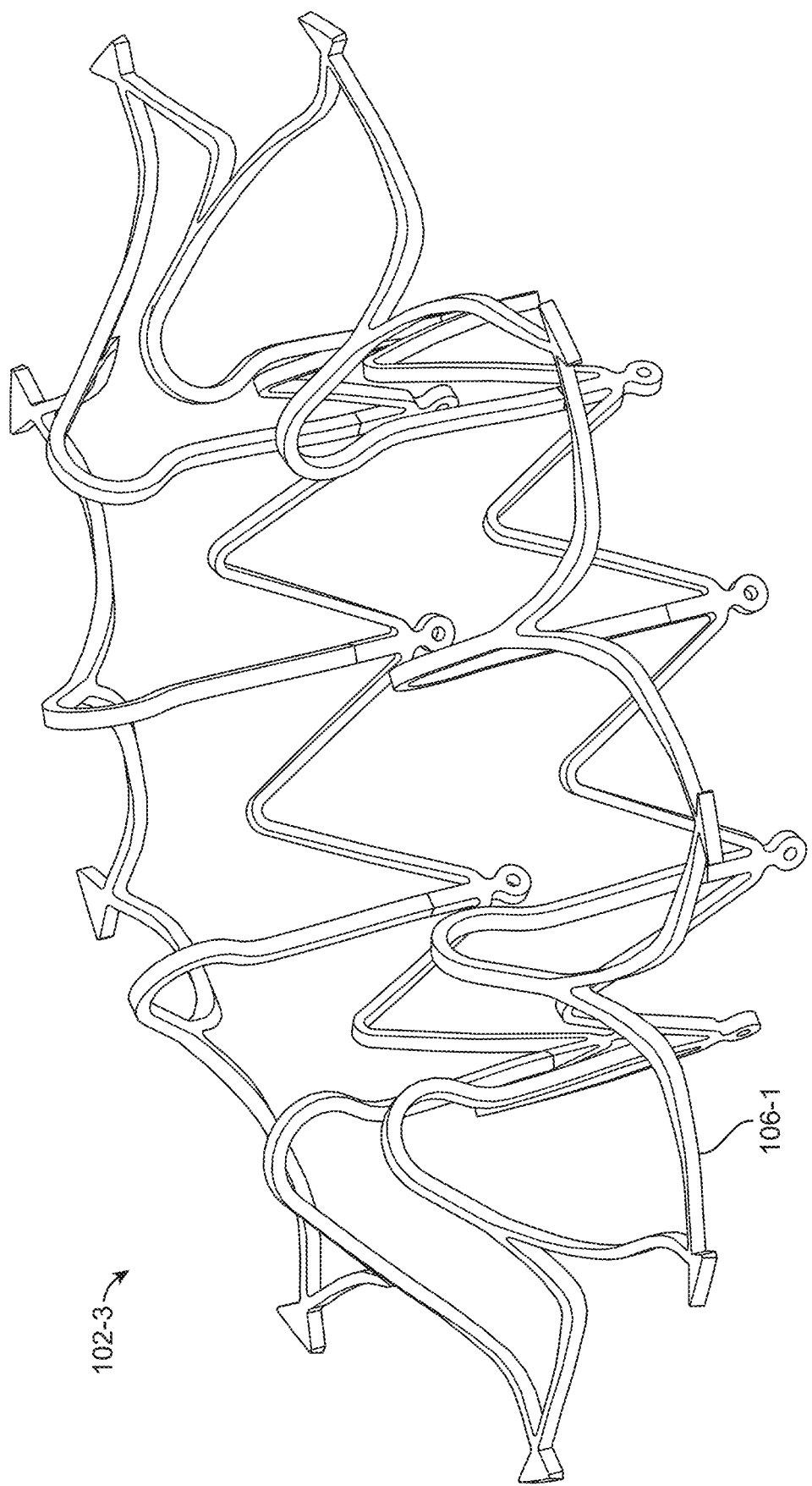
FIG. 53C illustrates a CAD drawing of a tilted side view of a support structure of a prosthetic tricuspid valve having three support structures, in accordance with an embodiment.
Figure 53E:
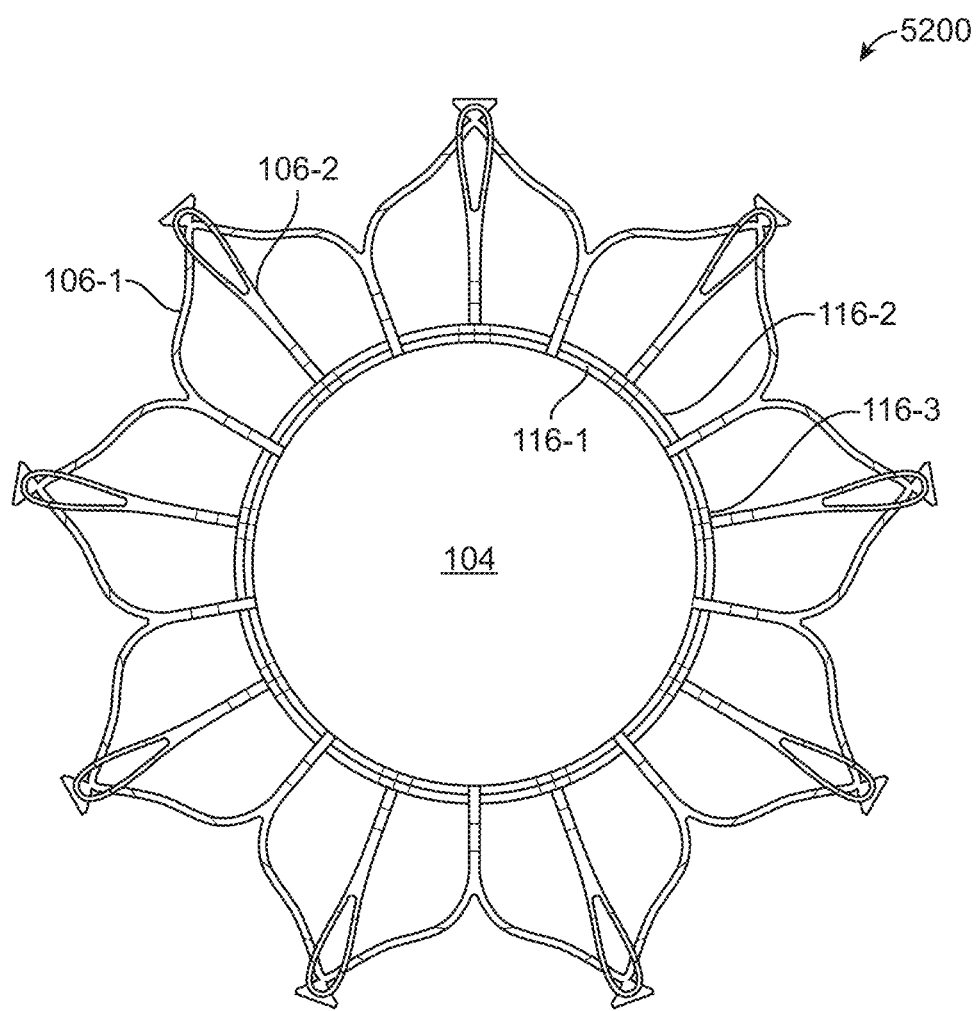
FIG. 53E illustrates a CAD drawing of a top-down view of a prosthetic tricuspid valve having three support structures, in accordance with an embodiment.
Figure 53F:
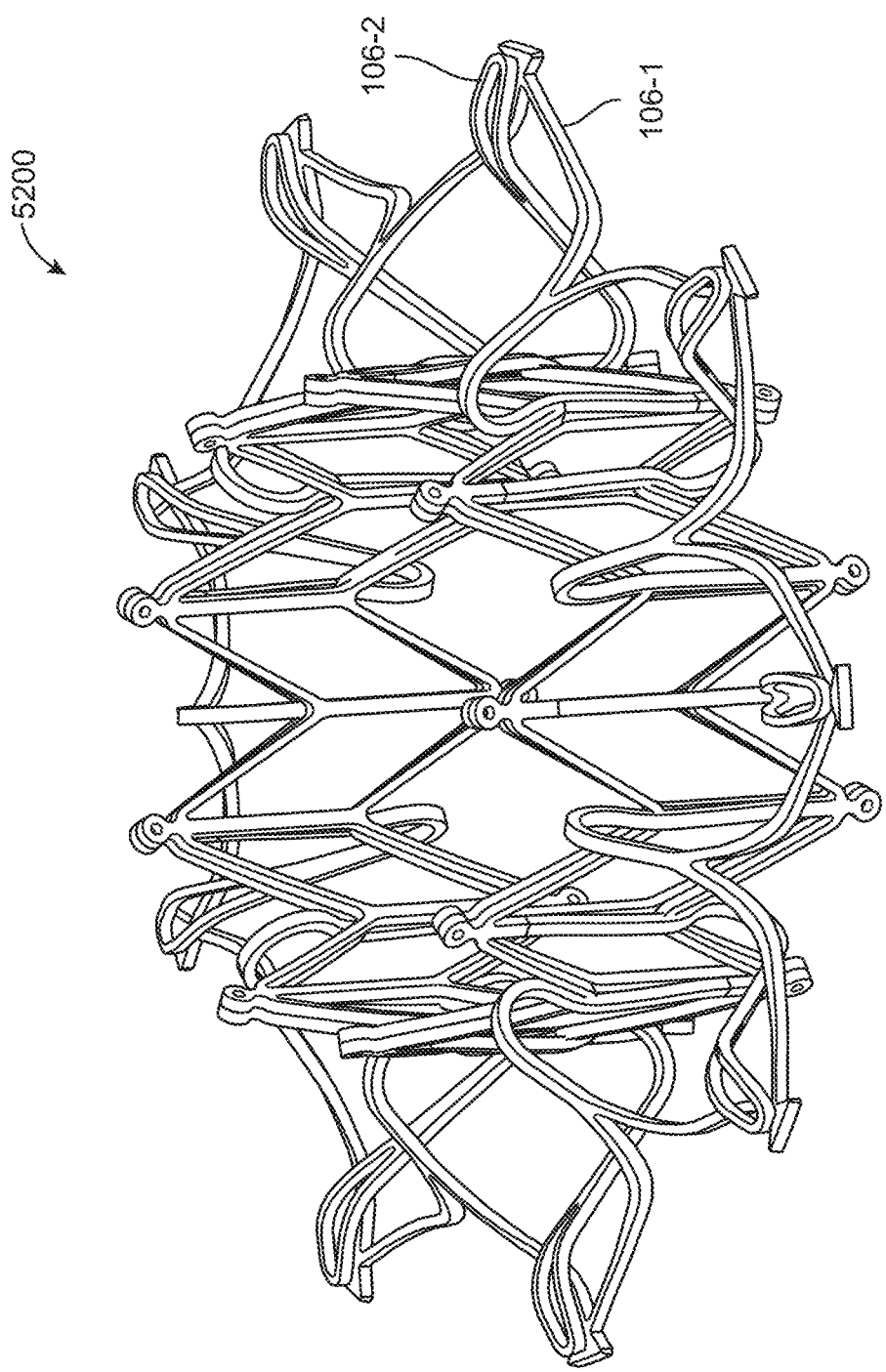
FIG. 53F illustrates a CAD drawing of a tilted side view of a prosthetic tricuspid valve having three support structures, in accordance with an embodiment.
Figure 53G:
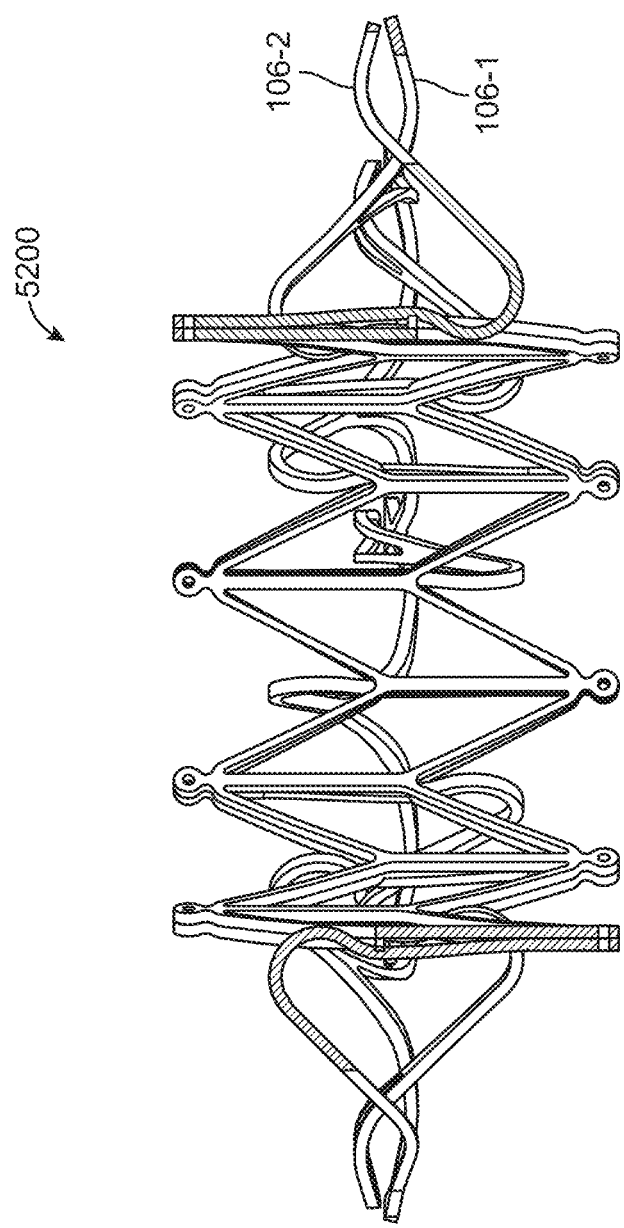
FIG. 53G illustrates a CAD drawing of another side view of a prosthetic tricuspid valve having three support structures, in accordance with an embodiment.

FIGS. 53A-G illustrate CAD drawings of different views of the prosthetic tricuspid valve 5200 having three support structures 102-1, 102-2, and 102-3, in accordance with an embodiment. FIG. 53A illustrates a CAD drawing of a tilted side view of the support structure 102-1 of the prosthetic tricuspid valve 5200 having three support structures 102-1, 102-2, and 102-3, in accordance with an embodiment. FIG. 53B illustrates a CAD drawing of a tilted side view of the support structure 102-2 of the prosthetic tricuspid valve 5200 having three support structures 102-1, 102-2, and 102-3, in accordance with an embodiment. FIG. 53C illustrates a CAD drawing of a tilted side view of the support structure 102-3 of the prosthetic tricuspid valve 5200 having three support structures 102-1, 102-2, and 102-3, in accordance with an embodiment. FIG. 53D illustrates a CAD drawing of a side view of the prosthetic tricuspid valve 5200 having three support structures 102-1, 102-2, and 102-3, in accordance with an embodiment. FIG. 53E illustrates a CAD drawing of a top-down view of the prosthetic tricuspid valve 5200 having three support structures 102-1, 102-2, and 102-3, in accordance with an embodiment. FIG. 53F illustrates a CAD drawing of a tilted side view of the prosthetic tricuspid valve 5200 having three support structures 102-1, 102-2, and 102-3, in accordance with an embodiment. FIG. 53G illustrates a CAD drawing of another side view of the prosthetic tricuspid valve 5200 having three support structures 102-1, 102-2, and 102-3, in accordance with an embodiment.

In the embodiment of the prosthetic tricuspid valve 5200 having three support structures 102-1, 102-2, and 102-3, the first support structure 102-1 does not form the atrial arms 106-1 or the ventricular arms 106-2. The second support structure 102-2 forms the ventricular arms 106-2. The third support structure 102-3 forms the atrial arms 106-1. The three support structures 102-1, 102-2, and 102-3 are configured to fit together to form the prosthetic tricuspid valve 5200. As described throughout this disclosure, at least one of the three support structures 102-1, 102-2, and 102-3 includes a cylindrical portion that defines an elongate central passageway 104 of the prosthetic tricuspid valve 5200. For example, in the implementation of the prosthetic tricuspid valve 5200 having three support structures 102-1, 102-2, and 102-3 depicted in FIGS. 52-53, each support structure of the three support structures 102-1, 102-2, and 102-3 includes a cylindrical portion, 116-1, 116-2, and 116-3, respectively, that define the elongate central passageway 104 of the prosthetic tricuspid valve 5200. However, in alternative embodiments, only one or two of the three support structures 102-1, 102-2, and 102-3 may include a cylindrical portion to define the elongate central passageway 104 of the prosthetic tricuspid valve 5200.

Like the prosthetic tricuspid valves 4600, 4800, and 5000, an advantage to forming the prosthetic tricuspid valve 5200 from the three support structures 102-1, 102-2, and 102-3 includes simpler manufacturing of the prosthetic tricuspid valve 5200. Additionally, like the prosthetic tricuspid valves 4800 and 5000, another advantage to forming the prosthetic tricuspid valve 5200 from the three support structures 102-1, 102-2, and 102-3 is that the leaflet elements can be formed from the first support structure 102-1 which does not form the atrial arms 106-1, thereby enabling an atrial sealing skirt as discussed above to be formed separately from the leaflet elements, by the third support structure 102-3 forming the atrial arms 106-1. By forming the atrial sealing skirt from the third support structure 102-3, separate from the leaflet elements formed from the first support structure 102-1, assembly of the individual support structures 102-1 and 102-3 is simpler, and the atrial sealing skirt can be laminated. However, assembly of the prosthetic tricuspid valve 5200 still includes an additional step of fitting the three support structures 102-1, 102-2, and 102-3 together to form the prosthetic tricuspid valve 5200. Another advantage to forming the prosthetic tricuspid valve 5200 from the three support structures 102-1, 102-2, and 102-3 is that there is improved load distribution because the first support structure 102-1 can provide additional reinforcement to the atrial arms 106-1 formed from the third support structure 102-3, and the first support structure 102-1 and the third support structure 102-3 can both provide additional reinforcement to the ventricular arms 106-2 formed from the second support structure 102-2. Furthermore, unlike the prosthetic tricuspid valves 4600, 4800, and 5000 described above, the arms 106 extend such that fulcrum points occur in multiple different locations apart from nodes receiving load forces, effectively yielding greater load distribution and thus less breakability of the prosthetic tricuspid valve 5200. However, disadvantageously, forming the prosthetic tricuspid valve 5200 from the three support structures 102-1, 102-2, and 102-3 causes the overall bulkiness and diameter of the prosthetic tricuspid valve 5200 to increase.

FIG. 54A illustrates a side view of overbite between an atrial arm 106-1 and a ventricular arm 106-2 of the prosthetic tricuspid valve 100 at rest, in accordance with an embodiment. In other words, FIG. 54A illustrates a side view of overbite between the atrial arm 106-1 and the ventricular arm 106-2 of the prosthetic tricuspid valve 100 when the prosthetic tricuspid valve 100 is not implanted in a native tricuspid valve.

FIG. 54B illustrates a side view of the atrial arm 106-1 and the ventricular arm 106-2 of the prosthetic tricuspid valve 100 when the prosthetic tricuspid valve 100 is implanted in a native tricuspid valve, in accordance with an embodiment. In other words, FIG. 54B illustrates a side view of the atrial arm 106-1 and the ventricular arm 106-2 of the prosthetic tricuspid valve 100 when the arms 106 are clamping onto a native leaflet of the native tricuspid valve in which the prosthetic tricuspid valve 100 is implanted. The amount of overbite between the atrial arm 106-1 and the ventricular arm 106-2 of the prosthetic tricuspid valve 100 when the prosthetic tricuspid valve 100 is at rest, as shown in FIG. 54A, determines the magnitude of the clamping force of the arms 106 on the native leaflet of the native tricuspid valve.

Figure 55:
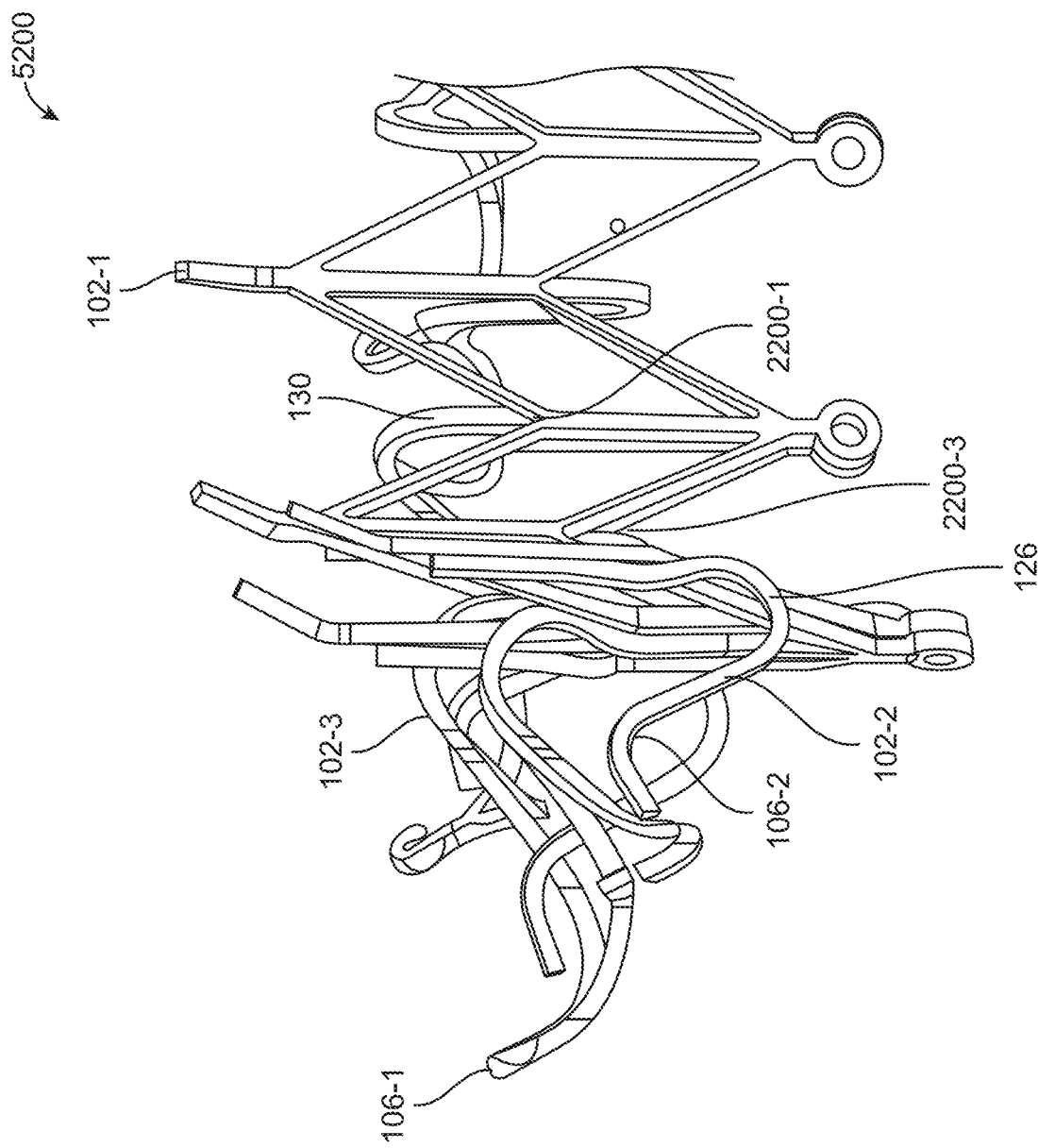
FIG. 55 illustrates a CAD drawing of a cut-away side view of a prosthetic tricuspid valve having three support structures, in accordance with an embodiment.

FIG. 55 illustrates a CAD drawing of a cut-away side view of the prosthetic tricuspid valve 5200 having three support structures 102-1, 102-2, and 102-3, in accordance with an embodiment. As mentioned above, the first support structure 102-1 does not form the atrial arms 106-1 or the ventricular arms 106-2. The second support structure 102-2 forms the ventricular arms 106-2, and the third support structure 102-3 forms the atrial arms 106-1. The three support structures 102-1, 102-2, and 102-3 are configured to fit together to form the prosthetic tricuspid valve 5200. Specifically, to fit the three support structures 102-1, 102-2, and 102-3 together to form the prosthetic tricuspid valve 5200, a radius of curvature of a secondary bend 130 of each atrial arm 106-1 is received by a V-shaped strut 2200-1 of the first support structure 102-1. Additionally, to fit the three support structures 102-1, 102-2, and 102-3 together to form the prosthetic tricuspid valve 5200, a radius of curvature of a secondary bend 126 of each ventricular arm 106-2 is received by a V-shaped strut 2200-1 of the support structure 102-1, and also contacts a mirror V-shaped strut 2200-3 of the support structure 102-3 that forms the atrial arms 106-1.

Furthermore, to enable the three support structures 102-1, 102-2, and 102-3 to fit together to form the prosthetic tricuspid valve 5200, dimensions of the three support structures 102-1, 102-2, and 102-3 can be determined relative to one another. For example, in some embodiments, a minimum inner diameter of the cylindrical portion(s) of the at least one support structure that defines the elongate central passageway 104 can be less than a maximum outer diameter of the elongate central passageway 104. As discussed above, in the implementation of the prosthetic tricuspid valve 5200, each support structure of the three support structures 102-1, 102-2, and 102-3 includes a cylindrical portion, 116-1, 116-2, and 116-3, respectively, that define the elongate central passageway 104 of the prosthetic tricuspid valve 5200. Therefore, in some embodiments, a minimum inner diameter of the cylindrical portions 116-1, 116-2, and 116-3 of the three support structures 102-1, 102-2, and 102-3, respectively, that define the elongate central passageway 104 can be less than a maximum outer diameter of the elongate central passageway 104. As another example, in some embodiments, a minimum diameter of a radius of curvature of each bend of each arm 106, where the arm 106 extends perpendicularly away from the central axis of the elongate central passageway 104, is less than the maximum outer diameter of the elongate central passageway 104. In other words, in some embodiments, a minimum diameter of a radius of curvature of the secondary bend 130 of each atrial arm 106-1 and of the secondary bend 126 of each ventricular arm 106-2 is less than the maximum outer diameter of the elongate central passageway 104. These relative dimensions can facilitate the three support structures 102-1, 102-2, and 102-3 fitting together to form the prosthetic tricuspid valve 5200.

Figure 56A:
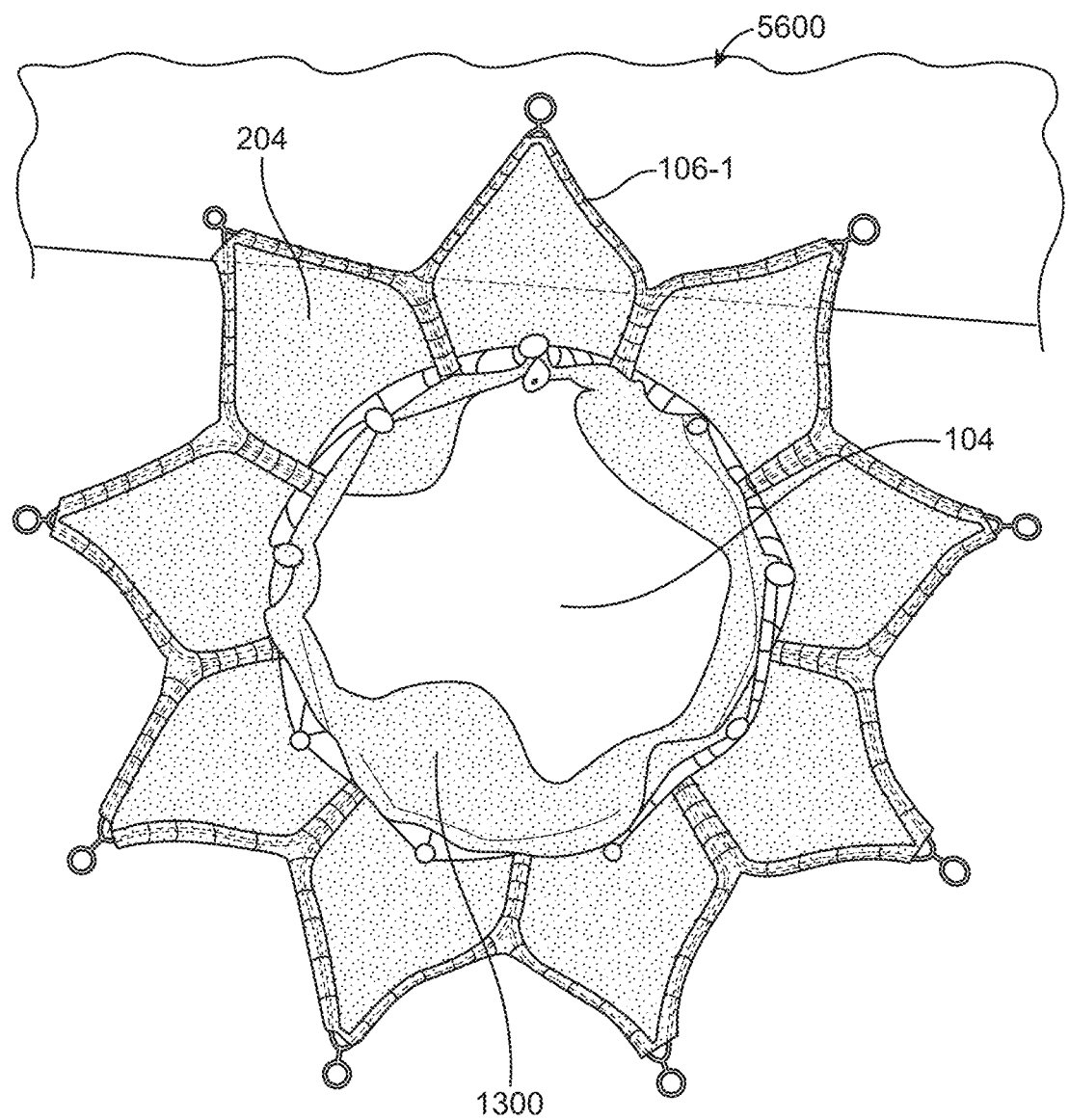
FIG. 56A is a top-down view of an image of a prototype prosthetic tricuspid valve clamping onto a sheet of paper oriented approximately perpendicular (e.g., 90°+/−45°) to the central axis of an elongate central passageway of the prosthetic tricuspid valve, in accordance with an embodiment.
Figure 56B:
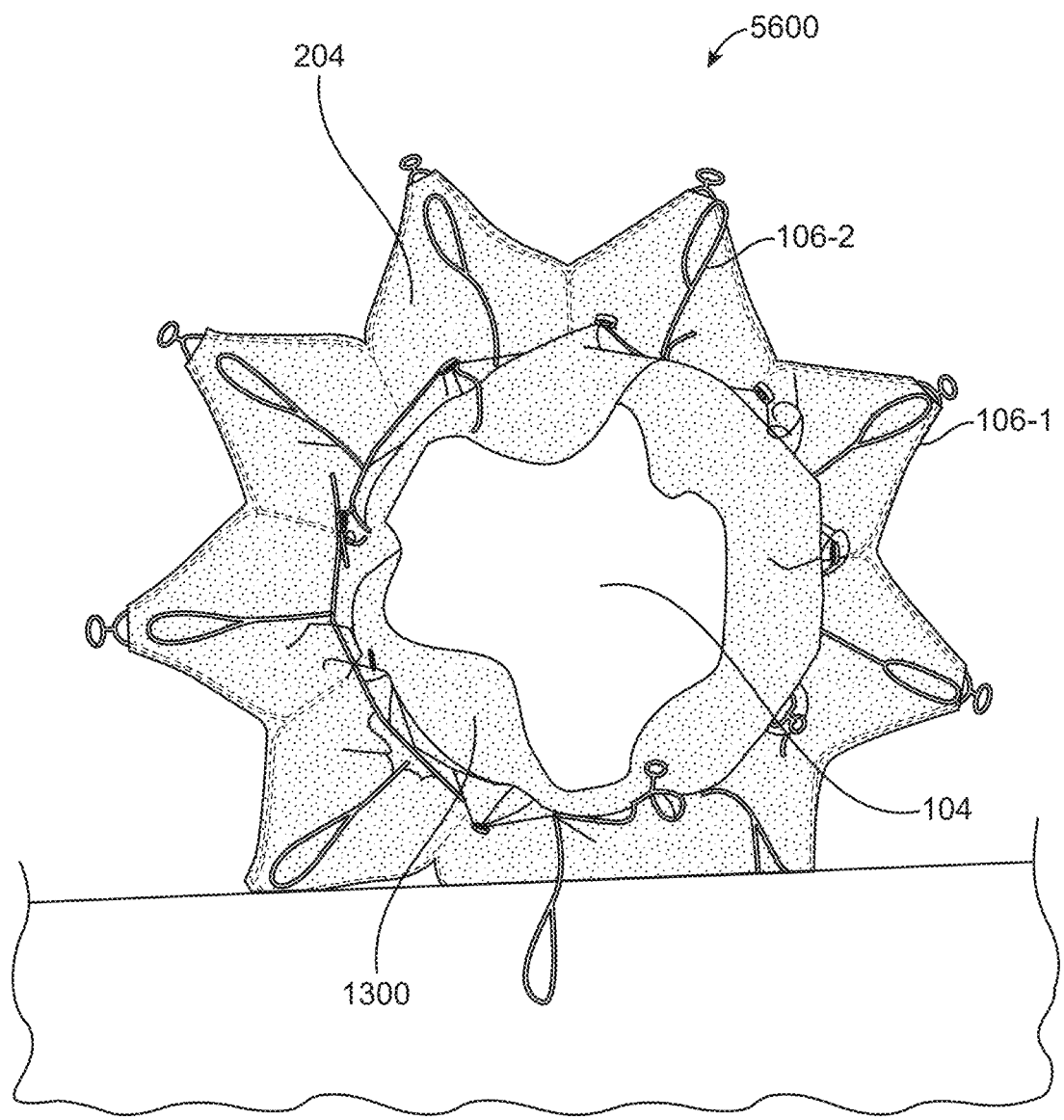
FIG. 56B is a bottom-up view of an image of a prototype prosthetic tricuspid valve clamping onto a sheet of paper oriented approximately perpendicular (e.g., 90°+/−45°) to the central axis of the elongate central passageway of the prosthetic tricuspid valve, in accordance with an embodiment.
Figure 56C:
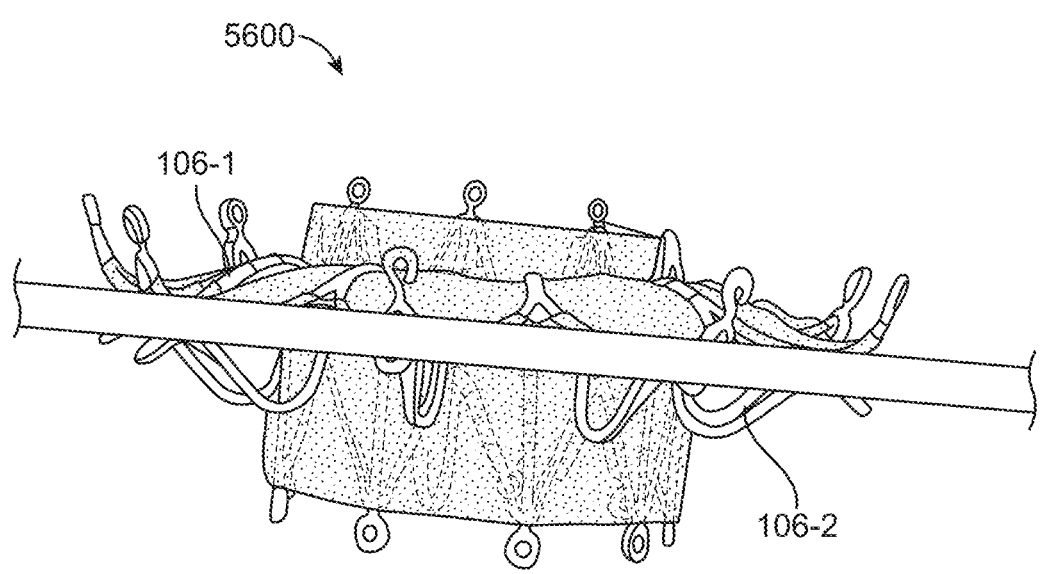
FIG. 56C is a side view of an image of a prototype prosthetic tricuspid valve clamping onto a sheet of paper oriented approximately perpendicular (e.g., 90°+/−45°) to the central axis of the elongate central passageway of the prosthetic tricuspid valve, in accordance with an embodiment.

FIGS. 56A-C are images of a prototype prosthetic tricuspid valve 5600, in accordance with an embodiment. Specifically, FIG. 56A is a top-down view of an image of the prototype prosthetic tricuspid valve 5600 clamping onto a sheet of paper oriented approximately perpendicular (e.g., 90°+/−45°) to the central axis of an elongate central passageway 104 of the prosthetic tricuspid valve 5600, in accordance with an embodiment. FIG. 56B is a bottom-up view of an image of the prototype prosthetic tricuspid valve 5600 clamping onto a sheet of paper oriented approximately perpendicular (e.g., 90°+/−45°) to the central axis of the elongate central passageway 104 of the prosthetic tricuspid valve 5600, in accordance with an embodiment. FIG. 56 is a side view of an image of the prototype prosthetic tricuspid valve 5600 clamping onto a sheet of paper oriented approximately perpendicular (e.g., 90°+/−45°) to the central axis of the elongate central passageway 104 of the prosthetic tricuspid valve 5600, in accordance with an embodiment.

Figure 57:
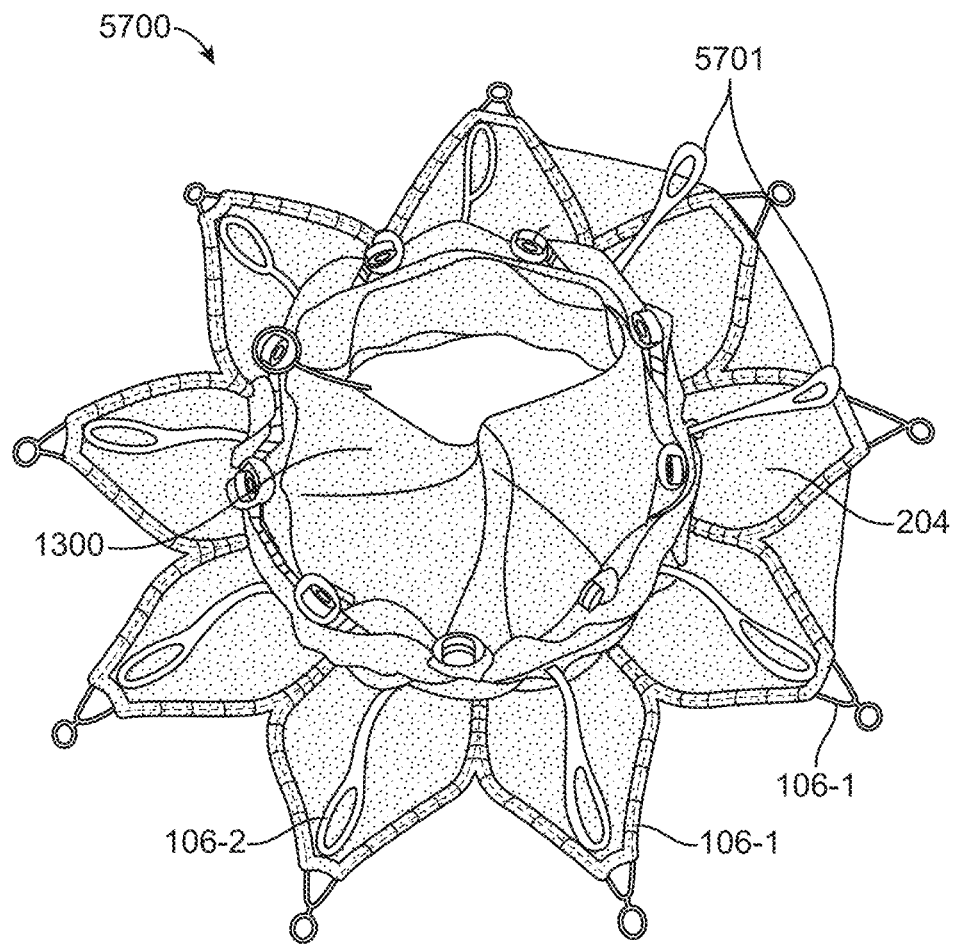
FIG. 57 is a bottom-up view of an image of a prototype prosthetic tricuspid valve, in accordance with an embodiment.

FIG. 57 is a bottom-up view of an image of a prototype prosthetic tricuspid valve 5700, in accordance with an embodiment. In the embodiment of the prosthetic tricuspid valve 5700 depicted in FIG. 57, two of the ventricular arms differ from the ventricular arms 106-2 described throughout this disclosure. Specifically, in the embodiment of the prosthetic tricuspid valve 5700 depicted in FIG. 57, ventricular-directed arms 5701 are ventricular arms that have been altered to differ from the ventricular arms 106-2 described throughout this disclosure. In particular, the distal segment 110 of each ventricular-directed arm 5701 has been altered to extend toward the ventricular end 120 of the cylindrical portion 116 of the at least one support structure 102. This extension of the distal segment 110 of each ventricular-directed arm 5701 toward the ventricular end 120 of the cylindrical portion 116 of the at least one support structure 102 enables the distal segment 110 of each ventricular-directed arm 5701 to contact a native leaflet of a native tricuspid valve on an atrial side of the native tricuspid valve, rather than on a ventricular side of the native tricuspid valve, thereby holding the native leaflet radially outward from the native tricuspid valve in an open position.

Configuring the ventricular-directed arms 5701 to hold a native leaflet radially outward from a native tricuspid valve in an open position can be useful in many different embodiments. For example, configuring the ventricular-directed arms 5701 to hold a native leaflet radially outward from a native tricuspid valve in an open position can be useful in embodiments in which the native leaflet is difficult to capture by the arms 106 for one reason or another (e.g., if the native leaflet is too small or restricted). As another example, configuring the ventricular-directed arms 5701 to hold a native leaflet radially outward from a native tricuspid valve in an open position can be useful in minimizing a number of echocardiography planes and/or viewpoints required during implantation of the prosthetic tricuspid valve (thereby simplifying the implantation procedure). In such embodiments, rather than attempt to capture all three native leaflets of the native tricuspid valve, one or more native leaflets can be pushed aside as described above, and the remaining native leaflets can be captured by the arms 106. While the prosthetic tricuspid valve 5700 includes two ventricular-directed arms 5701, in alternative embodiments, the prosthetic tricuspid valve 5700 can include any quantity of ventricular-directed arms 5701, such as, for example, zero, one, two, three, or more than three ventricular-directed arms 5701.

Figure 58:
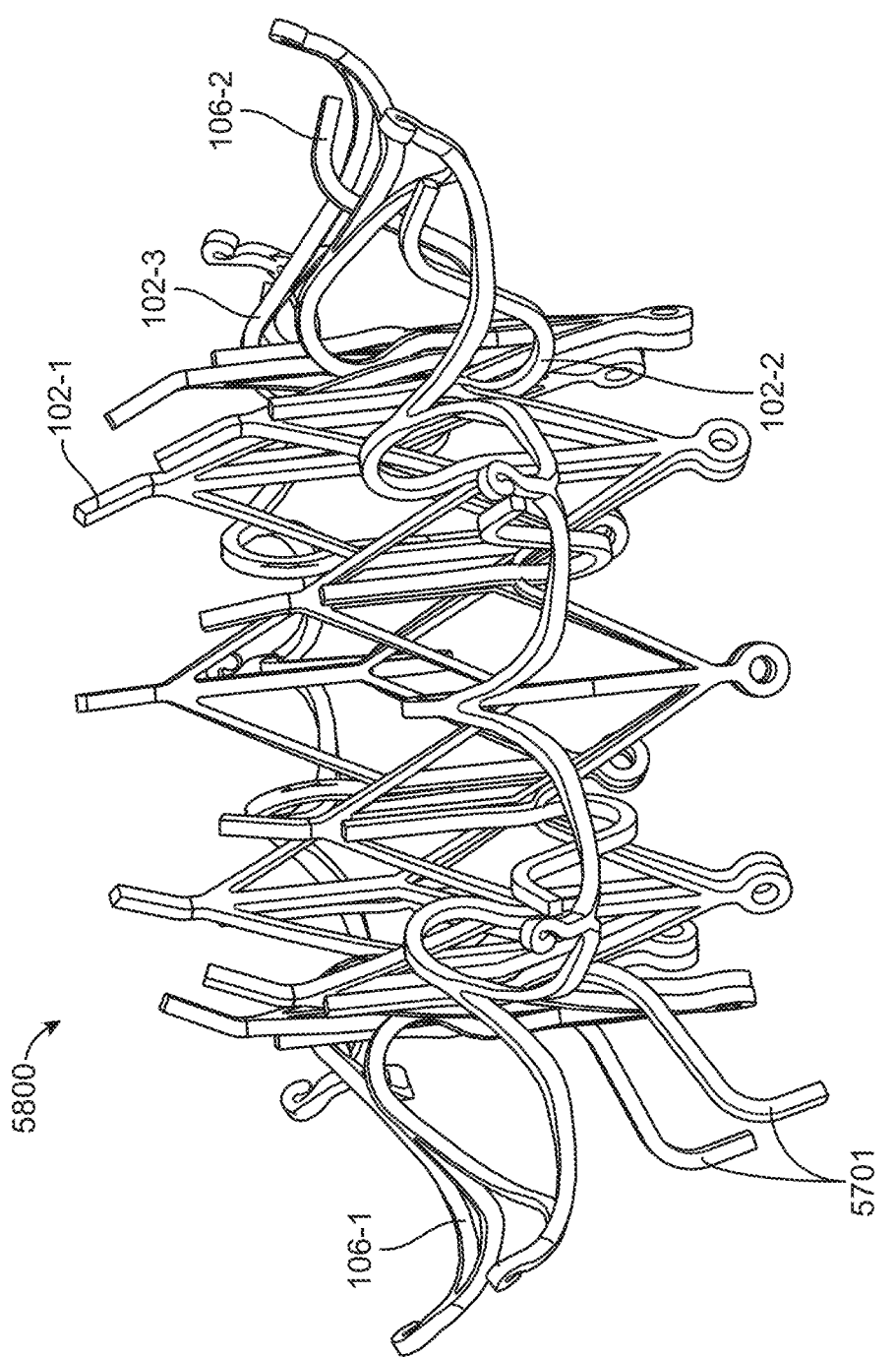
FIG. 58 illustrates a CAD drawing of a tilted side view of a prosthetic tricuspid valve having three support structures, in accordance with an embodiment.

FIG. 58 illustrates a CAD drawing of a tilted side view of the prosthetic tricuspid valve 5800 having three support structures 102-1, 102-2, and 102-3, in accordance with an embodiment. The prosthetic tricuspid valve 5800 is similar to the prosthetic tricuspid valve 5200 depicted in FIGS. 52, 53, and 55. However, the prosthetic tricuspid valve 5800 includes two ventricular-directed arms 5701, as described above with regard to FIG. 57. Like the ventricular arms 106-2, the ventricular-directed arms 5701 are formed from the second support structure 102-2.

FIG. 59 illustrates a view of a flattened support structure 102 of a prosthetic tricuspid valve, in accordance with an embodiment. As shown in FIG. 59, the support structure 102 includes an atrial end 118 and a ventricular end 120. A plurality of interlocking mechanisms 5900 are included at the atrial end 118 of the support structure 102. As discussed below with regard to FIG. 59, each interlocking mechanism 5900 of the support structure 102 is configured to interlock with a corresponding interlocking mechanism 3600 of a spreader arm 2300.

FIG. 60 illustrates loading, locking, and releasing of interlocking mechanisms 5900 of a support structure 102 of a prosthetic tricuspid valve, in accordance with an embodiment. Specifically, as shown in FIG. 60, each interlocking mechanism 5900 of the support structure 102 is interlocked with a corresponding interlocking mechanism 3600 of a spreader arm 2300.

Loading, locking, and releasing of the interlocking mechanisms 5900 of the support structure 102 is accomplished using an extension 3602 of each interlocking mechanism 3600 of each spreader arm 2300. Specifically, during loading of the interlocking mechanism 5900 of the support structure 102 with the corresponding interlocking mechanism 3600 of the spreader arm 2300, the extension 3602 of the interlocking mechanism 3600 of the spreader arm 2300 is partially retracted from the interlocking mechanism 5900 of the support structure 102, thereby pushing the interlocking mechanism 3600 of the spreader arm 2300 to the side and enabling the interlocking mechanism 5900 of the support structure 102 to snap into a locked position with the interlocking mechanism 3600 of the spreader arm 2300. During locking of the interlocking mechanism 5900 of the support structure 102 with the corresponding interlocking mechanism 3600 of the spreader arm 2300, the extension 3602 of the interlocking mechanism 3600 of the spreader arm 2300 is advanced fully over the interlocking mechanism 5900 of the support structure 102, thereby locking the interlocking mechanism 3600 of the spreader arm 2300 and the interlocking mechanism 5900 of the support structure 102 into the locked position. During releasing of the interlocking mechanism 5900 of the support structure 102 from the corresponding interlocking mechanism 3600 of the spreader arm 2300, the extension 3602 of the interlocking mechanism 3600 of the spreader arm 2300 is fully retracted from the interlocking mechanism 5900 of the support structure 102, thereby enabling the interlocking mechanism 5900 of the support structure 102 to expand and to release from the locked position with the interlocking mechanism 3600 of the spreader arm 2300.

Figure 61:
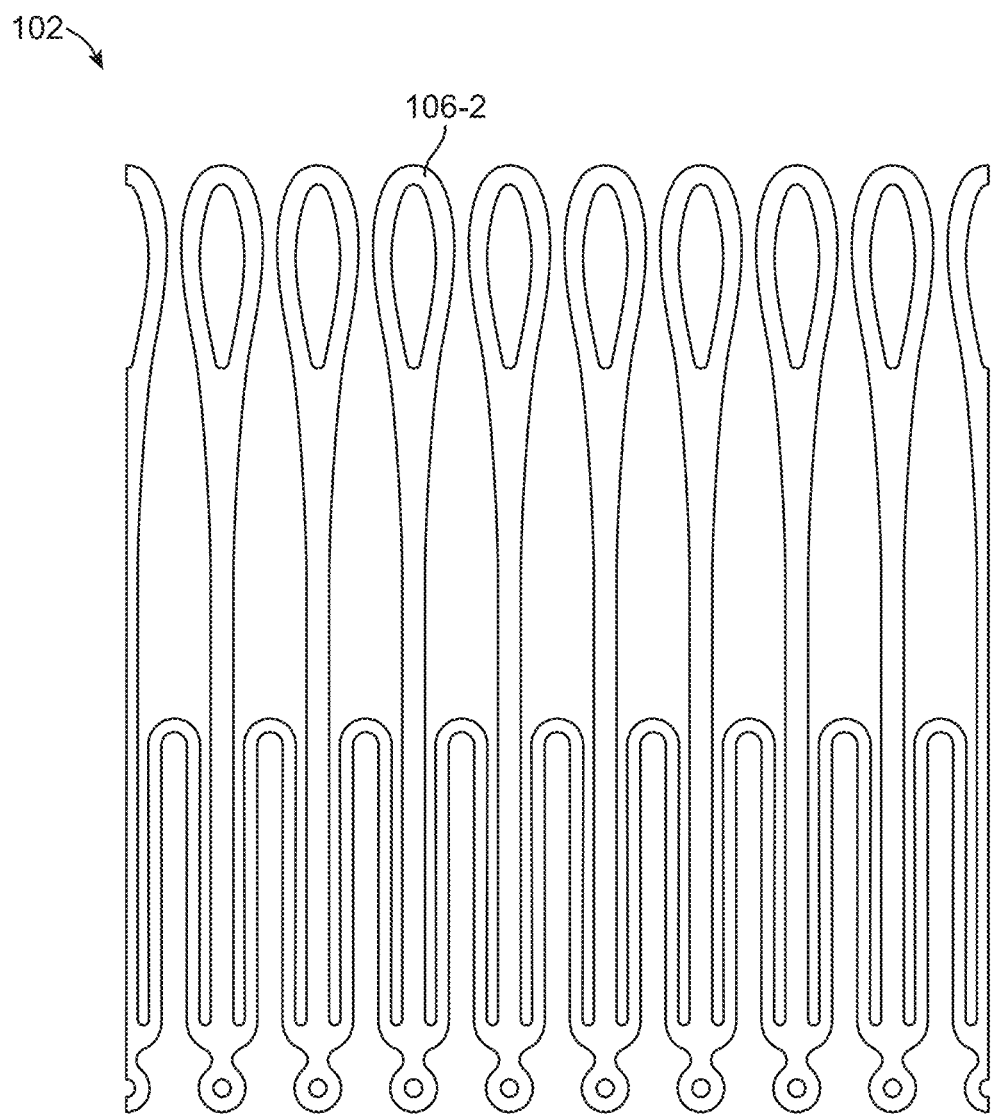
FIG. 61 illustrates a view of a flattened support structure configured to form ventricular arms of a prosthetic tricuspid valve, in accordance with an embodiment.

FIG. 61 illustrates a view of a flattened support structure 102 configured to form ventricular arms 106-2 of a prosthetic tricuspid valve, in accordance with an embodiment.

Figure 62A:
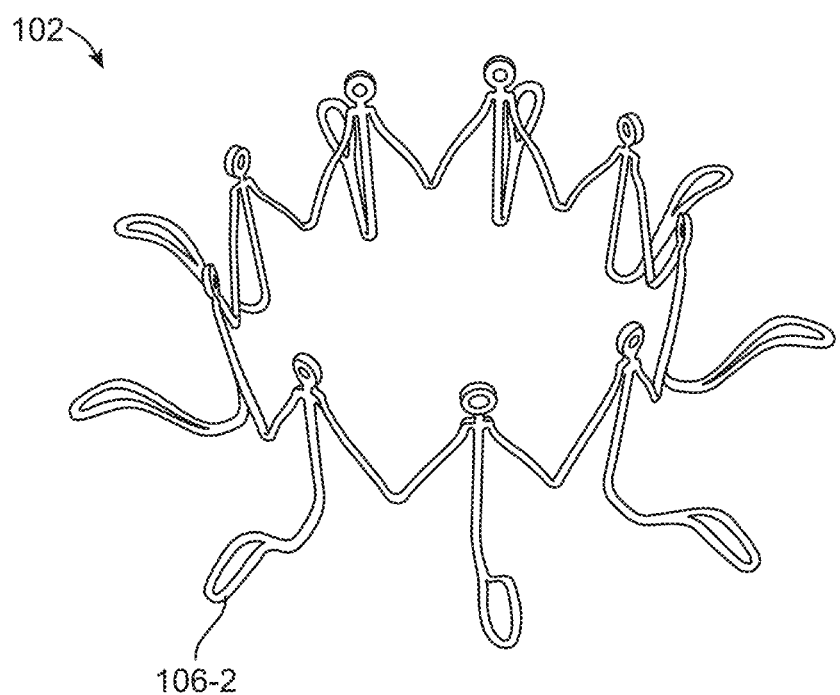
FIG. 62A is an image of a prototype support structure forming ventricular arms of a prosthetic tricuspid valve, in accordance with an embodiment.

FIG. 62A is an image of a prototype support structure 102 forming ventricular arms 106-2 of a prosthetic tricuspid valve, in accordance with an embodiment.

Figure 62B:
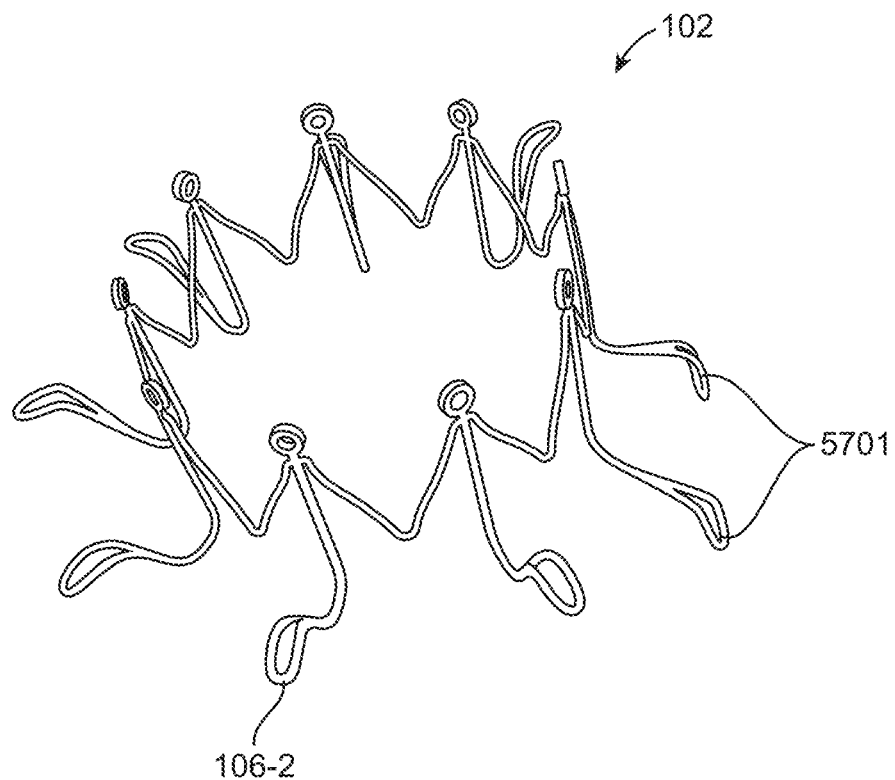
FIG. 62B is an image of a prototype support structure forming ventricular arms and ventricular-directed arms of a prosthetic tricuspid valve, in accordance with an embodiment.

FIG. 62B is an image of a prototype support structure 102 forming ventricular arms 106-2 and ventricular-directed arms 5701 of a prosthetic tricuspid valve, in accordance with an embodiment.

Figure 63B:
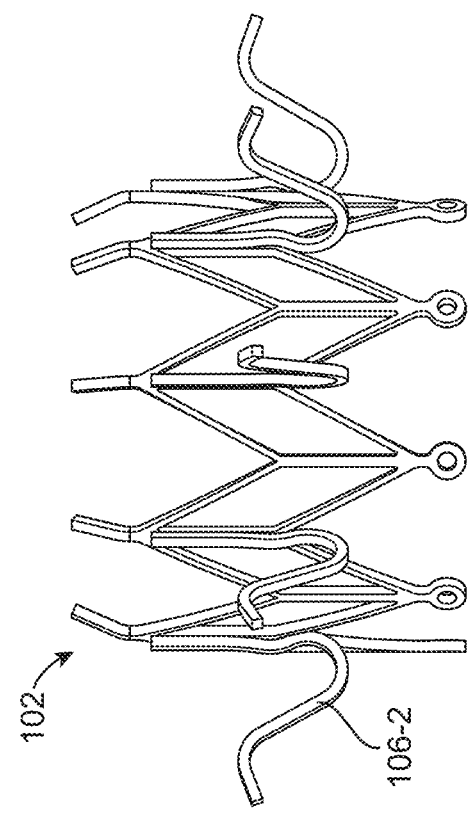
FIG. 63B illustrates a side view of a CAD drawing of a support structure forming ventricular arms of a prosthetic tricuspid valve, in accordance with an embodiment.
Figure 63A:
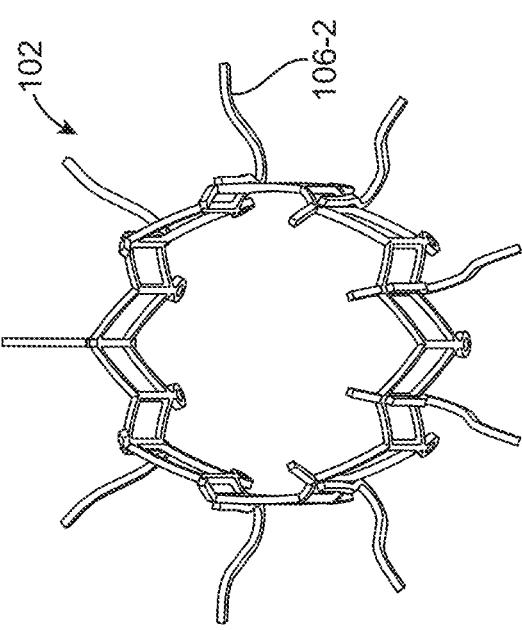
FIG. 63A illustrates a top-down view of a CAD drawing of a support structure forming ventricular arms of a prosthetic tricuspid valve, in accordance with an embodiment.

FIGS. 63A-B illustrate CAD drawings of a support structure 102 forming ventricular arms 106-2 of a prosthetic tricuspid valve, in accordance with an embodiment. Specifically, FIG. 63A illustrates a top-down view of a CAD drawing of a support structure 102 forming ventricular arms 106-2 of a prosthetic tricuspid valve, in accordance with an embodiment. FIG. 63B illustrates a side view of a CAD drawing of a support structure 102 forming ventricular arms 106-2 of a prosthetic tricuspid valve, in accordance with an embodiment.

Figure 64B:
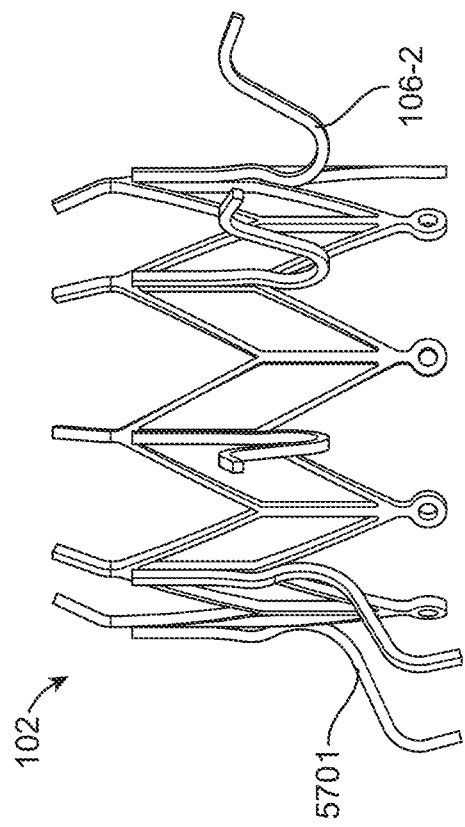
FIG. 64B illustrates a side view of a CAD drawing of a support structure forming ventricular arms and ventricular-directed arms of a prosthetic tricuspid valve, in accordance with an embodiment.
Figure 64A:
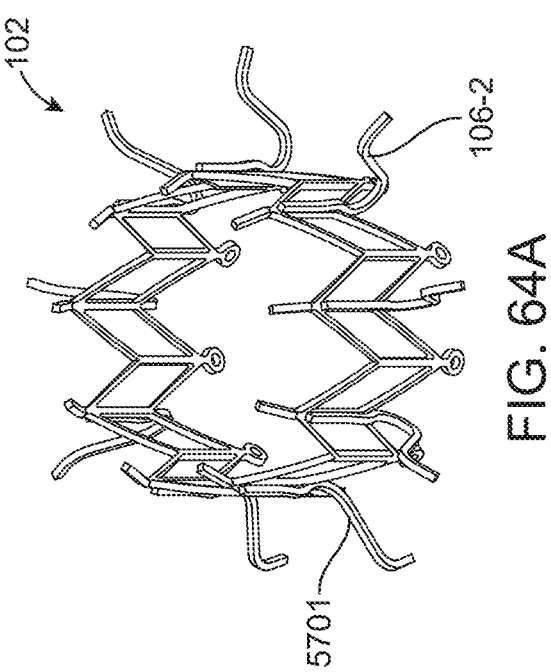
FIG. 64A illustrates a top-down view of a CAD drawing of a support structure forming ventricular arms and ventricular-directed arms of a prosthetic tricuspid valve, in accordance with an embodiment.

FIGS. 64A-B illustrate CAD drawings of a support structure 102 forming ventricular arms 106-2 and ventricular-directed arms 5701 of a prosthetic tricuspid valve, in accordance with an embodiment. Specifically, FIG. 64A illustrates a top-down view of a CAD drawing of a support structure 102 forming ventricular arms 106-2 and ventricular-directed arms 5701 of a prosthetic tricuspid valve, in accordance with an embodiment. FIG. 64B illustrates a side view of a CAD drawing of a support structure 102 forming ventricular arms 106-2 and ventricular-directed arms 5701 of a prosthetic tricuspid valve, in accordance with an embodiment.

Figure 65:
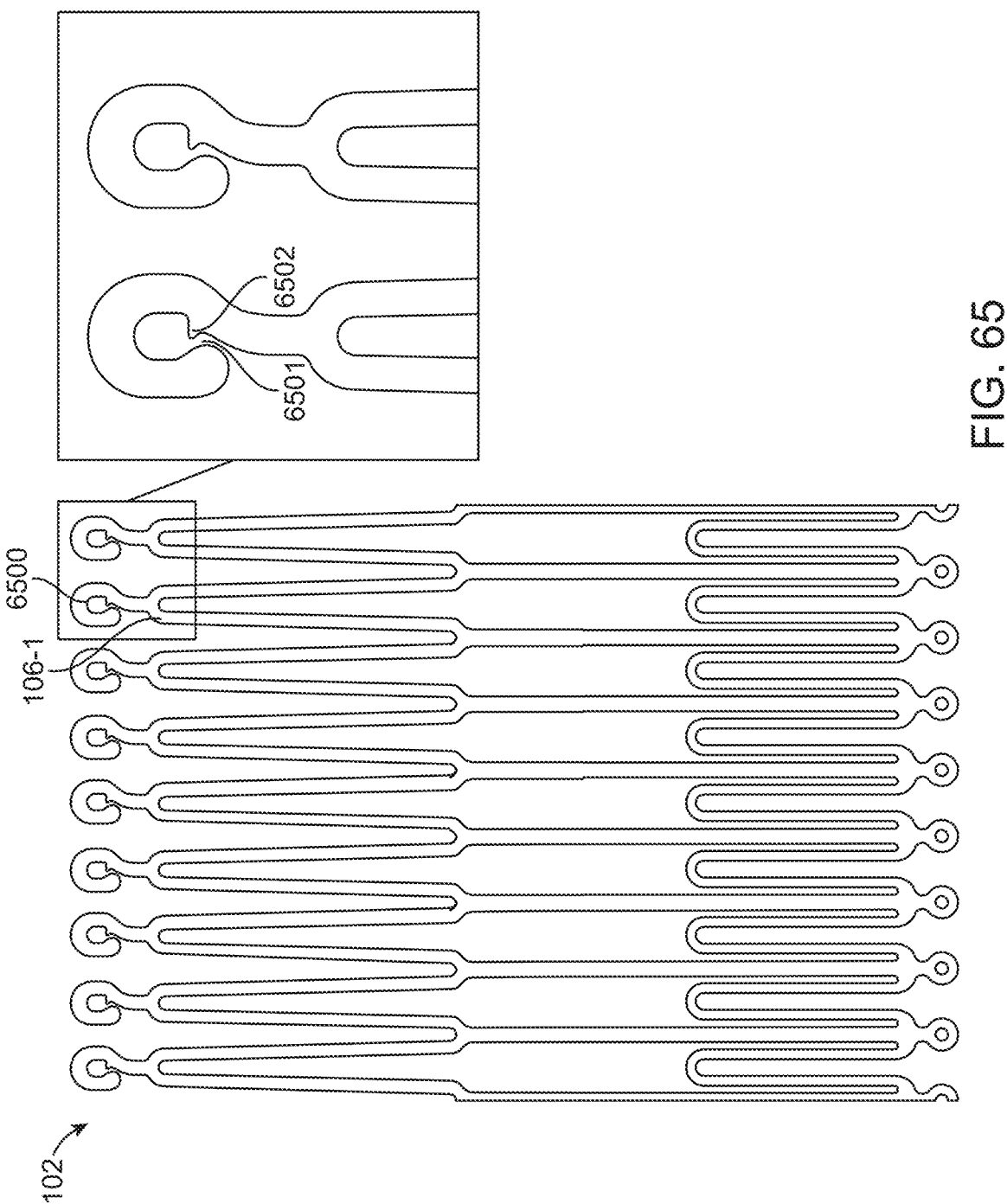
FIG. 65 illustrates a view of a flattened support structure configured to form atrial arms of a prosthetic tricuspid valve, in accordance with an embodiment.

FIG. 65 illustrates a view of a flattened support structure 102 configured to form atrial arms 106-1 of a prosthetic tricuspid valve, in accordance with an embodiment. As shown in FIG. 65, the tip 142 of each atrial arm 106-1 can include a locking mechanism 6500. Each locking mechanism 6500 of the support structure 102 is configured to lock in a corresponding restraint 410 (e.g., a suture).

During loading of the locking mechanisms 6500, a narrow opening 6501 of each locking mechanism 6500 enables the corresponding restraint 410 enter the locking mechanism 6500 and to lock into place. During locking of the locking mechanisms 6500, a tooth 6502 of each locking mechanism 6500 prevents the corresponding locked restraint 410 from exiting the locking mechanism 6500 via the narrow opening 6501 while the restraint 410 is under tension. During release of the locking mechanisms 6500, when tension is removed from the restraint 410, the restraint 410 is permitted to exit the locking mechanism 6500 via the narrow opening 6501.

Figure 66:
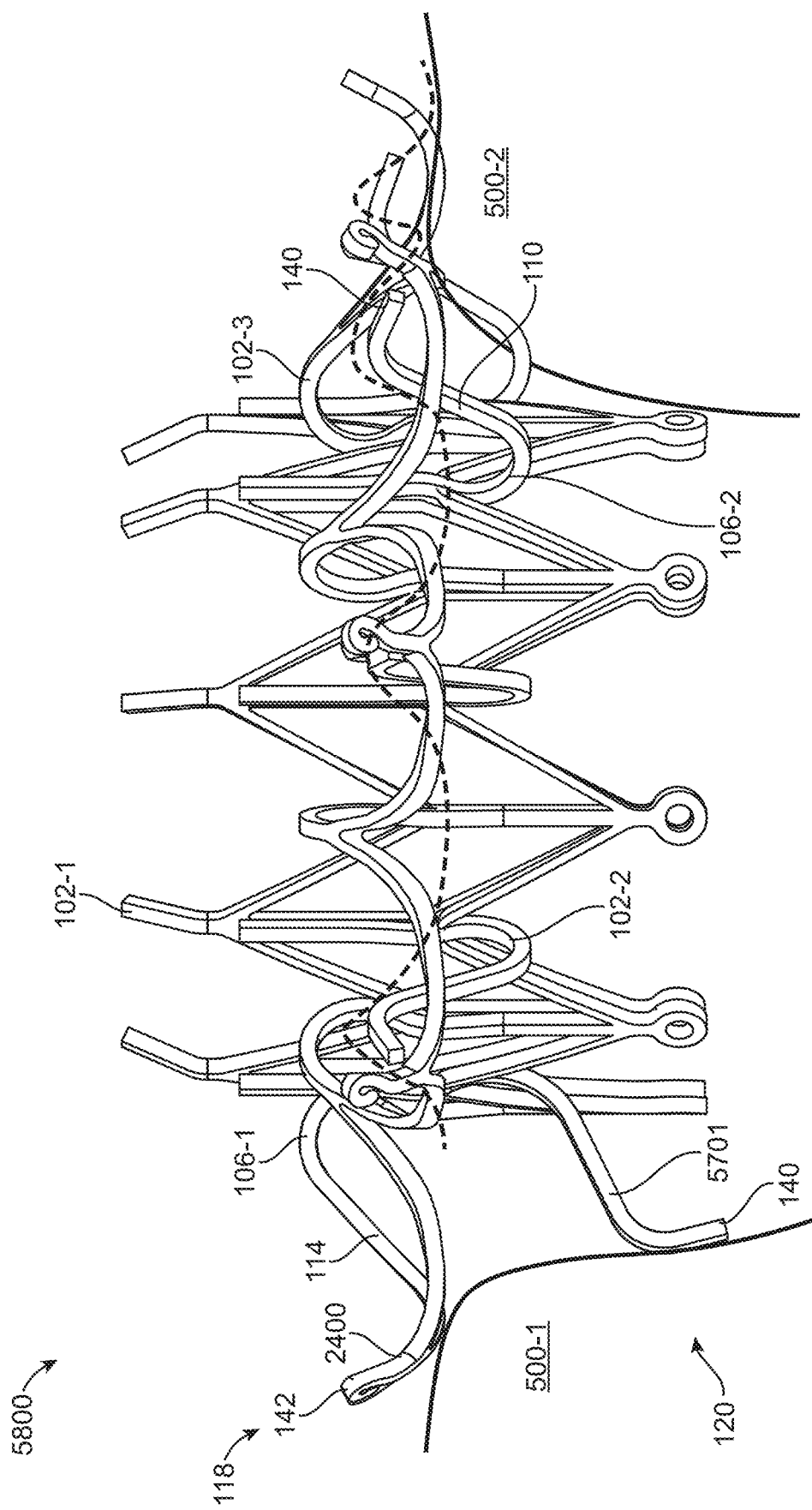
FIG. 66 illustrates a CAD drawing of a side view of a prosthetic tricuspid valve, in accordance with an embodiment.

FIG. 66 illustrates a CAD drawing of a side view of the prosthetic tricuspid valve 5800, in accordance with an embodiment. As also shown in FIG. 66, the distal segment 114 of each atrial arm 106-1 extends from the atrial end 118 of the cylindrical portion 116 of the support structures 102-1, 102-2, and 102-3, but extends toward the ventricular end 120 of the cylindrical portion 116 of the support structures 102-1, 102-2, and 102-3. Conversely, the distal segment 110 of each ventricular arm 106-2 extends from the ventricular end 120 of the cylindrical portion 116 of the support structures 102-1, 102-2, and 102-3, but extends toward the atrial end 118 of the cylindrical portion 116 of the support structures 102-1, 102-2, and 102-3. As a result, as discussed above, overbite occurs between the atrial arms 106-1 and the ventricular arms 106-2. The dotted line across the prosthetic tricuspid valve 5800 in FIG. 66 depicts points of overbite between the atrial arms 106-1 and the ventricular arms 106-2. As shown in FIG. 66, the overbite between the atrial arms 106-1 and the ventricular arms 106-2 enables the atrial arms 106-1 and the ventricular arms 106-2 to clamp a native leaflet 500-2 of a native tricuspid valve between them. Conversely, as shown in FIG. 66, the ventricular-directed arm 5701 is configured to hold a native leaflet 500-1 radially outward from a native tricuspid valve in an open position.

Additionally, as shown in FIG. 66, the tip 142 of each atrial arm 106-1 includes an extended segment 2400 with a third bend toward the atrial end 118 of the cylindrical portion 116 of the support structures 102-1, 102-2, and 102-3 for more atraumatic engagement of the atrial surfaces of the native leaflets. Similarly, as shown in FIG. 66, the tip 140 of the ventricular-directed arm 5701 can include an extended segment with a third bend toward the ventricular end 120 of the cylindrical portion 116 of the support structures 102-1, 102-2, and 102-3 for more atraumatic engagement of the atrial surface of the native leaflet 500-1. These third bends of the atrial arms 106-1 and the ventricular-directed arm 5701 can also prevent the atrial arms 106-1 and the ventricular-directed arm 5701 from embedding within tissue of the native leaflets.

Figure 67A:
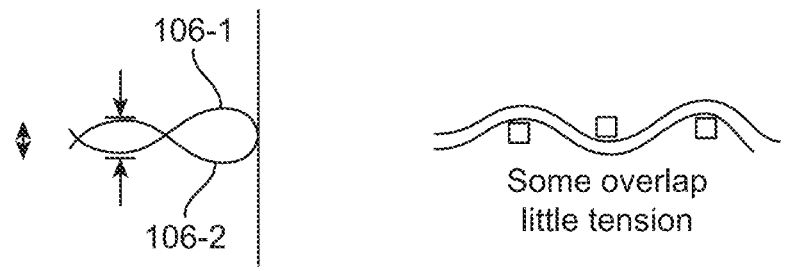
FIG. 67A illustrates a side view of a relatively small amount of overbite between an atrial arm and a ventricular arm of a prosthetic tricuspid valve, in accordance with an embodiment.
Figure 67B:
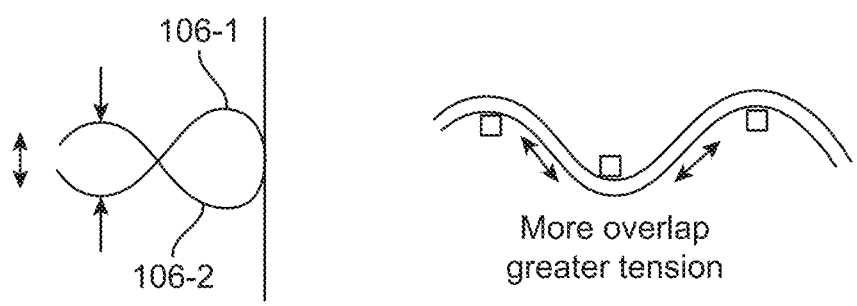
FIG. 67B illustrates a side view of a relatively moderate amount of overbite between an atrial arm and a ventricular arm of a prosthetic tricuspid valve, in accordance with an embodiment.
Figure 67C:
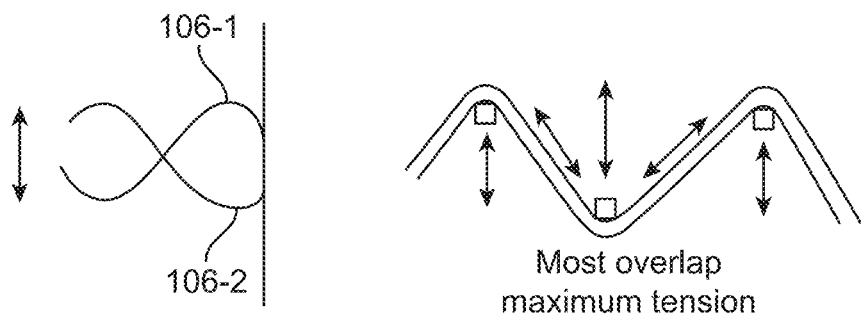
FIG. 67C illustrates a side view of a relatively large amount of overbite between an atrial arm and a ventricular arm of a prosthetic tricuspid valve, in accordance with an embodiment.

FIGS. 67A-C illustrate side views of overbite between an atrial arm 106-1 and a ventricular arm 106-2 of a prosthetic tricuspid valve, in accordance with an embodiment. Specifically, FIGS. 67A-C illustrate side views of varying amounts of overbite between the atrial arm 106-1 and the ventricular arm 106-2 of the prosthetic tricuspid valve, in accordance with an embodiment. The amount of overbite between the atrial arm 106-1 and the ventricular arm 106-2 of the prosthetic tricuspid valve determines the magnitude of the clamping force of the arms 106 on a native leaflet of a native tricuspid valve. Furthermore, the magnitude of the clamping force of the arms 106 on the native leaflet of the native tricuspid valve determines the amount of biodynamic movement of the prosthetic tricuspid valve within the native tricuspid valve throughout cardiac cycles of the heart.

FIG. 67A illustrates a side view of a relatively small amount of overbite between the atrial arm 106-1 and the ventricular arm 106-2 of the prosthetic tricuspid valve, in accordance with an embodiment. As a result of this relatively small amount of overbite between the atrial arm 106-1 and the ventricular arm 106-2 of the prosthetic tricuspid valve in FIG. 67A, a relatively small amount of tension can be exerted on a native leaflet clamped between the atrial arm 106-1 and the ventricular arm 106-2. Furthermore, as a result of this relatively small amount of tension exerted on the native leaflet clamped between the atrial arm 106-1 and the ventricular arm 106-2, the prosthetic tricuspid valve is able to demonstrate a relatively large amount of biodynamic movement within the native tricuspid valve throughout cardiac cycles of the heart.

FIG. 67B illustrates a side view of a relatively moderate amount of overbite between the atrial arm 106-1 and the ventricular arm 106-2 of the prosthetic tricuspid valve, in accordance with an embodiment. As a result of this relatively moderate amount of overbite between the atrial arm 106-1 and the ventricular arm 106-2 of the prosthetic tricuspid valve in FIG. 67B, a relatively moderate amount of tension can be exerted on a native leaflet clamped between the atrial arm 106-1 and the ventricular arm 106-2. Furthermore, as a result of this relatively moderate amount of tension exerted on the native leaflet clamped between the atrial arm 106-1 and the ventricular arm 106-2, the prosthetic tricuspid valve is able to demonstrate a relatively moderate amount of biodynamic movement within the native tricuspid valve throughout cardiac cycles of the heart.

FIG. 67C illustrates a side view of a relatively large amount of overbite between the atrial arm 106-1 and the ventricular arm 106-2 of the prosthetic tricuspid valve, in accordance with an embodiment. As a result of this relatively large amount of overbite between the atrial arm 106-1 and the ventricular arm 106-2 of the prosthetic tricuspid valve in FIG. 67C, a relatively large amount of tension can be exerted on a native leaflet clamped between the atrial arm 106-1 and the ventricular arm 106-2. Furthermore, as a result of this relatively large amount of tension exerted on the native leaflet clamped between the atrial arm 106-1 and the ventricular arm 106-2, the prosthetic tricuspid valve is able to demonstrate a relatively small amount of biodynamic movement within the native tricuspid valve throughout cardiac cycles of the heart.

Figure 68B:
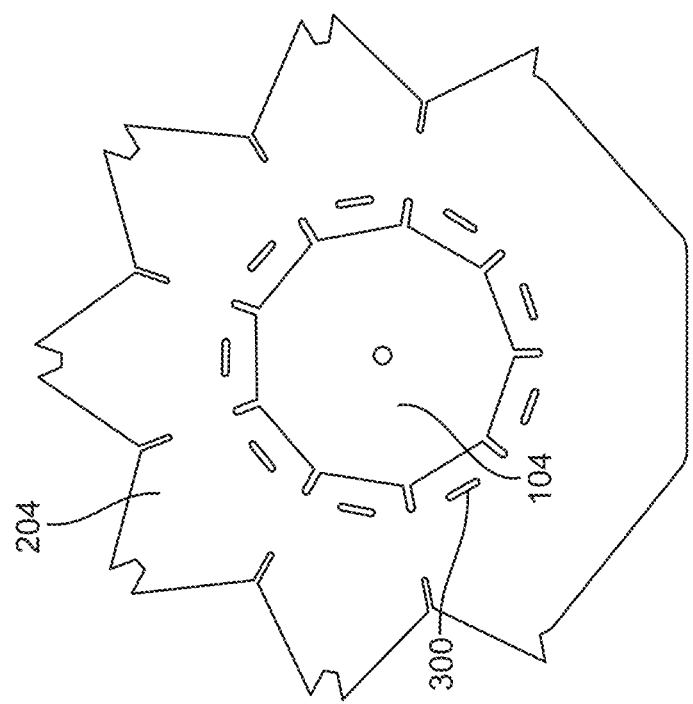
FIG. 68B illustrates an asymmetric implementation of an atrial sealing skirt, in accordance with an embodiment.
Figure 68A:
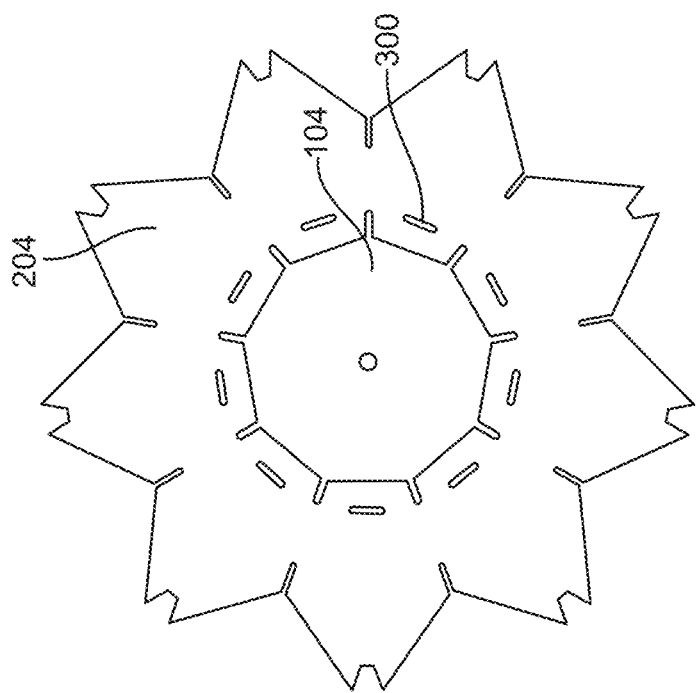
FIG. 68A illustrates a symmetric implementation of an atrial sealing skirt, in accordance with an embodiment.

FIGS. 68A-B illustrate different implementations of the atrial sealing skirt 204, in accordance with an embodiment. Specifically, FIG. 68A illustrates a symmetric implementation of the atrial sealing skirt 204, in accordance with an embodiment. FIG. 68B illustrates an asymmetric implementation of the atrial sealing skirt 204, in accordance with an embodiment.

The symmetric atrial sealing skirt 204 depicted in FIG. 68A can be used for symmetric prosthetic tricuspid devices, such as the prosthetic tricuspid devices depicted in FIGS. 62A and 64A-B. Specifically, the symmetric atrial sealing skirt 204 depicted in FIG. 68A can be used for prosthetic tricuspid devices having symmetrical ventricular arms (e.g., only ventricular arms 106-2).

Conversely, the asymmetric atrial sealing skirt 204 depicted in FIG. 68B can be used for asymmetric prosthetic tricuspid devices, such as the prosthetic tricuspid devices depicted in FIGS. 62B and 65A-B. Specifically, the asymmetric atrial sealing skirt 204 depicted in FIG. 68B can be used for prosthetic tricuspid devices having asymmetrical ventricular arms (e.g., ventricular arms 106-2 and ventricular-directed arm(s) 5701).

Tabs of the atrial sealing skirt 204 that line the elongate central passageway 104 can be folded down to join another portion of the cover 200 that runs along an inside of the cylindrical portion 116 of at least one support structure 102 of the prosthetic tricuspid valve. The fenestrations 300 of the atrial sealing skirt 204 can allow space for ventricular arms 106-2 to pass through the atrial sealing skirt 204 during assembly of the prosthetic tricuspid valve, such that the ventricular arms 106-2 are located exterior to the elongate central passageway 104 of the prosthetic tricuspid valve once the prosthetic tricuspid valve is assembled. In some embodiments, the asymmetric portion of the asymmetric atrial sealing skirt 204 of FIG. 68B can also include additional fenestrations 300 to be positioned within a native annulus of a native tricuspid valve when the prosthetic tricuspid valve is implanted in the native tricuspid valve.

FIG. 69A-B are images of support structures 102-2 and 102-3 of a prototype prosthetic tricuspid valve 6900, in accordance with an embodiment. Specifically, FIG. 69A is an image of a bottom-up view of support structures 102-2 and 102-3 of the prototype prosthetic tricuspid valve 6900, in accordance with an embodiment. FIG. 69B is an image of a side view of support structures 102-2 and 102-3 of the prototype prosthetic tricuspid valve 6900, in accordance with an embodiment.

Figure 74:
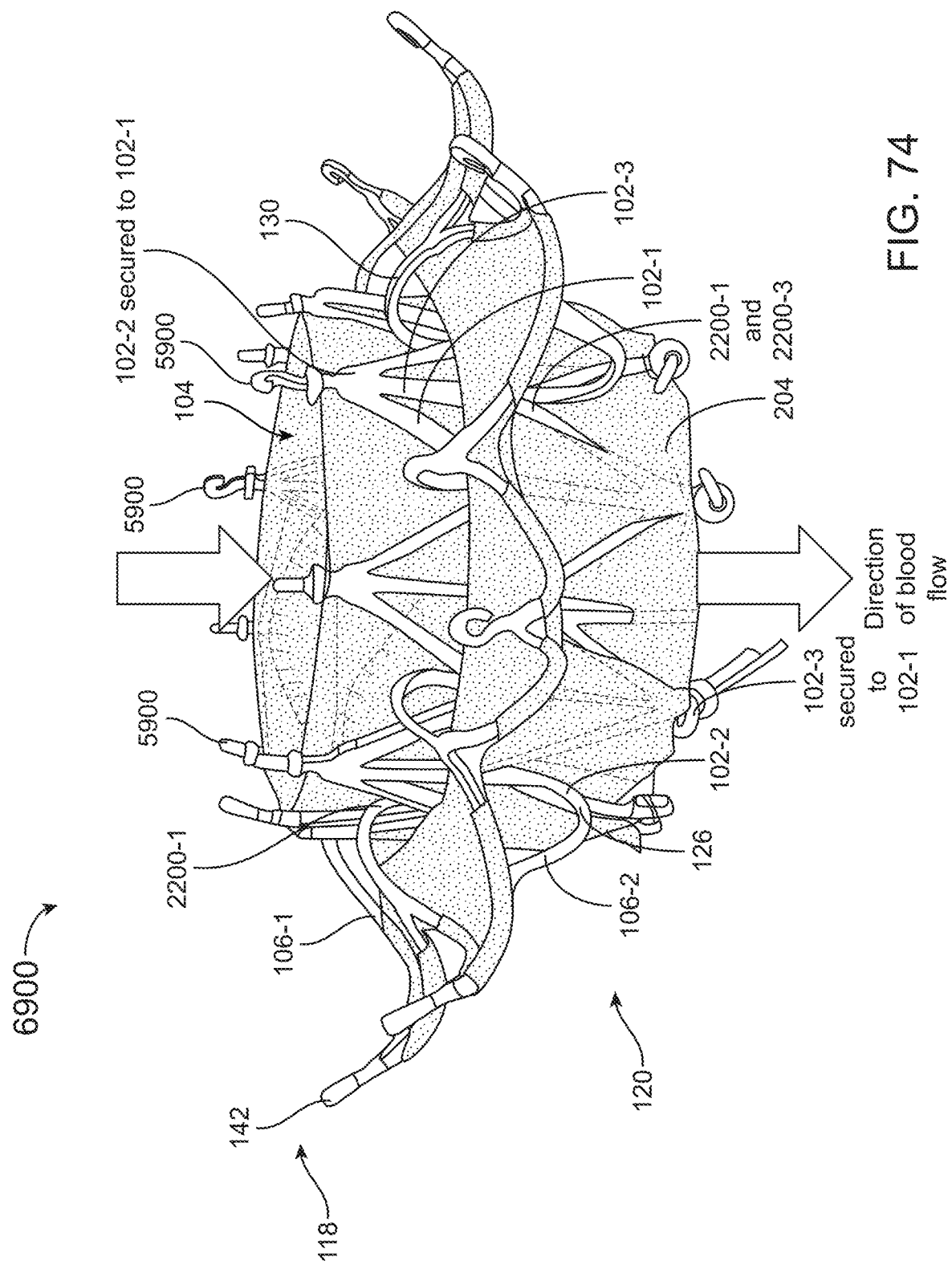
FIG. 74 is an image of a side view of a prototype prosthetic tricuspid valve, in accordance with an embodiment.

The prosthetic tricuspid valve 6900 is similar to the prototype prosthetic tricuspid valve 5600 of FIGS. 56A-C and includes three support structures 102-1, 102-2, and 102-3 (shown in FIG. 74). However, the images in FIGS. 69A-B depict only the support structures 102-2 and 102-3 of the prototype prosthetic tricuspid valve 6900. As discussed below, the first support structure 102-1 does not form the atrial arms 106-1 or the ventricular arms 106-2. The second support structure 102-2 forms the ventricular arms 106-2, and the third support structure 102-3 forms the atrial arms 106-1. As shown in FIGS. 69A-B, the symmetric atrial sealing skirt 204 of FIG. 68A covers the support structures 102-2 and 102-3 of the symmetric prototype prosthetic tricuspid valve 6900.

Figure 70B:
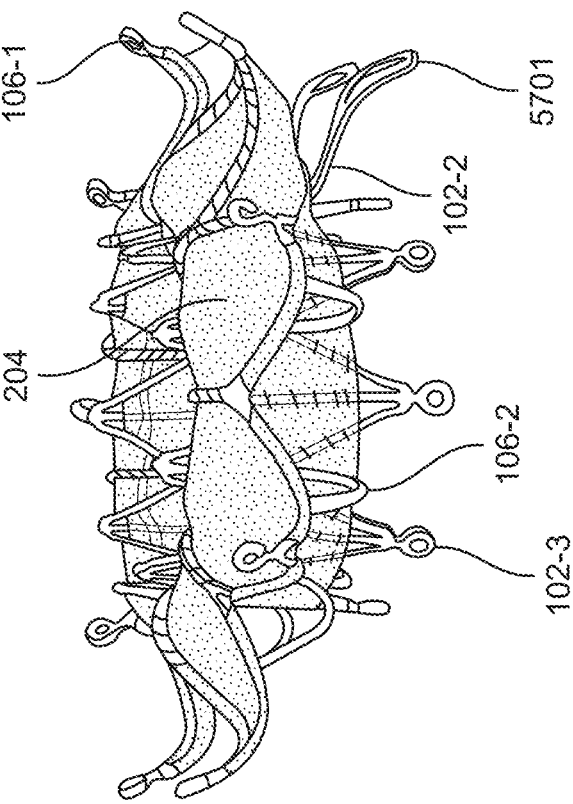
FIG. 70B is an image of a side view of support structures of a prototype prosthetic tricuspid valve, in accordance with an embodiment.
Figure 70A:
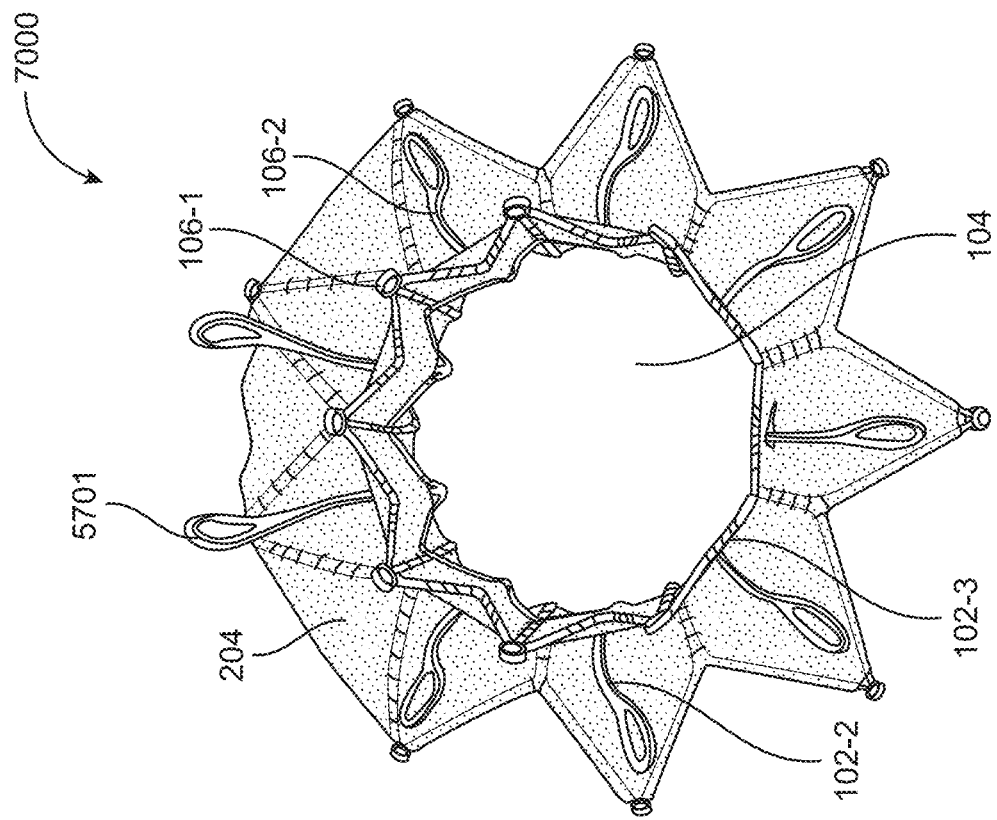
FIG. 70A is an image of a bottom-up view of support structures of a prototype prosthetic tricuspid valve, in accordance with an embodiment.

FIG. 70A-B are images of support structures 102-2 and 102-3 of a prototype prosthetic tricuspid valve 7000, in accordance with an embodiment. Specifically, FIG. 70A is an image of a bottom-up view of support structures 102-2 and 102-3 of the prototype prosthetic tricuspid valve 7000, in accordance with an embodiment. FIG. 70B is an image of a side view of support structures 102-2 and 102-3 of the prototype prosthetic tricuspid valve 7000, in accordance with an embodiment.

The prototype prosthetic tricuspid valve 7000 is similar to the prototype prosthetic tricuspid valve 5700 of FIG. 57 and includes three support structures 102-1, 102-2, and 102-3. However, the images in FIGS. 70A-B depict only the support structures 102-2 and 102-3 of the prototype prosthetic tricuspid valve 7000. As shown in FIGS. 70A-B, the asymmetric atrial sealing skirt 204 of FIG. 68B covers the support structures 102-2 and 102-3 of the symmetric prototype prosthetic tricuspid valve 7000.

Figure 71:
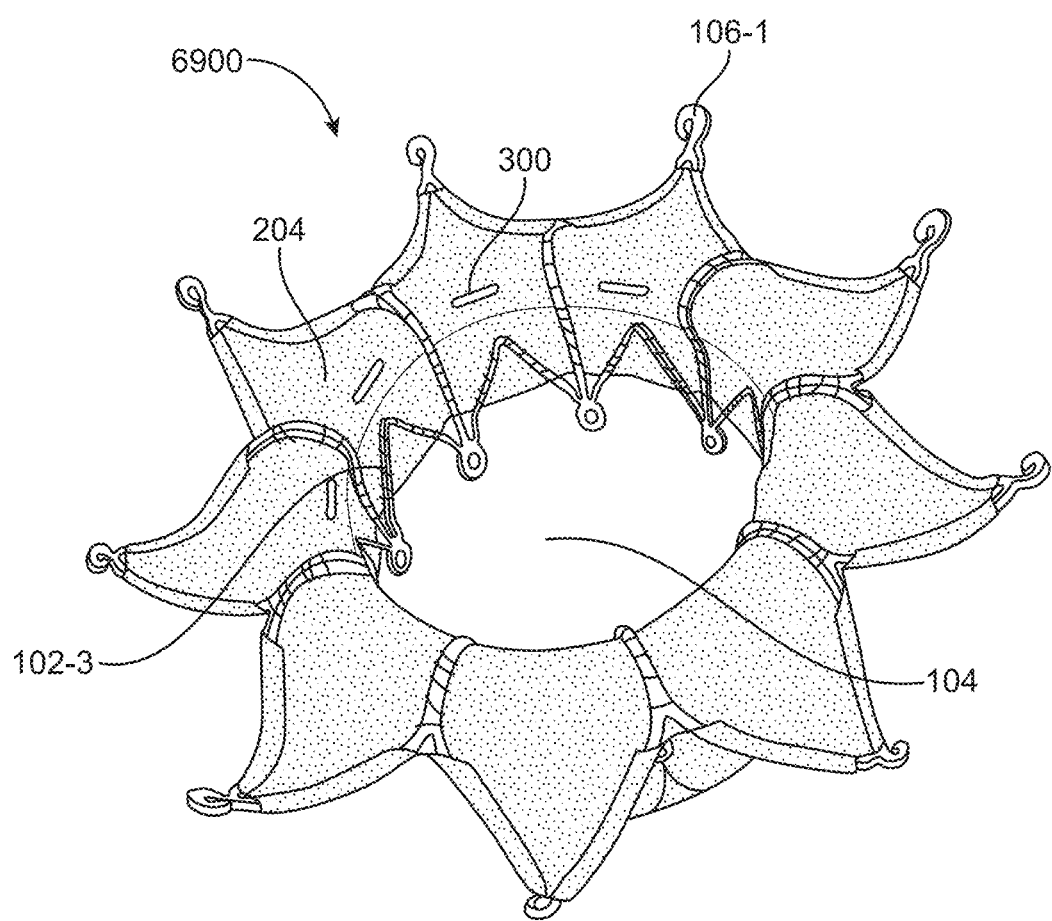
FIG. 71 is an image of a top-down view of a support structure of a prototype prosthetic tricuspid valve, in accordance with an embodiment.

FIG. 71 is an image of a top-down view of support structure 102-3 of the prototype prosthetic tricuspid valve 6900, in accordance with an embodiment. As shown in FIG. 71, the atrial sealing skirt 204 of the support structure 102-3 of prosthetic tricuspid valve 6900 includes fenestrations 300 configured to allow ventricular arms 106-2 to pass through the atrial sealing skirt 204 during assembly of the prosthetic tricuspid valve 6900, such that the ventricular arms 106-2 are located exterior to the elongate central passageway 104 of the prosthetic tricuspid valve 6900 once the prosthetic tricuspid valve 6900 is assembled.

Figure 72B:
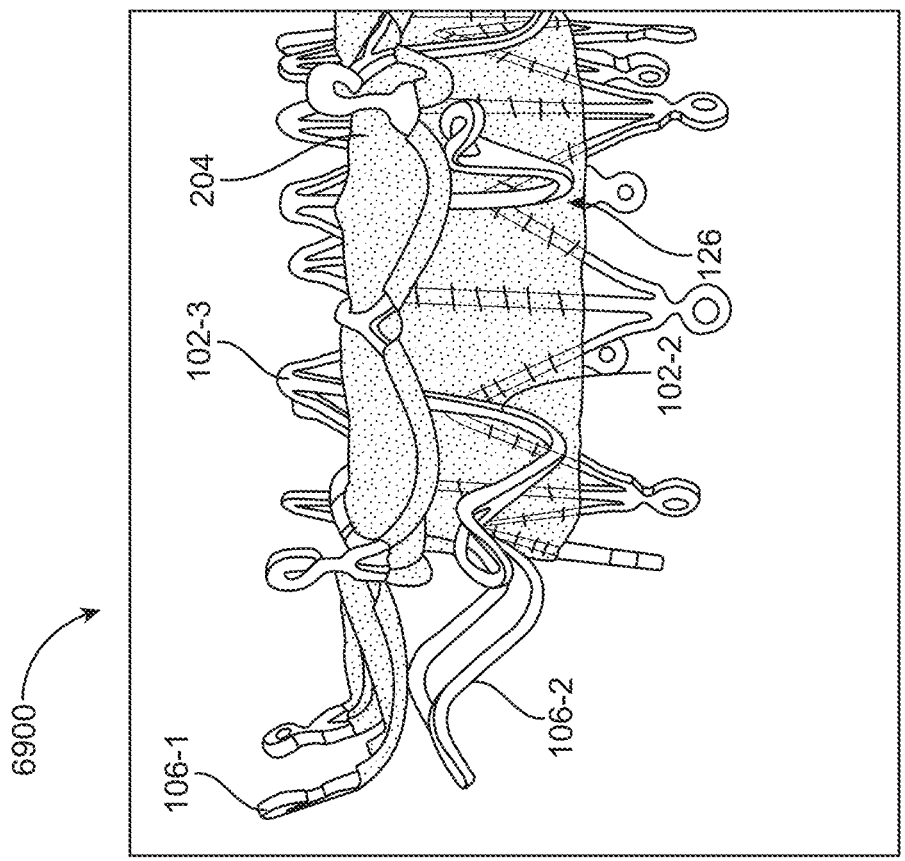
FIG. 72B is an image of a side view of support structures of a prototype prosthetic tricuspid valve, in accordance with an embodiment.
Figure 72A:
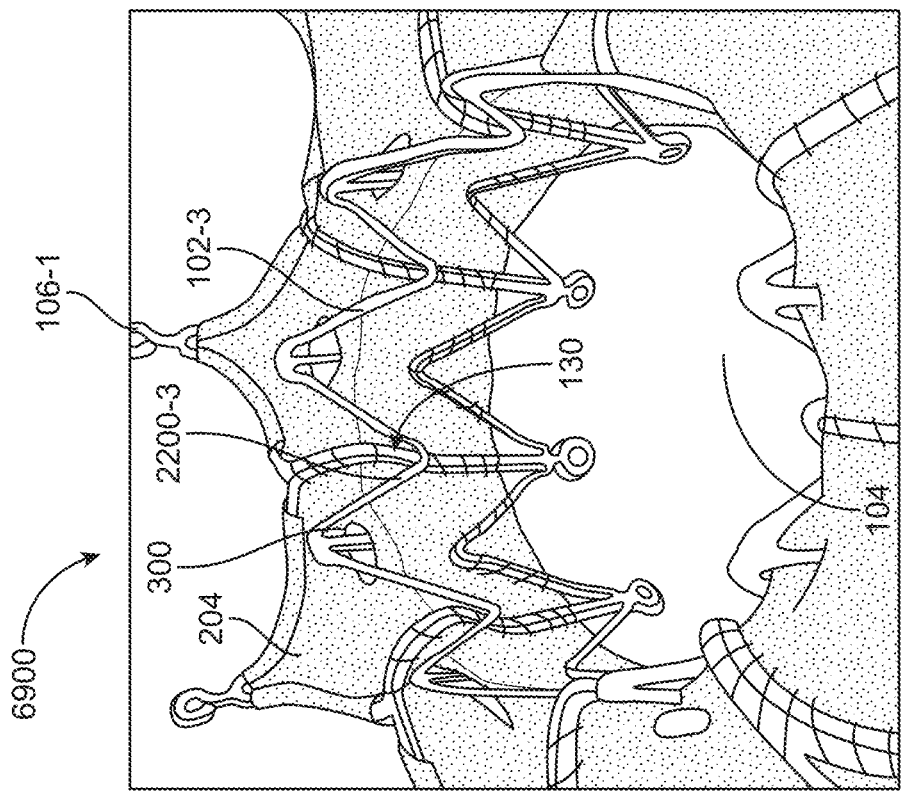
FIG. 72A is an image of a top-down view of support structures of a prototype prosthetic tricuspid valve, in accordance with an embodiment.

FIGS. 72A-B are images of support structures 102-2 and 102-3 of the prototype prosthetic tricuspid valve 6900, in accordance with an embodiment. Specifically, FIG. 72A is an image of a top-down view of support structures 102-2 and 102-3 of the prototype prosthetic tricuspid valve 6900, in accordance with an embodiment. FIG. 72B is an image of a side view of support structures 102-2 and 102-3 of the prototype prosthetic tricuspid valve 6900, in accordance with an embodiment.

As discussed above with regard to FIGS. 69A-B, the prosthetic tricuspid valve 6900 includes three support structures 102-1, 102-2, and 102-3 (shown in FIG. 74). However, the images in FIGS. 72A-B depict only the support structures 102-2 and 102-3 of the prototype prosthetic tricuspid valve 6900. As discussed below, the first support structure 102-1 does not form the atrial arms 106-1 or the ventricular arms 106-2. The second support structure 102-2 forms the ventricular arms 106-2, and the third support structure 102-3 forms the atrial arms 106-1.

The three support structures 102-1, 102-2, and 102-3 are configured to fit together to form the prosthetic tricuspid valve 6900. Specifically, to fit the three support structures 102-1, 102-2, and 102-3 together to form the prosthetic tricuspid valve 6900, a radius of curvature of a secondary bend 130 of each atrial arm 106-1 is received by a V-shaped strut 2200-1 of the first support structure 102-1 (shown in FIG. 74). Additionally, to fit the three support structures 102-1, 102-2, and 102-3 together to form the prosthetic tricuspid valve 6900, a radius of curvature of a secondary bend 126 of each ventricular arm 106-2 is received by a V-shaped strut 2200-1 of the support structure 102-1 (shown in FIG. 74), and also contacts a mirror V-shaped strut 2200-3 of the support structure 102-3 that forms the atrial arms 106-1.

Note that while the prosthetic tricuspid valve 6900 is configured to also include the support structure 102-1 (shown in FIG. 74) in addition to the support structures 102-2 and 102-3, in some embodiments, a prosthetic tricuspid valve does not require three support structures. Rather, in some embodiments, such as the embodiments of prosthetic tricuspid valves 4600, 4800, and 5000 a prosthetic tricuspid valve can include only two support structures. In such embodiments, there would simply be less reinforcement for the arms 106 of the prosthetic tricuspid valve, as described in detail above and below.

Figure 73:
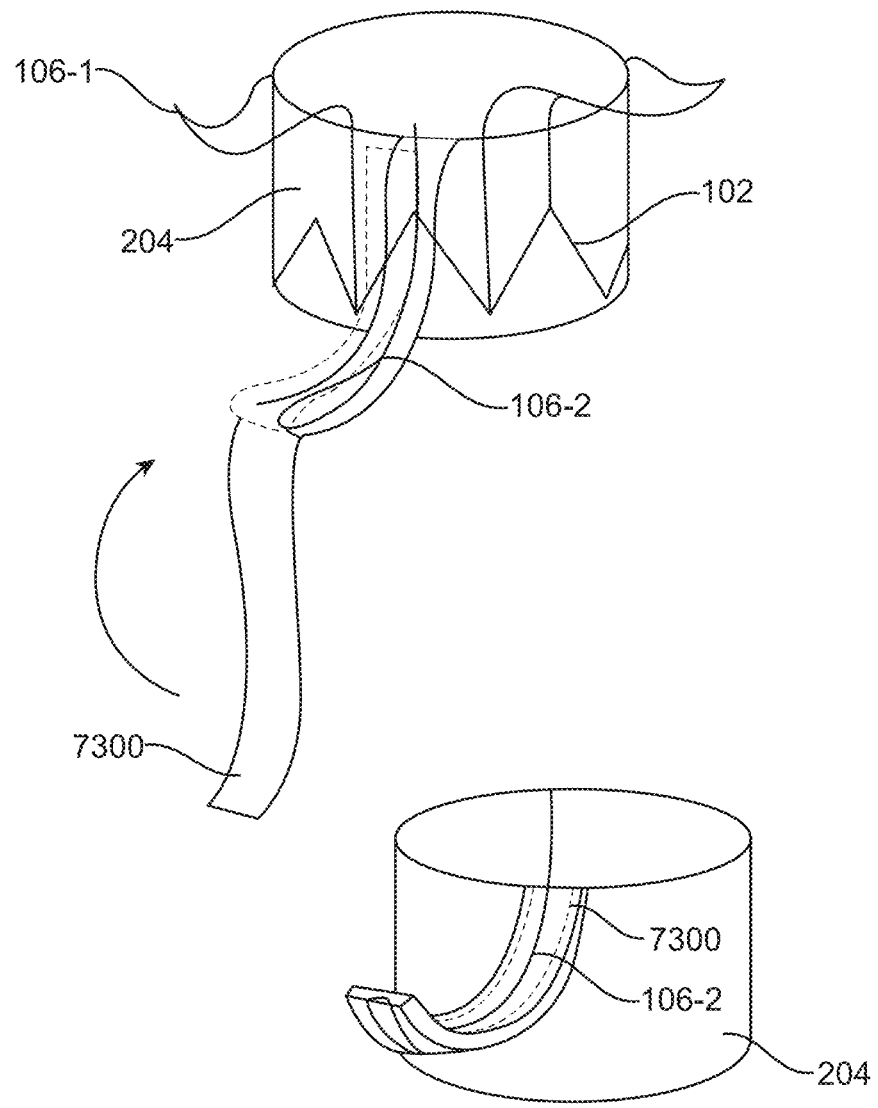
FIG. 73 illustrates an atrial sealing skirt including a ventricular arm sleeve configured to encapsulate a ventricular arm of a support structure, in accordance with an embodiment.

FIG. 73 illustrates an atrial sealing skirt 204 including a ventricular arm sleeve 7300 configured to encapsulate a ventricular arm 106-2 of a support structure 102, in accordance with an embodiment. As shown in FIG. 73, in some embodiments the atrial sealing skirt 204 can include one or more ventricular arm sleeves 7300, each ventricular arm sleeve 7300 configured to encapsulate a corresponding ventricular arm 106-2 of a support structure 102. Each ventricular arm sleeve 7300 can be configured, for example, as a ribbon extending from the atrial sealing skirt 204 covering the support structure 102. To encapsulate a ventricular arm 106-2, the ribbon extending from the atrial sealing skirt 204 can be folded over the ventricular arm 106-2, and stitched closed around the ventricular arm 106-2.

Encapsulation of a ventricular arm 106-2 by a ventricular arm sleeve 7300 can facilitate ingrowth of the ventricular arm 106-2 within a native tricuspid valve leaflet when the prosthetic tricuspid valve is implanted. Encapsulation of a ventricular arm 106-2 by a ventricular arm sleeve 7300 can also provide atraumatic contact between the ventricular arm 106-2 and a native tricuspid valve leaflet when the prosthetic tricuspid valve is implanted. Even further, encapsulation of a ventricular arm 106-2 by a ventricular arm sleeve 7300 can serve as a failsafe in preventing embolization in the event that the ventricular arm 106-2 fractures when the prosthetic tricuspid valve is implanted.

FIG. 74 is an image of a side view of the prototype prosthetic tricuspid valve 6900, in accordance with an embodiment. As discussed above with regard to FIGS. 69A-B, the prosthetic tricuspid valve 6900 includes three support structures 102-1, 102-2, and 102-3. The first support structure 102-1 does not form the atrial arms 106-1 or the ventricular arms 106-2. The second support structure 102-2 forms the ventricular arms 106-2, and the third support structure 102-3 forms the atrial arms 106-1.

The three support structures 102-1, 102-2, and 102-3 are configured to fit together to form the prosthetic tricuspid valve 6900. Specifically, to fit the three support structures 102-1, 102-2, and 102-3 together to form the prosthetic tricuspid valve 6900, a radius of curvature of a secondary bend 130 of each atrial arm 106-1 is received by a V-shaped strut 2200-1 of the first support structure 102-1. Additionally, to fit the three support structures 102-1, 102-2, and 102-3 together to form the prosthetic tricuspid valve 6900, a radius of curvature of a secondary bend 126 of each ventricular arm 106-2 is received by a V-shaped strut 2200-1 of the support structure 102-1, and also contacts a mirror V-shaped strut 2200-3 of the support structure 102-3 that forms the atrial arms 106-1.

Additionally, to secure the three support structures 102-1, 102-2, and 102-3 to one another to form the prosthetic tricuspid valve 6900, the support structures 102-2 and 102-3 are each secured to the support structure 102-1. Specifically, as depicted in FIG. 74, to secure the support structure 102-3 to the support structure 102-1, an eyelet 3502 (shown in FIG. 35) of each atrial arm 106-1 formed by the support structure 102-3 is secured to a corresponding eyelet of the support structure 102-1. As also depicted in FIG. 74, to secure the support structure 102-2 to the support structure 102-1, 3-point nodes of the support structure 102-2 are secured to the support structure 102-1.

FIGS. 75-79 illustrate different implementations of prosthetic tricuspid valves having different numbers of support structures, in accordance with an embodiment. Specifically, FIGS. 75-79 illustrate differential load distribution for different implementations of prosthetic tricuspid valves having different numbers of support structures, in accordance with an embodiment.

As shown in each of FIGS. 75-79, when prosthetic tricuspid valves are implanted in a native tricuspid valve throughout cardiac cycles of the heart, atrial-directed forces 7501 are incurred by the ventricular arms 106-2 of each prosthetic tricuspid valve as a result of ventricular systolic pressure loads from the heart. Conversely, ventricular-directed forces 7500 are incurred by the atrial arms 106-1 of each prosthetic tricuspid valve as a result of tensioning of native leaflets of the native tricuspid valve in response to the ventricular systolic pressure loads. As indicated by the magnitude of the arrows of the forces 7500 and 7501, the atrial-directed forces 7501 incurred by the ventricular arms 106-2 are much greater in magnitude than the ventricular-directed forces 7500 incurred by the atrial arms 106-1. As a result, and as discussed below, distribution of the atrial-directed forces 7501 incurred by the ventricular arms 106-2 is more essential to maintaining the integrity of the prosthetic tricuspid valve than distribution of the ventricular-directed forces 7500 are incurred by the atrial arms 106-1.

Depending upon the configuration of the prosthetic tricuspid valve, and particularly on the number of support structures comprising the prosthetic tricuspid valve, load nodes 7502 and fulcrum points 7503 can be differentially distributed throughout the prosthetic tricuspid valve, and therefore, the forces 7500 and 7501 can be differentially distributed throughout the prosthetic tricuspid valve. Each different configuration of the prosthetic tricuspid valve, and its load nodes 7502 and fulcrum points 7503, and therefore its distribution of the forces 7500 and 7501, are depicted in FIGS. 75-79.

Figure 75:
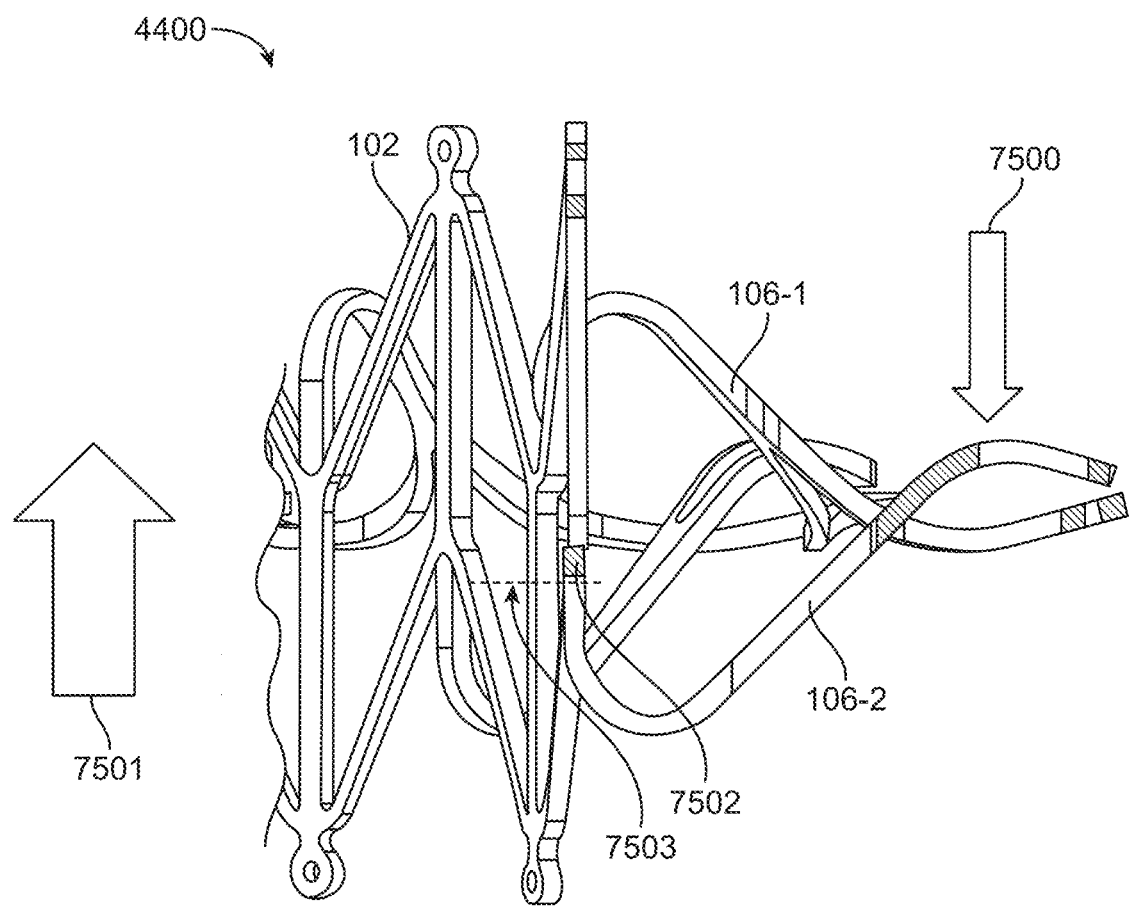
FIG. 75 illustrates load distribution for a prosthetic tricuspid valve having one support structure, in accordance with an embodiment.

FIG. 75 illustrates load distribution for the prosthetic tricuspid valve 4400 having one support structure 102, in accordance with an embodiment. In the embodiment of the prosthetic tricuspid valve 4400 having one support structure 102, both the atrial arms 106-1 and the ventricular arms 106-2 are formed from the one support structure 102.

As shown in FIG. 75, the prosthetic tricuspid valve 4400 has a single load node 7502 and a single fulcrum point 7503 located in the same general location of the one support structure 102. Additionally, there are no additional support structures supporting the ventricular arms 106-2. Thus, distribution of the atrial-directed forces 7501 incurred by the ventricular arms 106-2 is minimal, effectively resulting in greater breakability of the prosthetic tricuspid valve 4400.

Figure 76:
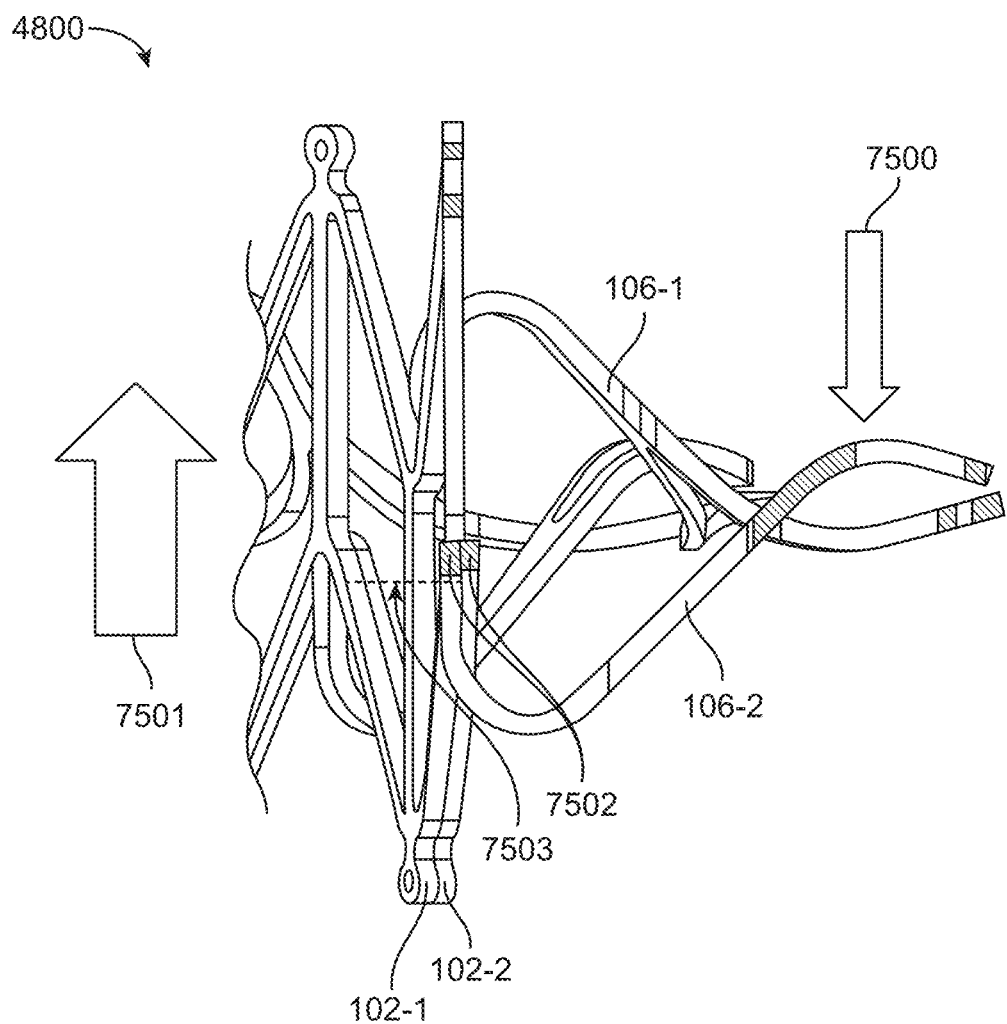
FIG. 76 illustrates load distribution for a prosthetic tricuspid valve having two support structures, in accordance with an embodiment.

FIG. 76 illustrates load distribution for the prosthetic tricuspid valve 4800 having two support structures 102-1 and 102-2, in accordance with an embodiment. In the first embodiment of the prosthetic tricuspid valve 4800 having two support structures 102-1 and 102-2, the ventricular arms 106-2 are formed from the first support structure 102-1 and the atrial arms 106-1 are formed from the second support structure 102-2.

As shown in FIG. 76, the prosthetic tricuspid valve 4800 has one load node 7502 located on each of the two support structures 102-1 and 102-2. The two load nodes 7502 are both located in the same general location of a single fulcrum point 7503. Additionally, the support structure 102-1 supports the atrial arms 106-1 formed by the support structure 102-2, rather than the ventricular arms 1061-2. Thus the majority of the improved load distribution in the prosthetic tricuspid valve 4800 occurs in the atrial arms 106-1, which is less important because the atrial arms 106-1 experience less force than the ventricular arms 106-2 when the prosthetic tricuspid valve 4800 is implanted in vivo as discussed above. Distribution of the atrial-directed forces 7501 incurred by the ventricular arms 106-2 is not improved relative to the prosthetic tricuspid valve 4400.

Figure 77:
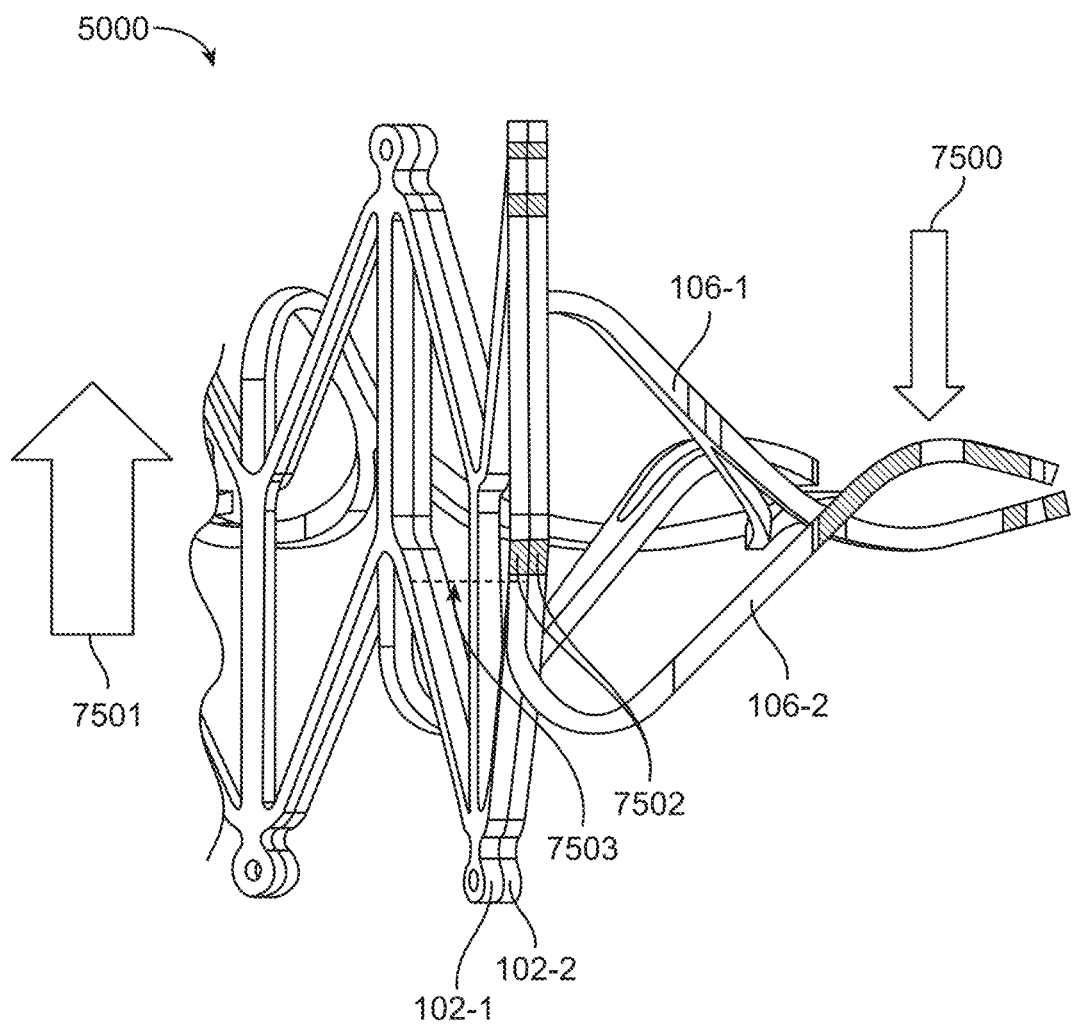
FIG. 77 illustrates load distribution for a prosthetic tricuspid valve having two support structures, in accordance with an embodiment.

FIG. 77 illustrates load distribution for the prosthetic tricuspid valve 5000 having two support structures 102-1 and 102-2, in accordance with an embodiment. In the embodiment of the prosthetic tricuspid valve 5000 having two support structures 102-1 and 102-2, the first support structure 102-1 does not form the atrial arms 106-1 or the ventricular arms 106-2. The second support structure 102-2 forms both the atrial arms 106-1 and the atrial arms 106-1.

As shown in FIG. 77, the prosthetic tricuspid valve 5000 has one load node 7502 located on each of the two support structures 102-1 and 102-2. The two load nodes 7502 are both located in the same general location of a single fulcrum point 7503. However, unlike the prosthetic tricuspid valve 4800, distribution of the atrial-directed forces 7501 incurred by the ventricular arms 106-2 is improved relative to the prosthetic tricuspid valves 4400 because the support structure 102-1 provides additional support to the ventricular arms 106-2 formed by the support structure 102-2. The support structure 102-1 also provides additional support to the atrial arms 106-1 formed by the support structure 102-2.

Figure 78:
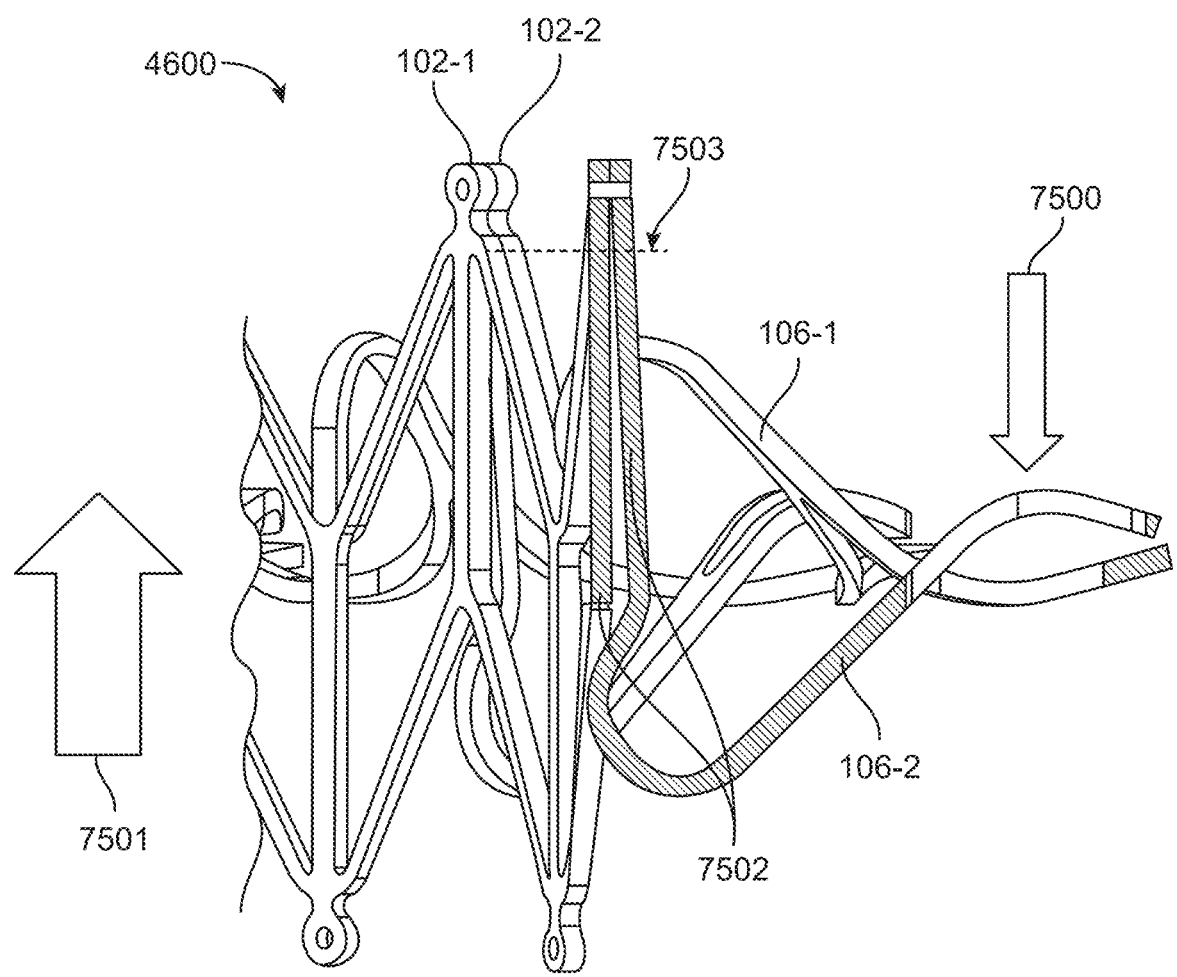
FIG. 78 illustrates load distribution for a prosthetic tricuspid valve having two support structures, in accordance with an embodiment.

FIG. 78 illustrates load distribution for the prosthetic tricuspid valve 4600 having two support structures 102-1 and 102-2, in accordance with an embodiment. In the embodiment of the prosthetic tricuspid valve 4600 having two support structures 102-1 and 102-2, the atrial arms 106-1 are formed from the first support structure 102-1 and the ventricular arms 106-2 are formed from the second support structure 102-2.

As shown in FIG. 78, the prosthetic tricuspid valve 4600 has one load node 7502 located on each of the two support structures 102-1 and 102-2. However, unlike the prosthetic tricuspid valves 4800 and 5000, the two load nodes 7502 are not located in the same general location. A single fulcrum point 7503 is located in the same general location of only one of the two load nodes 7502. Additionally, the support structure 102-1 provides additional support to the ventricular arms 106-2 formed by the support structure 102-2. As a result, distribution of the atrial-directed forces 7501 incurred by the ventricular arms 106-2 and of the ventricular-directed forces 7500 incurred by the atrial arms 106-1 is improved relative to the prosthetic tricuspid valves 4400, 4800, and 5000.

Figure 79:
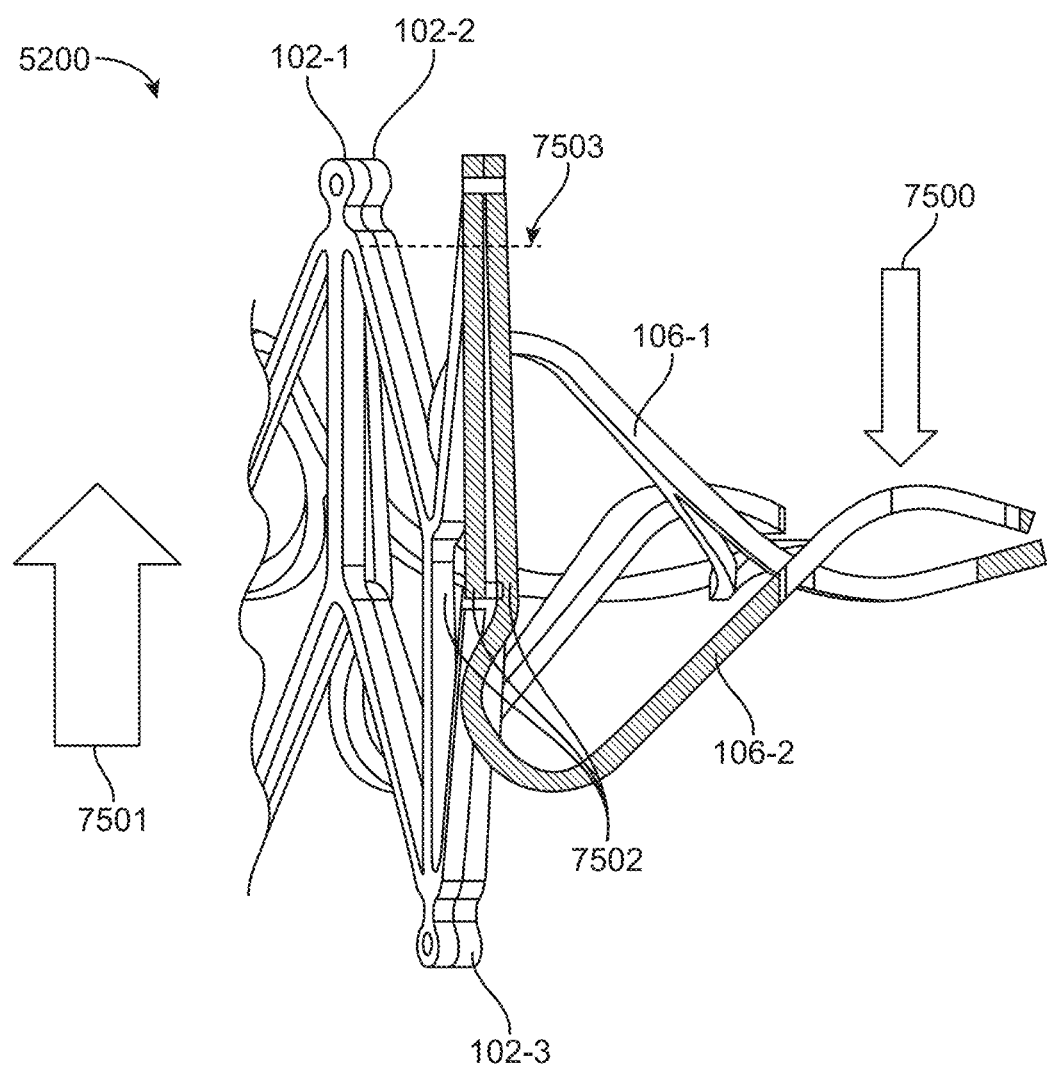
FIG. 79 illustrates load distribution for a prosthetic tricuspid valve having three support structures, in accordance with an embodiment.

FIG. 79 illustrates load distribution for the prosthetic tricuspid valve 5200 having three support structures 102-1, 102-2, and 102-3, in accordance with an embodiment. In the embodiment of the prosthetic tricuspid valve 5200 having three support structures 102-1, 102-2, and 102-3, the first support structure 102-1 does not form the atrial arms 106-1 or the ventricular arms 106-2. The second support structure 102-2 forms the ventricular arms 106-2. The third support structure 102-3 forms the atrial arms 106-1.

As shown in FIG. 79, the prosthetic tricuspid valve 5200 has one load node 7502 located on each of the three support structures 102-1, 102-2, and 102-3. The three load nodes 7502 are not located in the same general location of a single fulcrum point 7503. Additionally, the first support structure 102-1 can provide additional reinforcement to the atrial arms 106-1 formed from the third support structure 102-3, and the first support structure 102-1 and the third support structure 102-3 can both provide additional reinforcement to the ventricular arms 106-2 formed from the second support structure 102-2. As a result, distribution of the atrial-directed forces 7501 incurred by the ventricular arms 106-2 and of the ventricular-directed forces 7500 incurred by the atrial arms 106-1 is most improved in the prosthetic tricuspid valve 5200, relative to the prosthetic tricuspid valves 4400, 4800, 5000, and 4600.

Figure 80:
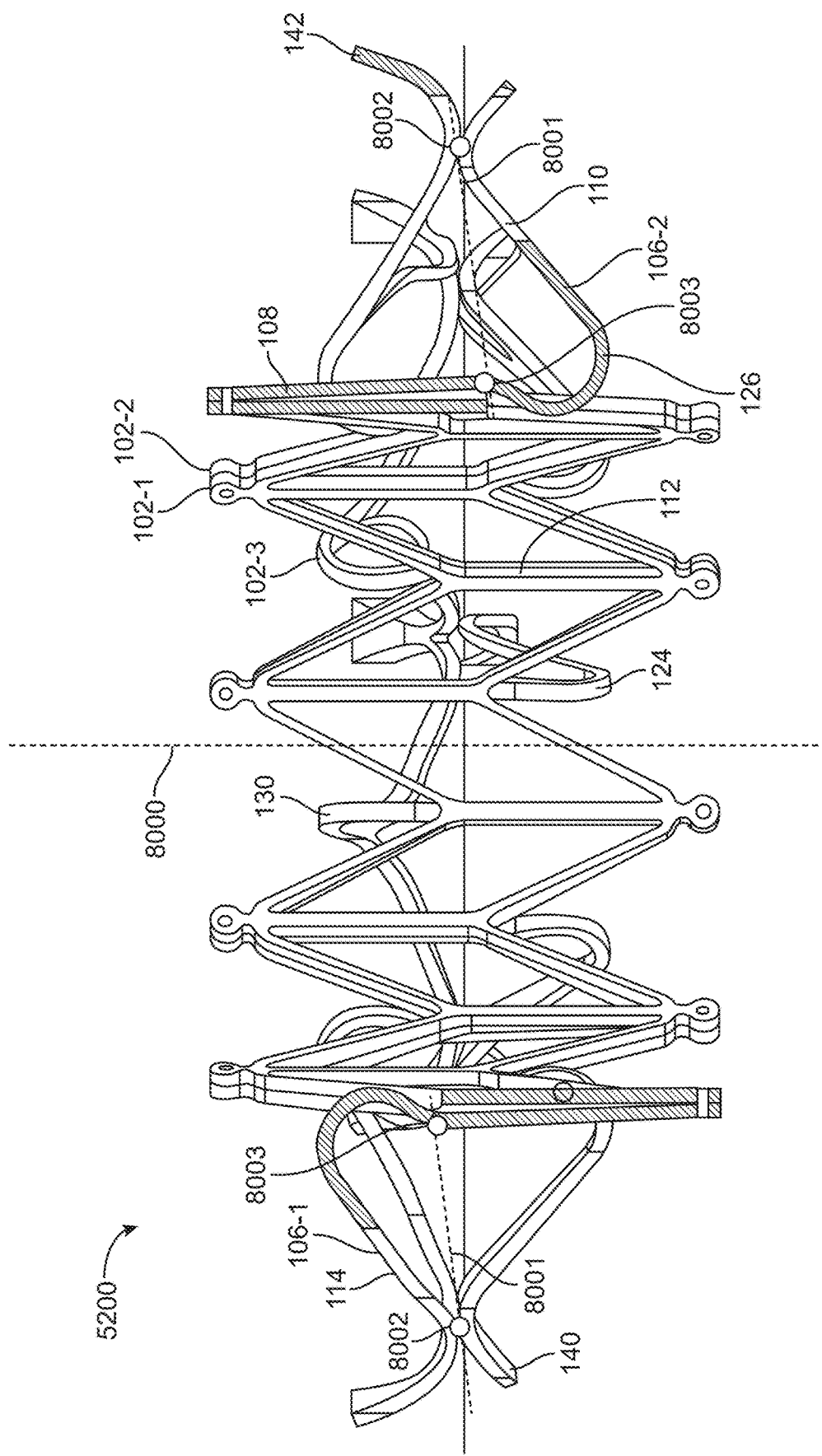
FIG. 80 illustrates a CAD drawing of a cut-away side view of a prosthetic tricuspid valve, in accordance with an embodiment.

FIG. 80 illustrates a CAD drawing of a cut-away side view of the prosthetic tricuspid valve 5200, in accordance with an embodiment. A central axis 8000 of the elongate central passageway 104 of the cylindrical portion 116 of at least one of the three support structures 102-1, 102-2, and 102-3 is shown in FIG. 80.

As discussed in detail above, the distal segment of each arm 106 (e.g., the distal segment 114 of each atrial arm 106-1 and the distal segment 110 of each ventricular arm 106-2) extends perpendicularly away from the central axis 8000 of the elongate central passageway 104 for attachment of the prosthetic tricuspid valve 5200 to an object (e.g., a native tricuspid valve leaflet). As referred to herein, a distal segment of an arm 106 extending "perpendicularly" away from the central axis 8000 of the elongate central passageway 104 refers to the distal segment of the arm 106 extending away from the central axis 8000 of the elongate central passageway 104 such that that a line 8001 drawn from a point of contact 8002 of the distal segment of the arm 106 with an object (e.g., a native tricuspid valve leaflet) to a longitudinal position 8003 along the exterior surface 147 of the cylindrical portion 116 of at least one of the three support structures 102-1, 102-2, and 102-3 from which the distal segment extends, is oriented approximately 90°+/−45° from the central axis 8000 of the elongate central passageway 104. In some embodiments, the point of contact 8002 of a distal segment of an arm 106 can be the tip 140 or 142 of the arm 106. In alternative embodiments in which a distal segment of an arm 106 includes an extended segment having a third bend, the point of contact 8002 of the distal segment of the arm 106 can be the extended segment, or more particularly, the third bend, of the arm 106. The point of contact 8002 of a distal segment of an arm 106 can also be any other portion of the distal segment of the arm 106. As discussed in further detail below, this approximate perpendicularity of the line 8001 from the point of contact 8002 of the distal segment to the longitudinal position 8003 along the exterior surface 147 of the cylindrical portion 116 from which the distal segment extends enables axial stabilization of the prosthetic tricuspid valve 5200 within the native tricuspid valve.

It is understood that any specific order or hierarchy of blocks in the processes disclosed is an illustration of example approaches. Based upon implementation preferences, it is understood that the specific order or hierarchy of blocks in the processes may be rearranged, or that not all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The subject technology is illustrated, for example, according to various aspects described above. The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that some or all steps, operations, or processes may be performed automatically, without the intervention of a user. Method claims may be provided to present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the appended claims. Moreover, nothing disclosed herein is intended to be dedicated to the public regardless of whether such disclosure is explicitly recited in the claims. No claims element is to be construed under the provisions of 35 U.S.C. § 112 (f) unless the element is expressly recited using the phrase "means for" or, in the case of a method, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Brief Description of the Drawings, and Claims of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims s reflect, inventive subject matter lies in less than all features of a single disclosed configuration or operation. The following claims are hereby incorporated into the Detailed Description, with each claims standing on its own to represent separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

Due to claim count limitations, the following subject matter has not been included in the claims below, but for clarity has been drafted in claim form, with reference to the below claims.

Claim A: The prosthetic heart valve of claim 1, wherein the at least one support structure is configured to biodynamically fix the prosthetic heart valve to the native leaflets such that the at least one support structure is moveable within a native annulus of the native heart valve responsive to changes in pressure on one or more sides of the native heart valve.

Claim B: The prosthetic heart valve of claim 11, wherein, in an implanted configuration in which the at least one support structure biodynamically fixes the prosthetic heart valve to the native leaflets of the native heart valve, the fenestration feature is disposed between the elongate central passageway and a native annulus of the native heart valve.

Claim C: The prosthetic heart valve of claim 10, wherein: the atrial set of arms is attached to the ventricular end of the cylindrical portion of the at least one support structure, the ventricular set of arms is attached to the atrial end of the cylindrical portion of the at least one support structure, and the one or more covers initiate at and are attached to the distal segment of each arm of the atrial set of arms, extend to and are attached to the proximal segment of each arm of the ventricular set of arms, extend through the cylindrical portion of the at least one support structure within the elongate central passageway, and extend around the cylindrical portion of the at least one support structure to attach to the proximal segment of each of the atrial set of arms.

Claim D: The prosthetic heart valve of claim C, wherein the one or more covers terminate at and attach to a location along the proximal segment of each arm of the atrial set of arms that is a common distance from the cylindrical portion of the at least one support structure.

Claim E: The prosthetic heart valve of claim C, wherein the one or more covers further extend and attach to the distal segment of each arm of the ventricular set of arms.

Claim F: The prosthetic heart valve of claim 23, wherein the one or more support structures comprise two support structures.

Claim G: The prosthetic heart valve of claim 23, wherein the one or more support structures comprise three support structures.

Claim H: A prosthetic heart valve, comprising: one or more support structures that define an elongate central passageway; and a valve structure attached to at least one support structure and disposed within the elongate central passageway for control of blood flow through the elongate central passageway, wherein at least one support structure comprises a plurality of arms that extend away from the elongate central passageway for attachment of the at least one support structure to native leaflets of a native heart valve of a heart.

Claim I: The prosthetic heart valve of claim H, wherein the plurality of arms include: an atrial set of arms that extend from an atrial end of at least one support structure before curving to extend away from the elongate central passageway; and a ventricular set of arms that extend from a ventricular end of at least one support structure before curving to extend away from the elongate central passageway.

Claim J: The prosthetic heart valve of claim I, wherein the atrial arms and the ventricular arms are configured to cooperate to hold the native leaflets of the native heart valve to maintain the elongate central passageway in a native annulus of the native heart valve without any direct attachment to the native annulus or to native cords associated with the native heart valve.

Claim K: A prosthetic heart valve, comprising: one or more support structures that define an elongate central passageway; and a plurality of leaflet elements attached to at least one support structure and disposed within the elongate central passageway, wherein at least one support structure is configured to biodynamically fix the prosthetic heart valve within, and separated from, a native annulus of a native heart valve of a heart.

Claim L: The prosthetic heart valve of claim K, wherein at least one support structure of the one or more support structures comprises a cylindrical portion comprising an atrial end and a ventricular end, the elongate central passageway is defined by the cylindrical portion of the at least one support structure, and the cylindrical portion of the at least one support structure is expandable to a maximum radial width that is less than a minimum radial width of the native annulus of the native heart valve.

Claim M: The prosthetic heart valve of claim K, wherein at least one support structure is configured to biodynamically fix the prosthetic heart valve within, and separated from, the native annulus of the native heart valve by grasping native leaflets of the native heart valve, without direct attachment to the native annulus or native cords associated with the native heart valve.

Claim N: The prosthetic heart valve of claim K, wherein the native heart valve is the tricuspid valve.

Claim O: The method of claim 26, further comprising detaching the plurality of restraints from the atrial plurality of arms.

Claim P: The method of claims 28 and/or 30, wherein the plurality of spreader arms extend from a mid layer within the sheath.

Claim Q: The method of claim P, wherein each restraint of the plurality of restraints extends from the sheath between a pair of the plurality of spreader arms.

Claim R: The method of claim 28, 30, P, and/or Q, wherein each spreader arm of the plurality of spreader arms includes an interlocking mechanism that maintains contact with the atrial end of the cylindrical portion of the at least one support structure.

What is claimed is:

1. A prosthetic heart valve, comprising:
   a support structure, wherein the support structure defines an elongate central passageway; and
   a plurality of leaflet elements attached to the support structure and disposed within the elongate central passageway for control of blood flow through the elongate central passageway,
   wherein the support structure is configured to biodynamically fix the prosthetic heart valve to native leaflets of a native heart valve of a heart such that the prosthetic heart valve is not attached to a native annulus of the native heart valve, and such that the prosthetic heart valve is configured to maintain axial stabilization within the native heart valve of the heart while the support structure moves within the native heart valve during cardiac cycles of the heart,
   wherein the support structure comprises a cylindrical portion comprising an atrial end and a ventricular end, the elongate central passageway is defined by the cylindrical portion of the support structure,
   wherein the support structure comprises an atrial set of arms and a ventricular set of arms,
   wherein a distal segment of each of the atrial set of arms and a distal segment of each of the ventricular set of arms extend perpendicularly away from a central axis of the elongate central passageway,
   wherein the atrial set of arms and the ventricular set of arms are configured to contact opposing sides of each native leaflet at locations radially inward from the native annulus such that at least a portion of each native leaflet is held radially away from the native annulus thereby permitting axial motion of the cylindrical portion of the support structure and the portion of each native leaflet, relative to the native annulus,
   wherein, during biodynamic movement of the prosthetic heart valve within the native heart valve during cardiac cycles of the heart, the ventricular set of arms are configured to resist the movement while the atrial set of arms maintain contact with the native leaflets and/or the atrial set of arms resist the movement while the ventricular set of arms maintain contact with the native leaflets, such that systolic and/or diastolic pressure load is at least partially absorbed by the motion of the native leaflets.

2. The prosthetic heart valve of claim 1, wherein:
   each arm of the atrial set of arms and the ventricular set of arms comprises a proximal segment that is proximal to the cylindrical portion of the support structure and the distal segment that is distal to the cylindrical portion of the support structure.

3. The prosthetic heart valve of claim 2, wherein the atrial and ventricular sets of arms are bent such that
   in an implanted configuration in which the support structure biodynamically fixes the prosthetic heart valve to the native leaflets of the native heart valve,
   in the event of motion of the cylindrical portion of the support structure toward the atrial side of the native heart valve due to a ventricular systolic pressure load, one or more arms of the ventricular set of arms resist the motion while one or more arms of the atrial set of arms relax to maintain contact with the atrial side of the native leaflets, and
   in the event of motion of the cylindrical portion of the support structure toward the ventricular side of the native heart valve due to a ventricular diastolic pressure load and/or an elimination of a previously applied ventricular systolic load, the one or more arms of the atrial set of arms resist the motion while the one or more arms of the ventricular set of arms relax to maintain contact with the ventricular side of the native leaflets.

4. The prosthetic heart valve of claim 2, wherein the arms of the atrial set of arms alternate with the arms of the ventricular set of arms around a circumference of the cylindrical portion of the support structure, and/or wherein the arms of the atrial set of arms and the arms of the ventricular set of arms extend across a cross-sectional plane of the cylindrical portion of the support structure.

5. The prosthetic heart valve of claim 4, comprising an overbite between the atrial set of arms and the ventricular set of arms over the cross-sectional plane of the cylindrical portion.

6. The prosthetic heart valve of claim 2, wherein:
   the distal segments of the arms of the atrial set of arms extend toward the ventricular end of the cylindrical portion of the support structure, thereby enabling the distal segments of the arms of the atrial set of arms to clamp the native leaflets on the atrial side of the native heart valve; and
   the distal segments of the arms of the ventricular set of arms extend toward the atrial end of the cylindrical portion of the support structure, thereby enabling the distal segments of the arms of the ventricular set of arms to clamp the native leaflets on the ventricular side of the native heart valve.

7. The prosthetic heart valve of claim 2, wherein:
   the distal segments of the arms of the atrial set of arms each have a tip that curves toward the atrial end of the cylindrical portion of the support structure, thereby reducing trauma to the native leaflets on the atrial side of the native heart valve at the points of contact of the atrial set of arms; and
   the distal segments of the arms of the ventricular set of arms each have a tip that curves toward the ventricular end of the cylindrical portion of the support structure, thereby reducing trauma to the native leaflets on the ventricular side of the native heart valve at the points of contact of the ventricular set of arms.

8. The prosthetic heart valve of claim 2, wherein the cylindrical portion of the support structure is radially collapsible for transcatheter implantation.

9. The prosthetic heart valve of claim 2, wherein the distal segments of the ventricular set of arms extend toward the ventricular end of the cylindrical portion of the support structure, thereby enabling the distal segments of the ventricular set of arms to contact one of the native leaflets on the atrial side of the native heart valve rather than on the ventricular side of the native heart valve, thereby holding the native leaflet radially outward from the native heart valve in an open position.

10. The prosthetic heart valve of claim 2, further comprising one or more covers that extend within the elongate central passageway and over one or more of the atrial set of arms and/or the ventricular set of arms.

11. The prosthetic heart valve of claim 10, further comprising a fenestration feature in a portion of the one or more covers.

12. The prosthetic heart valve of claim 11, wherein the fenestration feature comprises at least one of a radiopaque marker, an opening, a magnetic element, a one-way valve, a pop-up valve, a mechanically resizable opening, and increased porosity.

13. The prosthetic heart valve of claim 10, wherein the one or more covers extend asymmetrically and/or non-circularly within the elongate central passageway and over one or more of the atrial set of arms and the ventricular set of arms.

14. The prosthetic heart valve of claim 2, wherein the atrial set of arms is attached to the atrial end of the cylindrical portion of the support structure and/or the ventricular set of arms is attached to the ventricular end of the cylindrical portion of the support structure.

15. The prosthetic heart valve of claim 2, wherein the atrial set of arms is attached to the ventricular end of the cylindrical portion of the support structure and/or the ventricular set of arms is attached to the atrial end of the cylindrical portion of the support structure.

16. The prosthetic heart valve of claim 15, wherein the proximal segment of each arm of the atrial set of arms extends from the ventricular end of the cylindrical portion of the support structure toward the atrial end of the cylindrical portion of the support structure along an exterior surface of the cylindrical portion of the support structure, and the distal segment of each arm of the atrial set of arms extends perpendicularly away from the central axis of the elongate central passageway.

17. The prosthetic heart valve of claim 15, wherein the proximal segment of each arm of the ventricular set of arms extends from the atrial end of the cylindrical portion of the support structure toward the ventricular end of the cylindrical portion of the support structure along an exterior surface of the cylindrical portion of the support structure, and the distal segment of each arm of the ventricular set of arms extends perpendicularly away from the central axis of the elongate central passageway.

18. The prosthetic heart valve of claim 15, wherein:
in an implanted configuration in which the support structure biodynamically fixes the prosthetic heart valve to the native leaflets of the native heart valve, the ventricular set of arms extend from the atrial end of the cylindrical portion of the support structure, through a native annulus of the native heart valve, and into the ventricular side of the native heart valve to contact the native leaflets on the ventricular side of the native heart valve.

19. The prosthetic heart valve of claim 15, wherein:
in an implanted configuration in which the support structure biodynamically fixes the prosthetic heart valve to the native leaflets of the native heart valve, the atrial set of arms extend from the ventricular end of the cylindrical portion of the support structure, through a native annulus of the native heart valve, and into the atrium of the heart to contact the native leaflets on the atrial side of the native heart valve.

20. The prosthetic heart valve of claim 2, wherein:
the distal segments of the arms of the atrial set of arms extend from an atrial longitudinal position along the exterior surface of the cylindrical portion of the support structure, the distal segments of the arms of the ventricular set of arms extend from a ventricular longitudinal position along the exterior surface of the cylindrical portion of the support structure, and
the atrial longitudinal position is in closer proximity to the atrial end of the cylindrical portion of the support structure than the ventricular longitudinal position is to the atrial end of the cylindrical portion of the support structure.

21. The prosthetic heart valve of claim 2, wherein the cylindrical portion of the support structure comprises a cylindrical cage structure with openings, and wherein at least some portions of the cylindrical cage structure and the openings are configured to receive bends of the atrial set of arms and the ventricular set of arms, where the atrial set of arms and the ventricular set of arms extend perpendicularly away from the central axis of the elongate central passageway.

22. The prosthetic heart valve of claim 2, wherein a minimum inner diameter of the cylindrical portion of the support structure that defines the elongate central passageway is less than a maximum outer diameter of the elongate central passageway.

23. The prosthetic heart valve of claim 2, wherein a minimum diameter of a radius of curvature of each bend of the atrial set of arms and the ventricular set of arms, where the atrial set of arms and the ventricular set of arms extend perpendicularly away from the central axis of the elongate central passageway, is less than the maximum outer diameter of the elongate central passageway.

24. The prosthetic heart valve of claim 2, wherein the atrial set of arms is configured to contact the native leaflets on an atrial side of the native heart valve.

25. The prosthetic heart valve of claim 2, wherein the ventricular set of arms is configured to contact the native leaflets on a ventricular side of the native heart valve.

26. The prosthetic heart valve of claim 1, wherein the prosthetic heart valve comprises more than one support structure.

27. The prosthetic heart valve of claim 1, wherein the support structure is configured to biodynamically fix the prosthetic heart valve to the native leaflets of the native heart valve of the heart such that the prosthetic heart valve is responsive to alternating pressure differentials on either side of the native heart valve during cardiac cycles of the heart.

28. The prosthetic heart valve of claim 1, wherein the prosthetic heart valve is not rigidly fixed within the native heart valve.

29. The prosthetic heart valve of claim 1, wherein the atrial set of arms and the ventricular set of arms are configured to contact opposing sides of each native leaflet across a cross-sectional plane of the cylindrical portion of the support structure such that at least a portion of each native leaflet is held in a horizontal position relative to the native annulus thereby permitting axial motion of the cylindrical portion of the support structure, and the portion of each native leaflet, relative to the native annulus.

30. The prosthetic heart valve of claim 1, wherein the portion of each native leaflet held radially away from the native annulus is oriented at 90 degrees +/−45 degrees relative to the central axis of the elongate central passageway.

* * * * *